United States Patent [19]
Katakami et al.

[11] Patent Number: 5,332,739
[45] Date of Patent: Jul. 26, 1994

[54] PYRIMIDINEDIONE DERIVATIVES AND ANTIARRHYTHMIC AGENTS CONTAINING SAME

[75] Inventors: Tsutomu Katakami; Tatsuro Yokoyama; Michihiko Miyamoto; Haruki Mori; Nobuya Kawauchi; Tadahito Nobori; Joji Kamiya; Masaaki Ishii, all of Mobara, Japan

[73] Assignee: Mitsui Toatsu Chemicals, Incorporated, Tokyo, Japan

[21] Appl. No.: 971,059

[22] Filed: Nov. 2, 1992

Related U.S. Application Data

[63] Continuation of Ser. No. 690,821, Apr. 24, 1991, abandoned.

[30] Foreign Application Priority Data

Apr. 27, 1990 [JP] Japan .................. 2-112710
Nov. 13, 1990 [JP] Japan .................. 2-336080

[51] Int. Cl.$^5$ ............... A61K 31/50; A61K 31/505; C07D 403/04; C07D 239/42
[52] U.S. Cl. .................. 514/252; 544/295; 544/311; 544/312; 514/269
[58] Field of Search ............ 544/295; 514/252

[56] References Cited

U.S. PATENT DOCUMENTS 4,216,314  8/1980  Raabe et al. .................. 544/123
5,008,267  4/1991  Katakami et al. ............. 514/269

*Primary Examiner*—Mukund J. Shah
*Assistant Examiner*—Matthew V. Grumbling
*Attorney, Agent, or Firm*—Nixon & Vanderhye

[57] ABSTRACT

Pyrimidinedione derivatives of the formula:

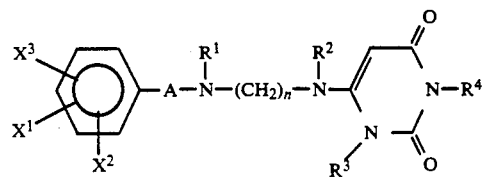

wherein $R^1$ and $R^2$ is so linked with each other as to make an alkylene chain and thus form a heterocyclic structure, A, $R^3$, $R^4$, $X^1$, $X^2$ and $X^3$ are substituents, respectively, and n is 2 or 3 have a basic backbone in which a phenyl group part and a pyrimidinedione part are linked by a structure comprising an alkyl chain and a heterocyclic ring having two nitrogen atoms. These compounds are useful for a medical treatment of cardiac arrhythmias.

11 Claims, No Drawings

PYRIMIDINEDIONE DERIVATIVES AND ANTIARRHYTHMIC AGENTS CONTAINING SAME

This is a continuation of application Ser. No. 690,821, filed Apr. 24, 1991 now abandoned.

BACKGROUND OF THE INVENTION

1. Field of the Invention

The present invention relates to novel pyrimidinedione derivatives and acid addition salts thereof, to methods of preparing the same and to pharmaceutical agents containing the same, which are effective for the treatment of cardiac dysfunctions such as arrhythmia and cardiac insufficiency.

2. Description of the Related Art

The mechanism of the occurrence of arrhythmia is complicated. Abnormalities in stimulation production and disorders in the conducting system or combinations thereof are considered to be responsible.

As to disorders in excitation conduction, the reentry theory is representative.

One of the conditions of occurrence of arrhythmia is irregularity in the refractory period in various parts of the heart. In addition, one-directional block, shortened refractory period, delay in conduction and the presence of circus movement are complicatedly involved.

Heretofore, various antiarrhythmic agents have been used for the treatment of arrhythmia.

The antiarrhythmic agents are classified into four groups according to their modes of action.

That is, E. M. Vaughan Williams (Vaughan Williams E. M.; "Advances in drug research, Vol 9", ed. by Harper N. J., Simmonds A. B., Academic Press, London, 1974, pages 69-101) have classified the antiarrhythmic agents into the following four groups in accordance with their actions against the action potential of cardiac muscle or against the ionic current which generates the action potential.

CLASS I

Sodium Channel Depressors

These agents are efficacious in repressing a sodium current. However, they have no or only minute effects on the retention time of the normal action potential and decrease the maximum rising velocity ($V_{max}$) of the sodium current. The antiarrhythmic agents which belong to this class have a high antiarrhythmic activity but at the same time strongly repress cardiac functions. Careful consideration is required in administering to patients with cardiac failure or hypotension.

CLASS II

Beta-Blocking Agents

The agents in this class, represented by propranolol, are efficacious in the beta-blocking action and are useful in treating patients with arrhythmia in which the sympathetic nerve is involved. However, the care must be taken for use since these agents have side-effects caused by the beta-blocking action, such as depression of cardiac functions, induction of bronchial asthmatic attack and hypoglycemic seizures.

CLASS III

Pharmaceutical Agents for Prolonging the Retention Time of the Action Current These agents are efficacious in remarkably prolonging the retention time of the action current of the cardiac muscle and in prolonging an effective refractory period. Re-entry arrhythmia is considered to be suppressed by the action of the pharmaceutical agents of Class III. The medicaments of this Class III include aminodarone and bretylium. However, all the agents have severe side effects, and therefore, careful consideration is required for use.

CLASS IV

Calcium Antagonists

These agents control a calcium channel and suppress arrhythmia due to automatic sthenia of sinoatrial nodes and to ventricular tachycardia in which atrial nodes are contained in the re-entry cycle.

Among these antiarrhythmic agents, pharmaceutical agents of the Class III type are considered to be particularly important and most efficacious, and known to be effective on ventricular arrhythmia which is most fatal.

SUMMARY OF THE INVENTION

Various medicinal agents have already been developed and utilized as antiarrhythmic agents.

Search for ideal antiarrhythmic agents has been pursued for treatment of arrhythmia which has complicated generating mechanisms and requires administration of such agents for a long period of time. However, satisfactory results have not been achieved so far.

The present invention has been accomplished in view of the present situation regarding antiarrhythmic agents. Thus, an object of the present invention is to provide a novel compound which is useful as a Class III type antiarrhythmic agent and to provide a process for producing the same.

Another object of the present invention is to provide a novel compound which is effective in improving cardiac dysfunction such as cardiac insufficiency and a process for the preparation of the same.

Still another object of the present invention is to provide a pharmaceutical agent, which contains the novel compound as an effective component, for the treatment of cardiac dysfunctions such as arrhythmia and cardiac. insufficiency.

In the course of the intensive study to solve the above-mentioned problems, the present inventors have found compounds of the formula (1) shown below and acid addition salts thereof. Furthermore, they have investigated the pharmacological properties of these compounds, and as a result, they have found that these compounds have pharmacological characteristics for markedly prolonging the retention time of the action potential of cardiomuscular cells and for markedly prolonging the ventricular refractory period in animal experiments using adult dogs. In consequence, the present invention has been achieved on the basis of the above-mentioned knowledge.

Furthermore, the present inventors have found that the compounds of the present invention have a positive inotropic action and are useful as therapeutic agents for cardiac insufficiency.

The compounds of the present invention can be utilized to provide antiarrhythmic agents and therapeutic agents for cardiac insufficiency.

DETAILED DESCRIPTION OF THE PREFERRED EMBODIMENTS

The compounds of the present invention are compounds represented by the following formula (1) and acid addition salts thereof:

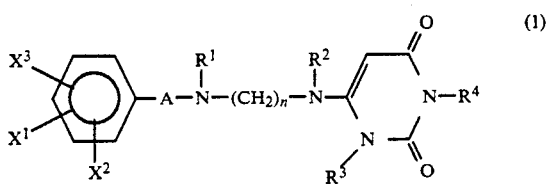

wherein A is $-(CH_2)_m-$, $-B-(CH_2)_k-$, $D-(CH_2)_l-$ or

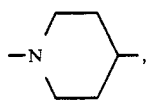

B is an oxygen atom, a sulfur atom,

and D is

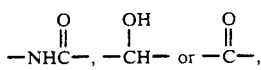

each of $R^1$ and $R^2$ is independently a hydrogen atom or a lower alkyl group (any one hydrogen atom of the alkyl group may be substituted by a substituent selected from the group consisting of a hydroxyl group and a benzoyloxy group), or $R^1$ and $R^2$ may be so linked with each other as to make an alkylene chain and thus form a heterocyclic structure, each of $R^3$ and $R^4$ is independently a hydrogen atom or a lower alkyl group, each of $X^1$, $X^2$ and $X^3$ is independently a hydrogen atom $-CO-R^6$, halogen atom lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^5$ is a hydrogen atom, lower alkylsulfonyl group or lower alkyl group, or $R^5$ may be so linked with $R^1$ as to make an alkylene chain and thus form a heterocyclic structure, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, m is 0, 1, 2, 3 or 4, k is 2, 3 or 4, and l is 0, 1, 2, 3 or 4.

In the compound of the formula (1), examples of the unsaturated lower alkyl group include a vinyl group, allyl group and propargyl group.

The lower alkyl group is a straight-chain or branched alkyl group having 1 to 5 carbon atoms, and examples of the lower alkyl group include methyl, ethyl, propyl, butyl, isopropyl, isobutyl, tertiary butyl and secondary buty groups.

Examples of the lower alkyl group substituted by the hydroxyl group include 2-hydroxyethyl, 3-hydroxypropyl, 2-hydroxypropyl and 4-hydroxybutyl groups.

Examples of the lower alkylsulfinyl group include a sulfinyl group substituted by the above-mentioned lower alkyl group.

Examples of the sulfamoyl group include methylsulfamoyl, dimethylsulfamoyl, ethylsulfamoyl and diethylsulfamoyl groups.

Examples of the lower alkyloxy group include oxygen atoms substituted by the above-mentioned lower alkyl groups.

Examples of the lower alkanoyloxy group include acetyloxy, propionyloxy, butyryloxy, isobutyryloxy and pivaloyloxy groups.

Examples of the lower alkyl group substituted by the benzoyloxy group include 2-benzoyloxyethyl, 3-benzoyloxypropyl and 2-benzoyloxypropyl groups.

Examples of the lower alkyl group substituted by the phenyl group include benzyl, 2-phenylethyl and 3-phenylpropyl groups.

Examples of the lower alkyl in the lower alkyloxycarbonyl group include those which are exemplified as the above-mentioned lower alkyl group.

Examples of the halogen atom include fluorine, chlorine, bromine and iodine atoms.

In tile lower alkyl group substituted by the halogen atom, the lower alkyl group substituted by the phenyl group, the lower alkyl group substituted by the lower alkyloxycarbonyl group, the unsaturated lower alkyl group substituted by the phenyl group and the unsaturated lower alkyl group substituted by the substituted phenyl group, no particular restriction is put on the substitution site of each substituent.

Examples of the lower alkylthio group include sulfur atoms substituted by the above-mentioned lower alkyl groups.

Examples of the lower alkanoylamino group include formylamino, acetylamino and propionylamino groups.

Examples of the lower alkylsulfonamido group include methansulfonamido and ethansulfonamido groups.

Examples of the mono- or di-lower alkylamino group include methylamino, ethylamino, dimethylamino and diethylamino groups.

Examples of the substituted-phenyl group include phenyl groups each substituted by a methylmercapto group, a halogen atom, a nitro group, an N,N-dimethylamino group or a methoxy group.

Examples of phenyl group-substituted lower alkylamino group include the above-mentioned mono- and di-lower alkylamino groups each substituted by a phenyl group, and no restriction is put on its substitution site.

Examples of the unsaturated lower alkyloxy group include vinyloxy, allyloxy and propargyloxy groups.

Examples of the alkylene chain for linking $R^1$ with $R^2$; or $R^1$ with $R^5$ include ethylene and propylene chains.

Examples of the lower alkanoyl group in the lower alkanoyloxy and lower alkanoylamino groups include formyl, acetyl, propionyl and butyryl groups.

Examples of the lower alkylsulfonyl group include methansulfonyl and ethanesulfonyl groups.

Examples of the cycloalkyl group include cyclopentyl and cyclohexyl groups.

Examples of the heterocyclic ring in $X^1$, $X^2$, $X^3$ and $R^6$ include pyridyl, pyrazolyl, pyrimidinyl, thienyl, furil, imidazolyl, triazolyl, tetrazolyl and pyrrolyl groups.

In case that the phenyl group in $R^6$ is substituted by a substituent, its substitution site is not particularly limited.

The expression "pharmaceutically acceptable" used to describe the pharmaceutically acceptable acid addition salts in the compounds of the above-mentioned formula (1) means that remarkable side effects or toxicity does not appear and that its pharmaceutical activities are not extinguished, when administered to men. These acid addition salts can be produced by neutralization of the corresponding free bases.

Examples of the acids from which these pharmaceutically acceptable salts can be prepared include organic acids and inorganic acids, such as hydrochloric acid, hydrobromic acid, phosphoric acid, sulfuric acid, nitric acid, methanesulfonic acid, maleic acid, oxalic acid, malonic acid, succinic acid, fumaric acid, tartaric acid, citric acid, lactic acid and benzenesulfonic acid.

Typical examples of the compounds of the present invention are as follows:

(1) 1,3-dimethyl-6-[4-(3-[2-fluorophenoxy]propyl)piperazin-1-yl]-2,4(1H,3H)-pyrimidinedione,
(2) 1,3-dimethyl-6-[4-(3-[3-fluorophenoxy]propyl)piperazin-1-yl]-2,4(1H,3H)-pyrimidinedione,
(3) 1,3-dimethyl-6-[4-(3-[4-fluorophenoxy]propyl)piperazin-]-yl]-2,4(1H,3H)-pyrimidinedione,
(4) 1,3-dimethyl-6-[4-(3-[2-aminophenoxy]propyl)piperazin-1-yl]-2,4(1H,3H)-pyrimidinedione,
(5) 1,3-dimethyl-6-[4-(3-[3-aminophenoxy]propyl)piperazin-1-yl]-2,4(1H,3H)-pyrimidinedione,
(6) 1,3-dimethyl-6-[4-(3-[4-aminophenoxy]propyl)piperazin-1-yl]-2,4(1H,3H)-pyrimidinedione,
(7) 1,3-dimethyl-6-[4-(3-[2-acetylphenoxy]propyl]piperazin-1-yl]-2,4(1H,3H)-pyrimidinedione,
(8) 1,3-dimethyl-6-[4-(3-[3-acetylphenoxy]propyl)piperazin-1-yl]-2 ,4(1H,3H)-pyrimidinedione,
(9) 1,3-dimethyl-6-[4-(3-[4-acetylphenoxy]propyl)piperazin-1-yl]-2,4(1H,3H)-pyrimidinedione,
(10) 1,3-dimethyl-6-[4-(3-[2-cyanophenoxy]propyl)piperazin-1-yl]-2,4(1H,3H)-pyrimidinedione,
(11) 1,3-dimethyl-6-[4-(3-[3-cyanophenoxy]propyl)piperazin-1-yl]-2,4(1H,3H)-pyrimidinedione,
(12) 1,3-dimethyl-6-[4-(3-[4-cyanophenoxy]propyl)piperazin-1-yl]-2,4(1H,3H)-pyrimidinedione,
(13) 1,3-dimethyl-6-[4-(3-[2-chlorophenoxy]propyl)piperazin-1-yl]-2,4(1H,3H)-pyrimidinedione,
(14) 1,3-dimethyl-6-[4-(3-[3-chlorophenoxy]propyl)piperazin-1-yl]-2,4(1H,3H)-pyrimidinedione,
(15) 1,3-dimethyl-6-[4-(3-[4-chlorophenoxy]propyl)piperazin-1-yl]-2,4(1H,3H)-pyrimidinedione,
(16) 1,3-dimethyl-6-[4-(3-[2-trifluoromethylphenoxy]propyl)piperazin-1-yl]-2,4(1H,3H)-pyrimidinedione,
(17) 1,3-dimethyl-6-[4-(3-[3-trifluoromethylphenoxy]propyl)piperazin-1-yl]-2,4(1H,3H)-pyrimidinedione,
(18) 1,3-dimethyl-6-[4-(3-[ 4-trifluoromethylphenoxy]propyl)piperazin-1-yl]-2,4(1H,3H)-pyrimidinedione,
(19) 1,3-dimethyl-6-[4-(3-[2-methanesulfonylaminophenoxy]propyl)piperazin-1-yl]-2,4(1H,3H)-pyrimidinedione,
(20) 1,3-dimethyl-6-[4-(3-[3-methanesulfonylaminophenoxy]propyl)piperazin-1-yl]-2,4(1H,3H)-pyrimidinedione,
(21) 1,3-dimethyl-6-[4-(3-[4-methanesulfonylaminophenoxy]propyl)piperazin-1-yl]-2,4(1H,3H)-pyrimidinedione,
(22) 1,3-dimethyl-6-[4-(3-[2-methoxyphenoxy]propyl)piperazin-1-yl]-2,4(1H,3H)-pyrimidinedione,
(23) 1,3-dimethyl-6-[4-(3-[3-methoxyphenoxy]propyl)piperazin-1-yl]-2,4(1H,3H)-pyrimidinedione,
(24) 1,3-dimethyl-6-[4-(3-[4-methoxyphenoxy]propyl)piperazin-1-yl]-2,4(1H,3H)-pyrimidinedione,
(25) 1,3-dimethyl-6-[4-(3-[2-methylthiophenoxy]propyl)piperazin-1-yl]-2,4(1H,3H)-pyrimidinedione,
(26) 1,3-dimethyl-6-[4-(3-[3-methylthiophenoxy]propyl)piperazin-1-yl]-2,4(1H,3H)-pyrimidinedione,
(27) 1,3-dimethyl-6-[4-(3-[4-methylthiophenoxy]propyl)piperazin-1-yl]-2,4(1H,3H)-pyrimidinedione,
(28) 1,3-dimethyl-6-[4-(3-[2-acetylaminophenoxy]propyl) piperazin-1-yl]-2,4(1H,3H)-pyrimidinedione,
(29) 1,3-dimethyl-6-[4-(3-[3-acetylaminophenoxy]propyl) piperazin-1-yl]-2,4(1H,3H)-pyrimidinedione,
(30) 1,3-dimethyl-6-[4-(3-[4-acetylaminophenoxy]propyl) piperazin-1-yl]-2,4(1H,3H)-pyrimidinedione,
(31) 1,3-dimethyl-6-[4-(3-[2-methanesulfonylphenoxy]propyl) piperazin-1-yl]-2,4(1H,3H)-pyrimidinedione,
(32) 1,3-dimethyl-6-[4-(3-[3-methanesulfonylphenoxy]propyl) piperazin-1-yl]-2,4(1H,3H)-pyrimidinedione,
(33) 1,3-dimethyl-6-[4-(3-[4-methanesulfonylphenoxy]propyl) piperazin-1-yl]-2,4(1H,3H)-pyrimidinedione,
(34) 1,3-dimethyl-6-[4-(3-phenoxypropyl)piperazin-1-yl]-2,4(1H,3H)-pyrimidinedione,
(35) 1,3-dimethyl-6-[4-(3-[2-methanesulfinylphenoxy]propyl) piperazin-1-yl]-2,4(1H,3H)-pyrimidinedione,
(36) 1,3-dimethyl-6-[4-(3-[2-carboxyphenoxy]propyl)-piperazin-1-yl]-2,4(1H,3H)-pyrimidinedione,
(37) 1,3-dimethyl-6-[4-(3-[4-trifluoroacetylaminophenoxy]propyl)piperazin-1-yl]-2,4(1H,3H)-pyrimidinedione,
(38) 1,3-dimethyl-6-[4-(3-[4-trifluoromethanesulfonylaminophenoxy]propyl)piperazin-1-yl]-2,4(1H,3H)-pyrimidinedione,
(39) 1,3-dimethyl-6-[4-(3-[4-ethanesulfonylaminophenoxy]propyl)piperazin-1-yl]-2,4(1H,3H)-pyrimidinedione,
(40) 1,3-dimethyl-6-[4-(3-[4-benzenesulfonylaminophenoxy] propyl)piperazin-1-yl]-2,4(1H,3H)-pyrimidinedione,
(41) 1,3-dimethyl-6-[4-(3-[4-methylsulfamoylphenoxy]propyl) piperazin-]-yl]-2,4(1H,3 H)-pyrimidinedione,
(42) 1,3-dimethyl-6-[4-(3-[4-(N'-methylureido)phenoxy]propyl) piperazin-1-yl]-2,4(1H,3H)-pyrimidinedione,
(43) 1,3-dimethyl-6-[4-(3-[2-methoxycarbonylphenoxy] propyl) piperazin-1-yl]-2,4(1H,3H)-pyrimidinedione,
(44) 1,3-dimethyl-6-[4-(3-[2-allyloxyphenoxy]propyl)-piperazin-1-yl]-2,4(1H,3H)-pyrimidinedione,
(45) 1,3-dimethyl-6-[4-(3-[2-vinyloxyphenoxy]propyl)-piperazin-1-yl]-2,4(1H,3H)-pyrimidinedione,
(46) 1,3-dimethyl-6-[4-(3-[2-dimethylsulfamoylphenoxy]propyl) piperazin-1-yl]-2,4(1H,3H)-pyrimidinedione,

(47) 1,3-dimethyl-6-[4-(3-[2-cyanomethylphenoxy]propyl) piperazin-1-yl]-2,4(1H,3H)-pyrimidinedione,
(48) 1,3-dimethyl-6-[4-(3-[2-methoxymethylphenoxy]propyl) piperazin-1-yl]-2,4(1H,3H)-pyrimidinedione,
(49) 1,3-dimethyl-6-[4-(3-[4-dimethanesulfonylaminophenoxy]propyl)piperazin-1-yl]-2,4(1H,3H)-pyrimidinedione,
(50) 1,3-dimethyl-6-[4-(3-[4-(1-imidazolyl)phenoxy]propyl) piperazin-1-yl]-2,4(1H,3H)-pyrimidinedione,
(51) 1,3-dimethyl-6-[4-(3-[4-(2-imidazolyl)phenoxy]propyl) piperazin-1-yl]-2,4(1H,3H)-pyrimidinedione,
(52) 1,3-dimethyl-6-[4-(3-[4-(1-tetrazolyl)phenoxy]propyl) piperazin-1-yl]-2,4(1H,3H)-pyrimidinedione,
(53) 1,3-dimethyl-6-[4-(3-[4-(1-triazolyl)phenoxy]propyl) piperazin-1-yl]-2,4(1H,3H)-pyrimidinedione,
(54) 1,3-dimethyl-6-[4-(3-[4-(N-methyl-N-methanesulfonylamino)phenoxy]propyl)piperazin-1-yl]-2,4(1H,3H)-pyrimidinedione,
(55) 1,3-dimethyl-6-[4-(3-[2-acetonyloxyphenoxy]propyl) piperazin-1-yl]-2,4(1H,3H)-pyrimidinedione,
(56) 1,3-dimethyl-6-[4-(3-[2-benzyloxycarbonylphenoxy]propyl) piperazin-1-yl]-2,4(1H,3H)-pyrimidinedione,
(57) 1,3-dimethyl-6-[4-(3-[2-azidophenoxy]propyl)piperazin-1-yl]-2,4(1H,3H)-pyrimidinedione,
(58) 1,3-dimethyl-6-[4-(3-[2-methanesulfonyloxyphenoxy]propyl)piperazin-1-yl]-2,4(1H,3H)-pyrimidinedione,
(59) 6-[4-(2-[2-aminophenyl]ethyl)piperazin-1-yl]-1,3-dimethyl-2,4(1H,3H)-pyrimidinedione,
(60) 6-[4-(3-[4-aminophenyl]propyl)piperazin-1-yl]-1,3-dimethyl-2,4(1H,3H)-pyrimidinedione,
(61) 6-[4-(3-[4-aminoanilino]propyl)piperazin-1-yl]-1,3-dimethyl-2,4(1H,3H)-pyrimidinedione,
(62) 1,3-dimethyl-6-[2-(N-[2-hydroxyethyl]-3-[4-aminophenyl]propylamino)ethylamino]-2,4(1H,3H)-pyrimidinedione,
(63) 6-[4-(2-[4-chlorophenoxy]ethyl)piperazin-1-yl]-1,3-dimethyl-2,4(1H,3H)-pyrimidinedione,
(64) 6-[4-(2-[4-acetylphenoxy]ethyl)piperazin-1-yl]-1,3-dimethyl-2,4(1H,3H)-pyrimidinedione,
(65) 6-[4-(2-[2-acetylphenoxy]ethyl)piperazin-1-yl]-1,3-dimethyl-2,4(1H,3H)-pyrimidinedione,
(66) 1,3-dimethyl-6-[4-(2-[4-methanesulfonylaminophenoxy]ethyl)piperazin-1-yl]-2,4(1H,3H)-pyrimidinedione,
(67) 6-[4-(2-[aminophenoxy]ethyl)piperazin-1-yl]-1,3-dimethyl-2,4(1H,3H)-pyrimidinedione,
(68) 1,3-dimethyl-6-[4-(2-phenoxyethyl)piperazin-1-yl]-2,4(1H,3H)-pyrimidinedione,
(69) 6-[4-(4-[4-chlorophenoxy]butyl)piperazin-1-yl]-1,3-dimethyl-2,4(1H,3H)-pyrimidinedione,
(70) 6-[4-(4-[4-acetylphenoxy]butyl)piperazin-1-yl]-1,3-dimethyl-2,4(1H,3H)-pyrimidinedione,
(71) 6-[4-(4-[2-acetylphenoxy]butyl)piperazin-1-yl]-1,3-dimethyl-2,4(1H,3H)-pyrimidinedione,
(72) 6-[4-(4-[4-cyanophenoxy]butyl)piperazin-1-yl]-1,3-dimethyl-2,4(1H,3H)-pyrimidinedione,
(73) 6-[4-(4-[4-aminophenoxy]butyl)piperazin-1-yl]-1,3-dimethyl-2,4(1H,3H)-pyrimidinedione,
(74) 6-[4-(4-[3-aminophenoxy]butyl)piperazin-1-yl]-1,3-dimethyl-2,4(1H,3H)-pyrimidinedione,
(75) 6-[4-(4-[2-aminophenoxy]butyl)piperazin-1-yl]-1,3-dimethyl-2,4(1H,3H)-pyrimidinedione,
(76) 6-[4-(4-[4-methanesulfonylaminophenoxy]butyl) piperazin-1-yl]-1,3-dimethyl-2,4(1H,3H)-pyrimidinedione,
(77) 6-[4-(4-[3-methanesulfonylaminophenoxy]butyl)-piperazin-1-yl]-1,3-dimethyl-2,4(1H,3H)-pyrimidinedione,
(78) 1-methyl-6-[4-(3-phenoxypropyl)piperazin-1-yl]-2,4(1H,3H)-pyrimidinedione,
(79) 6-[4-(3-phenoxypropyl)piperazin-1-yl]-2,4(1H,3H) pyrimidinedione,
(80) 3-methyl-6-[4-(3-phenoxypropyl)piperazin-1-yl]-2,4(1H,3H)-pyrimidinedione,
(81) 1-methyl-3-isopropyl-6-[4-(3-phenoxypropyl)piperazin-1-yl]-2,4(1H,3H)-pyrimidinedione,
(82) 1,3-diisopropyl-6-[4-(3-phenoxypropyl)piperazin-1-yl]-2,4(1H,3H)-pyrimidinedione,
(83) 3-isopropyl-6-[4-(3-phenoxypropyl)piperazin-1-yl]-2,4(1H,3H)-pyrimidinedione,
(84) 3-isobutyl-6-[4-(3-phenoxypropyl)piperazin-1-yl]-2,4(1H,3H)-pyrimidinedione,
(85) 1,3-diisopropyl-6-[4-(3-[4-cyanophenoxy]propyl)-piperazin-1-yl]-2,4(1H,3H)-pyrimidinedione,
(86) 1,3-diisopropyl-6-[4-(3-[4-chlorophenoxy]propyl)-piperazin-1-yl]-2,4(1H,3H)-pyrimidinedione,
(87) 1,3-diisopropyl-6-[4-(3-[2-cyanophenoxy]propyl)-piperazin-1-yl]-2,4(1H,3H)-pyrimidinedione,
(88) 1,3-diisopropyl-6-[4-(3-[2-acetylphenoxy]propyl)-piperazin-1-yl]-2,4(1H,3H)-pyrimidinedione,
(89) 3-isopropyl-6-[4-(3-[4-cyanophenoxy]propyl)piperazin-1-yl]-2,4(1H,3H)-pyrimidinedione,
(90) 3-isopropyl-6-[4-(3-[4-chlorophenoxy]propyl)piperazin-1-yl]-2,4(1H,3H)-pyrimidinedione,
(91) 3-isopropyl-6-[4-(3-[2-cyanophenoxy]propyl)piperazin-1-yl]-2,4(1H,3H)-pyrimidinedione,
(92) 1-isopropyl-6-[4-(3-[2-acetylphenoxy]propyl)piperazin-1-yl]-2,4(1H,3H)-pyrimidinedione,
(93) 6-[4-(3-[2-chlorophenoxy]propyl)piperazin-1-yl]2,4(1H,3H)-pyrimidinedione,
(94) 1-methyl-6-[4-(3-[4-chlorophenoxy]propyl)piperazin-1-yl]-2,4(1H,3H)-pyrimidinedione,
(95) 1,3-dimethyl-6-[4-(3-[3,5-dichlorophenoxy]propyl)-piperazin-1-yl]-2,4(1H,3H)-pyrimidinedione,
(96) 1,3-dimethyl-6-[4-(3-[3-chloro-4-fluorophenoxy]-propyl)piperazin-1-yl]-2,4(1H,3H)-pyrimidinedione,
(97) 1,3-dimethyl-6-[4-(3-[2-cyano-4-chlorophenoxy]-propyl)piperazin-1-yl]-2,4(1H,3H)-pyrimidinedione,
(98) 1,3-dimethyl-6-[4-(3-[2-chloro-4-methanesulfonylaminophenoxy]propyl)piperazin-1-yl]-2,4(1H,3H)-pyrimidinedione,
(99) 1,3-dimethyl-6-[4-(3-[2,6-dichloro-4-cyanophenoxy]propyl)piperazin-1-yl]-2,4(1H,3H)-pyrimidinedione,
(100) 1,3-dimethyl-6-[4-(3-[2-cinnamoylphenoxy]propyl) piperazin-1-yl]-2,4(1H,3H)-pyrimidinedione,
(101) 1,3-dimethyl-6-[2-(4-chloroanilino)ethylamino]-2,4(1H,3H)-pyrimidinedione,
(102) 1,3-dimethyl-6-[3-(4-chloroanilino)propylamino]-2,4(1H,3H)-pyrimidinedione,
(103) 1,3-dimethyl-6-[2-(4-acetylbenzylamino)ethylamino]-2,4(1H,3H)-pyrimidinedione,
(104) 1,3-dimethyl-6-[3-(4-acetylbenzylamino)propylamino]-2,4(1H,3H)-pyrimidinedione,
(105) 1,3-dimethyl-6-[4-(4-acetylbenzyl)piperazin-1-yl]-2,4(1H,3H)-pyrimidinedione,
(106) 1,3-dimethyl-6-[N-propyl-2-(4-cyanobenzylamino)ethylamino]-2,4(1H,3H)-pyrimidinedione,
(107) 1,3-dimethyl-6-[2-(N-ethyl-4-cyanobenzylamino)ethylamino]-2,4(1H,3H)-pyrimidinedione,
(108) 1,3-dimethyl-6-[2-(N-[2-hydroxyethyl]-4-cyanobenzylamino)ethylamino]-2,4(1H,3H)-pyrimidinedione, (109) 1,3-dimethyl-6-[2-(2-[2-acetylphenyl]ethylamino)ethylamino]-2,4(1H,3H)-pyrimidinedione,
(110) 1,3-dimethyl-6-[3-(2-[2-acetylphenyl]ethylamino)propylamino]-2,4(1H,3H)-pyrimidinedione,
(111) 1,3-dimethyl-6-[N-(2-hydroxyethyl)-2-(2-[4-chlorophenyl]ethylamino)ethylamino]-2,4(1H,3H)-pyrimidinedione,
(112) 1,3-dimethyl-6-[2-(N-ethyl-2-[4-methoxyphenyl]ethylamino)ethylamino]2,4(1H,3H)-pyrimidinedione,
(113) 1,3-dimethyl-6-[2-(N-[2-hydroxyethyl]-2-[4-methoxyphenyl]ethylamino)ethylamino]-2,4(1H,3H)-pyrimidinedione,
(114) 1,3-dimethyl-6-[4-(2-[4-methylphenyl]ethyl)piperazin-1-yl]-2,4(1H,3H)-pyrimidinedione,
(115) 1,3-dimethyl-6-[4-(2-[4-methyoxyphenyl]ethyl)homopiperazin-1-yl]-2,4(1H,3H)-pyrimidinedione,
(116) 1,3-dimethyl-6-[2-(N-[3-hydroxypropyl]-2-[4-methoxyphenyl]ethylamino)ethylamino]-2,4(1H,3H)-pyrimidinedione,
(117) 1,3-dimethyl-6-[2-(N-[3-benzoyloxypropyl]-2-[2-cyanophenyl]ethylamino)ethylamino]-2,4(1H,3H)-pyrimidinedione,
(118) 1,3-dimethyl-6-[4-(2-[3-fluorophenyl]ethyl)piperazin-1-yl]-2,4(1H,3H)-pyrimidinedione,
(119) 1,3-dimethyl-6-[4-(2-[2-fluorophenyl]ethyl)piperazin-1-yl]-2,4(1H,3H)-pyrimidinedione,
(120) 3-methyl-6-[4-(2-[4-fluorophenyl]ethyl)piperazin1-yl]-2,4(1H,3H)-pyrimidinedione,
(121) 1-methyl-6-[4-(2-[4-fluorophenyl]ethyl)piperazin-1-yl]-2,4(1H,3H)-pyrimidinedione,
(122) 1,3-diethyl-6-[2-(N-[2-hydroxyethyl]-2-phenylethylamino)ethylamino]-2,4(1H,3H)-pyrimidinedione,
(123) 1,3-diisopropyl-6-[2-(N-[2-hydroxyethyl]-2-[4-cyanophenyl]ethylamino)ethylamino]-2,4(1H,3H)-pyrimidinedione,
(124) 1,3-dimethyl-6-[2-(3-[4-chlorophenyl]propylamino)ethylamino]-2,4(1H,3H)-pyrimidinedione,
(125) 1,3-dimethyl-6-[3-(3-[4-chlorophenyl]propylamino)propylamino]-2,4(1H,3H)-pyrimidinedione,
(126) 1,3-dimethyl-6-[N-methyl-2-(3-[4-chlorophenyl]propylamino)ethylamino]-2,4(1H,3H)-pyrimidinedione,
(127) 1,3-dimethyl-6-[N-ethyl-2-(3-[4-chlorophenyl]propylamino)ethylamino]-2,4(1H,3H)-pyrimidinedione,
(128) 1,3-dimethyl-6-[N-propyl-2-(3-[4-methanesulfonylaminophenyl]propylamino)ethylamino]-2,4(1H,3H)-pyrimidinedione,
(129) 1,3-dimethyl-6-[N-(2-hydroxyethyl)-2-(3-[4-ethanesulfonylaminophenyl]propylamino)ethylamino]-2,4(1H,3H)-pyrimidinedione,
(130) 1,3-dimethyl-6-[N-(2-hydroxypropyl)-2-(3-[4-chlorophenyl]propylamino)ethylamino]-2,4(1H,3H)-pyrimidinedione,
(131) 1,3-dimethyl-6-[N-(2-hydroxy-1-methylethyl)-2-(3-[4-aminophenyl]propylamino)ethylamino]-2,4(1H,3H)-pyrimidinedione,
(132) 1,3-dimethyl-6-[2-(N-methyl-3-[4-propionylaminophenyl]propylamino)ethylamino]-2,4(1H,3H)-pyrimidinedione.
(133) 1,3-dimethyl-6-[2-(N-ethyl-3-phenylpropylamino)ethylamino]-2,4(1H,3H)-pyrimidinedione,
(134) 1,3-dimethyl-6-[2-(N-propyl-3-phenylpropylamino)ethylamino]-2,4(1H,3H)-pyrimidinedione,
(135) 1,3-dimethyl-6-[2-(N-[1-methylethyl]-3-[2-propionylphenyl]propylamino)ethylamino]-2,4(1H,3H)-pyrimidinedione,
(136) 1,3-dimethyl-6-[2-(N-butyl-3-[4-aminophenyl]propylamino) ethylamino]-2,4(1H,3H)-pyrimidinedione,
(137) 1,3-dimethyl-6-[2-(N-[t-butyl]-3-[4-aminophenyl]propylamino) ethylamino]-2,4(1H,3H)-pyrimidinedione,
(138) 1,3-dimethyl-6-[2-(N-[2-hydroxyethyl]-3-[4-bromophenyl]propylamino)ethylamino]-2,4(1H,3H)-pyrimidinedione,
(139) 1,3-dimethyl-6-[2-(N-[3-hydroxypropyl]-3-[4-ethanesulfonylphenyl]propylamino)ethylamino]-2,4(1H,3H)-pyrimidinedione,
(140) 1,3-dimethyl-6-[2-(N-[2-hydroxy-1-methylethyl]-3-[4-ureidephenyl]propylamino)ethylamino]-2,4(1H,3H)-pyrimidinedione,
(141) 1,3-dimethyl-6-[2-(N-[2-hydroxypropyl]-3-[2-acetylphenyl]propylamino)ethylamino]-2,4(1H,3H)-pyrimidinedione,
(142) 1,3-dimethyl-6-[2-(N-[4-hydroxybutyl]-3-[4-chlorophenyl]propylamino)ethylamino]-2,4(1H,3H)-pyrimidinedione,
(143) 1,3-dimethyl-6-[2-(N-[2-benzoyloxyethyl]-3-[4-allyloxyphenyl]propylamino)ethylamino]-2,4(1H,3H)-pyrimidinedione,
(144) 1,3-dimethyl-6-[N-methyl-2-(N-methyl-3-[4-hydroxyphenyl]propylamino)ethylamino]-2,4(1H,3H)-pyrimidinedione,
(145) 1,3-dimethyl-6-[N-methyl-2-(N-[2-hydroxyethyl]-3-[2-hydroxyphenyl]propylamino)ethylamino]-2,4(1H,3H)-pyrimidinedione,
(146) 1,3-dimethyl-6-[2-(N-[2-hydroxyethyl]-3-[2-benzoylphenyl]propylamino)ethylamino]-2,4(1H,3H)-pyrimidinedione,
(147) 1,3-dimethyl-6-[4-(3-[4-cyanophenyl]propyl)piperazin-1-yl]-2,4(1H,3H)-pyrimidinedione,
(148) 1,3-dimethyl-6-[4-(3-[4-cyanophenyl]propyl)homopiperazin-1-yl]-2,4(1H,3H)-pyrimidinedione,
(149) 3-methyl-6-[4-(3-[4-chlorophenyl]propyl)piperazin-1-yl]-2,4(1H,3H)-pyrimidinedione,
(150) 1-propyl-6-[2-(N-[2-hydroxyethyl]-3-[4-chlorophenyl]propylamino)ethylamino]-2,4(1H,3H)-pyrimidinedione,
(151) 1,3-dimethyl-6-[2-(4-[4-chlorophenyl]butylamino)ethylamino]-2,4(1H,3H)-pyrimidinedione,
(152) 6-[N-ethyl-2-(4-[4-(N,N'-dimethylureide)phenyl]butylamino) ethylamino]-1,3-dimethyl-2,4(1H,3H)-pyrimidinedione,
(153) 1,3-dimethyl-6-[N-(2-hydroxyethyl)-2-(4-[4-chlorophenyl]butylamino)ethylamino]-2,4(1H,3H)-pyrimidinedione, (154) 1,3-dimethyl-6-[2-(N-ethyl-4-[2-acetylphenyl]butylamino) ethylamino]-2,4(1H,3H)-pyrimidinedione,
(155) 1,3-dimethyl-6-[2-(N-[t-butyl]-4-[2-fluorophenyl]butylamino) ethylamino]-2,4(1H,3H)-pyrimidinedione,
(156) 1,3-dimethyl-6-[2-(N-[2-hydroxyethyl]-4-phenylbutylamino)ethylamino]-2,4(1H,3H)-pyrimidinedione,
(157) 1,3-dimethyl-6-[2-(N-[3-hydroxypropyl]-4-phenylbutylamino)ethylamino]-2,4(1H,3H)-pyrimidinedione,
(158) 1,3-dimethyl-6-[2-(3-phenoxypropylamino)ethylamino]-2,4(1H,3H)-pyrimidinedione, (159) 1,3-dimethyl-6-[4-(4-phenylbutyl)piperazin-1-yl]-2,4(1H,3H)-pyrimidinedione,
(160) 1,3-dimethyl-6-[4-(2-phenylethyl)piperazin-1-yl]-2,4(1H,3H)-pyrimidinedione,
(161) 1,3-dimethyl-6-[4-(3-phenylpropyl)piperazin-1-yl]-2,4(1H,3H)-pyrimidinedione,
(162) 1,3-dimethyl-6-[4-(3-oxo-3-phenylpropyl)piperazin-1-yl]-2,4(1H,3H)-pyrimidinedione,
(163) 1,3-dimethyl-6-[4-(2-[4-chlorophenyl]ethyl)piperazin-1-yl]-2,4(1H,3H)-pyrimidinedione,
(164) 1,3-dimethyl-6-[4-(4-oxo-4-[4-fluorophenyl]butyl)piperazin-1-yl]-2,4(1H,3H)-pyrimidinedione,
(165) 1,3-dimethyl-6-[4-(2-benzoylaminoethyl)piperazin-1-yl]-2,4(1H,3H)-pyrimidinedione,
(166) 1,3-dimethyl-6-[4-(3-hydroxy-3-phenylpropyl)piperazin-1-yl]-2,4(1H,3H)-pyrimidinedione,
(167) 1,3-dimethyl-6-[4-(2-oxo-2-[4-chlorophenyl]ethyl)piperazin-1-yl]-2,4(1H,3H)-pyrimidinedione,
(168) 1,3-dimethyl-6-[4-(2-hydroxy-2-[4-chlorophenyl]ethyl) piperazin-1-yl]-2,4(1H,3H)-pyrimidinedione,
(169) 1,3-dimethyl-6-[4-(4-[4-methanesulfonylaminophenyl]butyl)piperazin-1-yl]-2,4(1H,3H)-pyrimidinedione,
(170) 1,3-dimethyl-6-[4-(4-methanesulfonylaminobenzoyl)piperazin-1-yl]-2,4(1H,3H)-pyrimidinedione,
(171) 1,3-dimethyl-6-[4-(2-[4-methanesulfonylaminobenzoyloxy]ethyl)piperazin-1-yl]-2,4(1H,3H)-pyrimidinedione,
(172) 1,3-dimethyl-6-[4-(3-[4-methanesulfonylaminobenzoyloxy]propyl)piperazin-1-yl]-2,4(1H,3H)-pyrimidinedione,
(173) 1,3-dimethyl-6-[4-(2-[4-methanesulfonylaminobenzoylamino]ethyl)piperazin-1-yl]-2,4(1H,3H)-pyrimidinedione,
(174) 1,3-dimethyl-6-[4-(3-[2-(4-nitrocinnamoyl)-phenoxy]propyl)piperazin-1-yl]-2,4(1H,3H)-pyrimidinedione,
(175) 1,3-dimethyl-6-[4-(3-{2-[3-(4-pyridinyl)acryloyl]phenoxy}propyl)piperazin-1-yl]-2,4(1H,3H)-pyrimidinedione,
(176) 1,3-dimethyl-6-[4-(3-[2-(4-methylmercaptocinnamoyl)phenoxy]propyl)piperazin-1-yl]-2,4(1H,3H)-pyrimidinedione,
(177) 1,3-dimethyl-6-[4-(3-{2-[4-(N,N-dimethylamino)-cinnamoyl]phenoxy}propyl)piperazin-1-yl]-2,4(1H,3H)-pyrimidinedione,
(178) 1,3-dimethyl-6-[N-methyl-2-(N-methyl-4-[4-chlorophenyl]butylamino)ethylamino]-2,4(1H,3H)-pyrimidinedione,
(179) 1,3-dimethyl-6-[4-(4-[4-ethoxyphenyl]butyl)piperazin-1-yl]-2,4(1H,3H)-pyrimidinedione,
(180) 6-[2-(N-ethyl-4-[4-ethoxyphenyl]butylamino)ethylamino]-1,3-dimethyl-2,4(1H,3H)-pyrimidinedione,
(181) 1,3-dimethyl-6-[2-(2-[4-cyanophenoxy]ethylamino)ethylamino]-2,4(1H,3H)-pyrimidinedione,
(182) 1,3-dimethyl-6-[N-ethyl-2-(2-[4-cyanophenoxy]ethylamino) ethylamino]-2,4(1H,3H)-pyrimidinedione,
(183) 1,3-dimethyl-6-[4-(2-[4-acetylphenoxy]ethyl)piperazin-1-yl]-2,4(1H,3H)-pyrimidinedione,
(184) 1,3-dimethyl-6-[2-(3-[4-phenoxy]propylamino)ethylamino]-2,4(1H,3H)-pyrimidinedione,
(185) 1,3-dimethyl-6-[N-ethyl-2-(3-[4-phenoxy]propylamino)ethylamino]-2,4(1H,3H)-pyrimidinedione,
(186) 1,3-dimethyl-6-[2-(N-ethyl-3-[4-iodophenoxy]propylamino)ethylamino]-2,4(1H,3H)-pyrimidinedione,
(187) 1,3-dimethyl-6-[2-(N-[2-hydroxyethyl]-3-[4-trifluoroacetylphenoxy]propylamino )ethylamino]-2,4(1H,3H)-pyrimidinedione,
(188) 1,3-dimethyl-6-[N-methyl-2-(N-methyl-3-[4-acetylphenoxy]propylamino)ethylamino]-2,4(1H,3H)-pyrimidinedione,
(189) 1,3-dimethyl-6-[4-(3-[4-ethylthiophenoxy]propyl)-piperazin-1-yl]-2,4(1H,3H)-pyrimidinedione,
(190) 3-methyl-6-[4-(3-[4-chlorophenoxy]propyl)piperazin-1-yl]-2,4(1H,3H)-pyrimidinedione,
(191) 1,3-dimethyl-6-[4-(3-[3-formylphenoxy]propyl)-piperazin-1-yl]-2,4(1H,3H)-pyrimidinedione,
(192) 1,3-dimethyl-6-[4-(3-[2-formylphenoxy]propyl)-piperazin-1-yl]-2,4(1H,3H)-pyrimidinedione,
(193) 1,3-dimethyl-6-[2-(4-[4-cyanophenoxy]butylamino)ethylamino]-2,4(1H,3H)-pyrimidinedione,
(194) 1,3-dimethyl-6-[N-methyl-2-(N-methyl-4-[4-chlorophenoxy]butylamino)ethylamino]-2,4(1H,3H)-pyrimidinedione,
(195) 1,3-dimethyl-6-[4-(4-[4-acryloylphenoxy]butyl)-piperazin-1-yl]-2,4(1H,3H)-pyrimidinedione,
(196) 1,3-dimethyl-6-[2-(N-ethyl-2-[4-acetylphenylthio]ethylamino)ethylamino]-2,4(1H,3H)-pyrimidinedione,
(197) 1,3-dimethyl-6-[2-(N-[2-hydroxyethyl]-3-[4-acetylphenylthio]propylamino)ethylamino]-2,4(1H,3H)-pyrimidinedione,
(198) 1,3-dimethyl-6-[4-(3-[4-methylphenylthio]propyl)piperazin-1-yl]-2,4(1H,3H)-pyrimidinedione,
(199) 1,3-dimethyl-6-[N-methyl-2-(N-methyl-4-[4-trifluoromethylphenylthio]butylamino )ethylamino]-2,4(1H,3H)-pyrimidinedione,
(200) 1,3-dimethyl-6-[4-(4-chlorophenacyl)piperazin-1-yl]-2,4(1H,3H)-pyrimidinedione,
(201) 1,3-dimethyl-6-[4-(2-[4-chlorobenzoyl]ethyl)piperazin-1-yl]-2,4(1H,3H)pyrimidinedione,
(202) 1,3-dimethyl-6-[N-methyl-2-(N-methyl-4-[4-acetylphenylthio]butylamino)ethylamino]-2,4(1H,3H)-pyrimidinedione,
(203) 1,3-dimethyl-6-[4-(2-hydroxy-2-[4-cyanophenyl]ethyl) piperazin-1-yl]-2,4(1H,3H)-pyrimidinedione,
(204) 1,3-dimethyl-6-[4-(2-[4-cyanobezoyloxy]ethyl)-piperazin-1-yl]-2,4(1H,3H)-pyrimidinedione,
(205) 1,3-dimethyl-6-[2-(N-ethyl-3-[4-cyanobezoyloxy]propylamino)ethylamino] -2,4(1H,3H)-pyrimidinedione,
(206) 1,3-dimethyl-6-[2-(4-cyanobezoylamino)ethylamino]-2,4(1H,3H)-pyrimidinedione,
(207) 1,3-dimethyl-6-[4-(2-[4-cyanobezoylamino]ethyl)-piperazin-1-yl]-2,4(1H,3H)-pyrimidinedione,
(208) 1,3-dimethyl-6-[4-(N-[4-chlorophenyl]carbamoylmethyl)piperazin-1-yl]-2,4(1H,3H)-pyrimidinedione,
(209) 1,3-dimethyl-6-[4-(N-[4-chlorophenyl]carbamoylethyl)homopiperazin-1-yl]-2,4(1H,3H)-pyrimidinedione,
(211) 1,3-dimethyl-6-[4-(4-[N-(4-fluorophenyl)carbamoyl]butyl)piperazin-1-yl]-2,4(1H,3H)-pyrimidinedione,
(212) 1,3-dimethyl-6-[N-methyl-2-(N-methyl-2-[4-acetylanilino]ethylamino)ethylamino]-2,4(1H,3H)-pyrimidinedione,
(213) 1,3-dimethyl-6-[N-methyl-2-(N-[2-hydroxyethyl]-2-[4-acetylanilino]ethylamino)ethylamino]-2,4(1H,3H)-pyrimidinedione.
(214) 1,3-dimethyl-6-[2-(N-ethyl-2-[2-acetylanilino]ethylamino)ethylamino]-2,4(1H,3H)-pyrimidinedione, (215) 1,3-dimethyl-6-[3-(N-propyl-2-[2-acetylanilino]ethylamino)propylamino]-2,4(1H,3H)-pyrimidinedione,
(216) 1,3-dimethyl-6-[N-methyl-2-(N-methyl-2-[N-methyl-2-acetylanilino]ethylamino)ethylamino]-2,4(1H,3H)-pyrimidinedione,
(217) 1,3-dimethyl-6-[N-methyl-3-(N-methyl-2-[4-chloroanilino] ethylamino)propylamino]-2,4(1H,3H)-pyrimidinedione,
(218) 1,3-dimethyl-6-[2-(N-ethyl-3-[2-chloroanilino]propylamino)ethylamino]-2,4(1H,3H)-pyrimidinedione,
(219) 1,3-dimethyl-6-[2-(N-[2-hydroxyethyl]-3-[2-fluoroanilino]propylamino)propylamino]-2,4(1H,3H)-pyrimidinedione,
(220) 1,3-dimethyl-6-[4-(3-[4-acetylanilino]propyl)piperazin-1-yl]-2,4(1H,3H)-pyrimidinedione,
(221) 1,3-dimethyl-6-[4-(3-[N-methyl-4-acetylanilino]propyl)piperazin-1-yl]-2,4(1H,3H)-pyrimidinedione,
(222) 1,3-dimethyl-6-[4-(3-[N-propyl-4-chloroanilino]propyl)piperazin-1-yl]-2,4(1H,3H)-pyrimidinedione,
(223) 1,3-dimethyl-6-[4-(3-[N-methanesulfonyl-4-chloroanilino]propyl)piperazin-1-yl]-2,4(1H,3H)-pyrimidinedione,
(224) 1,3-dimethyl-6-[4-(3-[N-ethanesulfonyl-4-chloroanilino]propyl)piperazin-1-yl]-2,4(1H,3H)-pyrimidinedione,
(225) 1,3-dimethyl-6-[4-(3-[N-acetyl-4-fluoroanilino]propyl) piperazin-1-yl]-2,4(1H,3H)-pyrimidinedione,
(226) 1,3-dimethyl-6-[4-(3-[N-propionyl-4-fluoroanilino]propyl)piperazin-1-yl]-2,4(1H,3H)-pyrimidinedione,
(227) 1,3-dimethyl-6-[2-(1-[2-methoxyphenyl]piperazin-4-ylamino)ethylamino]- 2,4(1H,3H)-pyrimidinedione,
(228) 1,3-dimethyl-6-[2-(4-[4-methanesulfonylaminophenyl]piperazin-1-yl)ethylamino]-2,4(1H,3H)-pyrimidinedione,
(229) 1,3-dimethyl-6-[3-(4-[4-methanesulfonylaminophenyl]piperazin-1-yl)propylamino]-2,4(1H,3H)-pyrimidinedione,
(230) 1,3-dimethyl-6-[N-(2-hydroxyethyl)-2-{4-(4-methanesulfonylaminophenyl)piperazin-1-yl}ethylamino]-2,4(1H,3H)-pyrimidinedione,
(231) 1,3-dimethyl-6-[N-methyl-2-(4-[4-chlorophenyl]piperazin-1-yl)ethylamino]-2,4(1H,3H)-pyrimidinedione,
(232) 1,3-dimethyl-6-[4-(3-[2-acetyl-4-chlorophenyl]propyl)piperazin-1-yl]-2,4(1H,3H)-pyrimidinedione,
(233) 1,3-dimethyl-6-[2-(N-ethyl-2-[2-benzoyl-4-fluorophenyl]ethylamino)ethylamino]-2,4(1H,3H)-pyrimidinedione,
(234) 1,3-dimethyl-6-[4-(3-acetyl-4-methylphenyl)piperazin-1-yl]-2,4(1H,3H)-pyrimidinedione,
(235) 1,3-dimethyl-6-[4-(4-[2-acetyl-4-chlorophenoxy]butyl)piperazin-1-yl]-2,4(1H,3H)-pyrimidinedione,
(236) 1-methyl-6-[4-(3-[2-acetyl-4-chlorophenoxy]propyl)piperazin-1-yl]-2,4(1H,3H)-pyrimidinedione,
(237) 1,3-dimethyl-6-[4-(3-[2-cyano-4-(2-pyridinecarbonyl)phenoxy]propyl)piperazin-1-yl]-2,4(1H,3H)-pyrimidinedione,
(238) 1,3-dimethyl-6-[2-(N-[2-hydroxyethyl]-3-[4-benzoyl-2-cyanophenoxy]propylamino )ethylamino]-2,4(1H,3H)-pyrimidinedione,
(239) 1,3-dimethyl-6-[4-(3-[2-acetyl-4-cyanoanilino]propyl)piperazin-1-yl]-2,4(1H,3H)-pyrimidinedione,
(240) 1,3-dimethyl-6-[4-(3-[2-cyclopentanecarbonyl-4-cyanoanilino]propyl)piperazin-1-yl]-2,4(1H,3H)-pyrimidinedione,
(241) 1,3-dimethyl-6-[4-(3-[2-(2-chlorobenzoyl)-4-chloroanilino]propyl)piperazin-1-yl]-2,4(1H,3H)-pyrimidinedione,
(242) 1,3-dimethyl-6-[4-(3-[2-(2-pyridinecarbonyl)-4-chloroanilino]propyl)piperazin-1-yl]-2,4(1H,3H)-pyrimidinedione,
(243) 1,3-dimethyl-6-[4-(3-[2-(4-pyridinecarbonyl)-4-chloroanilino]propyl)piperazin-1-yl]-2,4(1H,3H)-pyrimidinedione,
(244) 1,3-dimethyl-6-[4-(3-[4-acetyl-2-chloroanilino]propyl)piperazin-1-yl]-2,4(1H,3H)-pyrimidinedione,
(245) 1,3-dimethyl-6-[4-(3-[4-propanoyl-2-cyanoanilino]propyl)piperazin-1-yl]-2,4(1H,3H)-pyrimidinedione,
(246) 1,3-dimethyl-6-[4-(3-[4-benzoyl-2-fluoroanilino]propyl)piperazin-1-yl]-2,4(1H,3H)-pyrimidinedione,
(247) 1,3-dimethyl-6-[4-(3-[3-acetyl-4-fluoroanilino]propyl)piperazin-1-yl]-2,4(1H,3H)-pyrimidinedione,
(248) 1,3-dimethyl-6-[2-(3-[4-acetyl-2-fluoroanilino]propylamino)ethylamino]-2,4(1H,3H)-pyrimidinedione,
(249) 1,3-dimethyl-6-[3-(N-[2-hydroxyethyl]-3-[4-propanoyl-2-chloroanilino]propylamino)propylamino]-2,4(1H,3H)-pyrimidinedione,
(250) 1,3-dimethyl-6-[4-(3-[2-benzoyl-4-chloroanilino]propyl)piperazin-1-yl]-2,4(1H,3H)-pyrimidinedione,
(251) 1,3-dimethyl-6-[4-(3-[3-fluoro-4-methanesulfonyloxyphenoxy]propyl)piperazin-1-yl]-2,4(1H,3H)-pyrimidinedione,
(252) 1,3-dimethyl-6-[4-(3-[3-fluoro-4-cyanoanilino]propyl)piperazin-1-yl]-2,4(1H,3H)-pyrimidinedione,
(253) 1,3-dimethyl-6-[4-(3-[3,5-difluoro-4-cyanophenoxy]propyl)piperazin-1-yl]-2,4(1H,3H)-pyrimidinedione,
(254) 1,3-dimethyl-6-[4-(3-[3,5-difluoro-4-cyanoanilino]propyl)piperazin-1-yl]-2,4(1H,3H)-pyrimidinedione,
(255) 1,3-dimethyl-6-[4-(3-[2-fluoro-4-cyanoanilino]propyl)piperazin-1 -yl]-2,4(1H,3H)-pyrimidinedione,
(256) 1,3-dimethyl-6-[2-(3-[2-methoxy-4-cyanophenoxy]propylamino)ethylamino]-2,4(1H,3H)-pyrimidinedione,
(257) 1,3-dimethyl-6-[3-(N-ethyl-3-[3-trifluoromethyl-4-cyanoanilino]propylamino)propylamino]-2,4(1H,3H)-pyrimidinedione,
(258) 1,3-dimethyl-6-[2-(4-[2-acetyloxy-4-chlorophenoxy]butyl]amino)ethylamino]-2,4(1H,3H)-pyrimidinedione,
(259) 1,3-dimethyl-6-[4-(3-[2-dimethylamino-4-cyanoanilino]propyl)homopiperazin-1-yl]-2,4(1H,3H)-pyrimidinedione,
(260) 1,3-dimethyl-6-[2-(2-[2-diethylamino-4-cyanoanilino]ethylamino)ethylamino]-2,4(1H,3H)-pyrimidinedione,
(261) 3-methyl-6-[2-(3-[2-hydroxy-4-chlorophenoxy]propylamino)ethylamino]-2,4(1H,3H)-pyrimidinedione,
(262) 1-ethyl-6-[4-(3-[2-bromo-4-cyanoanilino]propyl)piperazin-1-yl]-2,4(1H,3H)-pyrimidinedione,
(263) 1,3-dimethyl-6-[4-(N-[3-fluoro-4-acetylphenyl]carbamoylmethyl)piperazin-1-yl]-2,4(1H,3H)-pyrimidinedione,
(264) 1,3-dimethyl-6-[2-(3-[2-ethoxy-4-acetylphenylthio]propylamino)ethylamino]-2,4(1H,3H)-pyrimidinedione,
(265) 1,3-dimethyl-6-[4-(3-[2-ethanesulfonylamino-4-cyanophenoxy]propyl)piperazin-1-yl]-2,4(1H,3H)-pyrimidinedione, (266) 1,3-dimethyl-6-[4-(2-[3-fluoro-4-methoxyphenyl]ethyl)piperazin-1-yl]-2,4(1H,3H)-pyrimidinedione,
(267) 1,3-dimethyl-6-[2-(N-ethyl-3-[3-fluoro-4-methoxyphenyl]propylamino)ethylamino]-2,4(1H,3H)-pyrimidinedione,
(268) 1,3-dimethyl-6-[3-(N-[2-hydroxyethyl]-3-[3,5-difluorophenyl]propylamino)propylamino]-2,4(1H,3H)-pyrimidinedione,
(269) 1,3-dimethyl-6-[2-(N-[2-acetoxyethyl]-3-[2-dimethylaminophenyl]propylamino)ethylamino]-2,4(1H,3H)-pyrimidinedione,
(270) 1,3-dimethyl-6-[2-(N-ethyl-3-[2-ethoxyphenyl]propylamino)ethylamino]-2,4(1H,3H)-pyrimidinedione,
(271) 1,3-dimethyl-6-[3-(N-[2-acetyloxyethyl]-3-[2-ethanesulfonylaminophenyl]propylamino)propylamino]-2,4(1H,3H)-pyrimidinedione,
(272) 1,3-dimethyl-6-[4-(3-methylbenzyl)piperazin-1-yl]-2,4(1H,3H)-pyrimidinedione,
(273) 1,3-dimethyl-6-[2-(N-[2-hydroxyethyl]-3-[3-methoxyphenyl]propylamino)ethylamino]-2,4(1H,3H)-pyrimidinedione,
(274) 1,3-dimethyl-6-[4-(3-[2-acetyl-3-methylphenoxy]propyl)piperazin-1-yl]-2,4(1H,3H)-pyrimidinedione,
(275) 1,3-dimethyl-6-[4-(3-[4-acetyl-2-methylphenoxy]propyl)piperazin-1-yl]-2,4(1H,3H)-pyrimidinedione,
(276) 1,3-dimethyl-6-[4-(3-[4-benzoyl-2-chlorophenoxy]-propyl)piperazin-1-yl]-2,4(1H,3H)-pyrimidinedione,
(277) 1,3-dimethyl-6-[4-(3-[3-acetyl-4-cyanophenoxy]propyl)piperazin-1-yl]-2,4(1H,3H)-pyrimidinedione,
(278) 1,3-dimethyl-6-[4-(3-[2-benzoyl-4-cyanophenoxy]propyl)piperazin-1-yl]-2,4(1H,3H)-pyrimidinedione,
(279) 1,3-dimethyl-6-[4-(3-[2-(4-bromobenzoyl)phenoxy]-propyl)piperazin-1-yl]-2,4(1H,3H)-pyrimidinedione,
(280) 1,3-dimethyl-6-[4-(3-[2-(3-pyrazolylcarbonyl)phenoxy]propyl)piperazin-1-yl]-2,4(1H,3H)-pyrimidinedione,
(281) 1,3-dimethyl-6-[4-(3-[2-(2-pyrimidinecarbonyl)-4-cyanophenoxy]propyl)piperazin-1-yl]-2,4(1H,3H)-pyrimidinedione,
(282) 1,3-dimethyl-6-[4-(3-[2-(3-pyridinecarbonyl)-4-cyanophenoxy]propyl)piperazin-1-yl]-2,4(1H,3H)-pyrimidinedione,
(283) 1,3-dimethyl-6-[4-(3-[2-(4-pyridinecarbonyl)-4-cyanophenoxy]propyl)piperazin-1-yl]-2,4(1H,3H)-pyrimidinedione,
(284) 1,3-dimethyl-6-[4-(3-[2-(2-pyrimidinylcarbonyl)-4-cyanophenoxy]propyl)piperazin-1-yl]-2,4(1H,3H)-pyrimidinedione,
(285) 1,3-dimethyl-6-[4-(2-[2-acetyl-4-cyanophenoxy]ethyl)piperazin-1-yl]-2,4(1H,3H)-pyrimidinedione,
(286) 1,3-dimethyl-6-[4-(2-[2-benzoyl-4-cyanophenoxy]ethyl)piperazin-1-yl]-2,4(1H,3H)-pyrimidinedione,
(287) 1,3-dimethyl-6-[4-(2-[2-(4-bromobenzoyl)phenoxy]ethyl)piperazin-1-yl]-2,4(1H,3H)-pyrimidinedione,
(288) 1,3-dimethyl-6-[4-(2-[3-acetyl-4-chlorophenyl]ethyl)piperazin-1-yl]-2,4(1H,3H)-pyrimidinedione,
(289) 1,3-dimethyl-6-[4-(2-[2-chloro-4-acetyl]ethyl)piperazin-1-yl]-2,4(1H,3H)-pyrimidinedione,
(290) 1,3-dimethyl-6-[4-(2-[2-chloro-4-benzoyl]ethyl)piperazin-1-yl]-2,4(1H,3H)-pyrimidinedione,
(291) 1,3-dimethyl-6-[4-(3-[2-(2-hydroxybenzoyl)phenoxy]propyl)piperazin-1-yl]-2,4(1H,3H)-pyrimidinedione,
(292) 1,3-dimethyl-6-[4-(3-[2-(2-chlorobenzoyl)phenoxy]propyl)piperazin-1-yl]-2,4(1H,3H)-pyrimidinedione,
(293) 1,3-dimethyl-6-[4-(3-[2-(2-pyridinecarbonyl)phenylthio]propyl)piperazin-1-yl]-2,4(1H,3H)-pyrimidinedione,
(294) 3-methyl-6-[4-(3-[2-benzoylphenoxy]propyl)piperazin-1-yl]-2,4(1H,3H)-pyrimidinedione,
(295) 1,3-dimethyl-6-[2-(3-[2-benzoyl-4-chlorophenoxy]propylamino)ethylamino]-2,4(1H,3H)-pyrimidinedione,
(296) 1,3-dimethyl-6-[2-(N-ethyl-3-[4-benzoyl-2-chlorophenoxy]propylamino)ethylamino]-2,4(1H,3H)-pyrimidinedione,
(297) 1,3-dimethyl-6-[4-(2-[2-benzoyl-4-chlorophenylthio]ethyl)piperazin-1-yl]-2,4(1H,3H)-pyrimidinedione,
(298) 1,3-dimethyl-6-[4-(2-benzoyl-4-chlorophenyl)piperazin-1-yl]-2,4(1H,3H)-pyrimidinedione,
(299) 1,3-dimethyl-6-[3-(2-[3-pyridinecarbonyl]phenylamino)propylamino]-2,4(1H,3H)-pyrimidinedione,
(300) 1,3-dimethyl-6-[3-(2-benzoyl-3-chlorophenylamino)propylamino]-2,4(1H,3H)-pyrimidinedione,
(301) 1,3-dimethyl-6-[2-(2-benzoyl-4-chlorophenylamino)ethylamino]-2,4(1H,3H)-pyrimidinedione,
(302) 1,3-dimethyl-6-[2-(4-chloro-2-[3-pyridinecarbonyl]phenylamino)ethylamino]-2,4(1H,3H)-pyrimidinedione,
(303) 1,3-dimethyl-6-[4-(2-[2-benzoyl-4-cyanophenyl]ethyl)piperazin-1-yl]-2,4(1H,3H)-pyrimidinedione,
(304) 1,3-dimethyl-6-[4-(2-benzoyl-4-cyanobenzyl)piperazin-1-yl]-2,4(1H,3H)-pyrimidinedione,
(305) 1,3-dimethyl-6-[2-(2-benzoyl-4-cyanobenzylamino)ethylamino]-2,4(1H,3H)-pyrimidinedione,
(306) 1,3-dimethyl-6-[4-(3-[4-benzoyl-2-cyanophenyl]propyl)piperazin-1-yl]-2,4(1H,3H)-pyrimidinedione,
(307) 1,3-dimethyl-6-[4-(2-[4-benzoyl-2-chlorophenyl]ethyl)piperazin-1-yl]-2,4(1H,3H)-pyrimidinedione,
(308) 1,3-dimethyl-6-[4-(3-[4-methanesulfonamido-2-chlorophenyloxy]propyl)piperazin-1-yl]-2,4(1H,3H)-pyrimidinedione,
(309) 1,3-dimethyl-6-[4-(3-[4-acetamide-2-chlorophenoxy]propyl)piperazin-1-yl]-2,4(1H,3H)-pyrimidinedione,
(310) 1,3-dimethyl-6-[4-(3-[2-hydroxy-5-chlorophenoxy]-propyl)piperazin-1-yl]-2,4(1H,3H)-pyrimidinedione,
(311) 1,3-dimethyl-6-[4-(3-[2-allyloxy-5-acetylphenoxy]propyl)piperazin-1-yl]-2,4(1H,3H)-pyrimidinedione,
(312) 1,3-dimethyl-6-[4-(3-[4-methylthio-2-cyanophenoxy]propyl)piperazin-1-yl]-2,4(1H,3H)-pyrimidinedione,
(313) 1,3-dimethyl-6-[4-(3-[2-(α-hydroxybenzyl)phenyloxy]propyl)piperazin-1-yl]-2,4(1H,3H)-pyrimidinedione,
(314) 1,3-dimethyl-6-[4-(3-[3-trifluoromethyl-4-cyanophenoxy]propyl)piperazin-1-yl]-2,4(1H,3H)-pyrimidinedione,
(315) 1,3-dimethyl-6-[4-(3-[2-methoxycarbonyl-4-cyanophenoxy]propyl)piperazin-1-yl]-2,4(1H,3H)-pyrimidinedione,
(316) 1,3-dimethyl-6-[4-(3-[2-carboxy-4-fluorophenoxy]-propyl)piperazin-1-yl]-2,4(1H,3H)-pyrimidinedione, (317) 1,3-dimethyl-6-[4-(3-[2-amino-4-fluorophenoxy]-propyl)piperazin-1-yl]-2,4(1H,3H)-pyrimidinedione,
(318) 1,3-dimethyl-6-[4-(3-[4-methoxycarbonyl-2-fluorophenoxy]propyl)piperazin-1-yl]-2,4(1H,3H)-pyrimidinedione,
(319) 1,3-dimethyl-6-[4-(3-[2-cyano-4-fluorophenoxy]-propyl)piperazin-1-yl]-2,4(1H,3H)-pyrimidinedione,
(321) 1,3-dimethyl-6-[4-(3-[2-chloro-4-methoxyanilino]-propyl)piperazin-1-yl]-2,4(1H,3H)-pyrimidinedione,
(322) 1,3-dimethyl-6-[4-(3-[2-allyloxy-4-fluorophenoxy]propyl)piperazin-1-yl]-2,4(1H,3H)-pyrimidinedione,
(323) 1,3-dimethyl-6-[4-(3-[2-hydroxy-4-acetylphenoxy]propyl)piperazin-1-yl]-2,4(1H,3H)-pyrimidinedione,
(324) 1,3-dimethyl-6-[4-(3-[2-benzylamino-4-chlorophenoxy]propyl)piperazin-1-yl]-2,4(1H,3H)-pyrimidinedione,
(325) 1,3-dimethyl-6-[4-(3-[2-methoxy-4-chlorophenoxy]propyl)piperazin-1-yl]-2,4(1H,3H)-pyrimidinedione, and
(326) 1,3-dimethyl-6-[4-(3-[2,6-dichloro-4-cyanophenoxy]propyl)piperazin-1-yl]-2,4(1H,3H)-pyrimidinedione.

As shown in the above-mentioned formula (1), the compound of the present invention has a fundamental skeleton in which a phenyl moiety is linked with a pyrimidinedione moiety via the structure mainly comprising an alkyl chain containing at least two nitrogen atoms, and it can be presumed that the above-mentioned fundamental skeleton exerts pharmacological effects.

That is, when the compounds shown by the above-mentioned formula (1) were applied to the following arrhythmia pathological models, all the compounds demonstrated efficacy.

Atrial Fibrillation Model

Atrial fibrillation model animals were made in accordance with the method of A. L. Goldberger et al. (International Journal of Cardiology, Vol. 13, p. 47–55, 1986) by anesthetizing adult mongrel dogs with pentobarbital sodium (30 mg/kg, intravenous administration). Using these atrial fibrillation model animals, the effects of the compounds of the present invention on the atrial fibrillation model were investigated by administering the compounds intravenously at a dose of 0.1–10 mg/kg. As a result, it was confirmed that all the compounds of the present invention had therapeutic effects on atrial fibrillation.

Ventricular Tachycardia Model

Adult mongrel dogs were anesthetized with pentobarbital sodium (30 mg/kg, intravenous administration). A left thoracotomy was performed in the fourth intercostal space under artificial respiration, and the left anterior descending coronary artery was ligated at the border of the atrial appendage. The blood was then recirculated 120 minutes after the ligation, so that a cardiac infarction lesion was formed to readily induce tachycardia in each animal.

Thereafter, the ventricular tachycardia model animals were made by inducing ventricular tachycardia in accordance with the method of Lynch (Journal of Cardiovascular Pharmacology, Vol. 6, p. 1132–1141, 1984).

Using these model animals, it was confirmed that the compounds of the present invention had therapeutic effects on ventricular tachycardia when administered intravenously at a dose of 0.1 to 3 mg/kg.

As understood from the foregoing, the compounds of the present invention have effective therapeutic effects on the arrhythmia pathology model, i.e., atrial fibrillation model and ventricular tachycardia model, thus they are useful for the treatment and prevention of arrhythmia.

Furthermore, the effects of the compounds of the present invention on cardiac functions were investigated, so that the following results were obtained.

Mongrel dogs (body weights: 8–15 kg) were anesthetized with pentobarbital sodium (30 mg/kg, intravenous administration). A microsensor catheter was then inserted through the common carotid artery into the left ventricle of each animal so that primary differential values (dp/dt) of the inner pressure of the left ventricle and electrocardiograms were recorded. The compounds of the present invention were administered intravenously to the dogs (1 mg/kg) and changes in the dp/dt and electrocardiograms were investigated.

As a result, it was revealed that the compounds of the present invention significantly increased the values of dp/dt max and significantly extended QTc on the electrocardiograms.

Consequently, it was confirmed that the compounds of the present invention had an antiarrythmic action and particularly were useful as Class III type antiarrythmic agents. Furthermore, the significant increase in dp/dt max demonstrated that the compounds of the present invention had a positive inotropic action and accordingly they were useful as therapeutic agents for cardiac insufficiency.

As mentioned above, in general, most of patients with arrhythmia have deficiency in cardiac functions. In the case where, for example, antiarrythmic agents classified in Class I or II are given to such patients, the greatest care has to be taken for use because these agents exert more or less antiarrythmic action as well as a negative inotropic action (action to further repress cardiac functions) (Eivind S. Platous, Journal of Cardiovascular Pharmacology, Vol. 8, No. 3, p. 459, 1986).

On the contrary, as mentioned above, the compounds of the present invention have a positive inotropic action to significantly increase the dp/dt max, as well as an antiarrythmic action. Accordingly, it can be expected that these compounds provide satisfactory results to the arrhythmia patients whose cardiac functions are depressed.

Representative examples of processes for the production of the compounds of the formula (1) of the present invention will be described hereinafter, but the present invention should not be limited to these examples.

Of the compounds having the above-mentioned formula (1), a compound represented by the formula (2)

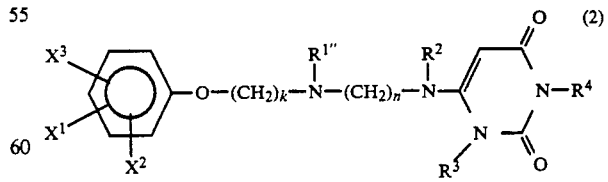

wherein each of $R^{1''}$ and $R^2$ is independently a hydrogen atom or a lower alkyl group (any one hydrogen atom of the alkyl group may be substituted by a substituent selected from the group consisting of a hydroxyl group and a benzoyloxy group), or $R^{1''}$ and $R^2$ may be so linked with each other as to make an alkylene chain and thus form a heterocyclic structure, $X^1$, $X^2$, $X^3$, $R^2$, $R^3$, $R^4$, k and n are defined as in the above-mentioned formula (1) can be prepared in accordance with a process containing the following step (a).

Step (a)

A compound represented by the formula (9)

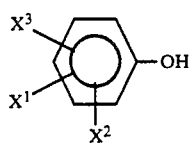

wherein $X^1$, $X^2$, $X^3$ are defined as in the above formula (1) and a compound represented by the formula (10)

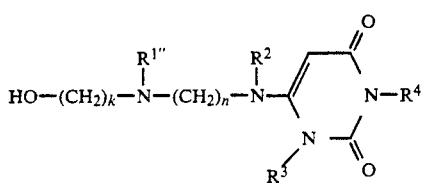

wherein $R^{1''}$ is defined as in the above formula (2), and $R^2$, $R^3$, $R^4$, n and k are defined as in the above formula (1) are dissolved or suspended in a suitable solvent or dispersant in the presence of a dehydration/condensation agent, and reaction is carried out in this state (the application of the Mitunobu's reaction; O. Mitunobu, Synthesis, pages 1-28, 1981), whereby the compound of the formula (2) can be obtained.

The reaction is carried out at a reflux temperature or less of the solvent or dispersant, and for example, the reaction temperature is preferably selected from the range of from $-10°$ to $80°$ C.

As the dehydration/condensation agents which can be used in the reaction, various kinds of dehydration/-condensation agents can be utilized which are usually used for the formation of an ether bond, and above all, a mixed condensation agent of diethyl azodicarboxylate and triphenylphosphine is preferable.

As the suitable solvent or dispersant used in the reaction, any one can be used without restriction, so long as it is inactive to this reaction. Examples of the usable solvent and dispersant include tetrahydrofuran, dimethylformamide, chloroform, dichloromethane and dioxane.

Next, of the compounds having the above-mentioned formula (1), a compound represented by the formula (4)

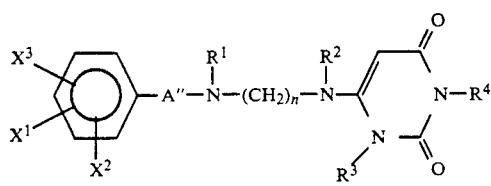

wherein $A''$ is $-B''(CH_2)_k-$ or

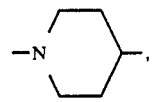

$B''$ is an oxygen atom, a sulfur atom or

and $R^5$ is a hydrogen atom or a lower alkylsulfonyl group or a lower alkyl group, or $R^5$ may be so linked with $R^1$ as to make an alkylene chain and thus form a heterocyclic structure, k is a value selected from 2, 3 and 4, and $X^1$, $X^2$, $X^3$, $R^1$, $R^2$, $R^3$, $R^4$ and n are defined as in the above-mentioned formula (1) can be prepared in accordance with a process containing the following step (b).

Step (b)

A compound represented by the formula (11)

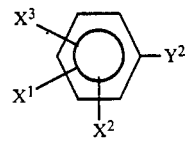

wherein $Y^2$ is a halogen atom, and $X^1$, $X^2$ and $X^3$ are defined as in the above formula (1) and a compound represented by the formula (12)

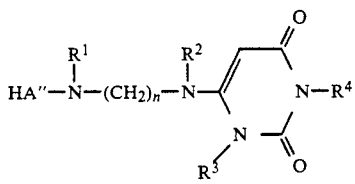

wherein $A''$ is defined as in the above formula (4), and $R^1$, $R^2$, $R^3$, $R^4$ and n are defined as in the above formula (1) are mixed with each other without using any solvent, or alternatively dissolved or suspended in a suitable solvent or dispersant to obtain the compound of the formula (4).

This reaction is carried out at a temperature of from room temperature to the reflux temperature of the reaction mixture solvent or dispersant, and for example, the reaction temperature is preferably selected from the range of from $20°$ to $150°$ C.

Furthermore, when a base is allowed to coexist in the reaction solution, the reaction can proceed more preferably.

As the suitable solvent or dispersant used in the reaction, any one can be used without restriction, so long as it is inactive to this reaction. Examples of the usable solvent and dispersant include alcohols such as methanol and ethanol, tetrahydrofuran, dimethylformamide, chloroform, dichloromethane, dioxane, benzene and dimethylsulfoxide.

Examples of the base having the effect of accelerating this reaction include triethylamine, pyridine, potassium carbonate, sodium carbonate and sodium hydroxide.

Next, of the compounds having the above-mentioned formula (1), a compound represented by the formula (3)

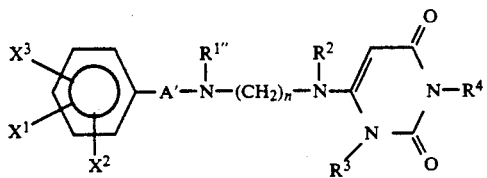

wherein A' is —(CH$_2$)$_m$—, —B'—(CH$_2$)$_k$— or

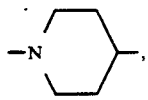

B' is an oxygen atom, a sulfur atom or

and R$^{5'}$ is a hydrogen atom or a lower alkylsulfonyl group or a lower alkyl group, (however, R$^{5'}$ does not form a heterocyclic structure together with R$^{1''}$), m is a value selected from 0, 1, 2, 3 and 4, k is a value selected from 2, 3 and 4, R$^{1''}$ is defined as in the above-mentioned formula (2), and R$^2$, R$^3$, R$^4$, X$^1$, X$^2$, X$^3$ and n are defined as in the above-mentioned formula (1) can be prepared in accordance with a process containing the following step (c).

Step (c)

A compound represented by the formula (13)

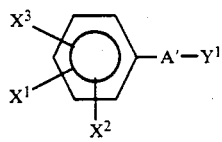

wherein Y$^1$ is a halogen atom or a substituent which can become a leaving group when reacted with a compound of the following formula (14), X$^1$, X$^2$, and X$^3$ are defined as in the above formula (1), and A' is defined as in the above formula (3) and a compound represented by the formula (14)

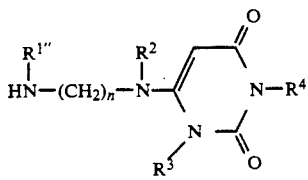

wherein R$^{1''}$ is defined as in the above formula (2), and R$^2$, R$^3$, R$^4$ and n are defined as in the above formula (1) are mixed with each other without using any solvent, or alternatively dissolved or suspended in a suitable solvent or dispersant, and in this state, reaction is carried out to obtain the compound of the formula (3).

This reaction is carried out at a temperature of from room temperature to the reflux temperature of the reaction mixture, and for example, the reaction temperature is preferably selected from the range of from 20° to 170° C.

Furthermore, when a base is allowed to coexist in the reaction solution, the reaction can proceed more preferably.

As the suitable solvent or dispersant used in the reaction, any one can be used without restriction, so long as it is inactive to this reaction. Examples of the usable solvent and dispersant include those which are enumerated in the paragraph regarding the previous step (b).

Examples of the base which is useful to accelerate this reaction include those which are enumerated in the paragraph regarding the previous step (b).

The compound represented by the formula (1) can also be prepared in accordance with a process containing the following step (d).

Step (d)

A compound represented by the formula (15)

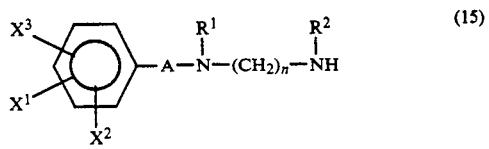

wherein A, X$^1$, X$^2$, X$^3$, R$^1$, R$^2$ and n are defined as in the above formula (1) and a compound represented by the formula (16)

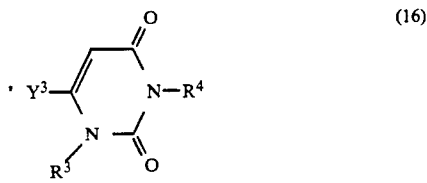

wherein Y$^3$ is a halogen atom or a substituent which can become a leaving group when reacted with a compound of the following formula (15), and R$^3$ and R$^4$ are defined as in the above formula (1) are mixed with each other without using any solvent, or alternatively dissolved or suspended in a suitable solvent or dispersant, and in this state, reaction is carried out to obtain the compound of the formula (1).

This reaction is carried out at a temperature of from room temperature to the reflux temperature of the reaction mixture, and for example, the reaction temperature is preferably selected from the range of from 20° to 150° C.

Furthermore, when a base is allowed to coexist in the reaction solution, the reaction can proceed more preferably.

As the suitable solvent or dispersant used in the reaction, any one can be used without restriction, so long as it is inactive to this reaction. Examples of the usable solvent and dispersant include those which are enumerated in the paragraph regarding the previous step (b).

Examples of the base which is useful to accelerate this reaction include those which are enumerated in the paragraph regarding the previous step (b).

Next, of the compounds having the above-mentioned formula (1), a compound represented by the formula (5)

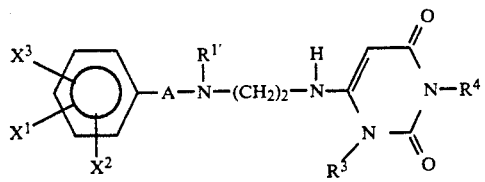 (5)

wherein each of $R^{1'}$ a hydrogen atom or a lower alkyl group (any one hydrogen atom of the alkyl group may be substituted by a substituent selected from the group consisting of a hydroxyl group and a benzoyloxy group), or, when A is $-B(CH_2)_k-$ and B is

$R^{1'}$ may be so linked with $R^5$ as A as to make an alkylene chain and thus make a heterocyclic structure, but does not the heterocyclic structure together with another moiety, A, B, $X^1$, $X^2$, $X^3$, $R^3$, $R^4$, $R^5$ and k are defined as in the above-mentioned formula (1) can be prepared in accordance with a process containing the following step (e).

Step (e)

A compound represented by the formula (17)

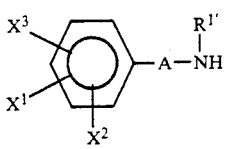 (17)

wherein A, $X^1$, $X^2$ and $X^3$ are defined as in the above formula (1), and $R^{1'}$ is defined as in the above formula (5) and a compound represented by the formula (18)

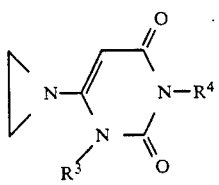 (18)

wherein $R^3$ and $R^4$ are defined as in the above formula (1) are mixed with each other without using any solvent, or alternatively dissolved or suspended in a suitable solvent or dispersant, and in this state, reaction is carried out to obtain the compound of the formula (5).

This reaction is carried out at a temperature of from room temperature to the reflux temperature of the reaction mixture, and for example, the reaction temperature is preferably selected from the range of from 20° to 180° C.

Furthermore, when an acid catalyst is allowed to coexist in the reaction solution, the reaction can proceed more preferably.

As the suitable solvent or dispersant used in the reaction, any one can be used without restriction, so long as it is inactive to this reaction. Examples of the usable solvent and dispersant include those which are enumerated in the paragraph regarding the previous step (b).

In addition, examples of the above-mentioned acid catalyst include p-toluenesulfonic acid and acidic ion exchange resins [e.g., trade name Umberlist such as Umberlist 15 made by Rohm & Hass Co., in U.S.A.].

Of the compounds having the above-mentioned formula (1), a compound represented by the formula (7)

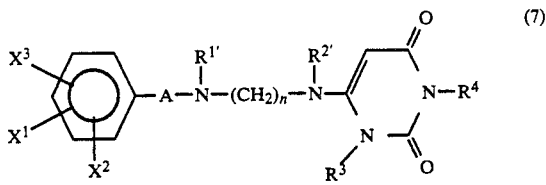 (7)

wherein each of $R^{1'}$ and $R^{2'}$ is independently a hydrogen atom or a lower alkyl group (any one hydrogen atom of the alkyl group may be substituted by a substituent selected from the group consisting of a hydroxyl group and a benzoyloxy group), or $R^{1'}$ is not linked with $R^{2'}$ to form an alkylene chain, $R^5$ is a hydrogen atom or a lower alkylsulfonyl group or a lower alkyl group, but with $R^5$ as A, when A is $-B(CH_2)_k-$ and B is

and A, B, $X^1$, $X^2$, $X^3$, $R^3$, $R^4$, $R^5$ m, k, l and n are defined as in the above-mentioned formula (1) can also be prepared in accordance with a process containing the following step (f).

Step (f)

That is, a compound represented by the formula (17) and a compound represented by the formula (19)

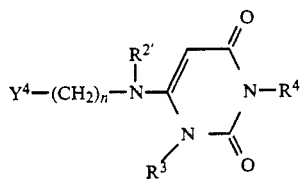 (19)

wherein $R^{2'}$ is defined as in the above formula (7), $R^3$, $R^4$ and n are defined as in the above-mentioned formula (1), and $Y^4$ is a halogen atom or a substituent which can become a leaving group when reacted with a compound of the aforesaid formula (17) are treated in the same manner as in the above-mentioned step (c) to obtain the compound of the formula (7).

Of the compounds having the above-mentioned formula (1), a compound represented by the formula (8)

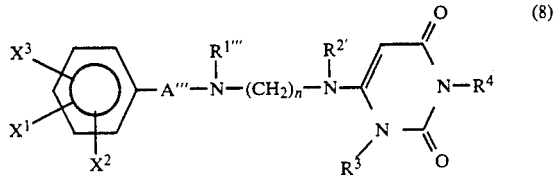 (8)

wherein $A'''$ is $-(CH_2)_m-$, $-B'''-(CH_2)_k-$ or $-D-(CH_2)_l-$ or

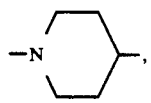

B''' is an oxygen atom, a sulfur atom,

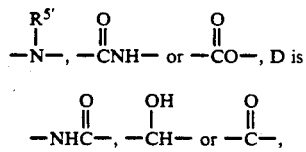

and each of R$^{1'''}$ and R$^{2'}$ is independently a hydrogen atom or a lower alkyl group, (any one hydrogen atom of the alkyl group may be substituted by a substituent selected from the group consisting of a hydroxyl group and a benzoyloxy group), or R$^{1'''}$ is linked neither with R$^{2'}$ nor with R$^5$, R$^{2'}$ is defined as in the above formula (7), X$^1$, X$^2$, X$^3$, R$^3$, R$^4$ and n are defined as in the above-mentioned formula (1), and R$^{5'}$ is defined as in the above formula (3) can also be prepared in accordance with a process containing the following step (g).

Step (g)

A compound represented by the formula (20)

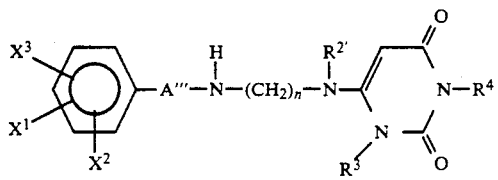 (20)

wherein R$^{2'}$ is defined as in the above formula (7), A''' is defined as in the above formula (8), and X$^1$, X$^2$, X$^3$, R$^3$, R$^4$ and n are defined as in the above-mentioned formula (1) a compound represented by the formula (21)

R$^{1'''}$—Y$^4$ (21)

wherein Y$^4$ is a halogen atom or a substituent which can become a leaving group when reacted with a compound of the following formula (20), and R$^{1'''}$ is defined as in the above formula (8) are treated in the same manner as in the above-mentioned step (c) to obtain the compound of the formula (8).

With regard to Y$^1$, Y$^3$ and Y$^4$ in the compounds used in the above-mentioned preparation methods, examples of the substituent which can become the leaving group include an arylsufonyloxy group such as a paratoluenesulfonyloxy group, and an alkylsulfonyloxy group such as a methanesulfonyloxy group.

In the above-mentioned formulae, R$^1$ is a group which may form a heterocyclic ring together with R$^2$ or R$^5$, and R$^{1'}$ is a group which may form a heterocyclic ring together with R$^5$ alone. Furthermore, R$^{1''}$ is a group which may form a heterocyclic ring together with R$^2$ alone.

Each of R$^{1'''}$, R$^{2'}$ and R$^{5'}$ is a group which does not form a heterocyclic ring together with another moiety.

The compound of the formula (18) can be prepared by a process containing the following step (f).

Step (f)

A compound represented by the formula (15) is reacted with 2-aminoethanol in the same manner as in the aforesaid step (d) in order to produce a compound having the following formula (21)

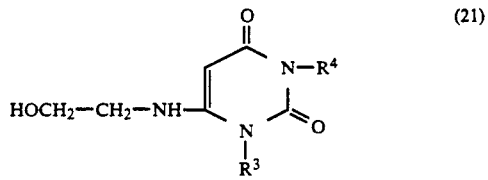 (21)

wherein R$^3$ and R$^4$ are defined as in the above formula (1), the thus produced compound is sulfonated with methane-sulfonyl chloride, p-toluenesulfonyl chloride or the like, or alternatively this compound is reacted with thionyl chloride, potassium tribromide or the like to form a halide, and then this sulfonated compound or halide is then stirred at room temperature or under heating in the presence of a base such as sodium hydride or sodium hydroxide in a solvent such as acetonitrile, chloroform, toluene, benzene, dimethyl sulfoxide or methanol, whereby the compound of the formula (18) can be obtained.

On the other hand, a pharmaceutically acceptable acid addition salt of the compound of the above-mentioned formula (1) can be produced by allowing the compound of the formula (1) to react with an inorganic or organic acid such as hydrochloric acid, hydrobromic acid, phosphoric acid, sulfuric acid, acetic acid, citric acid, maleic acid, fumaric acid, oxalic acid or methanesulfonic acid in water, an organic solvent or a mixture thereof.

When the compound of the formula (1) of the present invention or the acid addition salt thereof is used as a therapeutic agent to treat patients with cardiac malfunctions such as arrhythmia and cardiac insufficiency, the dose and form of the agent depend on properties of the compound of the present invention which is used as an active ingredient and depend on symptoms of the patients to be treated. For example, the therapeutic agent can be orally administered in a dose of from 10 to 1000 mg/day, preferably 10 to 500 mg/day for an adult in the form of tablets, granules, powders, suspensions or capsules, or parenterally in the form of depositories, injections, fluids for infusion, inhalations or plasters.

In the case of intravenous injection, for example, the dose of the compound regarding the present invention is from 1 to 1000 mg/day, preferably 1 to 300 mg/day for an adult.

A mixture of two or more of the compounds of the present invention may be contained in a pharmaceutical composition.

General processes for producing pharmaceutical compositions of the present invention include a method in which the compound of the present invention is dissolved in an appropriate amount of an oil selected from the group consisting of cotton seed oil, corn oil, peanut oil, olive oil and the like so as to prepare non-aqueous injections each containing 1 to 500 mg of the compound of the present invention; a method in which water is added to the compound of the present invention to form a solution, or alternatively the compound of the present invention is either suspended or emulsified in an appropriate surfactant so as to prepare aqueous injections each containing 1 to 500 mg of the compound of the present invention; or a method in which lactose, corn starch, crystallized cellulose or the like is added to the compound of the present invention and magnesium stearate is finally added thereto in order to prepare tablets each containing 1 to 1,000 mg of the compound of the present invention. However, the pharmaceutical preparations of the present invention can be obtained by any ordinary method in addition to the above-mentioned methods.

Now, the present invention will be described in more detail in reference to examples, but the scope of the present invention should not be limited to these examples.

REFERENCE EXAMPLE 1

Preparation of 1,3-dimethyl-6-[4-(3-hydroxypropyl)piperazin-1-yl]-2,4(1H,3H)-pyrimidinedione (compound a)

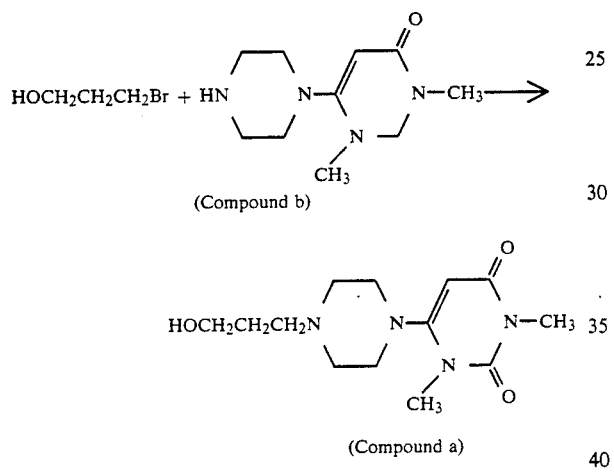

(Compound a)

14.1 g of 1,3-dimethyl-6-(1-piperazinyl)-2,4(1H,3H)-pyrimidinedione (compound b), 11.7 g of 3-bromo-1-propanol and 13 g of triethylamine were heated under reflux in 250 ml of ethanol for 20 hours to carry out reaction. After completion of the reaction, the resultant reaction mixture was then concentrated to dryness, and the resultant residue was dissolved in 300 ml of chloroform and then washed with 100 ml of water twice. The washed organic layer was dried over anhydrous magnesium sulfate and then treated with under reduced pressure, and the solvent was distilled off, thereby obtaining 20.5 g of a crude product. Next, ether was added to this crude product so as to achieve crystallization. The resultant crystals were recovered, washed and then dried to obtain 12.4 g (yield 69.8%) of 1,3-dimethyl-6-[4-(3-hydroxypropyl)piperazin-1-yl]-2,4(1H,3H)-pyrimidinedione (Compound a).

Analytical results of the obtained crystalline Compound a:

Melting point: 119°–121° C.

NMR (CDCl$_3$) δ ppm: 1.8 (dt, 2H), 2.7 (m, 6H), 3.02 (m, 4H), 3.36 (s, 3H), 3.43 (s, 3H), 3.82 (t, 2H), 4.34 (br, 1H), 5.26 (s, 1H).

IR $\nu_{max}^{KBr}$ (cm$^{-1}$): 3380, 3180, 2830, 1695, 1650, 1605, 1440, 1213, 1068, 1000, 921, 760.

REFERENCE EXAMPLE 2

Preparation of 1,3-dimethyl-6-[4-(3-[3-nitrophenoxy]propyl)piperazin-1-yl]-2,4(1H,3H)-pyrimidinedione (Compound c):

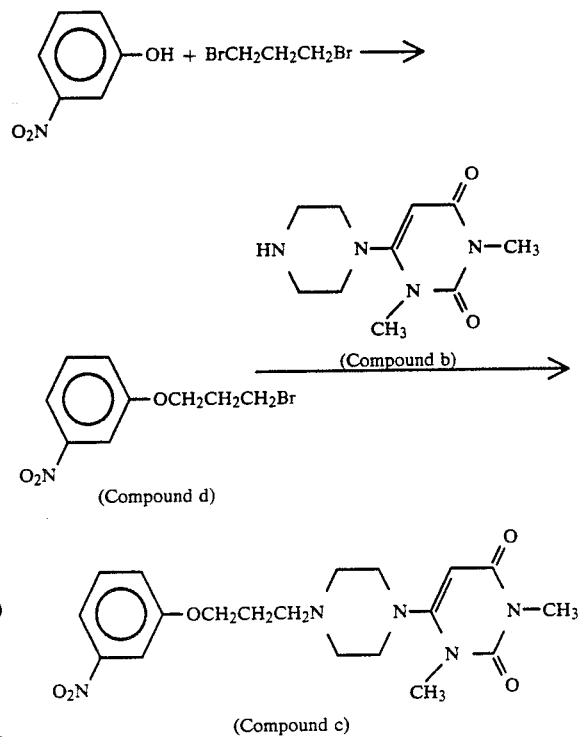

(1) Preparation of 3-(3-nitrophenoxy)propyl bromide (Compound d)

13.9 g of 3-nitrophenol, 101 g of 1,3-dibromopropane and 15.2 g of anhydrous potassium carbonate were reacted in 100 ml of methyl ethyl ketone for 2 hours by heating under reflux. After completion of the reaction, insoubles were removed from the reaction mixture by filtration, and the filtrate was then concentrated. Next, the resultant concentrate was dissolved in 300 ml of chloroform, and this chloroform solution was further washed with water. Afterward, the washed organic layer was dried over anhydrous magnesium sulfate and then treated with under reduced pressure to distill off the solvent, thereby obtaining 24.6 g of 3-(3-nitrophenoxy)propyl bromide (Compound d) in an oily state. This was used for a subsequent reaction without purifying.

(2) Preparation of 1,3-dimethyl-6-[4-(3-[3-nitrophenoxy]propyl)piperazin-1-yl]-2,4(1H,3H)-pyrimidinedione (Compound c):

1.69 g of the above oily compound d, 1.12 g of 1,3-dimethyl-6-(1-piperazinyl)-2,4(1H,3H)-pyrimidinedione (compound b) and 1 ml of triethylamine were heated under reflux in 20 ml of dioxane for 4 hours to carry out reaction. After completion of the reaction, insoubles were removed from the reaction mixture by filtration, and the filtrate was then concentrated. Next, the resultant residue (concentrate) was dissolved in chloroform, and the resultant chloroform solution was washed with water. Afterward, the washed organic layer was dried over anhydrous magnesium sulfate and then treated with under reduced pressure to distill off the solvent. The residue was further purified through a silica gel column chromatography (chloroform/methanol=100/1 to 25/1 in volume ratio) and then recrystallized from ethanol. The resultant crystals were collected by filtration, washed, and then dried, thereby obtaining 1.35 g of 1,3-dimethyl-6-[4-(3-[3-nitrophenoxy]propyl)piperazin-1-yl]-2,4(1H,3H)-pyrimidinedione (Compound c).

Analytical results of the crystals of the obtained Compound c:

Melting point: 164°–165° C.

NMR (CDCl$_3$) δ ppm: 1.8–2.2 (m, 2H), 2.4–2.8 (m, 6H), 2.8–3.8 (m, 4H), 3.34 (s, 3H), 3.42 (s, 3H), 4.15 (t, 2H), 5.25 (s, 1H), 7.1–8.0 (m, 4H).

Values of elemental analysis (as $C_{19}H_{25}N_5O_5$): Calcd. (%): C 56.57; H 6.25; N 17.36; Found (%): C 56.27; H 6.69; N 17.21.

REFERENCE EXAMPLE 3

Preparation of 1,3-dimethyl-6-[4-(3-[2-nitrophenoxy]propyl)piperazin-1-yl]-2,4(1H,3H)-pyrimidinedione (Compound c):

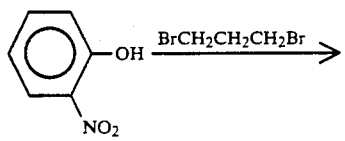

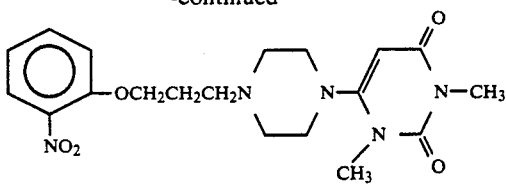

(Compound e)

The same procedure as in Reference Example 2-(1) and 2-(2) was effected except that 3-nitrophenol was replaced with 13.9 g of 2-nitrophenol, thereby obtaining crystals of 1,3-dimethyl-6-[4-(3-[2-nitrophenoxy]propyl)piperazin-1-yl]-2,4(1H,3H)-pyrimidinedione (Compound e).

Analytical results of the crystals of the obtained Compound e:

Melting point: 123.5°–125° C.

Values of elemental analysis (as $C_{19}H_{25}N_5O_5$): Calcd. (%): C 56.57; H 6.25; N 17.36; Found (%): C 56.74; H 5.85; N 17.46.

NMR (CDCl$_3$) δ ppm: 2.03 (m, 2H), 2.66 (m, 6H), 2.98 (m, 4H), 3.32 (s, 3H), 3.40 (s, 3H), 4.11 (t, 2H), 5.22 (s, 1H), 6.9–7.9 (m, 4H).

REFERENCE EXAMPLE 4

Preparation of 1,3-dimethyl-6-[4-(3-[4-nitrophenoxy]propyl)piperazin-1-yl]-2,4(1H,3H)-pyrimidinedione (Compound f):

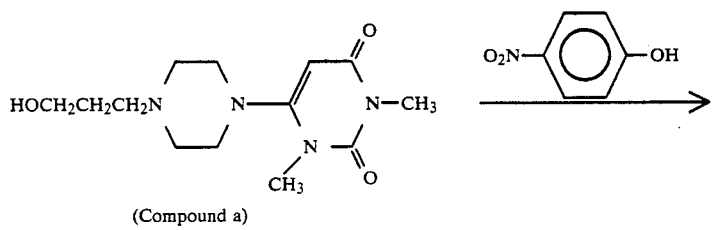

(Compound a)

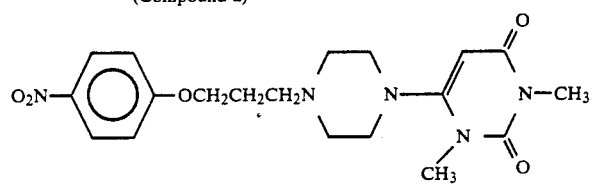

(Compound f)

2.0 g of the compound a obtained in Reference Example 1, 2.2 g of triphenylphosphine and 1.14 g of 4-nitrophenol were suspended in and mixed with 30 ml of anhydrous tetrahydrofuran, and 20 ml of an anhydrous tetrahydrofuran solution containing 1.42 g of diethyl azodicarboxylate was added to the resultant suspension at room temperature.

Next, the resultant mixture was stirred for 10 minutes and then concentrated to dryness, and the residue was purified through a silica gel column chromatograph (methanol/ethyl acetate=1/15 to 1/7 in volume ratio) to obtain 2.6 g (yield 80%) of 1,3-dimethyl-6-[4-(3-[4-nitrophenoxy]propyl)piperazin-1-yl]-2,4(1H,3H)-pyrimidinedione (Compound f).

Analytical results of the crystals of the obtained Compound f:

Melting point: 167°–170° C.

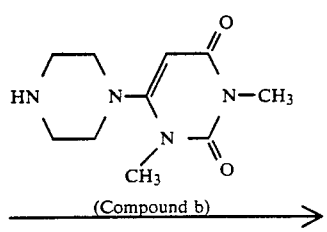

(Compound b)

Values of elemental analysis (as $C_{19}H_{25}N_3O_5$): Calcd. (%): C 56.57; H 6.25; N 17.36; Found (%): C 56.29; H 6.17; N 17.17.

REFERENCE EXAMPLE 5

Preparation of 1,3-dimethyl-6-[4-(3-[4-nitroanilino]propyl)piperazin-1-yl]-2,4(1H,3H)-pyrimidinedione (Compound g):

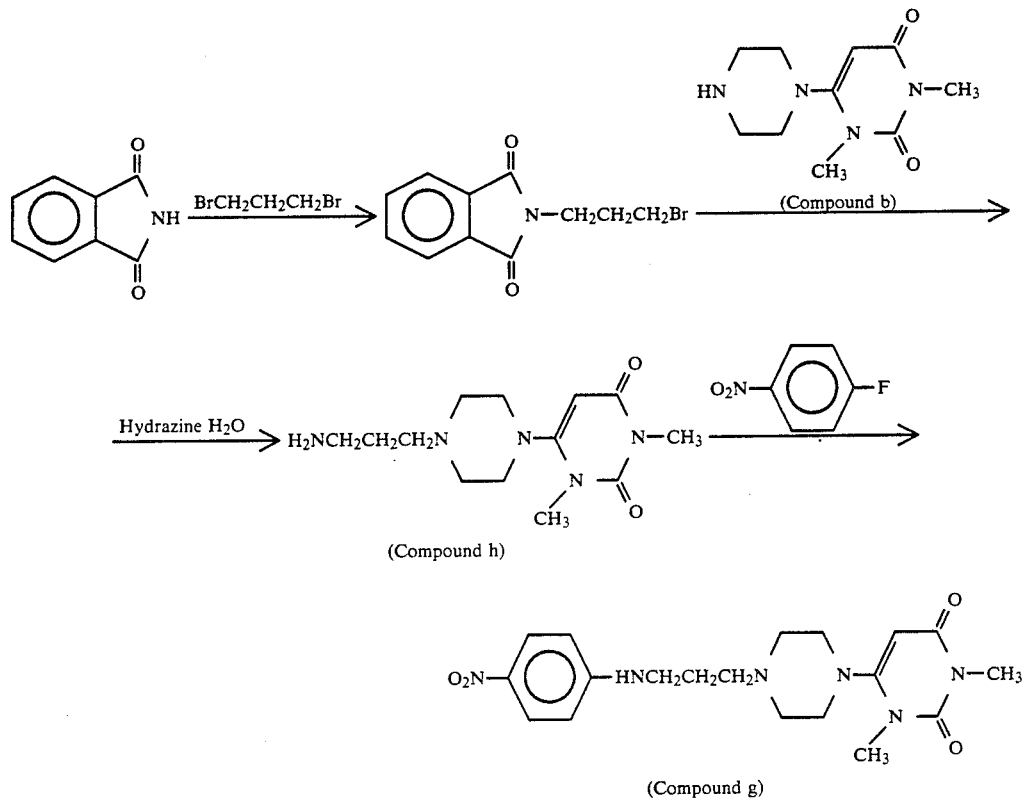

(1) Preparation of 1,3-dimethyl-6-[4-(3-aminopropyl)piperazin-1-yl]-2,4(1H,3H)-pyrimidinedione (Compound h):

18.52 g of potassium phthalimide and 200 g of 1,3-dibromopropane were suspended in 100 ml of dimethylformamide, and the suspension was then stirred at 120° C. for 6 hours under heating to react them. Next, insolubles were removed from the resultant reaction mixture by filtration, and the filtrate was then concentrated to dryness under reduced pressure. The residue was washed with hexane, and then recrystallized from ethanol/water, and the resultant crystals were collected by filtration, washed, and then dried, thereby obtaining 13.8 g of N-(3-bromopropyl)phthalimide.

Next, 13.0 g of this N-(3-bromopropyl)phthalimide, 10.3 g of 1,3-dimethyl-6-[1-piperazinyl]-2,4(1H,3H)-pyrimidinedione (Compound b) and 20 g of triethylamine were suspended in 200 ml of dioxane, and the resultant suspension was heated under reflux for 6 hours.

In addition, insolubles were removed from the resultant reaction mixture by filtration, and the filtrate was then concentrated to dryness under reduced pressure. The residue (which was obtained by concentration to dryness) was recrystallized from ethyl acetate/n-hexane, and the resultant crystals were collected by filtration, washed, and then dried, thereby obtaining 12.5 g of 1,3-dimethyl-6-[4-(3-phthaloylaminopropyl)piperazin-1-yl]-2,4(1H,3H)-pyrimidinedione.

Next, 12.5 g of the resultant crystals and 6.0 g of hydrazine hydrate were suspended in 200 ml of ethanol, and the suspension was then heated under reflux for 4 hours. After the suspension was allowed to stand for cooling, the appeared insolubles were removed therefrom by filtration, and the filtrate was then concentrated to dryness under reduced pressure. Furthermore, the residue (which was obtained by concentration to dryness) was dissolved in water, and dilute hydrochloric acid was then added thereto, so that a pH of the solution was adjusted to about 3. Insolubles formed at this time were removed by filtration, and a large amount of potassium carbonate was added to the filtrate and extraction was then carried out with chloroform. After completion of the extraction, the resultant organic layer was dried with anhydrous sodium sulfate and then treated under reduced pressure to distill off the solvent, thereby obtaining 6.80 g of colorless syrupy 1,3-dimethyl-6-[4-(3-aminopropyl)piperazin-1-yl]-2,4(1H,3H)-pyrimidinedione (Compound h). When this compound was allowed to stand overnight, crystallization was observed.

(2) Synthesis of 1,3-dimethyl-6-[4-(3-[4-nitroanilino]propyl)piperazin-1-yl]-2,4(1H,3H)-pyrimidinedione (Compound g):

2.50 g of the previously obtained compound h and 1.90 g of 4-nitrofluorobenzene were added to 20 ml of dimethyl sulfoxide, and the resultant mixture was then heated at 80° C. for 3 hours. After the mixture was allowed to stand for cooling, the precipitated crystals were collected by filtration, washed, and then dried to obtain 2.75 g of 1,3-dimethyl-6-[4-(3-[4-nitroanilino]- propyl)piperazin-1-yl]-2,4(1H,3H)-pyrimidinedione (Compound g).

Analytical results of the crystals of the obtained Compound g:

IR $\nu_{max}^{KBr}$ (cm$^{-1}$): 3280, 1635, 1592, 1450, 1425, 1295, 1105, 990, 840.

Values of elemental analysis (as $C_{19}H_{25}N_6O_4$): Calcd. (%): C 56.70; H 6.51; N 20.88; Found (%): C 56.19; H 6.88; N 20.50.

REFERENCE EXAMPLE 6

Preparation of 1,3-dimethyl-6-[4-(2-[4-nitrophenyl]ethyl)piperazin-1-yl]-2,4(1H,3H)-pyrimidinedione (Compound i):

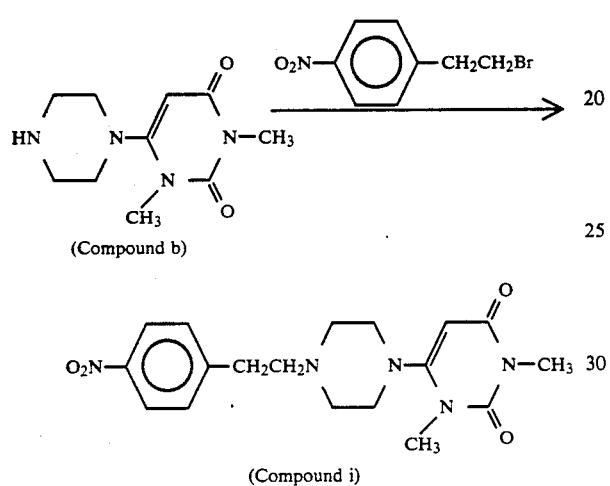

(Compound b)

(Compound i)

0.51 g of 4-nitrophenethyl bromide, 0.5 g of 1,3-dimethyl-6-[1-piperazinyl]-2,4(1H,3H)-pyrimidinedione (Compound b) and 0.5 ml of triethylamine were suspended in 5 ml of isopropanol, and the resultant suspension was heated under reflux for 8 hours. The solvent was distilled off from the resultant reaction mixture under reduced pressure, and the residue was then dissolved in chloroform. After washing with water, the washed organic layer was dried over anhydrous sodium sulfate. In addition, the dried organic layer was treated under reduced pressure, and the solvent was then distilled off. Afterward, the residue was purified through a silica gel column chromatograph (chloroform/methanol=50/1 to 20/1 in volume ratio) to obtain 0.58 g of 1,3-dimethyl-6-[4-(2-[4-nitrophenyl]ethyl)piperazin-1-yl]-2,4(1H,3H)-pyrimidinedione.

NMR (CDCl$_3$)δ ppm: 2.8 (m, 12H), 3.22 (s, 3H), 3.36 (s, 3H), 5.19 (s, 1H), 7.36 (d, 2H), 8.12 (d, 2H).

REFERENCE EXAMPLE 7

Preparation of 6-(1-aziridinyl)-1,3-dimethyl-2,4(1H,3H)-pyrimidinedione (Compound j):

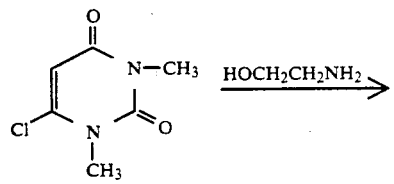 HOCH$_2$CH$_2$NH$_2$ →

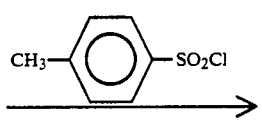

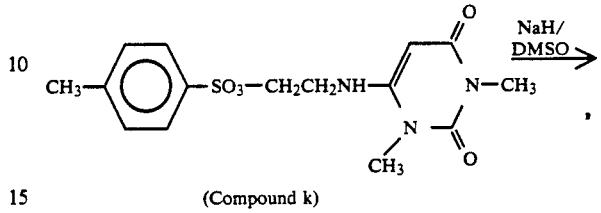

(Compound k)

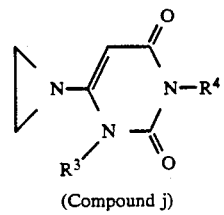

(Compound j)

(1) Preparation of 1,3-dimethyl-6-[2-(p-toluenesulfonyloxy)ethylamino)-2,4(1H,3H)-pyrimidinedione (Compound k)

On an oil bath, 35.0 g of 2-aminoethanol was heated up to 90° C. and it was removed from the oil bath, and 50.0 g of 6-chloro-1,3-dimethyl-2,4-dioxopyrimidine was added thereto in order to carry out reaction. This addition was effected at such a rate as to maintain a reaction temperature in the range of from 90° to 110° C. After completion of the addition, the reaction mixture was stirred for 10 minutes, and 300 ml of dioxane/methanol (10/1 in volume ratio) was then added thereto. The mixture was allowed to stand overnight, and the resultant crystals were washed with a small amount of dioxane and then dried, thereby obtaining 49.0 g of 1,3-methyl-6-(2-hydroxyethylamino)-2,4(1H,3H)-pyrimidinedione in the state of white crystals.

Next, the suspension prepared by suspending 49.0 g of the white crystals in 200 ml of pyridine was cooled to −5° C., and 40.0 g of p-toluenesulfonyl chloride was added thereto at such a rate that a reaction temperature did not rise in excess of 5° C. In order to completely extinguish the turbidity of the reaction solution, 51.0 g of p-toluenesulfonyl chloride were additionally used.

Furthermore, the resultant reaction mixture was poured into 1.5 liters of ice water containing 70 g of K$_2$CO$_3$, and it was then allowed to stand overnight. The resultant crystals were collected by filtration, washed with water, and then dried under reduced pressure, thereby obtaining 50.5 g of 1,3-dimethyl-6-[2-(p-toluenesulfonyloxy)ethylamino]-2,4(1H,3H)-pyrimidinedione (Compound k) in the state of light yellow crystals.

Analytical results of the crystals of the obtained Compound k:

Melting point: 146.0°–149.0° C.

IR $\nu_{max}^{KBr}$ (cm$^{-1}$): 3270, 1682, 1615, 1550, 1480, 1435, 1360, 1190, 1178, 1010, 903, 780.

(2) Synthesis of 6-(1-aziridinyl)-1,3-dimethyl-2,4(1H,3H)-pyrimidinedione (Compound j):

To 150 ml of anhydrous dimethyl sulfoxide (DMSO) containing 47.2 g of the previously obtained Compound k were slowly added 6.24 g of 60% oily sodium hydride at room temperature, and the resultant mixture was then stirred vigorously at room temperature for 5 hours. After cooling, a small amount of water was added thereto so as to bring the reaction to an end. The reaction mixture was poured into 1 liter of water containing 70 g of potassium carbonate, and then extracted with 200 ml of chloroform three times. Afterward, the organic layers were joined and dried over anhydrous sodium sulfate and then concentrated, and 300 ml of ether were added to the resultant concentrate. The mixture was then allowed to stand overnight.

Light yellow crystals which were precipitated by the overnight standing were collected by filtration, washed with ether, and then dried under reduced pressure to obtain 15.2 g of 6-(1-aziridinyl)-1,3-dimethyl-2,4(1H,3H)-pyrimidinedione (Compound j).

Analytical results of the crystals of the obtained Compound j:

Melting point: 126.0°–126.5° C.

IR $\nu_{max}^{KBr}$ (cm$^{-1}$): 1705, 1650, 1612, 1470, 1440, 1305, 1160, 783, 490.

$^1$H-NMR (CDCl$_3$) δ ppm 2.34 (s, 4H), 3.35 (s, 3H), 3.56 (s, 3H), 5.25 (s, 1H)

REFERENCE EXAMPLE 8

Preparation of 1,3-dimethyl-6-[2-(N-[2-hydroxyethyl]-3-[4-nitrophenyl]propylamino )ethylamino]-2,4(1H,3H)-pyrimidinedione (Compound l)

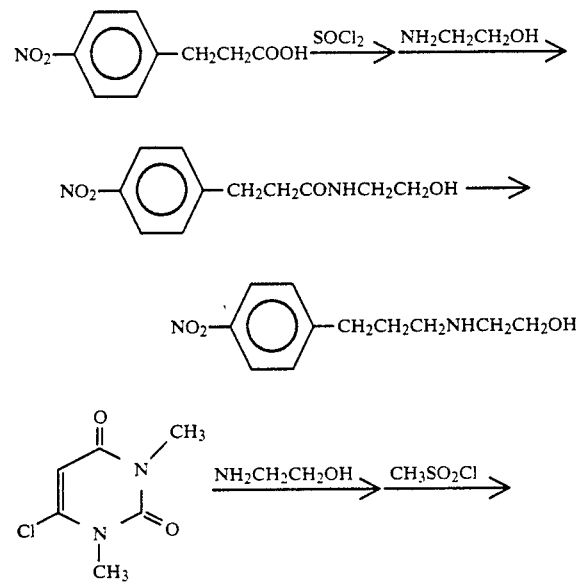

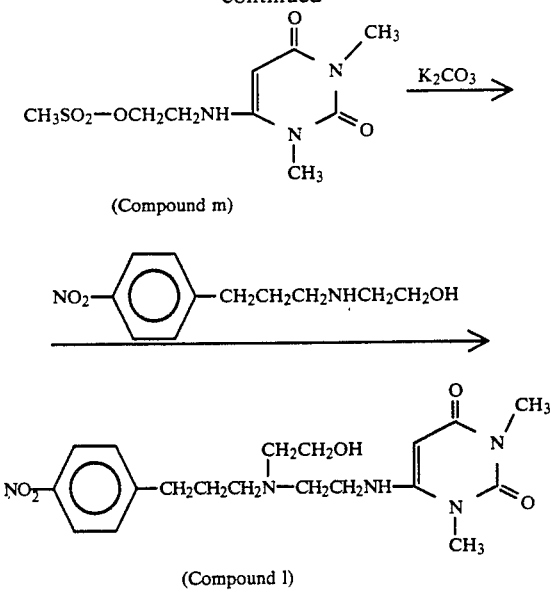

(Compound l)

(1) Preparation of N-(2-hydroxyethyl)-3-(4-nitrophenyl)propionylamide 60 g of 3-(4-nitrophenyl)propionic acid was suspended in 360 ml of chloroform, and 2.25 g of dimethylformamide was then added thereto. The resultant reaction mixture was heated up to a level of from 50° to 60° C., and 33.5 ml of thionyl chloride was slowly added dropwise thereto. After the addition, the solution was heated under reflux for 1 hour, and the solvent was then removed therefrom by distillation under reduced pressure. The thus obtained oily material was dissolved in 150 ml of chloroform. The resultant chloroform solution was added dropwise under ice cooling conditions, to a solution which was prepared by dissolving 28.2 g of ethanolamine and 42.5 g of potassium carbonate in 450 ml of water. After the addition, the solution was stirred for 1 hour, and the deposited crystals were collected by filtration and then recrystallized from 1 liter of ethyl acetate to obtain 56.1 g of N-(2-hydroxyethyl)-3-(4-nitrophenyl)propionylamide in the state of crystals which had a melting point of from 122° to 125° C.

(2) Preparation of N-(2-hydroxyethyl)-3-(4-nitrophenyl)propylamine 50 g of the previously obtained N-(2-hydroxyethyl)-3-(4-nitrophenyl)propionylamide and 31.8 g of sodium boron hydride were suspended in 500 ml of tetrahydrofuran, and 50.5 g of acetic acid was added dropwise thereto under ice cooling conditions. After completion of the addition, the solution was heated under reflux for 2 hours and then ice-cooled again, and 500 ml of water was added dropwise thereto. Afterward, 4N hydrochloric acid was added to the solution so as to adjust its pH to a level of from 5 to 6, and tetrahydrofuran was then distilled off under reduced pressure. Next, 425 ml of 4N hydrochloric acid was added to the resultant aqueous solution, and the solution was stirred at 60°–70° C. for 1 hour and then allowed to stand for cooling, so that the temperature of the solution was returned to room temperature. After washed with chloroform, the aqueous solution was adjusted to a pH of 11 by the use of a 16% aqueous sodium hydroxide solution, and extraction was carried out twice with 500 ml of chloroform. The chloroform extracts were joined and concentrated under reduced pressure, and the resultant residue was crystallized from 900 ml of toluene to obtain 38.6 g of crystalline N-(2-hydroxyethyl)-3-(4-nitrophenyl)-propylamine, which had a melting point of from 82.5° to 84.5° C.

(3) Preparation of 1,3-dimethyl-6-[2-methanesulfonyloxyethylamino)-2,4(1H,3H)-pyrimidinedione (Compound m)

52.4 g of 6-chloro-1,3-dimethyl-2,4(1H,3H)-pyrimidinedione was dissolved in 280 ml of pyridine, and 45.5 g of triethylamine and 21.3 g of aminoethanol were added thereto, followed by stirring at 90° C. for 4 hours. The reaction solution was cooled with ice so that its internal temperature might be in the range of from 0° to 4° C., and 55.8 g of methanesulfonyl chloride was added dropwise thereto, and the solution was then stirred at the same temperature for 3 hours. 1.2 liters of methanol were added to the solution, followed by stirring for further 2 hours. The crystals which had been deposited in the reaction solution were collected by filtration and then recrystallized from 3.5 liters of methanol to obtain 70.0 g of crystalline 1,3-dimethyl-6-[2-methanesulfonyloxyethylamino)-2,4(1H,3H)-pyrimidinedione (Compound m), which had a melting point of from 169° to 170° C.

(4) Preparation of 1,3-dimethyl-6-[2-(N-[2-hydroxyethyl]-3-[4-nitrophenyl]propylamino)ethylamino]-2,4(1H,3H)-pyrimidinedione (Compound l)

20.2 g of 1,3-dimethyl-6-[2-methanesulfonyloxyethylamino)-2,4(1H,3H)-pyrimidinedione (Compound m) synthesized in the previous section (3) and 15.1 g of potassium carbonate were suspended in 300 ml of acetonitrile, and the solution was then heated under reflux for 4 hours. Afterward, insolubles were removed therefrom by filtration, and the filtrate was concentrated under reduced pressure so that the total amount might be about 60 ml. Then, 18 g of N-(2-hydroxyethyl)-3-(4-nitrophenyl)propylamine obtained in the previous section (2), 36 ml of dimethylformamide and 0.69 g of p-toluenenesulfonic acid were then added thereto, and acetonitrile was distilled off under reduced pressure and the residue was stirred at 80° C. for 2 hours. The temperature of the reaction solution was returned to room temperature, and 900 ml of 0.1N hydrochloric acid was added thereto to dissolve insolubles. Afterward, a 0.5M aqueous potassium carbonate was added to the solution so as to make it alkaline, followed by stirring at room temperature for 3 hours to precipitate crystals. The crystals were then collected by filtration, dried and then recrystallized from ethanol to obtain 26.6 g of crystalline 1,3-dimethyl-6-[2-(N-[2-hydroxyethyl]-3-[4-nitrophenyl]propylamino)ethylamino]-2,4(1H,3H)-pyrimidinedione (Compound l), which had a melting point of from 125° to 126° C.

1H-NMR (CDCl3) δ ppm: 1.86 (m, 2H), 2.48-3.00 (m, 11H), 3.00-3.26 (m, 2H), 3.27 (s, 3H), 3.39 (s, 3H), 3.71 (m, 2H), 4.78 (s, 1H), 6.06 (m, 1H), 7.38 (d, 2H), 8.18 (d, 2H).

REFERENCE EXAMPLE 9

Preparation of 1,3-dimethyl-6-[4-(2-[2-nitrophenyl]ethyl)piperazin-1-yl]-2,4(1H,3H)-pyrimidinedione (Compound n)

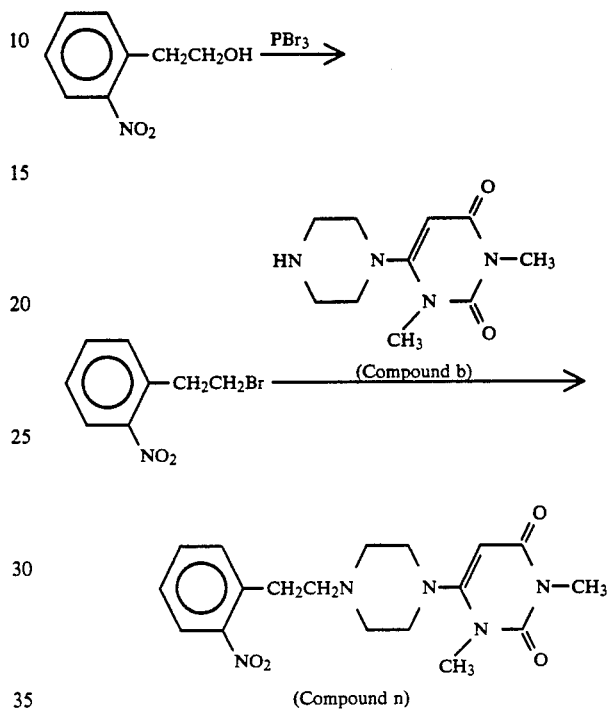

(Compound n)

(1) Preparation of 2-(2-nitrophenyl)ethyl bromide 2.5 ml of 2-(2-nitrophenyl)ethanol and 5.4 ml of PBr3 were stirred and mixed at 0° C. for 30 minutes to carry out reaction, and the resultant reaction mixture was diluted with 30 ml of benzene and the diluted mixture was then poured into 30 ml of water. The separated organic layer was separated, dried over anhydrous sodium sulfate, and then treated under reduced pressure to distill off the solvent, thereby obtaining 3 g of the crude product of 2-(2-nitrophenyl)ethyl bromide.

(2) Preparation of 1,3-dimethyl-6-[4-(2-[2-nitrophenyl]ethyl)piperazin-1-yl]-2,4(1H,3H)-pyrimidinedione (Compound n)

3.0 g of the previously obtained 2-(2-nitrophenyl)ethyl bromide, 3.2 g of 1,3-dimethyl-6-(piperazin-1-yl)2,4(1H,3H)-pyrimidinedione (Compound D) and 4.2 ml of triethylamine were added to 15 ml of isopropanol, and the resultant mixture was then treated in the same manner as in Reference Example 6 to obtain 2.2 g of 1,3-dimethyl-6-[4-(2-[2-nitrophenyl]ethyl)piperazin-1-yl]-2,4(1H,3H)-pyrimidinedione (Compound n).

Analytical results of the obtained Compound n:
NMR (CDCl3) δ ppm: 2.7-3.0 (m, 12H), 3.39 (s, 3H), 3.41 (s, 3H), 5.11 (s, 1H) 7.53 (m, 3H), 7.96 (m, 1H).

REFERENCE EXAMPLE 10

Synthesis of 1,3-dimethyl-6-[4-(4-[4-nitrophenyl]butyl)piperazin-1-yl]-2,4(1H,3H)-pyrimidinedione (Compound o)

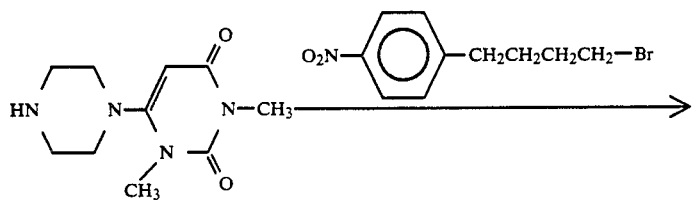

(Compound b)

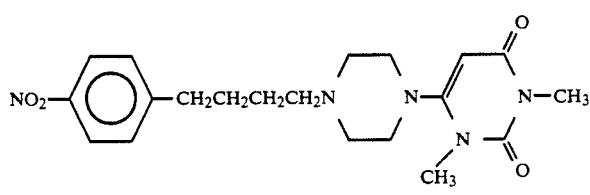

(Compound o)

The same treatment as in Reference Example 6 was effected except that 4-nitrophenethyl bromide was replaced with 0.55 g of 4-nitrophenylbutyl bromide, to obtain 0.59 g of 1,3-dimethyl-6-[4-(4-[4-nitrophenyl]butyl)piperazin-1-yl]-2,4(1H,3H)-pyrimidinedione (Compound o).

Analytical results of the obtained Compound o:
$^1$H-NMR (CDCl$_3$) δ ppm: 1.64 (m, 4H), 2.2–3.1 (m, 12H), 3.36 (s, 3H), 3.41 (s, 3H), 5.24 (s, 1H), 7.36 (d, 2H), 8.14 (d, 2H).

REFERENCE EXAMPLE 11

Synthesis of 1,3-dimethyl-6-[4-(3-[4-nitrophenyl]propyl)piperazin-1-yl]-2,4(1H,3H)-pyrimidinedione (Compound p)

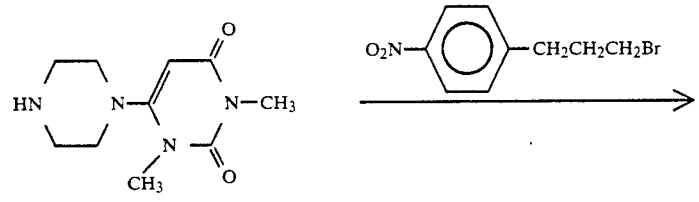

(Compound p)

The same treatment as in Reference Example 6 was effected except that 4-nitrophenethyl bromide was replaced with 0.51 g of 4-nitrophenylpropyl bromide, to obtain 0.2 g of 1,3-dimethyl-6-[4-(3-[4-nitrophenyl]propyl)piperazin-1-yl]-2,4(1H,3H)-pyrimidinedione (Compound p).

Analytical results of the obtained Compound p:
$^1$H-NMR (CDCl$_3$) δ ppm: 2.0 (m, 2H), 2.4–3.2 (m, 12H), 3.27 (s, 3H), 3.38 (s, 3H), 5.30 (s, 1H), 7.44 (d, 2H), 8.24 (d, 2H).

REFERENCE EXAMPLE 12

Synthesis of 1,3-dimethyl-6-[4-(3-[2-acetyl-4-nitrophenoxy]propyl)piperazin-1-yl]-2,4(1H,3H)-pyrimidinedione (Compound q)

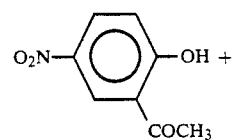

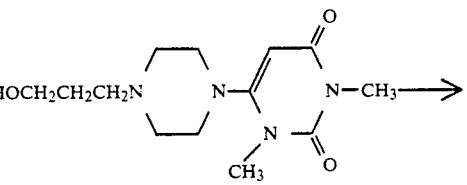

(Compound a)

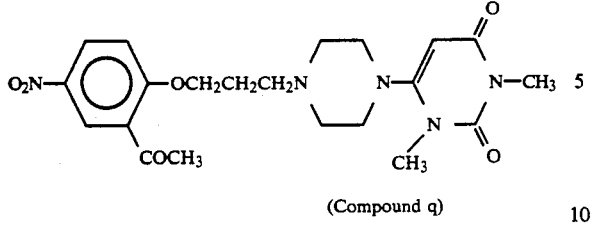

(Compound q)

NMR (CDCl₃) δ ppm: 8.47 (m, 1H), 7.54 (m, 1H), 6.91 (d, 1H), 5.23 (s, 1H), 4.26 (m, 2H), 3.37 (s, 3H), 3.30 (s, 3H), 2.98 (m, 4H), 2.60 (m, 6H), 2.63 (s, 3H), 2.16 (m, 2H).

REFERENCE EXAMPLE 13

Preparation of 1,3-dimethyl-6-[4-(3-[4-benzoyl-2-nitrophenoxy]-propyl)piperazin-1-yl]-2,4(1H,3H)-pyrimidinedione (Compound r)

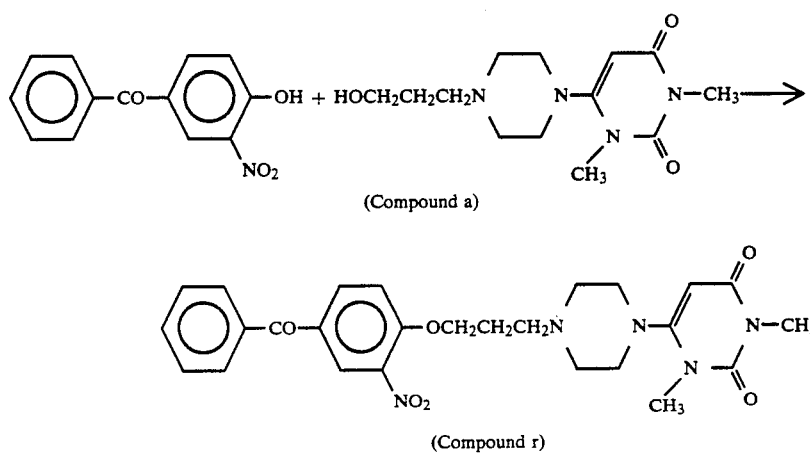

0.6g of 1,3-dimethyl-6-[4-(3-hydroxypropyl)piperazin-1-yl]-2,4(1H,3H)-pyrimidinedione (Compound a ), 0.54 g of 2-hydroxy-5-nitroacetophenone and 0.69 g of triphenylphosphine were suspended in and mixed with 10 ml of anhydrous tetrahydrofuran, and 0.42 ml of diethyl azodicarboxylate was added dropwise with stirring to the resultant suspension at room temperature.

Next, the resultant mixture was stirred at room temperature for 30 minutes and concentrated to dryness, and the residue was purified through a silica gel column chromatograph (chloroform/methanol=50/1 in volume ratio) to obtain 0.7 g of oily 1,3-dimethyl-6-[4-(3-[2-acetyl-4-nitrophenoxy]propyl)piperazin-1-yl]-2,4(1H,3H)-pyrimidinedione (Compound q).

Analytical results of the obtained Compound q:

The same procedure as in Reference Example 12 was effected except that 2-hydroxy-5-nitroacetophenone was replaced with 4-hydroxy-3-nitrobenzophenone, to obtain 1,3-dimethyl-6-[4-(3-[4-benzoyl-2-nitrophenoxy]-propyl)piperazin-1 -yl]-2,4(1H,3H)-pyrimidinedione (Compound r).

Analytical results of the obtained Compound r:

NMR (CDCl₃) δ ppm: 2.2 (m, 2H), 2.5–3.1 (m, 10H), 3.41 (s, 3H), 3.67 (s, 3H), 4.35 (t, 2H), 5.24 (s, 1H), 7.1–8.2 (m, 8H).

REFERENCE EXAMPLE 14

Preparation of 1,3-dimethyl-6-[4-(3-[2-benzoyl-4-nitrophenoxy]-propyl)piperazin-1-yl]-2,4(1H,3H)-pyrimidinedione (Compound s)

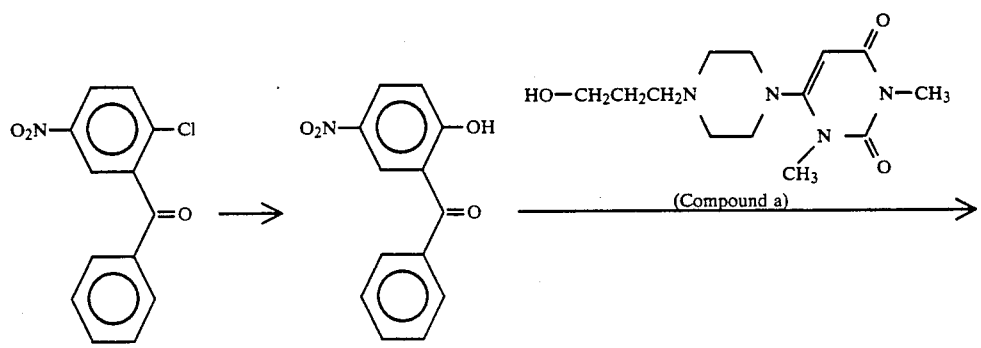

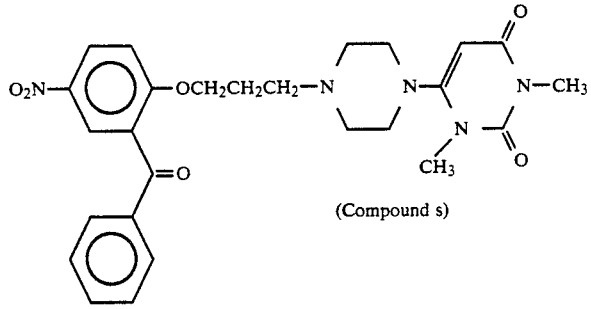

(Compound s)

(1) Preparation of 2-hydroxy-5-nitrobenzophenone:

3 g of 2-chloro-5-nitrobenzophenone and 1.1 g of potassium hydroxide were suspended in 30 ml of water to obtain a suspension, and this suspension was then heated to 150° C. and stirred for 5 hours in an autoclave.

After completion of the stirring the reaction solution was allowed to stand for cooling, and 30 ml of water was added thereto and hydrochloric acid was further added so as to make it acidic. Then, the precipitated crystals were collected by filtration.

The thus obtained crystals were further recrystallized from ethanol to prepare 2.3 g of 2-hydroxy-5-nitrobenzophenone.

Analytical results of the obtained crystals:
Melting point: 125°–126° C.
NMR (CDCl$_3$) δ ppm: 7.21 (m, 2H), 7.68 (m, 4H), 8.41 (m, 2H).
IR $\nu_{max}^{KBr}$ (cm$^{-1}$): 3040, 1600, 1520, 1330, 1280, 1210, 1080, 960, 690.

(2) Preparation of 1,3-dimethyl-6-[4-(3-[2-benzoyl-4-nitrophenoxy]-propyl)piperazin-1-yl]-2,4(1H,3H)-pyrimidinedione (Compound s)

The same procedure as in Reference Example 4 was effected so as to react 0.73 g of 2-hydroxy-5-nitrobenzophenone obtained in the above-mentioned section (1), 0.5 g of 1,3-dimethyl-6-[4-(3-hydroxypropyl)piperazin-1-yl]-2,4(1H,3H)-pyrimidinedione (Compound a), 0.58 g of triphenylphosphine and 0.34 ml of diethyl azodicarboxylate in 10 ml of anhydrous tetrahydrofuran, thereby obtaining 0.7 g of syrupy 1,3-dimethyl-6-[4-(3-[2-benzoyl-4-nitrophenoxy]propyl)piperazin-1-yl]-2,4(1H,3H)-pyrimidinedione (Compound s).

Analytical results of the obtained Compound s:
NMR (CDCl$_3$) δ ppm: 8.36 (m, 2H), 7.0–7.8 (m, 6H), 5.14 (s, 1H), 4.14 (t, 2H), 3.26 (s, 3H), 3.34 (s, 3H), 3.0 (m, 4H), 2.2–2.5 (m, 6H), 1.9 (m, 2H).

REFERENCE EXAMPLE 15

Preparation of 1,3-dimethyl-6-[4-(3-[4-chloro-2-nitrophenoxy]propyl)-piperazin-1-yl]-2,4(1H,3H)-pyrimidinedione(Compound t)

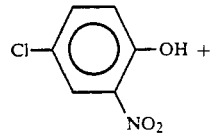

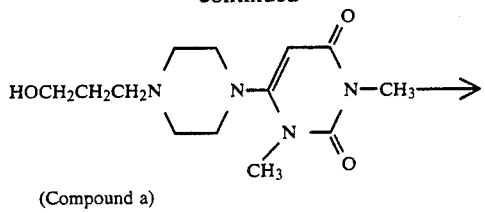

(Compound a)

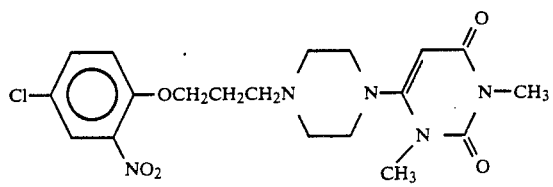

(Compound t)

In 15 ml of anhydrous tetrahydrofuran were suspended 0.80 g of 4-chloro-2-nitrophenol, 1.13 g of 1,3-dimethyl-6-[4-(3-hydroxypropyl)piperazin-1-yl]-2,4(1H,3H)-pyrimidinedione (Compound a) and 1.21 g of triphenylphosphine, and 0.80 g of diethyl azodicarboxylate was added to the resultant suspension. Afterward, the resultant mixture was treated in the same manner as in Reference Example 4 to obtain 1.43 g of crystalline 1,3-dimethyl-6-[4-(3-[4-chloro-2-nitrophenyloxy]propyl)piperazin-1-yl]-2,4(1H,3H)-pyrimidinedione (Compound t).

Analytical results of the crystals of the obtained Compound t:
Melting point: 162°–163° C.
Values of elemental analysis (as C$_{19}$H$_{24}$N$_5$O$_5$Cl·½H$_2$O): Calcd. (%): C 51.07; H 5.64; N 15.67; Cl 7.93 Found (%): C 51.11; H 5.68; N 15.64; Cl 7.94.
NMR (CDCl$_3$) δ ppm: 1.8–2.2 (m, 2H), 2.4–2.8 (m, 6H), 2.8–3.04 (m, 4H), 3.2–3.4 (m, 2H), 3.52 (s, 3H), 3.80 (s, 3H), 4.18 (t, 2H), 5.20 (S, 1H), 7.20 (d, 1H), 7.45 (dd, 1H), 7.81 (d, 1H).

REFERENCE EXAMPLE 16

Synthesis of 1,3-dimethyl-6-[4-(3-[2-chloro-4-nitrophenyloxy]-propyl)piperazin-1-yl]-2,4(1H,3H)-pyrimidinedione (Compound u)

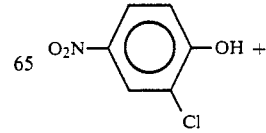

-continued

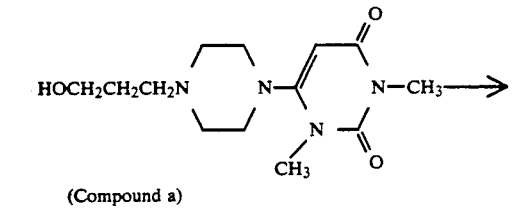
(Compound a)

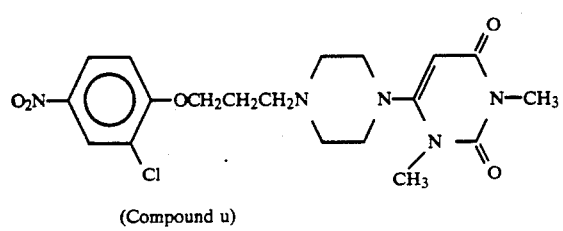
(Compound u)

In 70 ml of anhydrous tetrahydrofuran were suspended 2.4 g of 2-chloro-4-nitrophenol, 3.38 g of 1,3-dimethyl-6-[4-(3-hydroxypropyl)piperazin-1-yl]-2,4(1H,3H)-pyrimidinedione (Compound a) and 3.62 g of triphenylphosphine, and 2.4 g of diethyl azodicarboxylate was added to the resultant suspension. Afterward, the resultant mixture was treated in the same manner as in Reference Example 4 to obtain 2.5 g of light yellow crystals. The crystals were recrystallized from ethanol to obtain 2.07 g of crystalline 1,3-dimethyl-6-[4-(3-[2-chloro-4-nitrophenyloxy]propyl)piperazin-1-yl]-2,4(1H,3H)-pyrimidinedione (Compound u).

Analytical results of the crystals of the obtained Compound u:

Melting point: 133°–134° C.

Values of elemental analysis (as $C_{19}H_{24}N_5O_5Cl$): Calcd. (%): C 52.12; H 5.52; N 15.99; Cl 8.10 Found (%): C 51.99; H 5.72; N 15.70; Cl 8.01.

NMR (CDCl$_3$) δ ppm: 1.8–2.2 (m, 2H), 2.3–3.1 (m, 10H), 3.33 (s, 3H), 3.41 (s, 3H), 4.24 (t, 2H), 5.26 (s, 1H), 7.0–8.4 (m, 3H).

REFERNECE EXAMPLE 17

Synthesis of 1,3-dimethyl-6-[4-(3-[4-methylthio-2-nitrophenyloxy]propyl)piperazin-1-yl]-2,4(1H,3H)-pyrimidinedione (Compound v)

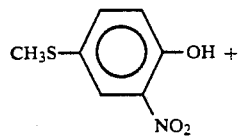

-continued

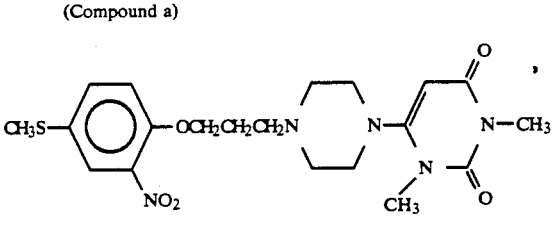
(Compound a)

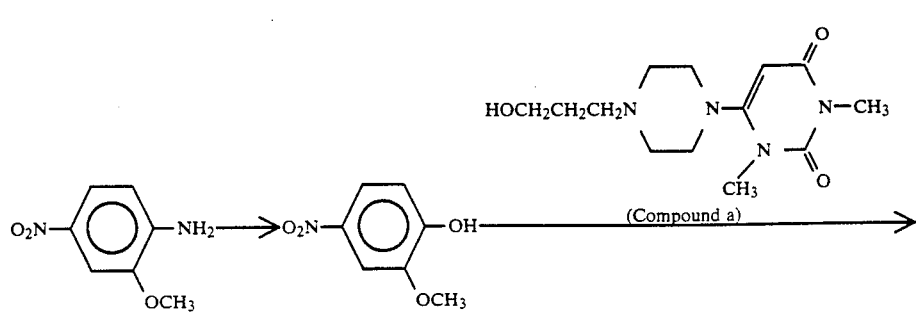
(Compound v)

In 30 ml of anhydrous tetrahydrofuran were suspended 1.5 g of 4-methylthio-2-nitrophenol, 2.0 g of 1,3-dimethyl-6-[4-(3-hydroxypropyl)piperazin-1-yl]-2,4(1H,3H)-pyrimidinedione (Compound a) and 2.2 g of triphenylphosphine, and 1.35 ml of diethyl azodicarboxylate was added to the resultant suspension. Afterward, the resultant mixture was treated in the same manner as in Reference Example 4 to obtain 2.9 g of crystalline 1,3-dimethyl-6-[4-(3-[4-methylthio-2-nitrophenyloxy]propyl)piperazin-1-yl]-2,4(1H,3H)-pyrimidinedione (Compound v).

Analytical results of the crystals of the obtained Compound v:

NMR (CDCl$_3$) δ ppm: 1.9–2.2 (m, 2H), 2.48 (s, 3H), 2.4–2.7 (m, 6H), 2.8–3.0 (m, 4H), 3.28 (m, 3H), 3.36 (s, 3H), 4.14 (m, 2H), 5.16 (s, 1H), 7.0 (d, 1H), 7.36 (dd, 1H), 7.62 (d, 1H).

REFERENCE EXAMPLE 18

Preparation of 1,3-dimethyl-6-[4-(3-[2-methoxy-4-nitrophenyloxy]propyl)piperazin-1-yl]-2,4(1H,3H)-pyrimidinedione (Compound w)

-continued

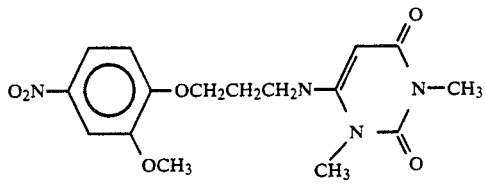

(Compound w)

(1) Preparation of 2-methoxy-4-nitrophenol 50 g of 2-amino-5-nitroanisole and 50 g of sodium hydroxide were dissolved in 450 ml of water, and the solution was then heated under reflux for 3 hours. Afterward, the solution was ice-cooled to precipitate crystals, and they were collected by filtration, dissolved in water, and then neutralized with 6N hydrochloric acid to precipitate crystals. The crystals were then collected by filtration, dissolved in chloroform, washed with water, and then dried over anhydrous sodium sulfate, and the resultant chloroform layer was concentrated under reduced pressure to obtain 4.5 g of the crystals of 2-methoxy-4-nitrophenol.

Analytical results of the obtained 2-methoxy-4-nitrophenol

Melting point: 102°–103° C.

(2) Preparation of 1,3-dimethyl-6-[4-(3-[2-methoxy-4-nitrophenyloxy]-propyl)piperazin-1-yl]-2,4(1H,3H)-pyrimidinedione (Compound w)

In 20 ml of anhydrous tetrahydrofuran were suspended 0.68 g of 2-methoxy-4-nitrophenol, 1.0 g of 1,3-dimethyl-6-[4-(3 -hydroxypropyl)piperazin-1-yl]-2,4(1H,3H)-pyrimidinedione (Compound a) and 1.1 g of triphenylphosphine, and 0.71 ml of diethyl azodicarboxylate was added to the resultant suspension. Afterward, the mixture was treated in the same manner as in Reference Example 4, followed by recrystallizing from methanol to obtain 1.35 g of oily 1,3-dimethyl-6-[4-(3-[2-methoxy-4-nitrophenyloxy]propyl)piperazin-1-yl]-2,4(1H,3H)-pyrimidinedione (Compound w).

Analytical results of the obtained Compound w:
NMR (CDCl$_3$) δ ppm: 1.9–3.3 (m, 12H), 3.43 (s, 3H), 3.5 (s, 3H), 4.06 (s, 3H), 4.26 (t, 2H), 5.35 (s, 1H), 7.05 (d, 1H), 7.8–8.15 (m, 2H).

REFERENCE EXAMPLE 19

Preparation of 1,3-dimethyl-6-[4-(2-[4-nitrophenoxy]ethyl)piperazin-1-yl]-2,4(1H,3H)-pyrimidinedione (Compound x)

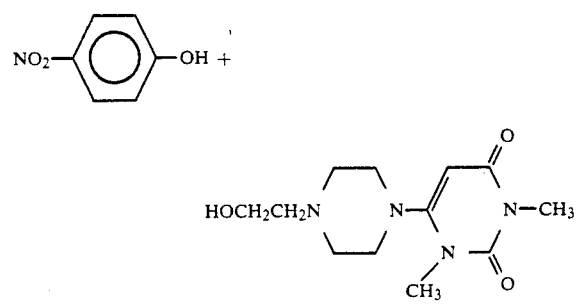

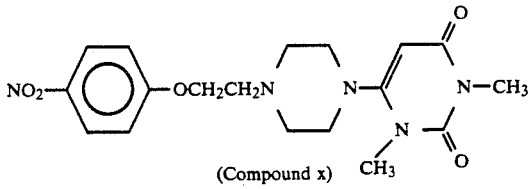

(Compound x)

To 100 ml of anhydrous tetrahydrofuran were added 5.37 g of 1,3-dimethyl-6-[4-(2-hydroxyethyl)piperazin-1-yl]-2,4(1H,3H)-pyrimidinedione, 3.20 g of 4-nitrophenol and 6.03 g of triphenylphosphine, and the resultant mixture and 50 ml of an anhydrous tetrahydrofuran solution containing 3.9 g of diethyl azodicarboxylate were treated in the same manner as in Reference Example 4, thereby obtaining 5.40 g of crystalline 1,3-dimethyl-6-[4-(2-[4-nitrophenoxy] ethyl)piperazin-1-yl]-2,4(1H,3H)-pyrimidinedione (Compound x).

Analytical results of the crystals of the obtained Compounds x:

IR $\nu_{max}^{KBr}$ (cm$^{-1}$): 1705, 1663, 1595, 1505, 1340, 1275, 1213, 1180, 1115, 1010, 862, 805, 750.

REFERENCE EXAMPLE 20

Preparation of 1,3-dimethyl-6-[4-(3-[2-hydroxy-5-nitrophenyloxy]-propyl)piperazin-1-yl]-2,4(1H,3H)-pyrimidinedione (Compound y)

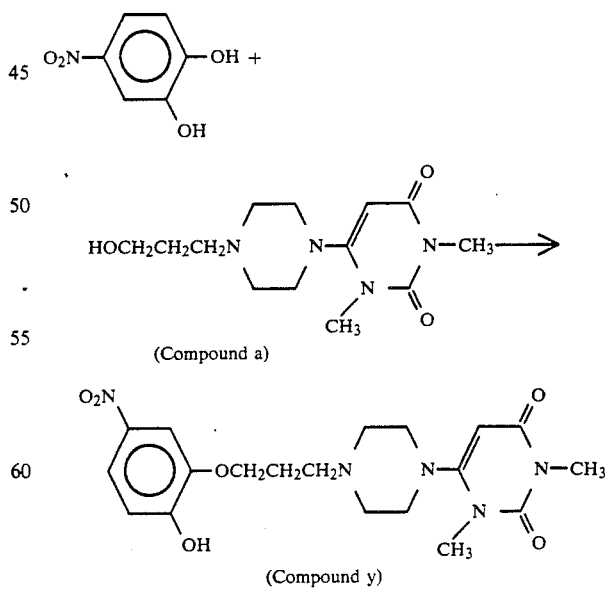

In 15 ml of anhydrous tetrahydrofuran were suspended 0.63 g of 2-nitrocatechol, 1.0 g of 1,3-dimethyl-6-[4-(3-hydroxypropyl)piperazin-1-yl]-2,4(1H,3H)- pyrimidinedione (Compound a) and 1.06 g of triphenylphosphine, and 0.71 g of diethyl azodicarboxylate was added to the resultant suspension. Afterward, the resultant mixture was treated in the same manner as in Reference Example 4 to obtain 0.65 g of light yellow crystals. The crystals were recrystallized from ethanol to obtain 0.55 g of crystalline 1,3-dimethyl-6-[4-(3-[2-hydroxy-5-nitrophenyloxy]propyl)piperazin-1-yl]-2,4(1H,3H)-pyrimidinedione (Compound y).

Analytical results of the crystals of the obtained Compound y:

Melting point: 171°–173° C.

Values of elemental analysis (as $C_{19}H_{25}N_5O_5$): Calcd. (%): C 54.40; H 6.00; N 16.69 Found (%): C 54.40; H 6.28; N 16.48

NMR (CDCl$_3$) δ ppm: 1.9–2.2 (m, 2H), 2.6–3.2 (m, 10H), 3.3 (s, 3H), 3.4 (s, 3H), 4.1 (t, 2H), 5.24 (s, 1H), 6.88–7.08 (m, 1H), 7.60–7.80 (m, 2H).

IR $\nu_{max}^{KBr}$ (cm$^{-1}$): 1700, 1620, 1500, 1340, 1285, 1280, 1140, 990, 870.

EXAMPLE 1

Preparation of 1,3-dimethyl-6-[4-(3-[4-fluorophenoxy]propyl)piperazin-1-yl]-2,4(1H,3H)-pyrimidinedione.hydrochloride (Compound 1)

(methanol/ethyl acetate=1/20 to 1/5 in volume ratio) to obtain 1.1 g of 1,3-dimethyl-6-[4-(3-[4-fluorophenoxy]propyl)piperazin-1-yl]-2,4(1H,3H)-pyrimidinedione.

Analytical results of the obtained pyrimidinedione derivative

Melting point: 121°–122° C.

NMR (CDCl$_3$) δ ppm: 1.8–2.1 (m, 2H), 2.4–2.7 (m, 6H), 2.8–3.1 (m, 4H), 3.29 (s, 3H), 3.36 (s, 3H), 3.95 (t, 2H), 5.24 (s, 1H), 6.7–7.1 (m, 4H).

1.0 g of this pyrimidinedione derivative was treated with a hydrochloric acid/methanol solution in an ordinary manner to obtain 0.3 g of crystalline 1,3-dimethyl-6-[4-(3-[4-fluorophenoxy]propyl)piperazin-1-yl]-2,4(1H,3H)-pyrimidinedione.hydrochloride (Compound 1).

Analytical results of the obtained Compound 1

Melting point: 234°–236° C.

Values of elemental analysis (as $C_{19}H_{26}N_4O_3F\cdot HCl\cdot \frac{1}{4}H_2O$):

Calcd. (%): C 54.68; H 6.40; N 13.42; F 4.55; Cl 8.49 Found (%): C 54.88; H 6.49; N 13.47; F 4.50; Cl 8.71.

IR $\nu_{max}^{KBr}$ (cm$^{-1}$): 1700, 1650, 1500, 1440, 1210, 1055, 860, 795.

EXAMPLE 2

The same procedure as in Example 1 was effected

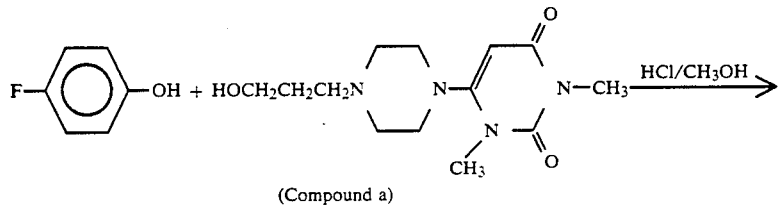

(Compound a)

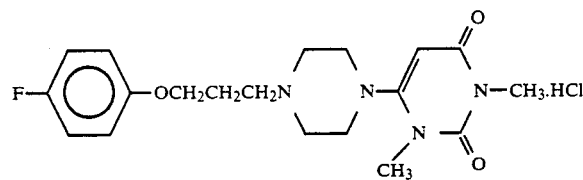

In 10 ml of anhydrous tetrahydrofuran were suspended 1.0 g of 1,3-dimethyl-6-[4-(3-hydroxypropyl)piperazin-1-yl]-2,4(1H,3H)-pyrimidinedione (Compound a) obtained in Reference Example 1, 1.1 g of triphenylphosphine and 0.47 g of 4-fluorophenol, and an anhydrous tetrahydrofuran solution containing 0.71 g of diethyl azodicarboxylate was added to the resultant suspension at room temperature. The mixture was stirred at room temperature for 10 minutes, and the solvent was then distilled off. The resultant residue was purified through a silica gel column chromatograph except that 4-fluorophenol was replaced with each corresponding phenol derivative, to obtain Compounds 2 to 63.

The analytical results of these compounds are set forth in Tables 1 to 18.

Furthermore, these Compounds 2 to 63 were treated with methanol solutions of acids shown in Tables 19 to 29, thereby obtaining corresponding acid addition salts 2'–63'.

The analytical results of these acid addition salts are set forth in Tables 19 to 29.

TABLE 1

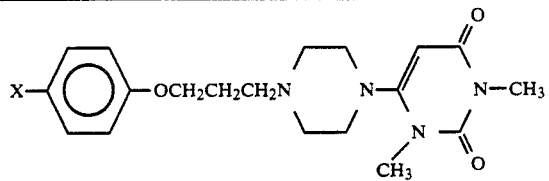

(for Compound Nos. 2-9)

| Comp. No. | —X | m.p. (°C.) | H-NMR (δppm) | Elemental Analysis (%) (calculated values) | | | |
|---|---|---|---|---|---|---|---|
| | | | | C | H | N | etc. |
| 2 | —CF$_3$ | 132–134 | (CDCl$_3$): 2.00(dt, 2H), 2.62(m, 6H), 2.96(m, 4H) 3.32(s, 3H), 3.37(s, 3H), 4.04(t, 2H) 5.22(s, 1H), 6.82(d, 2H), 7.52(d, 2H) | (56.33 55.81 | 5.91 5.91 | 13.14 13.24 | F 13.37) 13.12 |
| 3 | —CN | 133–134 | (CDCl$_3$): 2.00(m, 2H), 2.60(m, 6H), 2.96(m, 4H) 3.32(s, 3H), 3.38(s, 3H), 4.05(t, 2H) 5.27(s, 1H), 6.96(d, 2H), 7.61(d, 2H) | (62.65 62.84 | 6.57 6.77 | 18.26) 18.36 | |
| 4 | —COCH$_3$ | 127.5– 128.5 | (CDCl$_3$): 1.96(m, 4H), 2.50(m, 3H), 2.56(m, 6H) 2.92(m, 4H), 3.26(s, 3H), 3.33(s, 3H) 4.04(t, 2H), 5.15(s, 1H), 6.82(d, 2H) 7.82(d, 2H) | (62.98 62.56 | 7.05 7.47 | 13.99) 13.75 | |

TABLE 2

| Comp. No. | —X | m.p. (°C.) | H-NMR (δppm) | Elemental Analysis (%) (calculated values) | | | |
|---|---|---|---|---|---|---|---|
| | | | | C | H | N | etc. |
| 5 | —N⌒N (imidazole) | | (CDCl$_3$): 1.8–3.1(m, 12H), 3.33(s, 3H) 3.4(s, 3H), 4.1(t, 2H), 5.26(s, 1H) 6.9–7.8(m, 7H) | (62.26 62.01 | 6.65 6.81 | 19.80) 19.96 | |
| 6 | —N-N⌒N (triazole) | 168–170 | (CDCl$_3$): 2.04(m, 2H), 2.64(m, 6H), 3.00(m, 4H) 3.34(s, 3H), 3.40(s, 3H), 4.08(t, 2H) 5.24(s, 1H), 6.96(d, 2H), 7.54(d, 2H) 8.02(s, 1H), 8.40(s, 1H) | (59.28 59.18 | 6.40 6.42 | 23.04) 23.23 | |
| 7 | —SO$_2$CH$_3$ | 169–170 | (CDCl$_3$): 1.8–2.2(dt, 2H), 2.4–3.1(m, 10H) 3.02(s, 3H), 3.28(s, 3H), 3.36(s, 3H) 4.06(t, 2H), 5.23(s, 1H), 6.98(d, 2H) 7.84(d, 2H) | | | | |
| 8 | —SO$_2$N(CH$_3$)$_2$ | | (CDCl$_3$): 2.1(m, 2H), 2.3–3.2(m, 10H) 2.7(s, 6H), 3.3(s, 3H), 3.4(s, 3H) 4.1(t, 2H), 5.26(s, 1H), 7.03(d, 2H) 7.73(d, 2H) | (54.18 54.05 | 6.71 6.39 | 15.04 15.14 | S 6.89) 6.67 |
| 9 | —CO—C$_6$H$_5$ | | (CDCl$_3$): 2.1(m, 2H), 2.4–3.1(m, 10H) 3.31(s, 3H), 3.38(s, 3H), 4.11(t, 2H) 5.23(s, 1H), 7.0–8.0(m, 9H) | (67.51 67.33 | 6.54 6.81 | 12.11) 12.01 | |

TABLE 3

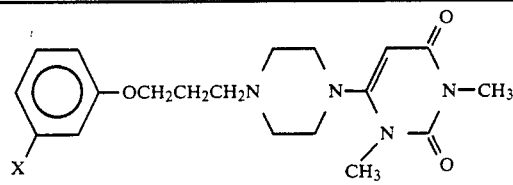

| Comp. No. | —X | m.p. (°C.) | H-NMR (δppm) | Elemental Analysis (%) (calculated values) | | | |
|---|---|---|---|---|---|---|---|
| | | | | C | H | N | etc. |
| 10 | —F | 155–156 | (CDCl$_3$): 1.8–2.1(m, 2H), 2.4–2.7(m, 6H) 2.8–3.0(m, 4H), 3.28(s, 3H), 3.35(s, 3H) | | | | |

TABLE 3-continued

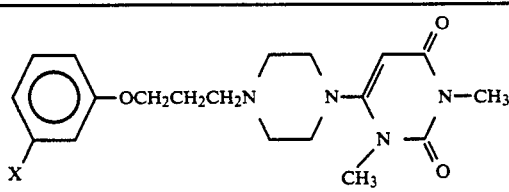

| Comp. No. | —X | m.p. (°C.) | H-NMR (δppm) | Elemental Analysis (%) (calculated values) C | H | N | etc. |
|---|---|---|---|---|---|---|---|
| 11 | —CF₃ | 116–118 | 3.94(t, 2H), 5.23(s, 1H), 6.4–7.3(m, 4H) | (56.33 | 5.91 | 13.14) | |
| | | | | 56.17 | 5.78 | 13.04 | |
| 12 | —CN | 141–142.5 | (CDCl₃): 2.00(m, 2H), 2.62(m, 6H), 3.35(s, 3H) 3.41(s, 3H), 4.09(t, 2H), 5.62(s, 1H) 7.0–7.6(m, 4H) | (62.65 | 6.57 | 18.26) | |
| | | | (CDCl₃): 2.02(m, 2H), 2.65(m, 6H), 3.33(s, 3H) 6.98–7.60(m, 4H) | 62.41 | 6.81 | 18.08 | |
| 13 | —COCH₃ | 103 | | (62.98 | 7.05 | 13.99) | |
| | | | | 62.93 | 7.45 | 13.75 | |

TABLE 4

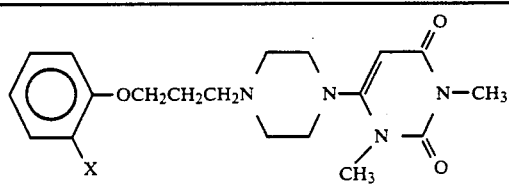

(for Compound Nos. 14–39)

| Comp. No. | —X | m.p. (°C.) | H-NMR (δppm) | Elemental Analysis (%) (calculated values) C | H | N | etc. |
|---|---|---|---|---|---|---|---|
| 14 | —F | 99–101 | (CDCl₃): 1.8–2.2(m, 2H), 2.4–2.8(m, 6H) 2.9–3.1(m, 4H), 3.33(s, 3H), 3.40(s, 3H) 4.14(t, 2H), 5.27(s, 1H), 6.8–7.3(m, 4H) | | | | |
| 15 | —CF₃ | 98–100 | (CDCl₃): 2.08(m, 2H), 2.72(m, 6H), 3.02(m, 4H) 3.32(s, 3H), 3.39(s, 3H), 4.10(t, 2H) 5.27(s, 1H), 7.04(m, 2H), 7.56(m, 2H) | | | | |
| 16 | —CN | 97–98 | (CDCl₃): 2.07(m, 2H), 2.64(m, 6H), 2.96(m, 4H) 3.33(s, 3H), 3.40(s, 3H), 4.14(t, 2H) 5.28(s, 1H), 7.04(m, 2H), 7.60(m, 2H) | (62.65 62.34 | 6.57 6.44 | 18.26) 18.11 | |

TABLE 5

| Comp. No. | -X | m.p. (°C.) | H-NMR (δppm) | Elemental Analysis (%) (calculated values) C H N etc. |
|---|---|---|---|---|
| 17 | —COCH₃ | 150–160 | (CDCl₃): 1.8–2.2 (m, 4H), 2.4–2.7 (m, 9H) 2.8–3.0 (m, 4H), 3.28 (s, 3H), 3.36 (s, 3H) 4.12 (t, 2H), 5.19 (s, 1H), 6.94 (d, 1H) 7.30 (dd, 1H), 7.42 (dd, 1H), 7.68 (dd, 1H) | (62.98 7.05 13.99) 62.83 7.48 13.91 |
| 18 | —NHCOCH₃ | 127 | (DMSO-d₆): 1.90 (m, 2H), 2.06 (s, 3H), 2.48 (m, 6H) 2.90 (m, 4H), 3.08 (s, 3H), 3.24 (s, 3H) 4.01 (t, 2H), 5.09 (s, 1H), 6.6–7.9 (m, 4H) 8.80 (br.s, 1H) | (60.71 7.04 16.86) 60.41 7.28 16.75 |
| 19 | —OCH₃ | 107–109 | (DCDl₃): 2.02 (m, 2H), 2.60 (m, 6H), 2.94 (m, 4H) 3.28 (s, 3H), 3.34 (s, 3H), 3.81 (s, 3H) 4.02 (t, 2H), 5.22 (s, 1H), 6.90 (s, 4H) | (61.84 7.27 14.42) 61.49 7.50 14.46 |

TABLE 6

| Comp. No. | -X | m.p. (°C.) | H-NMR (δppm) | Elemental Analysis (%) (calculated values) C H N etc. |
|---|---|---|---|---|
| 20 | —CH$_2$OCH$_3$ | | (CDCl$_3$): 1.8-2.1 (m, 2H), 2.5-2.7 (m, 6H) 2.8-3.0 (m, 4H), 3.25 (s, 3H), 3.3 (s, 3H) 3.35 (s, 3H), 4.0 (m, 2H), 4.4 (s, 2H), 5.2 (s, 1H), 6.7-7.3 (m, 4H) IR $\nu_{max}^{KBr}$ (cm$^{-1}$): 3060, 2930, 2800, 2770, 1680, 1630 1600, 1480, 1460, 1450, 1420, 1370, 1240, 1200, 990, 840 | |
| 21 | —COOCH$_3$ | | (CDCl$_3$): 2.6-2.9 (m, 10H), 3.3 (s, 3H), 3.36 (s, 3H) 3.90 (s, 3H), 4.12 (t, 2H), 5.22 (s, 1H) 6.7-7.8 (m, 4H) | (60.56 6.78 13.45) 60.17 6.51 13.81 |
| 22 | —SO$_2$N(CH$_3$)$_2$ | | (CDCl$_3$): 2.1 (m, 2H), 2.7-2.9 (m, 10H), 2.84 (br.s, 6H), 3.26 (s, 3H), 3.38 (s, 3H) 4.20 (m, 2H), 5.20 (s, 1H), 6.9-7.7 (m, 4H) | S (54.18 6.71 15.04 6.89) 54.25 6.92 15.14 6.77 |
| 23 | —CH$_2$CN | | (CDCl$_3$): 2.0 (m, 2H), 2.7-2.9 (m, 10H), 3.28 (s, 3H) 3.38 (s, 3H), 3.62 (br.s, 1H), 4.08 (t, 2H), 5.18 (s, 1H), 6.7-7.7 (m, 4H) | (63.46 6.85 17.62) 63.12 6.78 17.44 |

TABLE 7

| Comp. No. | -X | m.p. (°C.) | H-NMR (δppm) | Elemental Analysis (%) (calculated values) C H N etc. |
|---|---|---|---|---|
| 24 | —OCH$_2$CH=CH$_2$ | 103-105 | (CDCl$_3$): 1.8-2.1(m, 3H), 2.5-3.0(m, 9H) 3.28(s, 3H), 3.36(s, 3H), 4.00-4.20(m, 2H) 4.50-4.60(m, 2H), 5.14-5.50(m, 2H) 6.0(m, 1H), 6.86(m, 4H) | |
| 25 | —COCH(CH$_3$)$_2$ | | (CDCl$_3$): 1.14(d, 6H), 2.1(m, 3H), 2.6-3.0(m, 10H) 3.28(s, 3H), 3.46(s, 3H), 4.10(t, 2H) 5.22(s, 1H), 7.02(m, 2H), 7.14(m, 2H) | (64.46 7.53 13.07) 64.59 7.59 12.91 |
| 26 | —SOCH$_3$ | 106-108 | | S (57.12 6.71 13.32 7.62) 56.78 6.97 13.08 8.07 |
| 27 | 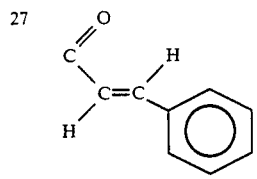 | | (CDCl$_3$): 1.8-2.0(m, 2H), 2.2-2.6(m, 6H) 2.7-2.9(m, 4H), 3.35(s, 6H), 4.0(t, 2H) 5.1(s, 1H), 6.9-7.1(m, 2H), 7.2-7.7(m, 9H) IR$\nu_{max}^{KBr}$(cm$^{-1}$): 3400, 2930, 2840, 2800, 1680, 1640, 1590, 1480, 1440, 1430, 1330, 1200, 1020, 1000, 970 | |

TABLE 8

| Comp. No. | -X | m.p. (°C.) | H-NMR (δppm) | Elemental Analysis (%) (calculated values) C H N etc. |
|---|---|---|---|---|
| 28 | —SCH$_3$ | 99-100 | (CDCl$_3$): 2.00(m, 2H), 240(s, 3H), 2.64(m, 6H) 2.93(m, 4H), 3.30(s, 3H), 3,36(s, 3H) 4.08(t, 2H), 5.19(s, 1H), 6.7-7.2(m, 4H) | S (59.38 6.98 13.85 7.93) 58.93 7.03 13.68 7.81) |
| 29 | —CO—C$_6$H$_5$ | 123-127 (decomposed) | (CDCl$_3$): 2.06(m, 2H), 2.2-3.0(m, 10H) 3.28(s, 3H), 3.34(s, 3H) 4.10(br.t, 2H), 5.20(s, 1H) 5.33(br.s, 2H), 6.6-7.9(m, 9H) | |
| 30 | —C(O)—C$_6$H$_5$ | | (CDCl$_3$): 1.65(m, 2H), 1.98-2.62(m, 6H) 3.29(s, 3H), 3.36(s, 3H), 3.90(m, 4H) 4.06(m, 2H), 5.19(s, 1H), 6.84-7.00(m, 9H) | (67.51 6.54 12.11) 67.69 6.22 11.97 |

TABLE 8-continued

| Comp. No. | —X | m.p. (°C.) | H-NMR (δppm) | Elemental Analysis (%) (calculated values) C | H | N | etc. |
|---|---|---|---|---|---|---|---|
| 31 | —COCH₂CH₂—⟨phenyl⟩ | | (CDCl₃): 2.0–2.2(m, 4H), 2.6–2.9(m, 10H) 3.28(s, 3H), 3.38(s, 3H), 4.18(t, 2H) 5.06(s, 1H), 5.10(m, 2H), 7.0–7.8(m, 9H) | (68.55 68.67 | 6.99 6.45 | 11.42) 11.38 | |
| 32 | —COCF₃ | | (CDCl₃): 2.0(m, 2H), 2.7–2.9(m, 10H) 3.22(s, 3H), 3.40(s, 3H), 4.26(t, 2H) 5.16(s, 1H), 6.9–7.0(m, 4H) | (55.50 55.28 | 5.55 5.71 | 12.33 12.14 | F 12.54) 13.01 |

TABLE 9

| Comp. No. | —X | m.p. (°C.) | H-NMR (δppm) | Elemental Analysis (%) (calculated values) C | H | N | etc. |
|---|---|---|---|---|---|---|---|
| 33 | —C(O)CH₂C(O)OC₂H | | (CDCl₃): 1.22(t, 3H), 2.0(m, 2H), 2.7–2.9(m, 10H) 3.24(s, 3H), 3.32(s, 3H), 3.94(s, 2H) 4.18(q, 2H), 4.3(m, 2H), 5.04(s, 1H) 6.7–7.8(m, 4H) | (61.00 60.79 | 6.83 6.65 | 11.86) 11.49 | |
| 36 | —N₃ | | (CDCl₃): 2.0(m, 2H), 2.6–2.8(m, 10H) 3.16(s, 3H), 3.32(s, 3H), 4.20(m, 2H) 5.21(s, 1H), 7.1–7.9(m, 4H) | (57.13 56.91 | 6.31 6.02 | 24.55) 24.86 | |

TABLE 10

| Comp. No. | —X | m.p. (°C.) | H-NMR (δppm) | Elemental Analysis (%) (calculated values) C | H | N | etc. |
|---|---|---|---|---|---|---|---|
| 37 | —C(O)—⟨2-pyridyl⟩ | | (CDCl₃): 1.9(m, 2H), 2.4–3.1(m, 10H) 3.32(s, 3H), 3.40(s, 3H) 3.97(t, 2H), 5.21(s, 1H) 7.10(m, 2H), 7.61(m, 4H) 8.78(d, 2H) | (64.78 64.51 | 6.31 6.55 | 15.11) 15.32 | |
| 38 | —C(O)—⟨4-pyridyl⟩ | | (CDCl₃): 2.0(m, 2H), 2.4–3.2(m, 10H) 3.31(s, 3H), 3.38(s, 3H) 4.10(m, 2H), 5.17(s, 1H) 7.1–8.0(m, 6H), 8.92(m, 2H) | (64.78 65.02 | 6.31 6.61 | 15.11) 14.98 | |
| 39 | —C(O)—⟨cyclopentyl⟩ | | (CDCl₃): 1.8–2.1(m, 6H), 2.3–3.2(m, 15H) 3.32(s, 3H), 3.40(s, 3H) 4.33(t, 2H), 5.14(s, 1H) 7.61(m, 1H), 8.22(m, 2H) | (66.06 66.22 | 7.54 7.34 | 12.33) 11.96 | |

TABLE 11

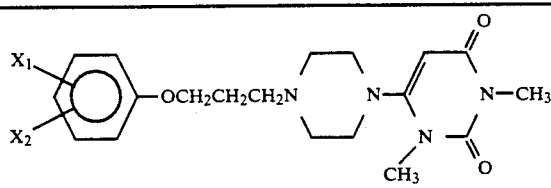

(for Compound Nos. 40–60)

| Comp. No. | Sub. Pos. | —X | m.p. (°C.) | H-NMR (δppm) | Elemental Analysis (%) (calculated values) C | H | N | etc. | |
|---|---|---|---|---|---|---|---|---|---|
| 40 | 3- 4- | —Cl —F | 153–155 | (CDCl₃): 1.9–2.2(m, 2H), 2.6–2.8(m, 6H) 3.0–3.2(m, 4H), 3.46(s, 3H) 3.54(s, 3H), 4.16(t, 2H) 5.43(s, 1H), 6.9–7.4(m, 3H) | (55.54 55.04 | 5.89 5.77 | 13.64 13.39 | F 4.62 4.50 | Cl 8.63) 8.66 |
| 41 | 2- | —CONH₂ | 187.5- | | | | | Cl | |

TABLE 11-continued

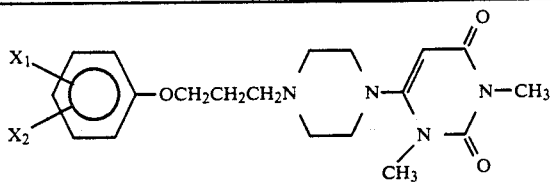

(for Compound Nos. 40–60)

| Comp. No. | Sub. Pos. | —X | m.p. (°C.) | H-NMR (δppm) | Elemental Analysis (%) (calculated values) C | H | N | etc. |
|---|---|---|---|---|---|---|---|---|
|  | 4- | —Cl | 189 |  | (55.11 | 6.01 | 16.07 | 8.13) |
|  |  |  |  |  | 55.03 | 6.06 | 15.93 | 7.88 |
| 42 | 3- | —CH$_3$ |  | (CDCl$_3$): |  |  |  | S |
|  | 4- | —SCH$_3$ |  | 2.1–2.7(m, 2H), 2.35(s, 3H) | (60.26 | 7.22 | 13.39 | 7.66) |
|  |  |  |  | 2.37(s, 3H), 2.4–2.7(m, 6H) | 60.39 | 6.92 | 13.81 | 7.75 |
|  |  |  |  | 2.8–3.0(m, 4H), 3.26(s, 3H) |  |  |  |  |
|  |  |  |  | 3.32(s, 3H), 3.90(t, 2H) |  |  |  |  |
|  |  |  |  | 5.17(s, 1H), 6.5–7.2(m, 3H) |  |  |  |  |

TABLE 12

| Comp. No. | Sub. Pos. | -X | m.p. (°C.) | H-NMR (δppm) | Elemental Analysis (%) (calculated values) C H N etc. |
|---|---|---|---|---|---|
| 43 | 2- | —Cl | 105–106 | (CDCl$_3$): | Cl |
|  | 4- | —Cl |  | 1.9–2.1 (m, 2H), 2.5–2.7 (m, 6H) | (53.40 5.66 13.11 16.59) |
|  |  |  |  | 2.8–3.1 (m, 4H), 3.29 (s, 3H) | 53.15 5.66 13.07 16.49 |
|  |  |  |  | 3.36 (s, 3H), 4.02 (m, 2H) |  |
|  |  |  |  | 5.18 (s, 1H), 6.7–7.4 (m, 3H) |  |
| 44 | 2- | —COCH$_3$ |  | (CDCl$_3$): |  |
|  | 4- | —SO$_2$CH$_3$ | 2.1 (m, 2H), 2.3–3.1 (m, 16H) |  |  |
|  |  |  |  | 3.27 (s, 3H), 3.35 (s, 3H) |  |
|  |  |  |  | 4.21 (m, 2H), 5.18 (s, 1H) |  |
|  |  |  |  | 7.10 (d, 1H), 7.96 (dd, 1H) |  |
|  |  |  |  | 8.17 (d, 1H) |  |
| 45 | 2- | —COCH$_3$ | 178–179 | (CDCl$_3$): | Cl |
|  | 4- | —Cl |  | 2.0 (t, 2H), 2.4–2.7 (m, 9H) | (56.80 6.44 13.25 8.38) |
|  |  |  |  | 2.8–3.0 (m, 4H), 3.24 (s, 3H) | 56.69 6.28 12.90 8.29 |
|  |  |  |  | 3.32 (s, 3H), 4.02 (t, 2H) |  |
|  |  |  |  | 5.18 (s, 1H), 6.85 (d, 1H), |  |
|  |  |  |  | 7.36 (dd, 1H), 7.62 (d, 1H) |  |
| 46 | 3- | —COOC$_2$H$_5$ |  | (CDCl$_3$): |  |
|  | 4- | —COOC$_2$H$_5$ |  | 1.34 (m, 6H), 1.96 (m, 2H) | (59.75 6.82 11.15) |
|  |  |  |  | 2.56 (m, 6H), 2.88 (m, 4H) | 56.39 6.28 10.92 |
|  |  |  |  | 3.27 (s, 3H), 3.35 (s, 3H) |  |
|  |  |  |  | 4.04 (t, 2H), 4.28 (m, 4H) |  |
|  |  |  |  | 5.23 (s, 1H), 6.92 (dd, 1H) |  |
|  |  |  |  | 7.04 (d, 1H), 7.76 (d, 1H) |  |

TABLE 12

| Comp. No. | Sub. Pos. | -X | m.p. (°C.) | H-NMR (δppm) | Elemental Analysis (%) (calculated values) C H N etc. |
|---|---|---|---|---|---|
| 47 | 2- | —COCH$_3$ | 207–208 | (CDCl$_3$ + DMSO-d$_6$): |  |
|  | 4- | —NHCOCH$_3$ |  | 2.08 (s, 4H), 2.60 (s, 8H) |  |
|  |  |  |  | 2.9–3.1 (m, 2H), 3.24 (s, 3H) |  |
|  |  |  |  | 3.36 (s, 3H), 3.52 (s, 3H) |  |
|  |  |  |  | 3.56 (s, 3H), 4.13 (m, 2H) |  |
|  |  |  |  | 5.18 (s, 1H), 6.96 (d, 1H) |  |
|  |  |  |  | 7.70 (m, 1H), 7.80 (m, 1H) |  |
|  |  |  |  | 9.72 (br.s, 1H) |  |
| 48 | 2- | —OCH$_3$ | 127–129 | (CDCl$_3$): |  |
|  | 4- | —OCH$_3$ |  | 1.80–2.10 (m, 2H), |  |
|  |  |  |  | 2.48–2.98 (m, 10H) |  |
|  |  |  |  | 3.28 (s, 3H), 3.34 (s, 3H) |  |
|  |  |  |  | 3.74 (s, 3H), 3.80 (s, 3H) |  |
|  |  |  |  | 3.96 (t, 2H), 5.24 (s, 1H) |  |
|  |  |  |  | 6.20–6.50 (m 2H), 6.76 (d, 1H) |  |
| 49 | 2- | —Br |  | (CDCl$_3$): |  |

TABLE 12-continued

| Comp. No. | Sub. Pos. | -X | m.p. (°C.) | H-NMR (δppm) | Elemental Analysis (%) (calculated values) C H N etc. | | | | |
|---|---|---|---|---|---|---|---|---|---|
| | 4- | —SO$_2$CH$_3$ | | 2.1 (m, 2H), 2.5-3.1 (m, 10H) 3.03 (s, 3H), 3.26 (s, 3H) 3.36 (s, 3H), 4.18 (t, 2H) 5.18 (s, 1H), 7.02 (d, 1H) 7.78 (dd, 1H), 8.04 (d, 1H) | (46.61 5.28 10.87 46.33 5.13 11.12 | Br 15.50 15.21 | S 6.22) 6.38 | | |

TABLE 14

| Comp. No. | Sub. Pos. | —X | m.p. (°C.) | H-NMR (δppm) | Elemental Analysis (%) (calculated values) | | | | |
|---|---|---|---|---|---|---|---|---|---|
| | | | | | C | H | N | | etc. |
| 50 | 2- 4- | —SO$_2$CH$_3$ —Cl | | (CDCl$_3$): 2.1(m, 2H), 2.7-2.9(m, 10H) 3.22(s, 3H), 3.31(s, 3H) 3.39(s, 3H), 4.27(t, 2H) 5.22(s, 1H), 7.16(d, 1H) 7.64(dd, 1H), 7.97(d, 1H) | (51.01 50.67 | 5.78 5.65 | 11.90 12.11 | Cl 7.53 7.76 | S 6.81) 6.54 |
| 51 | 2- 4- | 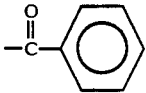 —Cl | | (CDCl$_3$): 1.68(m, 2H), 2.0-2.7(m, 6H) 2.88(m, 4H), 3.28(s, 3H) 3.36(s, 3H), 3.98(m, 2H) 5.20(s, 1H), 6.94(m, 1H) 7.2-7.6(m, 5H), 7.80(m, 2H) | (62.83 63.11 | 5.88 5.65 | 11.27 11.05 | Cl 7.13) 7.39 | |
| 52 | 2- 4- | 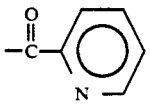 —Cl | | (CDCl$_3$): 1.8(m, 2H), 2.3-3.0(m, 10H) 3.30(s, 3H), 3.37(s, 3H) 3.94(t, 2H), 5.18(s, 1H) 6.94(m, 1H), 7.48(m, 3H) 8.00(m, 2H), 8.68(m, 1H) | (60.30 60.55 | 5.67 5.21 | 14.06 14.38 | Cl 7.12) 6.95 | |

TABLE 15

| Comp. No. | Sub. Pos. | —X | m.p. (°C.) | H-NMR (δppm) | Elemental Analysis (%) (calculated values) | | | |
|---|---|---|---|---|---|---|---|---|
| | | | | | C | H | N | etc. |
| 53 | 2- 4- | 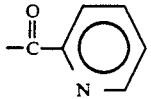 —Cl | | (CDCl$_3$): 1.9(m, 2H), 2.3-3.1(m, 10H) 3.36(s, 3H), 3.41(s, 3H) 4.00(t, 2H), 5.09(s, 1H) 7.44(m, 3H), 7.92(m, 2H) 8.81(m, 2H) | (60.30 59.75 | 5.67 5.12 | 14.06 13.65 | Cl 7.12) 7.59 |
| 54 | 2- 4- | 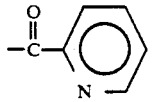 —OCH$_3$ | | (CDCl$_3$+DMSO-d$_6$): 2.0(m, 2H), 2.4-3.0(m, 10H) 3.11(s, 3H), 3.30(s, 3H) 3.40(s, 3H), 4.46(t, 2H) 5.30(s, 1H), 7.2-8.1(m, 5H) 8.54(m, 1H), 8.81(m, 1H) | (63.27 63.58 | 6.33 5.92 | 14.19) 14.23 | |
| 55 | 2- 4- | 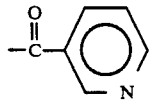 —OCH$_3$ | | (CDCl$_3$+DMSO-d$_6$): 2.0(m, 2H), 2.4-3.1(m, 10H) 3.09(s, 3H), 3.29(s, 3H) 3.40(s, 3H), 4.61(t, 2H) 5.19(s, 1H), 7.4(m, 2H) 7.8-8.4(m, 3H), 8.73(m, 2H) | (63.27 63.65 | 6.33 6.22 | 14.19) 14.10 | |

TABLE 16

| Comp. No. | Sub. Pos. | —X | m.p. (°C.) | H-NMR (δppm) | Elemental Analysis (%) (calculated values) | | | |
|---|---|---|---|---|---|---|---|---|
| | | | | | C | H | N | etc. |
| 56 | 2- 4- | —Cl 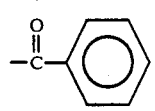 | | (CDCl$_3$): 2.1(m, 2H), 2.5-3.1(m, 10H) 3.33(s, 3H), 3.39(s, 3H) 4.23(t, 2H), 5.27(s, 1H) 6.9-8.0(m, 8H) | (62.83 62.56 | 5.88 5.95 | 11.27 11.51 | Cl 7.13 6.75 |
| 57 | 2- | —COOCH$_3$ | | (CDCl$_3$): | (64.60 | 6.20 | 10.76) | |

TABLE 16-continued

| Comp. No. | Sub. Pos. | —X | m.p. (°C.) | H-NMR (δppm) | Elemental Analysis (%) (calculated values) | | | |
|---|---|---|---|---|---|---|---|---|
| | | | | | C | H | N | etc. |
| | 4- | 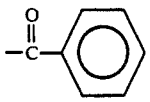 | | 2.1(m, 2H), 2.6–3.0(m, 10H) 3.30(s, 3H), 3.41(s, 3H) 3.90(s, 3H), 4.33(m, 2H) 5.04(s, 1H), 7.0–8.3(m, 8H) | 65.01 | 6.12 | 10.52 | |
| 58 | 2- 4- | —F 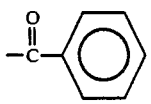 | | (CDCl$_3$): 2.1(m, 2H), 2.5–3.1(m, 10H) 3.28(s, 3H), 3.39(s, 3H) 4.20(t, 2H), 5.21(s, 1H) 6.9–7.9(m, 8H) | (64.99 64.38 | 6.08 6.15 | 11.66 11.09 | F 3.95) 4.05 |
| 59 | 2- 4- | —F —COCH$_3$ | | (CDCl$_3$): 1.97(m, 2H), 2.52(m, 3H) 2.5–3.1(m, 10H), 3.24(s, 3H) 3.33(s, 3H), 4.16(t, 2H) 5.15(s, 1H), 6.9–7.9(m, 3H) | (60.27 60.03 | 6.50 6.29 | 13.39 13.15 | F 4.54) 4.82 |

TABLE 17

| Comp. No. | Sub. Pos. | —X | m.p. (°C.) | H-NMR (δppm) | Elemental Analysis (%) (calculated values) | | | |
|---|---|---|---|---|---|---|---|---|
| | | | | | C | H | N | etc. |
| 60 | 2- 4- | —F 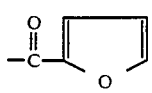 | | (CDCl$_3$): 2.1 (m, 2H), 2.4–3.1(m, 10H) 3.27(s, 3H), 3.35(s, 3H) 4.30(t, 2H), 5.18(s, 1H) 6.54(q, 1H), 6.9–8.0(m, 5H) | (61.27 61.58 | 5.78 5.39 | 11.91 11.65 | 4.04) 4.34 |

TABLE 16

| Comp. No. | Sub. Pos. | —X$^1$ —X$^2$ —X$^3$ | m.p. (°C.) | $^1$H-NMR (δppm) | Elemental Analysis (%) (calculated values) | | | |
|---|---|---|---|---|---|---|---|---|
| | | | | | C | H | N | etc. |
| 61 | 2- 4- 6- | —Br —SO$_2$CH$_3$ —Br | | (CDCl$_3$): 2.1(m, 2H), 2.6–3.2(m, 10H) 3.10(s, 3H), 3.26(s, 3H) 3.37(s, 3H), 4.12(m, 2H) 5.23(s, 1H), 8.07(s, 2H) | (40.42 40.87 | 4.41 4.59 | 9.43 9.10 | Br S 26.89 5.39) 27.35 5.01 |
| 62 | 2- 4- 6- | —I —SO$_2$CH$_3$ —I | | (CDCl$_3$): 2.1(m, 2H), 2.6–3.2(m, 10H) 3.08(s, 3H), 3.30(s, 3H) 3.38(s, 3H), 4.15(t, 3H) 5.25(s, 1H), 8.33(s, 2H) | | | | |
| 63 | 2- 4- 6- | —Br —SO$_2$CH$_3$ —COCH$_2$Br | | (CDCl$_3$): 2.1(m, 2H), 2.5(br.s, 2H) 2.6–3.2(m, 10H), 3.19(s, 3H) 3.38(s, 3H), 3.46(s, 3H) 4.27(t, 2H), 5.34(s, 1H) 7.66(m, 2H) | (41.52 40.96 | 4.44 4.33 | 8.80 8.39 | Br S 25.11 5.04) 25.65 4.81 |

TABLE 19

| Comp. No. | Acid | Molecular Formula | m.p. (°C.) | IR ν max (cm$^{-1}$) | Elemental Analysis (%) (calculated values) C H N etc. |
|---|---|---|---|---|---|
| 2' | HCl | C$_{20}$H$_{25}$H$_4$O$_3$F$_3$· HCl.2H$_2$O | 91–95 | (KBr): 1700, 1650, 1615, 1440 1330, 1255, 1160, 1065 840, 760 | Cl (48.15 6.06 11.23 7.11) 48.48 6.48 11.46 7.42 |
| 3' | HCl | C$_{20}$H$_{25}$N$_5$O$_3$· HCl | 238–241 (decom- | (KBr): 2930, 2410, 2210, 1690 | Cl |

TABLE 19-continued

| Comp. No. | Acid | Molecular Formula | m.p. (°C.) | IR ν max (cm⁻¹) | Elemental Analysis (%) (calculated values) C H N etc. |
|---|---|---|---|---|---|
| | | | posed) | 1640, 1620, 1435, 1252 1200, 1180, 1000, 860 800, 760 | (57.21 6.24 16.68 8.44) 57.04 6.52 16.69 8.52 |
| 4' | HCl | $C_{21}H_{28}N_4O_4$·HCl.1/3H$_2$) | 237 (decomposed) | | Cl (56.94 6.75 12.65 8.00) 56.88 6.52 12.66 8.29 |
| 5' | HCl | $C_{22}H_{28}N_6O_3$·2HCl.2H$_2$O | 190 (decomposed) | | Cl (49.53 6.42 15.75 13.29) 49.61 6.95 15.93 13.53 |
| 6' | (COOH)$_2$ | $C_{21}H_{27}N_7O_3$·(COOH)$_2$.H$_2$O | (decomposed) | (KBr): 3430, 1695, 1650, 1522 1440, 1252, 1055, 982 830 | (51.78 5.86 18.38) 51.59 5.31 17.98 |
| 7' | HCl | $C_{20}H_{28}N_4O_5S$·HCl | 249-253 | (KBr): 1645, 1470, 1430, 1290 1260, 1140, 965, 840, 760 | S Cl (50.79 6.18 11.84 6.78 7.50) 50.43 6.16 11.56 6.98 7.69 |

TABLE 20

| Comp. No. | Acid | Molecular Formula | m.p. (°C.) | IR ν max (cm⁻¹) | Elemental Analysis (%) (calculated values) C H N etc. |
|---|---|---|---|---|---|
| 8' | HCl | $C_{21}H_{31}N_5O_5S$·HCl.H$_2$O | 238-241 | | S Cl (48.50 6.59 13.47 6.17 6.82) 47.98 6.45 13.57 6.48 7.13 |
| 9' | (COOH)$_2$ | $C_{26}H_{30}N_4O_4$·(COOH)$_2$.H$_2$O | 184-186 | (KBr): 2550, 1700, 1650, 1640 1600, 760, 700 | (58.94 6.01 9.82) 58.85 5.71 9.65 |
| 10' | HCl | $C_{19}H_{25}N_4O_3F$·HCl.½H$_2$O | 220-222 | (KBr): 1700, 1640, 1500, 1280 1200, 1140, 980, 760 | F Cl (54.68 6.40 13.42 4.55 8.49) 54.88 6.49 13.47 4.50 8.68 |
| 11' | HCl | $C_{20}H_{25}N_4O_3F_3$·HCl.½H$_2$O | 206-208.5 | (KBr): 1695, 1640, 1490, 1450 1440, 1330, 1260, 1120 790, 760 | Cl (50.90 5.77 11.87 7.51) 51.08 5.80 11.91 8.10 |
| 12' | HCl | $C_{20}H_{25}N_5O_3$·HCl | 246-248 | (KBr): 2420, 2220, 1690, 1650 1480, 1430, 1390, 1267 1155, 802, 760, 680 | Cl (57.21 6.24 16.68 8.44) 56.97 6.46 16.50 8.31 |
| 13' | (COOH)$_2$ | $C_{21}H_{28}N_4O_4$·(COOH)$_2$.H$_2$O | 145 | (KBr): 3490, 1695, 1648, 1490 1440, 1277, 1207, 795 760, 708 | (54.33 6.34 11.02) 54.46 6.44 11.09 |

TABLE 21

| Comp. No. | Acid | Molecular Formula | m.p. (°C.) | IR ν max (cm⁻¹) | Elemental Analysis (%) (calculated values) C H N etc. |
|---|---|---|---|---|---|
| 14' | HCl | $C_{19}H_{25}N_4O_3F$·HCl.1.5H$_2$O | 219-220 | (KBr): 1690, 1640, 1440, 1400 1200, 1110, 930 780, 760 | F Cl (51.88 6.64 12.74 4.32 8.06) 51.68 7.05 12.74 4.32 8.23 |
| 15' | HCl | $C_{20}H_{25}N_4O_3F_3$·HCl.H$_2$O | 205-211 | | Cl (49.95 5.87 11.65 7.36) 50.49 6.16 11.68 7.90 |
| 16' | HCl | $C_{20}H_{25}N_5O_3$·HCl.H$_2$O | 251-255 | (KBr): 2220, 1700, 1650, 1600 1497, 1435, 1295, 1270 980, 790 | Cl (54.85 6.44 15.99 8.10) 54.72 6.59 15.70 8.20 |
| 17' | HCl | $C_{21}H_{28}N_4O_4$·HCl.H$_2$O | 224 (decomposed) | | (55.44 6.87 12.32 7.79) 55.69 7.22 12.40 8.18 |
| 18' | HCl | $C_{21}H_{29}N_5O_4$·HCl.½H$_2$) | 260-261 (decomposed) | (KBr): 3400, 1690, 1648, 1530 1440, 1395, 1260, 1208 1116, 762 | Cl (54.72 6.78 15.19 7.69) 54.93 7.14 15.01 8.06 |
| 19' | (COOH)$_2$ | $C_{20}H_{28}N_4O_4$·(COOH)$_2$.2H$_2$O | 178 (decomposed) | (KBr:) 3420, 1698, 1650, 1505 1440, 1395, 1254, 1222 1202, 1125, 1026, 750 720 | (51.36 6.60 10.89) 50.98 6.35 10.67 |

TABLE 22

| Comp. No. | Acid | Molecular Formula | m.p. (°C.) | IR ν max (cm$^{-1}$) | Elemental Analysis (%) (calculated values) C H N etc. |
|---|---|---|---|---|---|
| 20' | (COOH)$_2$ | C$_{21}$H$_{30}$N$_4$O$_4$· (COOH)$_2$·2H$_2$O | 135–137 | | (52.27 6.87 10.69) 52.50 6.47 10.19 |
| 21' | (COOH)$_2$ | C$_{21}$H$_{28}$N$_4$O$_5$· (COOH)$_2$·2H$_2$O | 153–155 | (KBr:) 2550, 1720, 1700, 1630 1600, 1300, 760 | (52.31 6.18 10.61) 52.36 6.37 10.56 |
| 22' | (COOH)$_2$ | C$_{21}$H$_{31}$N$_5$O$_5$S· (COOH)$_2$·1.5H$_2$O | 158–163 (decomposed) | (KBr): 3400, 2500, 2240, 1700 1630, 1600, 760 | (47.42 6.23 12.02) 47.33 6.26 12.16 |
| 23' | (COOH)$_2$ | C$_{21}$H$_{27}$N$_5$O$_3$· (COOH)$_2$·H$_2$O | 181–183 (decomposed) | (KBr): 3400, 2500, 2240, 1700 1630, 1600, 760 | (54.65 6.18 13.85) 55.06 6.35 13.59 |
| 24' | (COOH)$_2$ | C$_{22}$H$_{30}$N$_4$O$_4$· (COOH)$_2$·½H$_2$O | 182–185 | | (56.13 6.47 10.90) 56.28 6.69 11.02 |
| 25' | (COOH)$_2$ | C$_{23}$H$_{32}$N$_4$O$_4$· (COOH)$_2$·H$_2$O | 139–141 | (KBr): 2550, 1720, 1700, 1630 1590, 1340, 760 | (55.96 6.76 10.44) 55.60 6.71 10.72 |
| 26' | (COOH)$_2$ | C$_{20}$H$_{28}$N$_4$O$_4$S· (COOH)$_2$·H$_2$O | 160–166 (decomposed) | (KBr): 3430, 1698, 1648, 1470 1442, 1395, 1280, 1236 1202, 1030, 760 | S (49.99 6.10 10.60 6.07) 49.63 6.30 10.14 5.55 |

TABLE 23

| Comp. No. | Acid | Molecular Formula | m.p. (°C.) | IR ν max (cm$^{-1}$) | Elemental Analysis (%) (calculated values) C H N etc. |
|---|---|---|---|---|---|
| 27' | HCl | C$_{28}$H$_{32}$N$_4$O$_4$·HCl | 233–236 | | Cl (64.05 6.35 10.67 6.75) 64.24 6.80 10.51 6.96 |
| 28' | HCl | C$_{20}$H$_{32}$N$_4$O$_3$S· HCl·H$_2$O | 215 | (KBr): 3370, 2930, 2550, 1690 1485, 1470, 1440, 1392 1279, 1242, 1073, 982 750 | S Cl (52.33 6.81 12.21 6.98 7.72) 52.22 6.89 12.08 6.99 7.66 |
| 29' | (COOH)$_2$ | C$_{27}$H$_{32}$N$_4$O$_5$· (COOH)$_2$·H$_2$O | | (KBr): 2950, 2550, 1720, 1690 1650, 1600, 760, 750, 700 | (57.99, 6.04 9.33) 58.00 5.85 9.39 |
| 30' | HCl | C$_{26}$H$_{30}$N$_4$O$_4$· HCl·H$_2$O | 212–214 (decomposed) | (KBr): 1700, 1670, 1650, 770 760, 700 | Cl (60.40 6.43 10.84 6.86) 60.25 6.64 10.88 7.62 |
| 31' | HCl | C$_{28}$H$_{34}$N$_4$O$_4$·HCl | 218–222 (decomposed) | (KBr): 2520, 1700, 1650, 1610 1600, 760, 700 | Cl (61.93 6.50 10.32 6.53) 61.63 6.77 10.58 6.61 |
| 32' | HCl | C$_{21}$H$_{25}$N$_4$O$_4$F$_3$· HCl·2H$_2$O | | (KBr): 2570, 1710, 1690, 1640 1600, 1340, 1170, 760 720 | Cl (47.87 5.74 10.63 6.73) 47.88 6.19 10.29 6.66 |

TABLE 24

| Comp. No. | Acid | Molecular Formula | m.p. (°C.) | IR ν max (cm$^{-1}$) | Elemental Analysis (%) (calculated values) C H N etc. |
|---|---|---|---|---|---|
| 33' | (COOH)$_2$ | C$_{24}$H$_{32}$N$_4$O$_6$· (COOH)$_2$·2H$_2$O | 162–166 (decomposed) | (KBr): 2550, 1730, 1720, 1700 1650, 1630, 1600, 760 | (52.17 6.40 9.36) 52.15 6.09 9.92 |
| 36' | (COOH)$_2$ | C$_{19}$H$_{25}$N$_7$O$_3$· (COOH)$_2$·2H$_2$O | 159–162 | (KBr): 2950, 2250, 2100, 1690 1640, 1600, 760 | (49.70 5.76 19.32) 49.53 5.79 18.84 |
| 37' | (COOH)$_2$ | C$_{25}$H$_{29}$N$_5$O$_4$· 2(COOH)$_2$· 2.5H$_2$O | 110 | (KBr): 2600, 1740, 1700, 1640 1610 | (50.58 5.56 10.17) 50.56 5.56 10.20 |
| 38' | (COOH)$_2$ | C$_{25}$H$_{29}$N$_5$O$_4$· 2(COOH)$_2$· 2H$_2$O | 153–156 | (KBr): 2600, 1740, 1710, 1650 1600 | (51.25 5.49 10.30) 51.44 5.91 10.02 |

TABLE 25

| Comp. No. | Acid | Molecular Formula | m.p. (°C.) | IR ν max (cm$^{-1}$) | Elemental Analysis (%) (calculated values) C H N etc. |
|---|---|---|---|---|---|
| 39' | (COOH)$_2$ | C$_{25}$H$_{34}$N$_4$O$_4$·(COOH)$_2$·2H$_2$O | 180–182 (decomposed) | (KBr): 1730, 1700, 1660, 1600 750 | (55.85 6.94 9.65) 55.92 6.61 9.48 |
| 40' | HCl | C$_{19}$H$_{24}$N$_4$O$_3$FCl·HCl·½H$_2$O | 250–253 (decomposed) | | F Cl (50.51 5.69 12.40 4.20 15.69) 50.46 5.77 12.19 4.13 15.70 |
| 41' | HCl | C$_{20}$H$_{26}$N$_5$O$_4$Cl·HCl·2H$_2$O | 144–149 | | Cl (47.25 6.15 13.78 13.95) 47.53 6.27 13.68 13.83 |
| 42' | HCl | C$_{21}$H$_{30}$N$_4$O$_3$S·HCl·½H$_2$O | 185–188 | (KBr): 1690, 1650, 1430, 1240 1175, 1045, 980, 760 | S Cl (54.36 6.95 12.07 6.91 7.64) 54.61 7.27 12.11 6.99 7.90 |
| 43' | HCl | C$_{19}$H$_{24}$N$_4$O$_3$Cl$_2$·HCl | 267 | (KBr): 3420, 1700, 1650, 1605 1490, 1460, 1390, 1290 1260, 1060, 980, 790 | Cl (49.20 5.45 12.08 22.93) 48.73 5.31 12.09 22.76 |
| 44' | (COOH)$_2$ | C$_{22}$H$_{30}$N$_4$O$_6$S·(COOH)$_2$·H$_2$O | 145–151 (decomposed) | (KBr): 3000, 2550, 1750, 1740 1710, 1600, 1350, 1120 850, 800 | S (49.14 5.84 9.55 5.47) 49.26 6.20 10.13 5.11 |

TABLE 26

| Comp. No. | Acid | Molecular Formula | m.p. (°C.) | IR ν max (cm$^{-1}$) | Elemental Analysis (%) (calculated values) C H N etc. |
|---|---|---|---|---|---|
| 45' | HCl | C$_{20}$H$_{27}$N$_4$ClO$_4$·HCl·H$_2$O | 232 (decomposed) | | Cl (50.32 6.33 11.74 14.85) 50.17 6.49 11.12 15.05 |
| 46' | HCl | C$_{25}$H$_{34}$N$_4$O$_7$·HCl·H$_2$O | 156.8–159 | (KBr): 1690, 1645, 1510, 1440 1330, 1150, 1000, 800 730 | Cl (53.91 6.69 10.06 6.36) 54.34 7.18 10.11 6.55 |
| 47' | HCl | C$_{23}$H$_{31}$N$_5$O$_5$·2HCl·1.5H$_2$O | 186–205 (decomposed) | | Cl (49.55 6.51 12.56 12.72) 49.71 6.89 12.40 12.12 |
| 48' | HCl | C$_{21}$H$_{30}$N$_4$O$_5$·HCl·H$_2$O | | | Cl (53.32 7.03 11.84 7.49) 52.88 7.37 11.50 7.94 |
| 49' | (COOH)$_2$ | C$_{20}$H$_{27}$N$_4$)$_5$SBr·(COOH)$_2$·H$_2$O | 145–150 (decomposed) | (KBr): 2950, 2500, 1720, 1700 1630, 1590, 1300, 1140 850, 800, 590 | Br S (42.38 5.01 8.99 12.82 5.14) 41.93 4.95 8.55 12.76 4.59 |
| 50' | (COOH)$_2$ | C$_{20}$H$_{27}$N$_4$O$_5$SCl·(COOH)$_2$·1.5H$_2$O | 196–198 | (KBr): 2900, 2540, 1730, 1700 1650, 1610, 1310, 1140 830, 720 | Br S (44.94 5.49 9.53 6.03 5.45) 45.03 5.06 9.05 5.86 5.17 |

TABLE 27

| Comp. No. | Acid | Molecular Formula | m.p. (°C.) | IR ν max (cm$^{-1}$) | Elemental Analysis (%) (calculated values) C H N etc. |
|---|---|---|---|---|---|
| 51' | (COOH)$_2$ | C$_{26}$H$_{29}$N$_4$O$_4$Cl·(COOH)$_2$·3H$_2$O | 167–170 (decomposed) | KBr): 2600, 1740, 1700, 1660 1650, 760, 700, 660 | Cl (52.46 5.82 8.74 5.53) 52.62 5.72 8.75 5.30 |
| 52' | (COOH)$_2$ | C$_{25}$H$_{28}$N$_5$O$_4$Cl·2(COOH)$_2$·3H$_2$O | 120–123 | KBr): 2600, 1730, 1690, 1640 1600, 800, 760 | Cl (47.58 5.23 9.57 4.84) 47.95 4.75 9.61 4.88 |
| 53' | (COOH)$_2$ | C$_{25}$H$_{28}$N$_5$O$_4$Cl·2(COOH)$_2$·1.5H$_2$O | 145–147 (decomposed) | KBr): 2550, 1720, 1690, 1660 1600, 800, 760 | Cl (49.40 5.00 9.93 5.03) 49.64 5.20 9.43 5.12 |
| 54' | (COOH)$_2$ | C$_{26}$H$_{31}$N$_5$O$_5$·2(COOH)$_2$·2H$_2$O | 100–104 (decomposed) | KBr): 1740, 1700, 1630, 1610 760, 690 | (50.77 5.54 9.87) 50.42 5.26 10.14 |
| 55' | (COOH)$_2$ | C$_{26}$H$_{31}$N$_5$O$_5$·2(COOH)$_2$·2H$_2$O | 109–112 (decomposed) | KBr): 1730, 1700, 1630, 1610 760, 700 | (50.77 5.54 9.87) 50.38 6.00 10.11 |
| 56' | HCl | C$_{26}$H$_{29}$N$_4$O$_4$Cl·HCl | 204–206 (decomposed) | KBr): 2450, 1700, 1650, 1610 1500, 1280, 1060, 960 | Cl (54.84 6.02 9.86 12.45) 55.07 6.10 10.10 12.00 |

TABLE 27-continued

| Comp. No. | Acid | Molecular Formula | m.p. (°C.) | IR ν max (cm⁻¹) | Elemental Analysis (%) (calculated values) C H N etc. |
|---|---|---|---|---|---|
| | | | | 790, 760, 740 | |

TABLE 28

| Comp. No. | Acid | Molecular Formula | m.p. (°C.) | IR ν max (cm⁻¹) | Elemental Analysis (%) (calculated values) C H N etc. |
|---|---|---|---|---|---|
| 57' | (COOH)$_2$ | C$_{28}$H$_{32}$N$_4$O$_6$·(COOH)$_2$·H$_2$O | 180–192 (decomposed) | KBr: 3300, 3050, 1770, 1710 1690, 1640, 1440, 1280 840, 800, 760, 705 | (55.72 5.92 8.66) 55.98 6.20 9.13 |
| 58' | (COOH)$_2$ | C$_{26}$H$_{29}$N$_4$O$_4$F·(COOH)$_2$ 1.5H$_2$O | 183–185 | KBr: 3460, 1700, 1440, 1280 1110, 800, 760, 700 | (56.28 5.73 9.38) 56.12 5.66 9.20 |
| 59' | (COOH)$_2$ | C$_{21}$H$_{27}$N$_4$O$_4$F·(COOH)$_2$.2H$_2$O | 140–143 | KBr: 3450, 2550, 1690, 1620 1510, 1270, 800, 760, 710 | (50.73 6.11 10.29) 50.57 5.73 10.10 |
| 60' | (COOH)$_2$ | C$_{24}$H$_{27}$N$_4$O$_5$F·(COOH)$_2$ | 179–180 | KBr: 3400, 2550, 1720, 1700 1620, 1430, 1310, 1290 1105, 790, 700 | (55.71 5.22 10.00) 55.39 5.22 9.95 |
| 61' | (COOH)$_2$ | C$_{20}$H$_{26}$N$_4$O$_5$SBr$_2$·(COOH)$_2$.H$_2$O | 167–171 (decomposed) | KBr: 2900, 2600, 1700, 1630 1305, 1150, 800, 600 | Br S (37.62 4.31 7.98 22.75 4.56) 37.69 4.24 7.98 21.46 4.02 |
| 62' | (COOH)$_2$ | C$_{20}$H$_{26}$N$_4$O$_5$SI$_2$·(COOH)$_2$.H$_2$O | 164–167 | KBr: 2950, 2500, 1700, 1650 1640, 1310, 1150, 800 530 | I S (33.18 3.80 7.04 31.87 4.03) 33.31 3.71 7.18 31.39 4.05 |

TABLE 29

| Comp. No. | Acid | Molecular Formula | m.p. (°C.) | IR ν max (cm⁻¹) | Elemental Analysis (%) (calculated values) C H N etc. |
|---|---|---|---|---|---|
| 63' | (COOH)$_2$ | C$_{22}$H$_{28}$N$_4$O$_6$SBr$_2$·(COOH)$_2$.H$_2$O | 160–163 (decomposed) | (KBr): 2950, 2500, 1740, 1700 1640, 1620, 1310, 1150 800, 660 | Br S (38.72 4.33 7.53 21.47 4.31) 38.60 4.35 7.41 21.43 4.56 |

EXAMPLE 3

Preparation of 6-[4-(3-[4-chlorophenoxy]propyl)piperazin-1-yl]-1,3-dimethyl-2,4(1H,3H)-pyrimidinedione.hydrochloride (Compound 64)

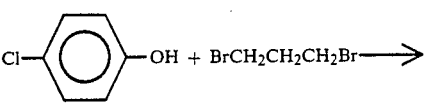

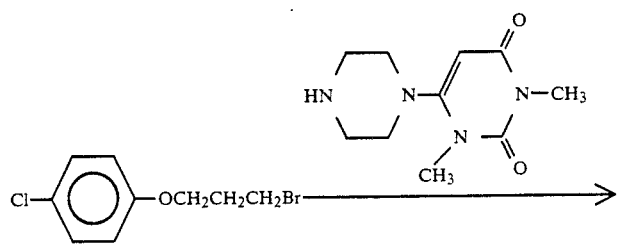

-continued

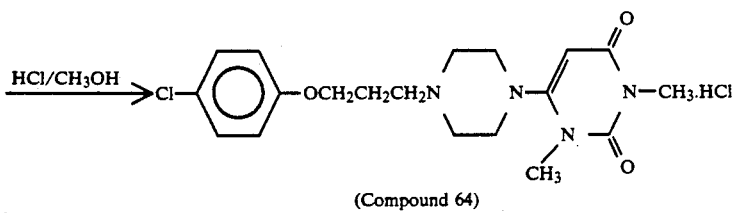
(Compound 64)

10 g of potassium carbonate was added to 30 ml of a methyl ketone solution containing 15.9 g of p-chlorophenol, and the solution was then heated with stirring at 60° C. for 1 hour. Afterward, 30 ml of a methyl ethyl ketone solution containing 50 g of 1,3-dibromopropane was added dropwise; After the addition, the solution was heated under reflux for 3 hours. The reaction solution was then cooled and a precipitate was removed therefrom, and the solution was evaporated to dryness under reduced pressure to obtain 23.2 g of 4-chlorophenoxypropyl bromide.

3 ml of triethylamine was added to 10 ml of an ethanol solution containing 2.5 g of 3-(4-chlorophenoxy)-propyl bromide and 1.3 g of 1,3-dimethyl-6-(1-piperazinyl)-2,4(1H,3H)-pyrimidinedione, and the solution was then heated under reflux for 3 hours. Afterward, the reaction solution was concentrated to dryness, and the resultant residue was dissolved in chloroform and then washed with water. The thus obtained chloroform solution was dried and then concentrated, and the residue was recrystallized from ethanol/hexane, thereby preparing 1.96 g (yield: 86%) of 6-[4-(3-[4-chlorophenoxy]propyl)piperazin-1-yl]-1,3-dimethyl-2,4(1H,3H)-pyrimidinedione.

Melting point: 130°–131° C.

Values of elemental analysis (as $C_{19}H_{25}N_4O_3Cl$): Calcd. (%): C 58.09; H 6.41; N 14.26; Cl 9.02 Found (%): C 57.62; H 6.48; N 13.93; Cl 9.11.

NMR (CDCl$_3$) δ ppm: 1.94 (m, 2H), 2.60 (m, 6H), 2.96 (m, 4H), 3.32 (s, 3H), 3.38 (s, 3H), 3.98 (t, 2H), 5.25 (s, 1H), 6.7–7.3 (m, 4H).

6-[4-(3-[4-chlorophenoxy]propyl)piperazin-1-yl]-1,3-dimethyl-2,4(1H,3H)-pyrimidinedione obtained above was treated with an HCl/methanol solution in an ordinary manner to prepare 6-[4-(3-[4-chlorophenoxy]propyl)piperazin-1-yl]-1,3-dimethyl-2,4(1H,3H)-pyrimidinedione.hydrochloride (Compound 64).

Melting point: 253°–254° C.

Values of elemental analysis (as $C_{19}H_{26}N_4Cl_2O_3$): Calcd. (%): C 53.15; H 6.10; N 13.05; Cl 16.51 Found (%): C 53.16; H 6.26; N 12.68; Cl 16.54

EXAMPLE 4

Preparation of 1,3-dimethyl-6-[4-(2-phenoxyethyl)piperazin-1-yl]-2,4(1H,3H)-pyrimidinedione.hydrochloride (Compound 65)

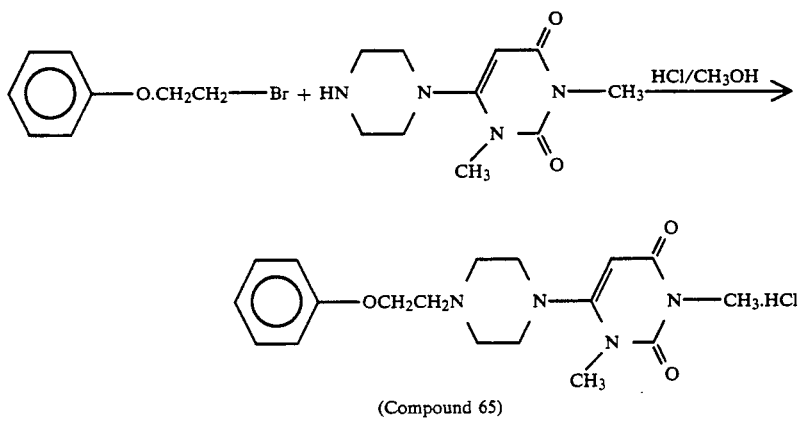
(Compound 65)

1.12 g of 1,3-dimethyl-6-(1-piperazinyl)-2,4(1H,3H)pyrimidinedione and 1.4 g of phenoxyethyl bromide were dissolved in 5 ml of ethanol, and 1.0 g of triethylamine was then added, followed by heating under reflux for 1 hour. Furthermore, 0.6 g of phenoxyethyl bromide was added, and the solution was heated under reflux for 2 hours. The precipitated crystals were collected by filtration, washed with water, dried and then recrystallized from hexane/ethanol to obtain 1.1 g (yield: 63%) of 1,3-dimethyl-6-[4-(2-phenoxyethyl)piperazin-1-yl]-2,4(1H,3H)-pyrimidinedione.

Melting point: 132°–134° C.

NMR (CDCl$_3$) δ ppm: 2.6–3.1 (m, 10H), 3.36 (s, 3H), 3.41 (s, 3H), 4.14 (t, 2H), 5.26 (s, 1H), 6.8–7.4 (m, 5H)

Values of elemental analysis (as $C_{18}H_{24}N_4O_3$): Calcd. (%): C 62.77; H 7.02; N 16.27 Found (%): C 62.69; H 7.35; N 16.25.

1,3-dimethyl-6-[4-(2-phenoxyethyl)piperazin-1-yl]-2,4(1H,3H)-pyrimidinedione obtained above was treated with an HCl/methanol solution in an ordinary manner to prepare 1,3-dimethyl-6-[4-(2-phenoxyethyl)piperazin-1-yl]-2,4(1H,3H)-pyrimidinedione.hydrochloride (Compound 65).

Values of elemental analysis: (as $C_{18}H_{24}N_4O_3.HCl.H_2O$): Calcd. (%): C 54.20; H 6.82; N 14.05; Cl 8.89 Found (%): C 53.58; H 7.06; N 13.82; Cl 9.52.

IR $\nu_{max}^{KBr}$ (cm$^{-1}$): 3430, 1695, 1640, 1600, 1490, 1438, 1240, 1200, 752, 691

EXAMPLE 5

Preparation of 4-[3-(4-[1,3-dimethyl-2,4-dioxo-1,2,3,4-tetrahydropyrimidin-6-yl]piperazin-1-yl)propyloxy]-N-methylbenzenesulfonamide.hydrochloride (Compound 66)

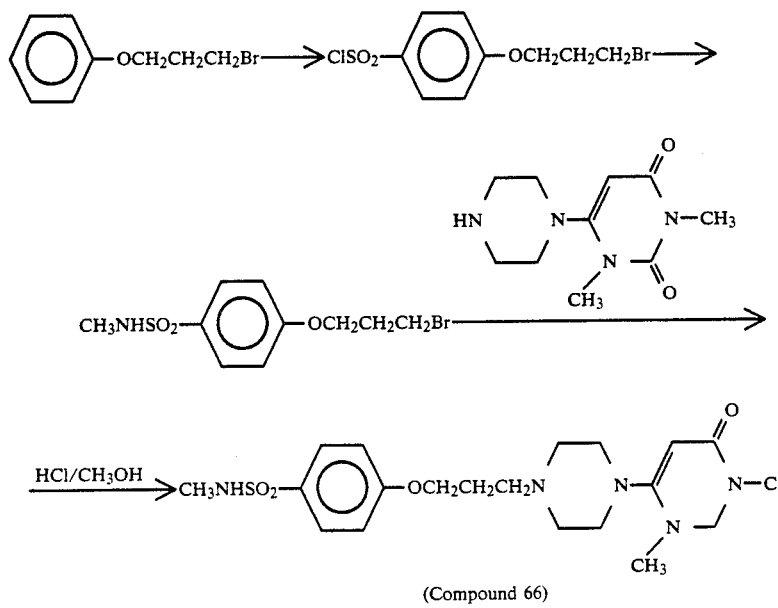

(Compound 66)

(1) Synthesis of 4-(3-bromopropoxy)benzenesulfonic acid chloride 20 ml of a chloroform solution containing 5.8 g of 3-phenoxypropyl bromide was cooled to −10° C., and 3.6 ml of chlorosulfuric acid was added thereto, followed by stirring at room temperature for 1 hour. The reaction solution was poured onto ice, and extraction was performed with 100 ml of chloroform. Water washing, drying and concentration were successively carried out to obtain 3.4 g (yield: 40%)of 4-(3-bromopropoxy)-benzenesulfonic acid chloride in an oily state.

(2) Synthesis of 4-(3-bromopropoxy)-N-methylbenzenesulfonamide 3.4 g of 4-(3-bromopropoxy)benzenesulfonic acid chloride was suspended in water, and 6.2 ml a 20% aqueous methylamine solution was added to the suspension under ice cooling. The solution was stirred at room temperature for 2 hours and then extracted with chloroform (50 ml×2), and drying and concentration followed to obtain 2.9 g (yield: 87%) of 4-(3-bromopropoxy)-N-methylbenzenesulfonamide in an oily state.

NMR (CDCl$_3$) δ ppm: 2.4 (m, 2H), 2.66 (s, 3H), 3.63 (t, J=6 Hz, 2H), 4.2 (t, J=6 Hz, 2H), 7.03 (d, J=8 Hz, 2H), 7.83 (d, J=8 Hz, 2H).

(3) Synthesis of 4-[3-(4-[1,3-dimethyl-2,4-dioxo-1,2,3,4-tetrahydropyrimidin-6-yl]piperazin-1-yl)propoxy]-N-methylbenzenesulfonamide.hydrochloride (Compound 66)

This desired sulfonamide derivative was synthesized from 4-(3-bromopropoxy)-N-methylbenzenesulfonamide in the same manner as in Example 3.

NMR (CDCl$_3$) δ ppm: 1.7–2.3 (m, 2H), 2.3–3.4 (m, 12H), 3.15 (s, 3H), 3.3 (s, 3H), 3.31 (s, 3H), 4.13 (t, J=6 Hz, 2H), 5.16 (s, 1H), 7.1 (d, J=8 Hz, 2H), 7.73 (d, J=8 Hz, 2H).

The sulfonamide derivative obtained above was treated with an HCl/methanol solution in an ordinary manner to prepare 4-[3-(4-[1,3-dimethyl-2,4-dioxo-1,2,3,4-tetrahydropyrimidin-6-yl]piperazin-1-yl)propoxy]-N-methyl]benzenesulfonamide.hydorchloride (Compound 66).

Melting point: 249°–251° C.

Values of elemental analysis (as C$_{20}$H$_{29}$N$_5$O$_5$S.HCl.½H$_2$O): Calcd. (%): C 48.33; H 6.29; N 14.09; S 6.45; Cl 7.13 Found (%): C 48.31; H 6.67; N 13.75; S 6.85; Cl 7.46.

EXAMPLE 6

Synthesis of 6-[4-(3-[4-aminophenoxy]propyl)piperazin-1-yl]-1,3-dimethyl-2,4(1H,3H)-pyrimidinedione.hydrochloride (Compound 67)

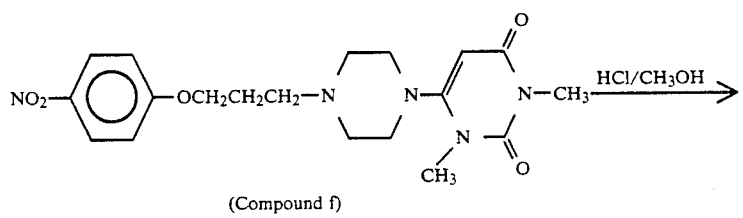

(Compound f)

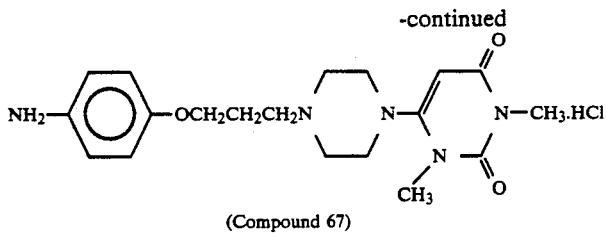

(Compound 67)

2 g of 1,3-dimethyl-6-[4-(3-[4-nitrophenoxy)propyl)-piperazin-1-yl]-2,4(1H,3H)-pyrimidinedione (Compound f) obtained in Reference Example 4 was suspended in 300 ml of methanol and 500 mg of 10% Pd/c solution was added to the suspension, and hydrogenation was then carried out at ordinary pressure for 30 minutes. The catalyst was removed by filtration, and the solvent was distilled off, thereby obtaining 1.54 g of 6-[4-(3-[4-aminophenoxy)propyl)piperazin-1-yl]-1,3-dimethyl-2,4(1H,3H)-pyrimidinedione.

This product was treated with a hydrochloric acid/methanol solution in an ordinary manner, and the resultant hydrochloride was then recrystallized from methanol/ethyl acetate to prepare 6-[4-(3-[4-aminophenoxy]propyl)piperazin-1-yl]-1,3-dimethyl-2,4(1H,3H)-pyrimidinedione.hydrochloride (Compound 67).

Melting point: 260° C.

Values of elemental analysis (as $C_{19}H_{27}N_5O_3 \cdot 2HCl \cdot \frac{1}{2}H_2O$): Calcd. (%): C 50.11; H 6.64; N 15.38; Cl 15.57 Found (%): C 49.71; H 6.84; N 15.29; Cl 15.86.

EXAMPLE 7

Synthesis of 1,3-dimethyl-6-[4-(3-[4-methanesulfonylaminophenoxy]propyl)piperazin-1-yl]-2,4(1H,3H)-pyrimidinedione.-hydrochloride (Compound 68)

washed with chloroform (500 ml×2), made weakly acidic with concentrated hydrochloric acid and then washed with chloroform (50 ml). In succession, potassium carbonate was added to this solution to adjust its pH to 7, and the solution was extracted with chloroform (50 ml×3), dried over sodium sulfate and then concentrated to obtain 0.9 g of crystalline 1,3-dimethyl-6-[4-(3-[4-methanesulfonylaminophenoxy]propyl)piperazin-1-yl]-2,4(1H,3H)-pyrimidinedione.

Melting point: 162.5°–163° C.

NMR (CDCl₃) δ ppm: 1.96 (m, 2H), 2.58 (m, 6H), 2.95 (s, 3H), 2.80–3.10 (m, 4H), 3.33 (s, 3H), 3.38 (s, 3H), 3.98 (t, J=6 Hz, 2H), 5.30 (s, 1H), 7.10 (ABq, J=10.5 Hz, 4H).

Values of elemental analysis (as $C_{20}H_{29}N_5O_5S$): Calcd. (%): C 53.20; H 6.47; N 15.51; S 7.10 Found (%): C 53.52; H 6.82; N 15.18; S 7.03.

0.7 g of this 1,3-dimethyl-6-[4-(3-[4-methanesulfonylaminophenoxy]propyl)piperazin-1-yl]-2,4(1H,3H)-pyrimidinedione was treated with HCl/methanol in an ordinary manner, thereby obtaining 0.6 g of 1,3-dimethyl-6-[4-(3-[4-methanesulfonylaminophenoxy]propyl)-piperazin-yl]-2,4(1H,3H)-pyrimidinedione.hydrochloride (Compound 68).

Melting point: 263°–267° C. (decomposed)

Values of elemental analysis (as $C_{20}H_{29}N_5O_5S \cdot HCl \cdot \frac{1}{2}$

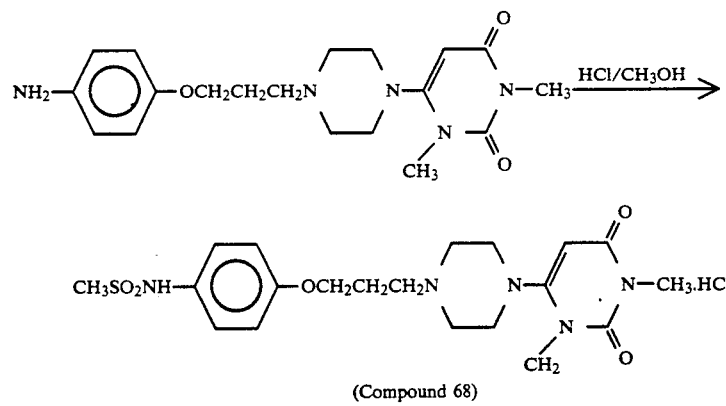

(Compound 68)

20 ml of a dioxane solution containing 1.1 g of 6-[4-(3-[4-aminophenoxy]propyl)piperazin-1-yl]-1,3-dimethyl-2,4(1H,3H)-pyrimidinedione obtained in Example 6 and 1.8 ml of pyridine was cooled to 0° C., and 0.95 ml of trimethylsilyl chloride was further added, followed by stirring at the same temperature for 5 minutes and then at room temperature for 30 minutes. The reaction solution was cooled to 0° C. again, and 0.6 ml of methanesulfonyl chloride was added dropwise thereto. The solution was stirred at the same temperature for 5 minutes and further at room temperature for 1 hour, and then cooled on an ice water bath. Afterward, 10 ml of ice water was added dropwise, and 50 ml of water and 70 ml of a 1N aqueous sodium hydroxide solution were further added. The resultant aqueous solution was H₂O): Calcd. (%): C 48.33; H 6.29; N 14.09; Cl7.13; S 6.45 Found (%): C 48.65; H 6.48; N 14.09; Cl7.26; S 6.27.

EXAMPLE 8

Preparation of 6-[4-(3-[2-aminophenoxy]propyl)piperazin-1-yl]-1,3-dimethyl-2,4(1H,3H)-pyrimidinedione.oxalate (Compound 69)

6.05 g of the Compound e obtained in Reference Example 3 was treated in the same manner as in Example 6, thereby obtaining 5.51 g of crystalline 6-[4-(3-[2- aminophenoxy]propyl)piperazin-1-yl]-1,3-dimethyl-2,4(1H,3H)-pyrimidinedione (Compound 69').

Analytical results of the obtained Compound 69'
Melting point: 117°–118° C.
NMR (CDCl₃) δ ppm: 2.0 (m, 2H), 2.4–2.7 (m, 6H), 2.8–3.1 (m, 4H), 3.31 (s, 3H), 3.37 (s, 3H), 3.44 (br, 2H), 4.06 (t, 2H), 5.22 (s, 1H), 6.7 (m, 4H).

3.64 g of this pyrimidinedione derivative (Compound 69') was treated with an oxalic acid/methanol solution in an ordinary manner, thereby obtaining 5.20 g of crystalline 6-[4-(3-[2-aminophenoxy]propyl)piperazin-1-yl]-1,3-dimethyl-2,4(1H,3H)-pyrimidinedione.oxalate (Compound 69).

Analytical results of the obtained Compound 69:
Melting point: 113° C.
Values of elemental analysis (as $C_{19}H_{27}N_5O_3S.2-(COOH)_2.1.5H_2O$): Calcd. (%): C 47.58; H 5.90; N 12.06 Found (%): C 47.25; H 6.38; N 11.81.

EXAMPLE 9

Preparation of 6-[4-(3-[3-aminophenoxy]propyl)piperazin-1-yl]-1,3-dimethyl-2,4(1H,3H)-pyrimidinedione.oxalate (Compound 70)

2.82 g of the Compound c obtained in Reference Example 2 was treated in the same manner as in Example 6, thereby obtaining 0.23 g of crystalline 6-[4-(3-[3-aminophenoxy]propyl)piperazin-1-yl]-1,3-dimethyl-2,4(1H,3H)-pyrimidinedione (Compound 70').

Analytical results of the obtained Compound 70'
Melting point: 169°–170° C.
Values of elemental analysis (as $C_{19}H_{27}N_5O_3$): Calcd. (%): C 61.11; H 7.29; N 18.75 Found (%): C 60.92; H 7.55; N 18.86

0.22 g of this pyrimidinedione derivative (Compound 70') was treated with an oxalic acid/methanol solution in an ordinary manner, thereby obtaining 0.28 g of crystalline 6-[4-(3-[3-aminophenoxy]propyl)piperazin-1-yl]-1,3-dimethyl-2,4 (1H,3H)-pyrimidinedione.oxalate (Compound 70).

Analytical results of the obtained Compound 70:
Melting point: 110° C.
Values of elemental analysis (as $C_{19}H_{27}N_5O_3S.1.5-(COOH)_2.H_2O$): Calcd. (%): C 50.19; H 6.13; N 13.30 Found (%): C 50.00; H 6.46; N 12.96

EXAMPLE 10

Preparation of 6-[4-(3-[4-aminoanilino]propyl)piperazin-1-yl]-1,3-dimethyl-2,4(1H,3H)-pyrimidinedione.hydrochloride (Compound 71)

1.2 g of the Compound g obtained in Reference Example 5 was treated in the same manner as in Example 6, thereby obtaining 1.02 g of 6-[4-(3-[4-aminoanilino]-propyl) piperazin-1-yl]-1,3-dimethyl-2,4(1H,3H)-pyrimidinedione.

Analytical results of the obtained pyrimidinedione derivative
NMR (CDCl₃) δ ppm: 1.9 (m, 2H), 2.4–3.0 (m, 12H), 3.31 (s, 3H), 3.40 (s, 3H), 5.10 (s, 1H), 6.33 (d, 2H), 6.81 (d, 2H).

0.90 g of this pyrimidinedione derivative was treated with a hydrochloric acid/methanol solution in an ordinary manner to obtain 0.5 g of crystalline 6-[4-(3-[4-aminoanilino]propyl)piperazin-1-yl]-1,3-dimethyl-2,4 (1H,3H)-pyrimidinedione.hydrochloride (Compound 71).

Analytical results of then obtained Compound 71:
Melting point: 265°–268° C.
Values of elemental analysis (as $C_{19}H_{28}N_6O_2.3HCl.\frac{1}{2}H_2O$): Calcd. (%): C 46.49; H 6.57; N 17.12; Cl 21.67 Found (%): C 46.33; H 6.63; N 16.80; Cl 20.62.
IR $\nu_{max}^{KBr}$ (cm$^{-1}$): 3450, 2550, 1690, 1650, 1480, 1440, 1200, 970, 800, 760.

EXAMPLE 11

Preparation of 1,3-dimethyl-6-[4-(3-[2-methanesulfonylaminophenoxy]propyl)piperazin-1-yl]-2,4(1H,3H)pyrimidinedione.-hydrochloride (Compound 72)

The Compound 69' obtained in Example 8 was treated in the same manner as in Example 7, thereby obtaining 1,3-dimethyl-6-[4-(3-[2-methanesulfonylaminophenoxy]-propyl)piperazin-1-yl]-2,4(1H,3H)-pyrimidinedione.

Analytical results of the obtained pyrimidinedione derivative
Melting point: 157°–158.5° C.
Values of elemental analysis (as $C_{20}H_{29}N_5O_5S$): Calcd. (%): C 53.20; H 6.47; N 15.51; S 7.10 Found (%): C 53.46; H 6.54; N 15.24; S 7.29

This pyrimidinedione derivative was treated with a hydrochloric acid/methanol solution in an ordinary manner to obtain 1,3-dimethyl-6-[4-(3-[2-methanesulfonylaminophenoxy]propyl)piperazin-]-yl]-2,4(1H,3H)-pyrimidinedione.hydrochloride (Compound 72).

Analytical results of the obtained Compound 72:
Melting point: 275°–276° C. (decomposed)
Values of elemental analysis (as $C_{20}H_{29}N_5O_5S.HCl$): Calcd. (%): C 46.23; H 6.20; Cl7.26; N 14.35; S 6.57 Found (%): C 48.63; H 6.43; Cl7.73; N 14.09; S 6.91.
IR $\nu_{max}^{KBr}$ (cm$^{-1}$): 3420, 3100, 2430, 1707, 1640, 1500, 1465, 1431, 1323, 1150, 1109, 995, 755.

EXAMPLE 12

Preparation of 1,3-dimethyl-6-[4-(3-[3-methanesulfonylaminophenoxy]propyl)piperazin-1-yl]-2,4(1H,3H)-pyrimidinedione.-hydrochloride (Compound 73)

The Compound 70' obtained in Example 9 was treated in the same manner as in Example 7, thereby obtaining 1,3-dimethyl-6-[4-(3-[3-methanesulfonylaminophenoxy]-propyl)piperazin-1-yl]-2,4(1H,3H)-pyrimidinedione.

Analytical results of the obtained pyrimidinedione derivative
Melting point: 141°–142° C.
NMR (DMSO-d₆) δ ppm: 1.78 (m, 2H), 2.36 (m, 6H), 2.6–3.4 (m, 4H), 2.78 (s, 3H), 2.94 (s, 3H). 3.08 (s, 3H), 3.74 (m, 2H), 4.84 (s, 1H), 6.2–7.0 (m, 4H), 9.18 (brs, 1H).

Values of elemental analysis (as $C_{20}H_{29}N_5O_5S$): Calcd. (%): C 53.20; H 6.47; N 15.51; S 7.10 Found (%): C 52.92; H 6.37; N 15.56; S 6.80.

This pyrimidinedione derivative was treated with a hydrochloric acid/methanol solution in an ordinary manner to obtain 1,3-dimethyl-6-[4-(3-[3-methanesulfonylaminophenoxy]propyl)piperazin-1-yl]-2,4(1H,3H)-pyrimidinedione.hydrochloride (Compound 73).

Analytical results of the obtained Compound 73:
Melting point: 223.5°–225° C.
Values of elemental analysis (as $C_{20}H_{29}N_5O_5S.HCl.\frac{1}{2}H_2O$): Calcd. (%): C 48.33; H 6.29; N 14.09; Cl7.13; S 6.45 Found (%): C 48.47; H 6.35; N 14.06; Cl7.33; S 6.54

IR $\nu_{max}^{KBr}$ (cm$^{-1}$): 3030, 2580, 1710, 1649, 1495, 1450, 1324, 1153, 988, 764, 690.

EXAMPLE 13

Preparation of
6-[4-(3-phenoxypropyl)piperazin-1-yl]-2,4(1H,3H)-pyrimidinedione.hydrochloride (Compound 74)

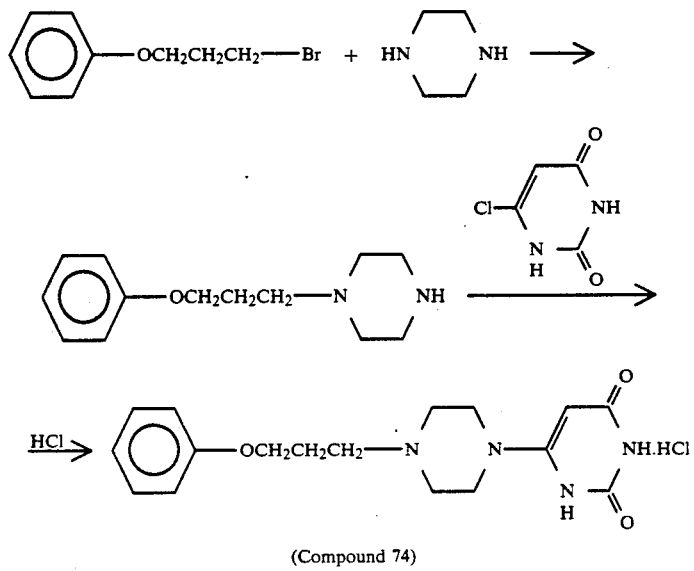

(Compound 74)

(1) Synthesis of 1-(3-phenoxypropyl)piperazine:

15.1 g of phenoxypropyl bromide and 60 g of piperazine were dissolved in 150 ml of dioxane, and the solution was heated at 80°-90° C. for 1 hour. The precipitated crystals were removed by filtration, and the filtrate was then concentrated. Afterward, the resultant residue was dissolved in chloroform and then washed with water. Chloroform was distilled off to obtain 15 g of 1-(3-phenoxypropyl)piperazine.

(2) Preparation of
6-[4-(3-phenoxypropyl)piperazin-1-yl]-2,4(1H,3H)-pyrimidinedione.hydrochloride (Compound 74)

1.1 g of 1-(3-phenoxypropyl)piperazine, 0.8 ml of triethylamine and 0.59 g of 6-chloro-2,4(1H,3H)-pyrimidinedione were dissolved in 15 ml of dioxane, followed by heating under reflux for 1 hour. After cooling, the precipitated crystals were collected by filtration, and then washed with water and hot ethanol to obtain 1.0 g (yield 66% ) of 6-[4-(3-phenoxypropyl)piperazin-1-yl]-2,4(1H,3H)-pyrimidinedione.

Analytical results of the obtained pyrimidinedione derivative

Melting point: 242°-244° C.

NMR (DMSO-d$_6$) δ ppm: 1.7-2.1 (m, 2H), 2.9-3.7 (m, 10H), 4.02 (t, 2H), 4.66 (s, 1H), 6.8-7.4 (m, 5H), 10.43 (brs, 2H).

Values of elemental analysis (as C$_{17}$H$_{22}$N$_4$O$_3$): Calcd. (%): C 61.80; H 6.71; N 16.96 Found (%): C 61.86; H 6.73; N 16.88.

6-[4-(3-phenoxypropyl)piperazin-1-yl]-2,4(1H,3H)pyrimidinedione obtained above was treated with an HCl/methanol solution in an ordinary manner to prepare 6-[4-(3-phenoxypropyl)piperazin-1-yl]-2,4(1H,3H)-pyrimidinedione.hydrochloride (Compound 74).

Melting point: 250° C. or more

Values of elemental analysis (as C$_{17}$H$_{22}$N$_4$O$_3$.HCl): Calcd. (%): C 55.66; H 6.32; N 15.27; Cl 9.66; Found (%): C 55.42; H 6.32; N 15 10; Cl 11.13.

IR $\nu_{max}^{KBr}$ (cm$^{-1}$): 1720, 1650, 1490, 1400, 1250, 1170, 965, 760, 695, 535.

EXAMPLE 14

Preparation of
6-[4-(2-[4-chlorophenoxy]ethyl)piperazin-1-yl]-1,3-dimethyl-2,4(1H, 3H)-pyrimidinedione.hydrochloride (Compound 75)

The same treatment as in Example 13 was effected except that phenoxyethyl bromide was replaced with 2-(4-chlorophenoxy)ethyl bromide, thereby obtaining the crystals of 6-[4-(2-[4-chlorophenoxy]ethyl)piperazin-1-yl]-1,3-dimethyl-2,4(1H,3H)-pyrimidinedione.

Analytical results of the obtained pyrimidinedione derivative

Melting point: 130°-132° C.

NMR (CDCl$_3$) δ ppm: 2.6-3.1 (m, 10H), 3.52 (s, 3H), 3.38 (s, 3H), 4.04 (t, 2H), 5.22 (s, 1H), 6.7-7.4 (m, 4H).

Values of elemental analysis (as C$_{18}$H$_{23}$ClN$_4$O$_3$): Calcd. (%): C 57.07; H 6.12; Cl 9.36; N 14.79; Found (%): C 56.70; H 6.41; Cl 9.40; N 14.53.

1.0 g of this pyrimidinedione derivative was treated with an HCl/methanol solution in an ordinary manner to obtain 5.20 g of crystalline 6-[4-(2-[4-chlorophenoxy]-ethyl)piperazin-1-yl]-1,3-dimethyl-2,4(1H,3H)-pyrimidinedione.hydrochloride (Compound 75).

Analytical results of the obtained Compound 75:

Melting point: 139° C. (decomposed).

Values of elemental analysis (as C$_{18}$H$_{23}$ClN$_4$O$_3$.2HCl.2H$_2$O): Calcd. (%): C 44.32; H 5.99; Cl 21.80; N 11.49; Found (%): C 44.06; H 6.13; Cl 22.31; N 11.28.

IR $\nu_{max}^{KBr}$ (cm$^{-1}$): 3385, 3080, 2950, 2590, 1730, 1496, 1244, 1097, 843, 800, 761, 588.

EXAMPLE 15

Preparation of
6-[4-(3-[4-chlorophenoxy]propyl)piperazin-1-yl]-2,4(1H,3H)-pyrimidinedione.hydrochloride
(Compound 76)

The same treatment as in Example 13 was effected except that phenoxypropyl bromide was replaced with 3-(4-chlorophenoxy)propyl bromide, thereby obtaining the crystals of 6-[4-(3-[4-chlorophenoxy]propyl)piperazin-1-yl]-2,4(1H,3H)-pyrimidinedione.

Analytical results of the obtained pyrimidinedione derivative

Melting point: 246°–250° C.

NMR (CF$_3$COOH) δppm: 2.2–2.7 (m, 2H), 3.1–4.6 (m, 12H), 5.75 (s, 1H), 6.86 (d, 2H), 7.33 (d, 2H).

1.0 g of this pyrimidinedione derivative was treated with an HCl/methanol solution in an ordinary manner to obtain the crystals of 6-[4-(3-[4-chlorophenoxy]propyl)piperazin-1-yl]-2,4(1H,3H)-pyrimidinedione.hydrochloride (Compound 76).

Analytical results of the obtained Compound 76:

Melting point: 265°–268° C.

IR $\nu_{max}^{KBr}$(cm$^{-1}$): 1700, 1640, 1485, 1240, 1085, 960.

EXAMPLE 16

Preparation of
1,3-dimethyl-6-[4-(3-[4-trifluoroacetylaminophenoxy]propyl)piperazin-1-yl]-2,4(1H,3H)-pyrimidinedione.hydrochloride (Compound 77)

ganic layer was then separated. The aqueous layer was neutralized and then extracted with 50 ml of chloroform, and the extract layer was mixed with the organic layer previously separated and the mixture was dried and then concentrated to obtain 0.52 g (yield: 38%) of 1,3-dimethyl-6-[4-(3-[4-trifluoroacetylaminophenoxy]propyl)piperazin-1-yl]-2,4(1H,3H)-pyrimidinedione.

Analytical results of the obtained pyrimidinedione derivative

Melting point: 231°–234° C.

NMR (CDCl$_3$) δ ppm: 1.94 (m, 2H), 2.56 (m, 6H), 2.92 (m, 4H), 3.29 (s, 3H), 3.35 (s, 3H), 3.99 (t, J=6.5 Hz, 2H), 5.26 (s, 1H), 6.88 (d, J=9.5 Hz, 2H), 7.46 (d, J=9.5 Hz, 2H), 8.11 (br. s, 1H).

Values of elemental analysis (as C$_{21}$H$_{26}$N$_5$O$_4$F$_3$): Calcd. (%): C 53.73; H 5.58; N 14.92; F 12.14; Found (%): C 53.56; H 5.89; N 14.77; F 11.55.

IR $\nu_{max}^{KBr}$ (cm$^{-1}$): 3440, 1720, 1700, 1632, 1605, 1515, 1288, 1240, 1200, 1159, 1002, 833, 810.

This pyrimidinedione derivative was treated with an HCl/methanol solution in an ordinary manner to obtain the crystals of 1,3-dimethyl-6-[4-(3-[4-trifluoroacetylaminophenoxy]propyl)piperazin-1-yl]-2,4(1H,3H)-pyrimidinedione.hydrochloride (Compound 77).

Analytical results of the obtained Compound 77:

Melting point: 255° C. or more.

Values of elemental analysis (as C$_{21}$H$_{26}$N$_5$O$_4$F$_3$.HCl): Calcd. (%): C 49.86; H 5.38; N 13.84; Cl 7.01; Found (%): C 49.70; H 5.74; N 13.87; Cl 7.10.

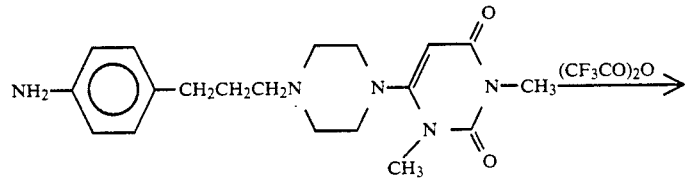

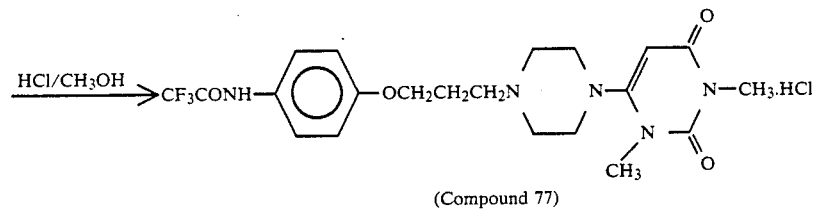

(Compound 77)

0.5 ml of anhydrous trifluoroacetic acid was added dropwise at 0° C. to 20 ml of a dichloromethane solution containing 1.1 g of 6-[4-(3-[4-aminophenoxy]propyl)piperazin-1-yl]-1,3-dimethyl-2,4(1H,3H)-pyrimidinedione obtained in Example 6, and the solution was then stirred at the same temperature for 10 minutes and further at room temperature for 1 hour. Next, the reaction mixture was diluted with 100 ml of chloroform and 50 ml of a 0.5N aqueous sodium hydroxide solution so as to dissolve insolubles therein, and the resultant organic layer was then separated.

IR $\nu_{max}^{KBr}$ (cm$^{-1}$): 3450, 1730, 1705, 1650, 1515, 1440, 1240, 1205, 1160.

EXAMPLE 17

Preparation of
1,3-dimethyl-6-[4-(3-[4-trifluoromethanesulphonylaminophenoxy]propyl)piperazin-1-yl]-2,4(1H,3H)-pyrimidinedione.hydrochloride
(Compound 78)

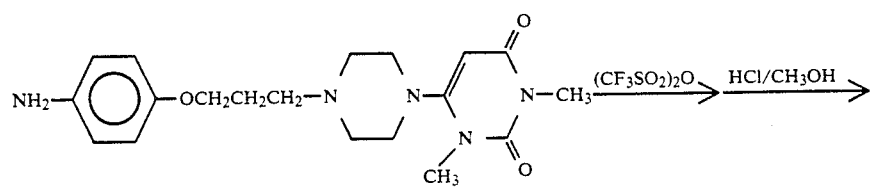

-continued

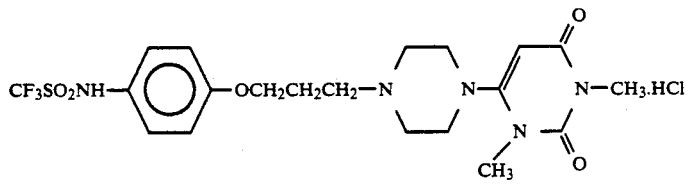

(Compound 78)

5 ml of a dichloromethane solution containing 0.65 ml of anhydrous trifluoromethanesulfonic acid was added at −78° C. to 25 ml of a dichloromethane solution containing 1.3 g of 6-[4-(3-[4-aminophenoxy]propyl)piperazin-1-yl]-1,3-dimethyl-2,4(1H,3H)-pyrimidinedione obtained in Example 6, and the temperature of the solution was then gradually elevated to room temperature, while it was stirred. 20 ml of dichloromethane and a 2% aqueous potassium carbonate solution were added to the reaction solution, followed by stirring until insolubles were dissolved therein. After the separation of the resultant organic layer, the aqueous layer was neutralized and then extracted with chloroform (50 ml×2), and the extract layers were joined and mixed with the organic layer previously obtained. The mixture was dried over sodium sulfate and then concentrated to obtain 1.1 g (yield: 62.5%) of 6-[4-(3-[4-trifluoromethanesulfonylaminophenoxy]propyl)piperazin-1-yl]-2,4(1H,3H)-pyrimidinedione in a crystalline state.

Analytical results of the obtained pyrimidinedione derivative

Melting point: 193.5°–195.5° C.

NMR (CDCl$_3$) δ ppm: 1.98 (m, 2H), 2.60 (m, 6H), 2.96 (m, 4H), 3.32 (s, 3H), 3.40 (s, 3H), 4.00 (t, J=6 Hz, 2H), 5.33 (s, 1H), 5.62 (br. s, 1H), 6.90 (d, J=10 Hz, 2H), 7.30 (d, J=10 Hz, 2H).

Values of elemental analysis (as $C_{20}H_{26}N_5O_5SF_3$): Calcd. (%): C 47.52; H 5.18; N 13.85; F 11.27; S 6.34; Found (%): C 47.38; H 5.52; N 13.63; F 10.64; S 6.56.

IR $\nu_{max}^{KBr}$ (cm$^{-1}$): 3430, 1700, 1630, 1508, 1380, 1210, 1150, 605.

This pyrimidinedione derivative was treated with an HCl/methanol solution in an ordinary manner to obtain the crystals of 1,3-dimethyl-6-[4-(3-[4-trifluoromethanesulphonylaminophenoxy]propyl)piperazin-1-yl]-2,4(1H,3H)-pyrimidinedione.hydrochloride (Compound 78).

Analytical results of the obtained Compound 78:
Amorphous crystals
Values of elemental analysis (as $C_{20}H_{26}N_5O_5SF_3 \cdot 1.1HCl \cdot H_2O$): Calcd. (%): C 42.62; H 5.20; N 12.43; Cl 6.92; S 5.69; Found (%): C 42.48; H 5.66; N 11.34; Cl 7.11; S 5.83.

EXAMPLE 18

Preparation of 1,3-dimethyl-6-[4-(3-[4-ethanesulphonylaminophenoxy]propyl)piperazin-1-yl]-2,4(1H,3H)-pyrimidinedione.hydrochloride (Compound 79)

The same treatment as in Example 17 was effected except that anhydrous trifluoromethanesulfonic acid was replaced with anhydrous ethanesulfonic acid, thereby obtaining the crystals of 1,3-dimethyl-6-[4-(3-[4-ethanesulphonylaminophenoxy]propyl)piperazin-1-yl]-2,4(1H,3H)-pyrimidinedione.

Analytical results of the obtained pyrimidinedione derivative

Melting point: 144°–145° C.

NMR (CDCl$_3$) δ ppm: 1.38 (t, 3H), 2.00 (m, 2H), 2.60 (m, 6H), 3.00 (m, 4H), 3.06 (q, 2H), 3.34 (s, 3H), 3.41 (s, 3H), 4.04 (t, 2H), 5.31 (s, 1H), 6.91–7.26 (m, 4H).

Values of elemental analysis (as $C_{21}H_{31}N_5O_5$): Calcd. (%): C 54.18; H 6.71; N 15.04; S 6.89; Found (%): C 53.61; H 6.87; N 15.10; S 6.85.

IR $\nu_{max}^{KBr}$ (cm$^{-1}$): 1690, 1642, 1513, 1337, 1153, 1002, 910, 800, 730.

This pyrimidinedione derivative was treated with an HCl/methanol solution in an ordinary manner to obtain the crystals of 1,3-dimethyl-6-[4-(3-[4-ethanesulphonylaminophenoxy]propyl)piperazin-1-yl]-2,4(1H,3H)-pyrimidinedione.hydrochloride (Compound 79).

Analytical results of the obtained Compound 79:
Melting point: 258.5°–260.6° C. (decomposed)
Values of elemental analysis (as $C_{21}H_{31}N_5O_5S \cdot HCl$): Calcd. (%): C 50.24; H 6.24; N 13.95; S 6.39; Cl 7.06; Found (%): C 49.61; H 6.76; N 13.89; S 6.37; Cl 7.08.

EXAMPLE 19

Preparation of 6-[4-(3-[4-benzenesulphonylaminophenoxy]propyl)piperazin-1-yl]-1,3-dimethyl-2,4(1H,3H)-pyrimidinedione.hydrochloride (Compound 80)

The same treatment as in Example 17 was effected except that anhydrous trifluoromethanesulfonic acid was replaced with anhydrous benzenesulfonic acid, thereby obtaining the crystals of 6-[4-(3-[4-benzenesulphonylaminophenoxy]propyl)piperazin-1-yl]-1,3-dimethyl-2,4(1H,3H)-pyrimidinedione.

Analytical results of the obtained pyrimidinedione derivative

Melting point: 137°–139° C.

NMR (CDCl$_3$/DMSO-d$_6$=4/1) δ ppm: 1.92 (m, 2H), 2.60 (m, 6H), 2.98 (m, 4H), 3.29 (s, 3H), 3.39 (s, 3H), 3.97 (m, 2H), 5.21 (s, 1H), 6.72 (d, 2H), 7.48 (m, 2H), 7.48 (m, 3H), 7.76 (m, 2H), 9.52 (br. s, 1H).

Values of elemental analysis (as $C_{25}H_{31}N_5O_5S \cdot \frac{1}{2}H_2O$): Calcd. (%): C 57.46; H 6.17; N 13.40; S 6.13; Found (%): C 57.73; H 6.47; N 13.08; S 5.98.

This pyrimidinedione derivative was treated with an HCl/methanol solution in an ordinary manner to obtain the crystals of 6-[4-(3-[4-benzenesulphonylaminophenoxy]-propyl)piperazin-1-yl]-1,3-dimethyl-2,4(1H,3H)-pyrimidinedione.hydrochloride (Compound 80).

Analytical results of the obtained Compound 80:
Melting point: 162.5°–166.5° C.

Values of elemental analysis (as $C_{25}H_{31}N_5O_5S \cdot HCl \cdot H_2O$): Calcd. (%): C 52.86; H 6.03; N 12.33; S 5.64; Cl 6.24; Found (%): C 52.72; H 6.55; N 11.79; S 5.46; Cl 5.88.

IR $\nu_{max}^{KBr}$ (cm$^{-1}$): 3180, 1705, 1660, 1620, 1512, 1332, 1250, 1167, 802, 762, 587.

EXAMPLE 20

Preparation of 1,3-dimethyl-6-[4-(3-[4-(N'-methylureido)phenoxy]propyl)piperazin-1-yl]-2,4(1H,3H)-pyrimidinedione.hydrochloride (Compound 81)

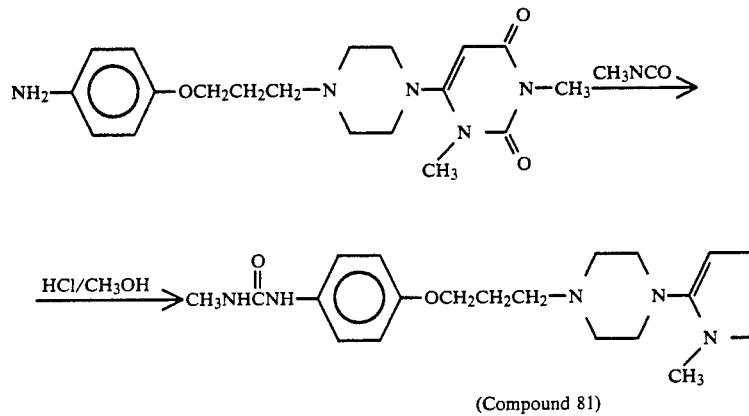

(Compound 81)

1.5 g of 6-[4-(3-[4-aminophenoxy]propyl)piperazin-1-yl]-1,3-dimethyl-2,4(1H,3H)-pyrimidinedione obtained in Example 6 was dissolved in a mixed solvent of tetrahydorfuran/dichloromethane (15 ml/10 ml), and 0.26 ml of methyl isocyanate was added to the solution at room temperature, followed by stirring for 20 hours. The precipitated crystals were collected by filtration, and then washed with a small amount of cooled dichloromethane, thereby obtaining 1.55 g (yield: 90%) of 1,3-dimethyl-6-[4-(3-[4-(N'-methylureido)phenoxy]propyl)piperazin-1-yl]-2,4(1H,3H)-pyrimidinedione.

Analytical results of the obtained pyrimidinedione derivative

Melting point: 178.5°–181.5° C.

NMR (CDCl$_3$) δ ppm: 1.92 (m, 2H), 2.56 (m, 6H), 2.74 (d, 3H), 2.93 (m, 4H), 3.28 (s, 3H), 3.35 (s, 3H), 3.91 (t, 2H), 5.21 (s, 1H), 5.30 (m, 1H), 6.76–7.24 (m, 4H).

Values of elemental analysis (as C$_{21}$H$_{30}$N$_6$O$_4$·C$_2$H$_5$OH): Calcd. (%): C 57.97; H 7.61; N 17.63; Found (%): C 57.95; H 7.91; N 17.75.

This pyrimidinedione derivative was treated with an HCl/methanol solution in an ordinary manner to obtain the crystals of 1,3-dimethyl-6-[4-(3-[4-(N'-methylureido)phenoxy]propyl)piperazin-1-yl]-2,4(1H,3H)-pyrimidinedione.hydrochloride (Compound 81).

Analytical results of the obtained Compound 81:

Melting point: 265.5°–266.5° C.

Values of elemental analysis (as C$_{21}$H$_{30}$N$_6$O$_4$·HCl·H$_2$O): Calcd. (%): C 52.01; H 6.86; N 17.33; Cl 7.31; Found (%): C 52.75; H 7.00; N 17.88; Cl 6.60.

IR $\nu_{max}^{KBr}$ (cm$^{-1}$): 3360, 1690, 1650, 1612, 1550, 1505, 1440.

EXAMPLE 21

Preparation of 6-[4-(4-[4-chlorophenoxy]butyl)piperazin-1-yl]-1,3-dimethyl-2,4(1H,3H)-pyrimidinedione.hydrochloride (Compound 82)

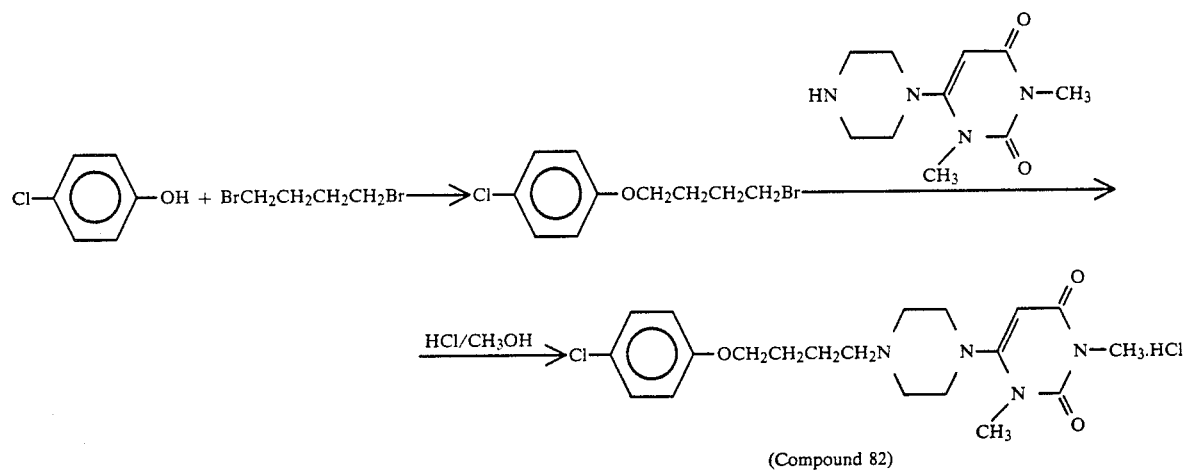

(Compound 82)

13 g of p-chlorophenol, 40 g of 1,4-dibromobutane and 15.5 g of potassium carbonate were suspended in methyl ethyl ketone, and the solution was then heated under reflux for 3 hours. After cooling, the precipitate was removed by filtration, and the filtrate was then concentrated. 3 ml of triethylamine was added to 40 ml of an ethanol solution containing 2.6 g of the resultant concentrate and 1.3 g of 1,3-dimethyl-6-(1-piperazinyl)-2,4(1H,3H)pyrimidinedione, and the solution was then heated under reflux for 3 hours. After cooling, the reaction solution was concentrated, and the precipitated crystals were then collected by filtration, washed with water and ethanol, and then dried to obtain 1.2 g (yield 50 %) of 6-[4-(4-[4-chlorophenoxy]butyl)piperazin-1-yl]-1,3-dimethyl-2,4(1H,3H)-pyrimidinedione.

Analytical results of the obtained pyrimidinedione derivative

NMR (CDCl$_3$) δ ppm: 1.5–2.0 (m, 4H), 2.4–2.7 (m, 6H), 2.8–3.1 (m, 4H), 3.32 (s, 3H), 3.38 (s, 3H), 3.94 (t, J=7 Hz, 2H), 6.82 (d, J=10 Hz, 2H), 7.24 (d, J=10 Hz, 2H).

This pyrimidinedione derivative was treated with an HCl/methanol solution in an ordinary manner to obtain the crystals of 6-[4-(4-[4-chlorophenoxy]butyl)piperazin-1-yl]-1,3-dimethyl-2,4(1H,3H)-pyrimidinedione.hydrochloride (Compound 82).

Analytical results of the obtained Compound 82:
Melting point: 200°–202° C.
Values of elemental analysis (as C$_{20}$H$_{27}$N$_4$O$_3$Cl.HCl.½H$_2$O): Calcd. (%): C 53.45; H 6.73; N 12.38; Cl 15.23; Found (%): C 53.10; H 6.46; N 12.38; Cl 15.67.

EXAMPLE 22

Preparation of 1,3-dimethyl-6-[4-(3-[4-dimethanesulfonylaminophenoxy]propyl)piperazin-1-yl]-2,4(1H,3H)-pyrimidinedione.hydrochloride (Compound 83)

15 ml of a chloroform solution containing 1.0 g of 6-[4-(3-[4-aminophenoxy]propyl)piperazin-1-yl]-1,3-dimethyl-2,4(1H,3H)-pyrimidinedione obtained in Example 6 and 2.5 ml of triethylamine was added to 5 ml of a chloroform solution containing 1.5 g of methanesulfonyl chloride, and the solution was then stirred at room temperature for 30 minutes. Afterward, water was added to the solution, and this solution was then subjected to separation, drying, concentration and purification through a silica gel column chromatograph (chloroform/methanol=50/1). Next, the thus obtained 1,3-dimethyl-6-[4-(3-[4-dimethanesulfonylaminophenoxy]propyl)piperazin-1-yl]-2,4(1H,3H)-pyrimidinedione was treated with an HCl/methanol solution in an ordinary manner to obtain 0.75 g of crystalline 1,3-dimethyl-6-[4-(3-[4-dimethanesulfonylaminophenoxy]propyl)piperazin-1-yl]-2,4(1H,3H)-pyrimidinedione.hydrochloride (Compound 83).

Analytical results of the obtained Compound 83:
Melting point: 223°–227° C.
Values of elemental analysis (as C$_{21}$H$_{31}$N$_5$O$_7$S$_2$.1.5HCl): Calcd. (%): C 43.10; H 5.61; N 11.99; S 10.97; Cl 9.10; Found (%): C 42.82; H 6.00; N 11.74; S 11.90; Cl 8.72.

EXAMPLE 23

Preparation of 1,3-dimethyl-6-[4-(2-[2-benzoylphenyl]ethyl)piperazin-1-yl]-2,4(1H,3H)-pyrimidinedione.oxalate (Compound 84)

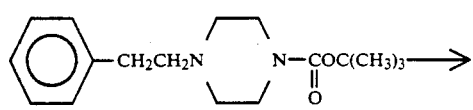

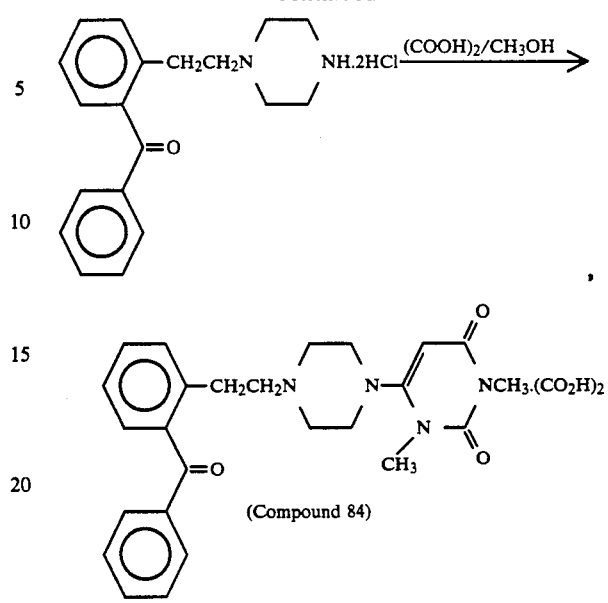

(Compound 84)

(1) Synthesis of 1-(2-[2-benzoylphenyl]ethyl)piperazine.hydrochloride 1.1 g of 1-(t-butyloxycarbonyl)-4-(2-phenylethyl)piperazine was dissolved in 8 ml of tetrahydrofuran, and 2.8 ml of butyllithium (1.6N, a hexane solution) was added dropwise to the solution at −30° C. followed by stirring for 30 minutes. Next, 0.88 ml of benzoyl chloride was added thereto, and the solution was stirred for 3 hours, poured into ice water, and then extracted with 50 ml of chloroform. The resultant chloroform layer was washed with water, dried over anhydrous sodium sulfate, and then concentrated, and the residue was separated through a silica gel column chromatograph (hexane/ethyl acetate=1/1). The resultant oil dissolved in 10 ml of ether, and 4.8 ml of a 4N hydrochloric acid/dioxane solution was added thereto, followed by stirring at room temperature for 30 minutes. The precipitated crystals were collected by filtration, whereby 0.36 g of 1-2-[2-benzoylphenyl]ethyl)piperazine.hydrochloride was obtained.

(2) Preparation of 1,3-dimethyl-6-[4-(2-[2-benzoylphenyl]ethyl)piperazin-1-yl]-2,4 (1H,3H) -pyrimidinedione.oxalate (Compound 84)

0.34 g of 1-(2-[2-benzoylphenyl]ethyl)piperazine.hydrochloride, 0.20 g of 6-chloro-1,3-dimethyl-2,4(1H,3H)-pyrimidinedione and 0.6 ml of triethylamine were dissolved in 10 ml of isopropylalcohol, and the solution was heated under reflux with stirring for 6 hours.

After standing for cooling, the solution was concentrated under reduced pressure, and 50 ml of chloroform was added thereto. Next, the chloroform solution was washed with water twice, dried over anhydrous sodium sulfate, and then concentrated. The resultant residue was purified through a silica gel column chromatograph (chloroform/methanol=50/1), thereby obtaining 0.31 g of 1,3-dimethyl-6-[4-(2-[2-benzoylphenyl]ethyl)piperazin-1-yl]-2,4(1H,3H)-pyrimidineione.

Analytical results of the obtained pyrimidinedione derivative

NMR (CDCl$_3$) δ ppm: 2.3–3.1 (m, 12H), 3.34 (s, 3H), 3.39 (s, 3H), 4.96 (s, 1H), 7.1–8.0 (m, 9H).

0.28 g of this pyrimidinedione derivative was treated with an oxalic acid/methanol solution in an ordinary manner to obtain 0.22 g of 1,3-dimethyl-6-[4-(2-[2-benzoylphenyl]ethyl)piperazin-1-yl]-2,4(1H,3H)-pyrimidinedione.oxalate (Compound 84).

Analytical results of the obtained Compound 84
Melting point: 178°–179° C. (decomposed).
IR $\nu_{max}^{KBr}$ (cm$^{-1}$): 2550, 1700, 1640, 840, 760, 700.
Values of elemental analysis (as C$_{25}$H$_{28}$N$_4$O$_3$·(CO$_2$H)$_2$·1.5H$_2$O) Calcd. (%): C 59.07; H 6.05; N 10.19; Found (%): C 59.04; H 6.23; N 9.73.

EXAMPLE 24

Preparation of 1,3-dimethyl-6-[4-(2-[2-acetylphenyl]ethyl)piperazin-1-yl]-2,4(1H,3H)-pyrimidinedione.oxalate (Compound 85)

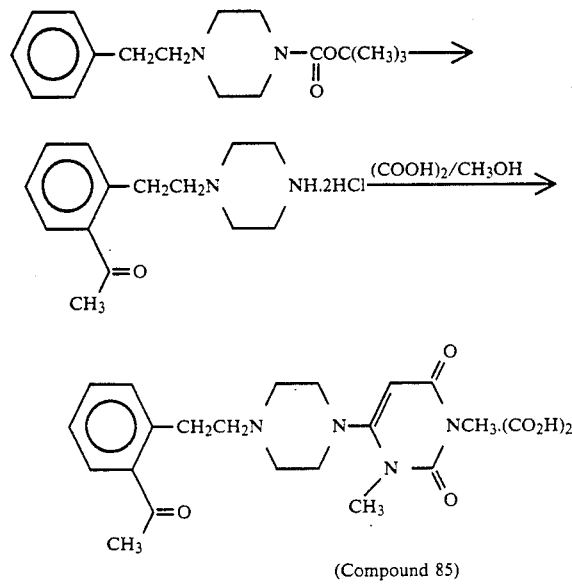

(Compound 85)

(1) Preparation of 1-[2-(2-acetylphenyl)ethyl]-piperazine.hydrochloride

The same procedure as in the section (1) of Example 23 was effected except that benzoyl chloride was replaced with 1.0 ml of anhydrous acetic acid, thereby obtaining 0.52 g of 1-[2-(2-acetylphenyl)ethyl]-piperazine.hydrochloride.

(2) Preparation of 1,3-dimethyl-6-[4-(2-[2-acetylphenyl]ethyl)piperazin-1-yl]-2,4(1H,3H)-pyrimidinedione.oxalate (Compound 85):

The same procedure as in the section (2) of Example 23 was effected except that 1-2-[2-benzoylphenyl]ethyl)piperazine.hydrochloride was replaced with 0.28 g of 1-[2-(2-acetylphenyl)ethyl]piperazine.hydrochloride, thereby obtaining 0.39 g of 1,3-dimethyl-6-[4-(2-[2-acetylphenyl]ethyl)piperazin-1-yl]-2,4(1H,3H)-pyrimidinedione.

Analytical results of the obtained pyrimidinedione derivative

NMR (CDCl$_3$) δ ppm: 2.08 (s, 3H), 2.8 (m, 10H), 3.30 (s, 3H), 3.36 (s, 3H), 3.5 (m, 2H), 5.18 (s, 1H), 7.19 (m, 4H).

0.36 g of this pyrimidinedione derivative was treated with an oxalic acid/methanol solution in an ordinary manner to obtain 0.30 g of 1,3-dimethyl-6-[4-(2-[2-acetylphenyl]ethyl)piperazin-1-yl]-2,4(1H,3H)-pyrimidinedione.oxalate (Compound 85).

Analytical results of the obtained Compound 85
Melting point: 195°–197° C. (decomposed).
IR $\nu_{max}^{KBr}$ (cm$^{-1}$): 3000, 1710, 1670, 1640, 1620, 720.
Values of elemental analysis (as C$_{20}$H$_{26}$N$_4$O$_3$·(CO$_2$H)$_2$·½H$_2$O): Calcd. (%): C 56.28; H 6.23; N 11.93; Found (%): C 59.14; H 6.61; N 11.50.

EXAMPLE 25

Production of Tablets Containing, as an Effective Ingredient, 6-[4-(3-[4-chlorophenoxy]propyl)piperazin-1-yl]-1,3-dimethyl-2,4(1H,3H)-pyrimidinedione.hydrochloride (Compound 64) which can be obtained by the procedure of Example 3

With 20 g of corn starch were sufficiently mixed 1 g of the above pyrimidinedione derivative.hydrochloride (Compound 64) and 123 g of lactose, and the mixture was further mixed with a solution prepared by dissolving 5 g of hydroxypropyl cellulose in 100 ml of water, so as to form grains, followed by drying the grains at 50° C. for 4 hours. Afterward, 1 g of magnesium stearate was added to the dried grains and then mixed sufficiently. The mixture was then formed into tablets by the use of a tableting machine, the weight of each tablet being 150 mg.

EXAMPLE 26

Preparation of Capsules Containing, as an Effective Component, 6-[4-(3-[4-chlorophenoxy]propyl)piperazin-1-yl]-1,3-dimethyl-2,4(1H,3H)-pyrimidinedione.hydrochloride (Compound 64) which can be obtained by the procedure of Example 3

With 25 g of corn starch were sufficiently mixed 5 g of the above pyrimidinedione derivative.hydrochloride (Compound 64) and 120 g of lactose, and hard capsules were filled with the reactant mixture by the use of a capsule filling machine to obtain capsules, the content of the mixture in each capsule being 150 mg.

EXAMPLE 27

Preparation of an Injection Containing, as an Effective Component, 6-[4-(3-[4-chlorophenoxy]propyl)piperazin-1-yl]-1,3-dimethyl-2,4(1H,3H)-pyrimidinedione.hydrochloride (Compound 64) which can be obtained by the procedure of Example 3

In a suitable amount of distilled water for injection were dissolved 20 mg of the above pyrimidinedione derivative.hydrochloride (Compound 64) and 0.85 g of sodium chloride, and the total volume of the liquid was then regulated to be 100 ml, thereby preparing an injection.

EXAMPLE 28

Synthesis of 1,3-dimethyl-6-[2-(3-phenoxypropylamino)ethylamino]-2,4(1H,3H)-pyrimidinedione.bromate (Compound 86)

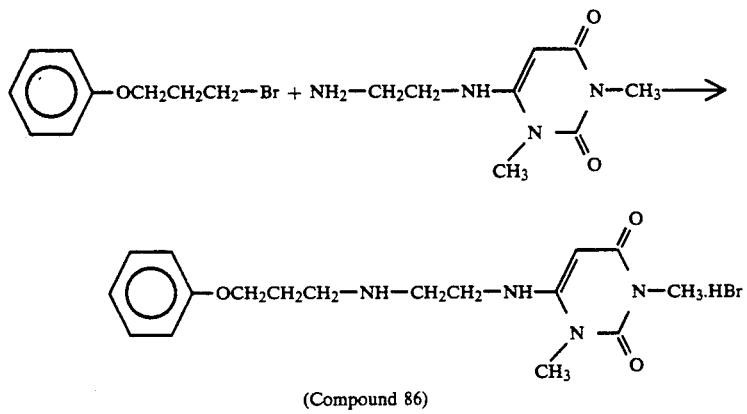

(Compound 86)

0.99 g of 1,3-dimethyl-6-[2-aminoethylamino]-2,4(1H,3H)-pyrimidinedione was dissolved in 25 ml of dimethylformamide, and 0.6 g of triethylamine was added to the solution. Heating was then made so as to attain a temperature of from 60° to 70° C., and 1.08 g of 3-phenoxypropyl bromide was added dropwise slowly to the solution. After completion of the addition, the solution was heated and stirred at 80° C. for 3 hours, and the reaction solution was then concentrated to dryness.

Afterward, 50 ml of dichloromethane was added to the residue, and insolubles were then removed therefrom by filtration. The resultant filtrate was concentrated, purified through a silica gel column chromatograph (dichloromethane/methanol = 100/3 to 100/6 in volume ratio), and then recrystallized from hexane/methanol to prepare 0.14 g of 1,3-dimethyl-6-[2-(3-phenoxypropylamino) ethylamino]-2,4(1H,3H)-pyrimidinedione.bromate (Compound 86).

Analytical results of the crystals of the obtained Compound 86:

Melting point: 218°–220° C.

IR $v_{max}^{KBr}$ (cm$^{-1}$): 3260, 2780, 2700, 1700, 1620, 1590, 1550, 1480, 780, 755.

Values of elemental analysis (as $C_{17}H_{24}N_4O_3 \cdot HBr \cdot \frac{1}{2} H_2O$): Calcd. (%): C 48.35; H 6.21; N 13.27; Br 18.92; Found (%): C 48.55; H 6.37; N 13.40; Br 18.16.

EXAMPLE 29

Synthesis of 1,3-dimethyl-6-[4-(4-phenylbutyl)piperazin-1-yl]-2,4(1H,3H)-pyrimidinedione.hydrochloride (Compound 87)

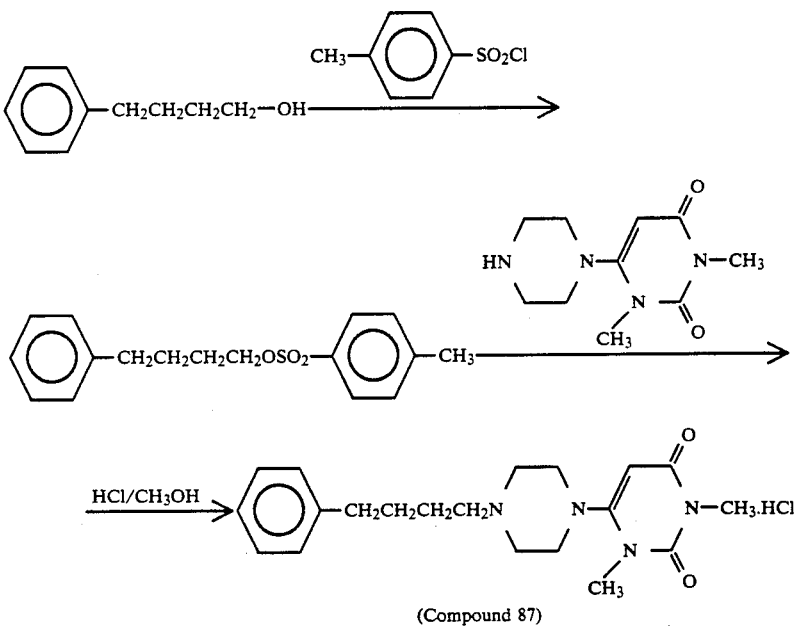

(Compound 87)

(1) Synthesis of 4-phenylbutyl p-trienesulfonate 4.0 g of 4-phenyl-1-butanol and 5 ml of pyridine were dissolved in 30 ml of methylene chloride, and 6.1 g of p-toluenesulfonyl chloride was added thereto at 0° C., followed by stirring at room temperature overnight. Next, 2 ml of water was added, and the solution was stirred for 2 hours. After 50 ml of methylene chloride was added, the solution was washed with water, a 1N aqueous sodium hydroxide solution and a saturated sodium chloride solution in this order. The resultant organic layer was dried over anhydrous magnesium sulfate, and the solvent was distilled off under reduced pressure, so that 6.07 g of 4-phenylbutyl p-trienesulfonate was obtained in a colorless oily state.

Analytical results of the obtained ester derivative $^1$H-NMR (CDCl$_3$) δ ppm: 1.70 (m, 4H), 2.42 (s, 3H), 2.50 (m, 2H), 4.04 (m, 2H), 7.0–7.90 (m, 9H).

(2) Synthesis of 1,3-dimethyl-6-[4-(4-phenylbutyl)piperazin-1-yl]-2,4(1H,3H)-pyrimidinedione.hydrochloride (Compound 87)

A mixture of 1.0 g of 4-phenylbutyl p-trienesulfonate and 0.67 g of 1,3-dimethyl-6-(1-piperazinyl)-2,4-(1H,3H)-pyrimidinedione was heated at 100° C. for 2 hours. After standing for cooling, the reaction mixture was dissolved in 100 ml of chloroform, and the resultant chloroform solution was then washed with an aqueous saturated sodium hydrogencarbonate solution and a saturated sodium chloride solution in this order, followed by drying over anhydrous magnesium sulfate. The dried solution was concentrated to dryness under reduced pressure, and the residue was purified through a silica gel column chromatograph (chloroform/methanol=100/3 to 100/6 in volume ratio), thereby obtaining 0.56 g of 1,3-dimethyl-6-[4-(4-phenylbutyl)piperazin-1-yl]-2,4(1H,3H)-pyrimidinedione in a colorless oily state.

Analytical results of the obtained pyrimidinedione derivative $^1$H-NMR (DMSO-d$_6$) δ ppm: 1.70 (m, 4H), 2.63 (t, 2H), 2.9–3.70 (m, 16H), 5.23 (s, 1H), 7.27 (m, 5H).

1.0 g of this pyrimidinedione derivative was treated with a hydrochloric acid/methanol solution in an ordinary manner to obtain 0.3 g of crystalline 1,3-dimethyl-6-[4-(4-phenylbutyl)piperazin-1-yl]-2,4(1H,3H)-pyrimidinedione.hydrochloride (Compound 87).

Analytical results of the obtained Compound 87:
Melting point: 227.5°–231° C.
IR $\nu_{max}^{KBr}$ (cm$^{-1}$): 2920, 2380, 1690, 1645, 1610, 1490, 1428.
Values of elemental analysis (as C$_{20}$H$_{28}$N$_4$O$_2$.HCl.½H$_2$O): Calcd. (%): C 59.77; H 7.52; N 13.94; Cl 8.82; Found (%): C 60.04; H 7.63; N 13.87; Cl 8.85.

EXAMPLE 30

Synthesis of 1,3-dimethyl-6-[4-(2-phenylethyl)-piperazin-1-yl]-2,4(1H,3H)-pyrimidinedione.hydrochloride (Compound 88)

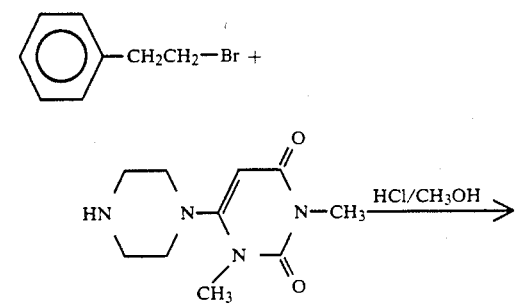

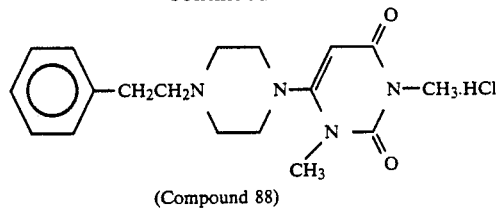

(Compound 88)

The same treatment as in Example 4 was effected except that phenoxyethyl bromide was replaced with 1.85 g of phenethyl bromide, thereby obtaining 1.16 g of crystalline 1,3-dimethyl-6-[4-(2-phenylethyl)piperazin-1-yl]-2,4(1H,3H)-pyrimidinedione.

Analytical results of the obtained pyrimidinedione derivative

Melting point: 115°–116° C.
$^1$H-NMR (CDCl$_3$) δ ppm: 2.6–3.4 (m, 12H), 3.34 (s, 3H), 3.40 (s, 3H), 5.25 (s, 1H), 7.2–7.4 (m, 5H).
Values of elemental analysis (as C$_{18}$H$_{24}$N$_4$O$_2$): Calcd. (%): C 65.83; H 7.37; N 17.06; Found (%): C 65.41; H 7.26; N 17.20.

0.4 g of this pyrimidinedione derivative was treated with a hydrochloric acid/methanol solution in an ordinary manner to obtain 0.44 g of the crystals of 1,3-dimethyl-6-[4-(2-phenylethyl)piperazin-1-yl]-2,4(1H,3H)-pyrimidinedione.hydrochloride (Compound 88).

Analytical results of the obtained Compound 88:
Melting point: 194° C. (decomposed).
IR $\nu_{max}^{KBr}$ (cm$^{-1}$): 3470, 3400, 2930, 1710, 1640, 1580, 1510, 1430, 1380, 1230.
Values of elemental analysis (as C$_{18}$H$_{24}$N$_4$O$_2$.2HCl.½H$_2$O): Calcd. (%): C 52.69; H 6.63; N 13.65; Cl 17.28; Found (%): C 52.67; H 7.00; N 13.77; Cl 17.14.

EXAMPLE 31

Synthesis of 1,3-dimethyl-6-[4-(3-phenylpropyl)piperazin-1-yl]-2,4(1H,3H)-pyrimidinedione.hydrochloride (Compound 89)

(Compound 89)

The same treatment as in Example 4 was effected except that phenoxyethyl bromide was replaced with 2.0 g of 3-phenylpropyl bromide, thereby obtaining 1,3-dimethyl-6-[4-(3-phenylpropyl)piperazin-1-yl]-2,4(1H,3H)-pyrimidinedione. This pyrimidinedione derivative was treated with a hydrochloric acid/methanol solution in an ordinary manner to obtain 1.04 g of crystalline 1,3-dimethyl-6-[4-(3-phenylpropyl)piperazin-1-yl]-2,4(1H,3H)-pyrimidinedione.hydrochloride (Compound 89).

Analytical results of the obtained Compound 89:
Melting point: 251°–253° C. (decomposed).
IR $\nu_{max}^{KBr}$ (cm$^{-1}$): 3350, 2920, 2420, 1700, 1645, 1500, 1450, 1430, 750.
Values of elemental analysis (as $C_{19}H_{26}N_4O_2 \cdot HCl$): Calcd. (%): C 60.23; H 7.18; N 14.79; Cl 9.36; Found (%): C 59.73; H 7.21; N 14.62; Cl 9.79.

EXAMPLE 32

Synthesis of 1,3-dimethyl-6-[4-(3-oxo-3-phenylpropyl)piperazin-1-yl]-2,4(1H,3H)-pyrimidinedione.hydrochloride (Compound 90)

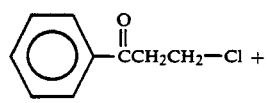

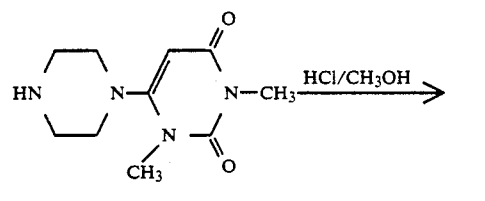

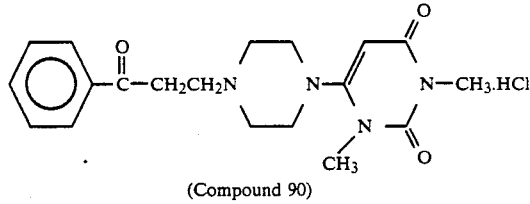

(Compound 90)

In 15 ml of dioxane were dissolved 1.68 g of 3-chloropropiophenone, 2.24 g of 1,3-dimethyl-6-(1-piperazinyl)-2,4(1H,3H)-pyrimidinedione and 1.6 ml of triethylamine, and the solution was then stirred at 80° C. for 1 hour. Next, the solvent was distilled off, and the resultant residue was dissolved in chloroform, washed with water, and then concentrated to dryness. The residue was further recrystallized from methanol, thereby obtaining 2.58 g of the crystals of 1,3-dimethyl-6-[4-(3-oxo-3-phenylpropyl)piperazin-1-yl]-2,4(1H,3H)-pyrimidinedione.

Analytical results of the obtained pyrimidinedione derivative
Melting point: 146°–148° C.
Values of elemental analysis (as $C_{19}H_{24}N_4O_3 \cdot CH_3OH$): Calcd. (%): C 61.84; H 7.26; N 14.42; Found (%): C 61.53; H 6.80; N 14.65.

2.3g of this pyrimidinedione derivative was treated with a hydrochloric acid/methanol solution in an ordinary manner to obtain 2.0 g of crystalline 1,3-dimethyl-6-[4-(3-oxo-3-phenylpropyl)piperazin-1-yl]-2,4(1H,3H)-pyrimidinedione.hydrochloride (Compound 90).

Analytical results of the obtained Compound 90:
Melting point: 195°–198° C.

IR $\nu_{max}^{KBr}$ (cm$^{-1}$): 1680, 1630, 1430, 1340, 1155, 1125, 970, 755, 695.
Values of elemental analysis (as $C_{19}H_{24}N_4O_3 \cdot HCl \cdot CH_3OH$): Calcd. (%): C 56.53; H 6.88; N 13.18; Cl 8.34; Found (%): C 56.50; H 7.16; N 13.29; Cl 8.92.

EXAMPLE 33

Synthesis of 1,3-dimethyl-6-[4-(2-[4-chlorophenyl]-ethyl)piperazin-1-yl]-2,4(1H,3H)-pyrimidinedione.hydrochloride (Compound 91)

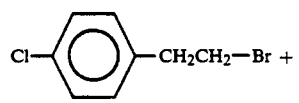

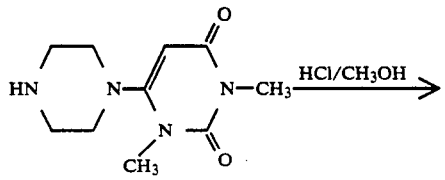

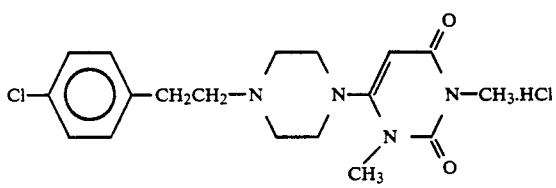

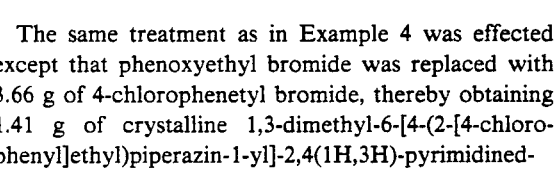

(Compound 91)

The same treatment as in Example 4 was effected except that phenoxyethyl bromide was replaced with 3.66 g of 4-chlorophenetyl bromide, thereby obtaining 1.41 g of crystalline 1,3-dimethyl-6-[4-(2-[4-chlorophenyl]ethyl)piperazin-1-yl]-2,4(1H,3H)-pyrimidinedione.

Analytical results of the obtained pyrimidinedione derivative
Melting point: 124°–126° C.
$^1$H-NMR (DMSO-d$_6$) δ ppm: 2.4–3.8 (m, 12H), 3.10 (s, 3H), 3.22 (s, 3H), 5.09 (s, 1H), 7.25 (s, 4H).
Values of elemental analysis (as $C_{18}H_{23}ClN_4O_2$): Calcd. (%): C 59.58; H 6.39; N 15.44; Cl 9.77; Found (%): C 59.37; H 6.47; N 15.68; Cl 9.71.

0.83 g of this pyrimidinedione derivative was treated with a hydrochloric acid/methanol solution in an ordinary manner to obtain 1.22 g of the crystals of 1,3-dimethyl-6-[4-(2-[4-chlorophenyl]ethyl)piperazin-1-yl]-2,4(1H,3H)-pyrimidinedione.hydrochloride (Compound 91).

Analytical results of the obtained Compound 91:
Melting point: 140° C. (decomposed).
IR $\nu_{max}^{KBr}$ (cm$^{-1}$): 3430, 2925, 2675, 1700, 1640, 1495, 1440, 1395, 1230, 1095, 1020, 975.
Values of elemental analysis (as $C_{18}H_{24}N_4O_2 \cdot 2HCl \cdot CH_3OH$): Calcd. (%): C 48.78; H 6.25; N 11.98; Cl 22.73; Found (%): C 48.75; H 6.70; N 11.95; Cl 22.86.

EXAMPLE 34

Synthesis of 1,3-dimethyl-6-[4-(4-oxo-4-[4-fluorophenyl]butyl)piperazin-1-yl]-2,4(1H,3H)-pyrimidinedione.hydrochloride (Compound 92)

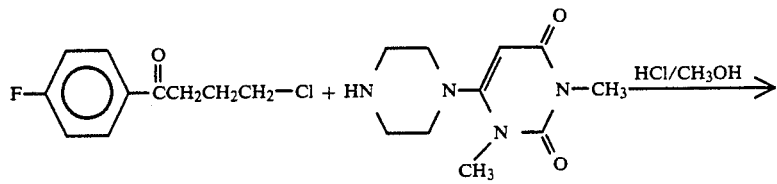

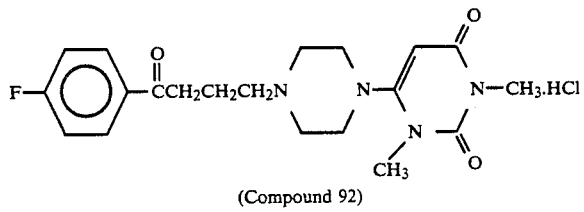

(Compound 92)

The same treatment as in Example 32 was effected except that 3-chloropropiophenone was replaced with 2.0 g of 4-chloro-1-(4-fluorophenyl)-1-butanone, thereby obtaining 1.0 g of crystalline 1,3-dimethyl-6-[4-(4-oxo-4-[4-fluorophenyl]butyl)piperazin-1-yl]-2,4(1H,3H)-pyrimidinedione.

Analytical results of the obtained pyrimidinedione derivative

Melting point: 145°–148° C.

$^1$H-NMR (CDCl$_3$) δ ppm: 1.8–2.2 (m, 2H), 2.3–3.2 (m, 12H), 3.32 (s, 3H), 3.37 (s, 3H), 5.2 (s, 1H), 7.2–8.2 (m, 4H).

0.5 g of this pyrimidinedione derivative was treated with a hydrochloric acid/methanol solution in an ordinary manner to obtain 0.51 g of the crystals of 1,3-dimethyl-6-[4-(4-oxo-4-[4-fluorophenyl]butyl)piperazin-1-yl]-2,4(1H,3H)-pyrimidinedione.hydrochloride (Compound 92).

Analytical results of the obtained Compound 92:

Melting point: 238°–241° C.

IR $\nu_{max}^{KBr}$ (cm$^{-1}$): 1680, 1640, 1420, 1200, 1150, 980, 755.

Values of elemental analysis (as C$_{19}$H$_{24}$N$_4$O$_3$.HCl.½H$_2$O): Calcd. (%): C 55.36; H 6.27; N 12.91; Cl 8.17; Found (%): C 55.90; H 6.60; N 12.74; Cl 7.70.

EXAMPLE 35

Synthesis of 1,3-dimethyl-6-[4-(N-benzoyl-2-aminoethyl)piperazin-1-yl]-2,4(1H,3H)-pyrimidinedione.hydrochloride (Compound 93):

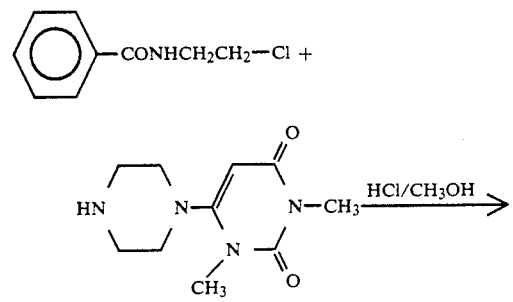

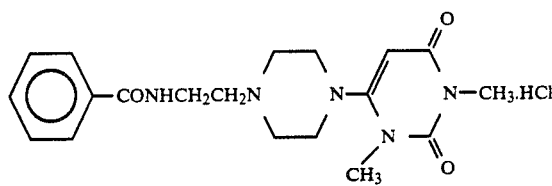

(Compound 93)

In 20 ml of dioxane were suspended 2.76 g of N-(2-chloroethyl)benzamide, 1.12 g of 1,3-dimethyl-6-(1-piperazinyl)-2,4(1H,3H)-pyrimidinedione, 3.75 g of sodium iodide and 1.4 ml of triethylamine, and the solution was heated under reflux with stirring for 15 hours. Afterward, the solvent was distilled off, and the resultant residue was dissolved in chloroform, washed with water, and then concentrated to dryness. The residue was purified through a silica gel column chromatograph (chloroform/methanol=100/1 to 100/5 in volume ratio), thereby obtaining 1.25 g of the crystals of 1,3-dimethyl-6-[4-(N-benzoyl-2-aminoethyl)piperazin-1-yl]-2,4(1H,3H)-pyrimidinedione.

Analytical results of the obtained pyrimidinedione derivative

Melting point: 191°–193° C.

$^1$H-NMR (CDCl$_3$) δ ppm: 2.4–3.2 (m, 10H), 3.34 (s, 3H), 3.42 (s, 3H), 3.5–3.8 (q, 2H), 5.24 (s, 1H), 6.83 (br, 1H), 7.4–7.9 (m, 5H).

1.2 g of this pyrimidinedione derivative was treated with a hydrochloric acid/methanol solution in an ordinary manner to obtain 1.13 g of the crystals of 1,3-dimethyl-6-[4-(N-benzoyl-2-aminoethyl)piperazin-1-yl]-2,4 (1H,3H)-pyrimidinedione.hydrochloride (Compound 93).

Analytical results of the obtained Compound 93:

Melting point: 247°–252° C.

IR $\nu_{max}^{KBr}$ (cm$^{-1}$): 1650, 1535, 1286, 1150, 1015, 920, 750, 710.

Values of elemental analysis (as C$_{19}$H$_{25}$N$_5$O$_3$HCl): Calcd. (%): C 55.95; H 6.43; N 17.17; Cl 8.69; Found (%): C 56.33; H 6.56; N 17.18; Cl 8.43.

EXAMPLE 36

Synthesis of 1,3-dimethyl-6-[4-(2-oxo-2-[4-chlorophenyl]ethyl)piperazin-1-yl]-2,4(1H,3H)-pyrimidinedione.hydrochloride (Compound 94)

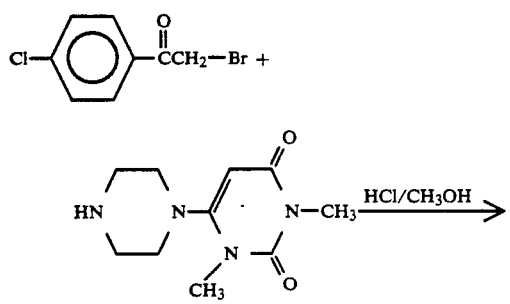

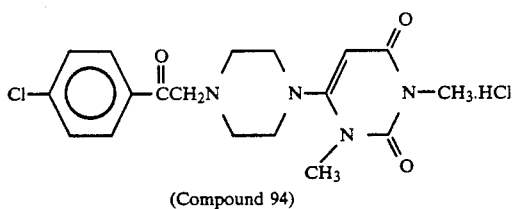

(Compound 94)

The same treatment as in Example 32 was effected except that 3-chloropropiophenone was replaced with 2.4 g of 2-bromo-4'-chloroacetophenone, thereby obtaining 2.5 g of the crystals of 1,3-dimethyl-6-[4-(2-oxo-2-[4-chlorophenyl]ethyl)piperazin-1-yl]-2,4(1H,3H)-pyrimidinedione.

Analytical results of the obtained pyrimidinedione derivative

Melting point: 181°–184° C.

$^1$H-NMR (CDCl$_3$) δ ppm: 2.6–3.2 (m, 8H), 3.33 (s, 3H), 3.43 (s, 3H), 3.87 (s, 2H), 5.26 (s, 1H), 7.37 (d, 2H), 7.99 (d, 2H).

1.2 g of this pyrimidinedione derivative was treated with a hydrochloric acid/methanol solution in an ordinary manner to obtain 1.26 g of the crystals of 1,3-dimethyl-6-[4-(2-oxo-2-[4-chlorophenyl]ethyl)piperazin-1-yl]-2,4(1H,3H)-pyrimidinedione.hydrochloride (Compound 94).

Analytical results of the obtained Compound 94:

Melting point: 192°–197° C.

IR $\nu_{max}^{KBr}$(cm$^{-1}$): 1700, 1630, 1430, 1220, 1095, 960, 795, 750.

Values of elemental analysis (as C$_{18}$H$_{21}$N$_4$O$_3$Cl.HCl.CH$_3$OH): Calcd. (%): C 51.36; H 5.67; N 12.61; Cl 15.96; Found (%): C 50.95; H 6.05; N 12.38; Cl 15.71.

EXAMPLE 37

Synthesis of 1,3-dimethyl-6-[4-(3-[2-chlorophenoxy]-propyl)piperazin-1-yl]-2,4(1H,3H)-pyrimidinedione.hydrochloride (Compound 95):

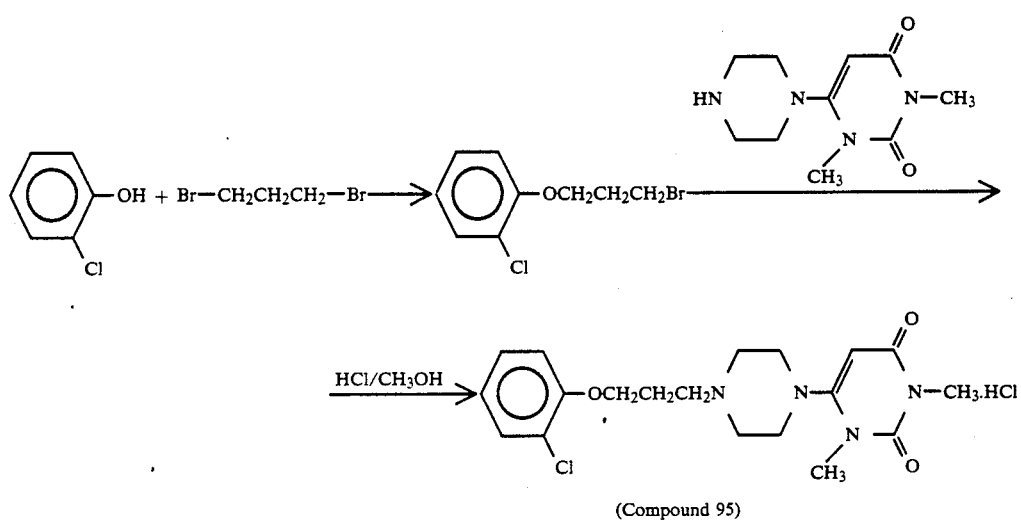

(Compound 95)

The same treatment as in Example 3 was effected except that 4-chlorophenol was replaced with 2-chlorophenol, thereby obtaining 8.2 g of the crystals of 1,3-dimethyl-6-[4-(3-[2-chlorophenoxy]propyl)piperazin-1-yl]-2,4(1H,3H)-pyrimidinedione.

Analytical results of the obtained pyrimidinedione derivative $^1$H-NMR (DMSO-d$_6$) δ ppm: 2.1–2.5 (m, 2H), 3.0–3.7 (m, 16H), 4.13 (t, 2H), 5.24 (s, 1H), 6.8–7.5 (dd, 4H).

4.1 g of this pyrimidinedione derivative was treated with a hydrochloric acid/methanol solution in an ordinary manner to obtain 2.1 g of the crystals of 1,3-dimethyl-6-[4-(3-[2-chlorophenoxy]propyl)piperazin-1-yl]-2,4(1H,3H)-pyrimidinedione.hydrochloride (Compound 95).

Analytical results of the obtained Compound 95:

Melting point: 246°–247.5° C. (decomposed).

Values of elemental analysis (as C$_{19}$H$_{25}$N$_4$O$_3$Cl.HCl.H$_2$O): Calcd. (%): C 52.90; H 6.54; N 12.99; Cl 16.44; Found (%): C 53.01; H 6.47; N 12.55; Cl 16.46.

EXAMPLE 38

Synthesis of 1,3-dimethyl-6-[4-(3-[3-chlorophenoxy]-propyl)piperazin-1-yl]-2,4(1H,3H)-pyrimidinedione.hydrochloride (Compound 96)

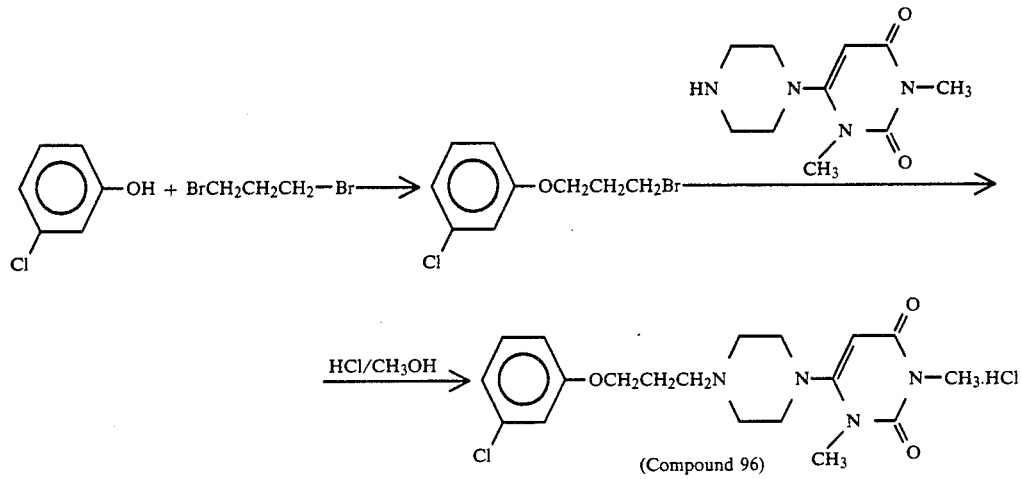

(Compound 96)

The same treatment as in Example 3 was effected except that 4-chlorophenol was replaced with 3-chlorophenol, thereby obtaining 17.5 g of the crystals of 1,3-dimethyl-6-[4-(3-[3-chlorophenoxy]propyl)piperazin-1-yl]-2,4(1H,3H)-pyrimidinedione.

Analytical results of the obtained pyrimidinedione derivative

Melting point: 136°–137° C.

$^1$H-NMR (CDCl$_3$+DMSO-d$_6$) δ ppm: 1.8–2.1 (m, 2H), 2.5–2.8 (m, 6H), 2.9–3.1 (m, 4H), 3.28 (s, 3H), 3.35 (s, 3H), 4.07 (t, 2H), 5.22 (s, 1H), 6.8–7.3 (m, 4H).

Values of elemental analysis (as C$_{19}$H$_{25}$N$_4$ClO$_3$): Calcd. (%): C 58.09; H 6.41; N 14.26; Cl 9.02; Found (%): C 58.05; H 6.38; N 14.40; Cl 9.64.

1.0 g of this pyrimidinedione derivative was treated with a hydrochloric acid/methanol solution in an ordinary manner to obtain 0.82 g of the crystals of 1,3-dimethyl-6-[4-(3-[3-chlorophenoxy]propyl)piperazin-1-yl]-2,4(1H,3H)-pyrimidinedione.hydrochloride (Compound 96).

Analytical results of the obtained Compound 96:

Melting point: 249°–252° C. (decomposed).

Values of elemental analysis (as C$_{19}$H$_{25}$N$_4$ClO$_3$.HCl): Calcd. (%): C 53.15; H 6.10; N 13.05; Cl 16.51; Found (%): C 53.15; H 6.24; N 13.04; Cl 16.62.

EXAMPLE 39

Synthesis of 1,3-dimethyl-6-[4-(3-[3,5-dichlorophenoxy]propyl)piperazin-1-yl]-2,4(1H,3H)-pyrimidinedione.hydrochloride (Compound 97)

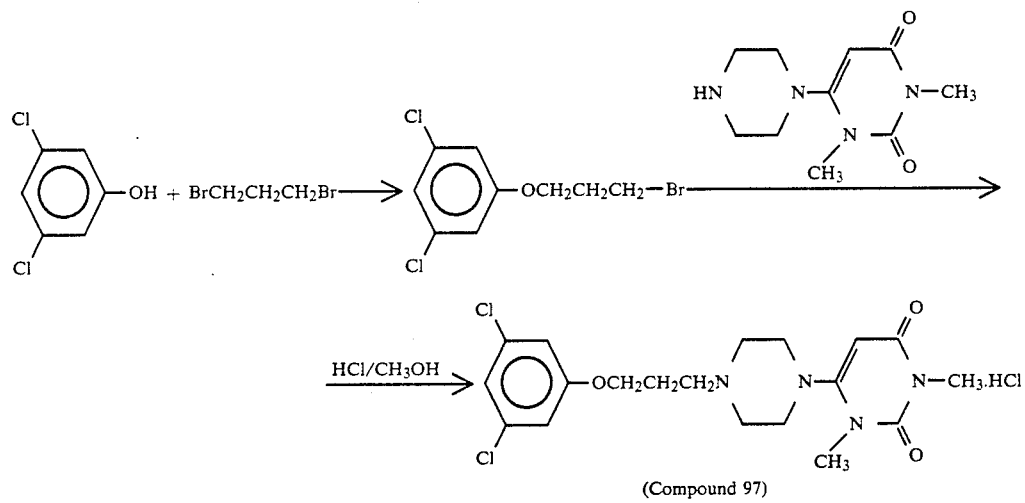

(Compound 97)

The same treatment as in Example 3 was effected except that 4-chlorophenol was replaced with 3,5-dichlorophenol, thereby obtaining 12.5 g of the crystals of 1,3-dimethyl-6-[4-(3-[3,5-dichlorophenoxy]propyl)-piperazin-1-yl]-2,4(1H,3H)-pyrimidinedione.

Analytical results of the obtained pyrimidinedione derivative

Melting point: 120°–121° C.

$^1$H-NMR (DMSO-d$_6$) δ ppm: 1.8–2.1 (m, 2H), 2.4–2,8 (m, 6H), 2.8–3.0 (m, 4H), 3.14 (s, 3H), 3.28 (s, 3H), 3.42 (m, 2H), 4.08 (t, 2H), 5.16 (s, 1H), 7.02 (s, 2H), 7.08 (s, 1H).

Values of elemental analysis (as C$_{19}$H$_{24}$N$_4$Cl$_2$O$_3$): Calcd. (%): C 53.40; H 5.66; N 13.11; Cl 16.59; Found (%): C 53.05; H 5.57; N 13.13; Cl 16.83.

1.8 g of this pyrimidinedione derivative was treated with a hydrochloric acid/methanol solution in an ordinary manner to obtain 1.5 g of the crystals of 1,3-dimethyl-6-[4-(3-[3,5-dichlorophenoxy]propyl)piperazin-1-yl]-2,4(1H,3H)-pyrimidinedione.hydrochloride (Compound 97).

Analytical results of the obtained Compound 97:
Melting point: 252°–255° C. (decomposed).
Values of elemental analysis (as $C_{19}H_{24}N_4Cl_2O_3 \cdot HCl$): Calcd. (%): C 49.20; H 5.43; N 12.08; Cl 22.93; Found (%): C 49.11; H 5.45; N 12.13; Cl 22.35.

EXAMPLE 40

Synthesis of 1,3-dimethyl-6-[4-(3-[4-methylthiophenoxy]propyl)piperazin-1-yl]-2,4 (1H,3H)-pyrimidinedione.hydrochloride (Compound 98):

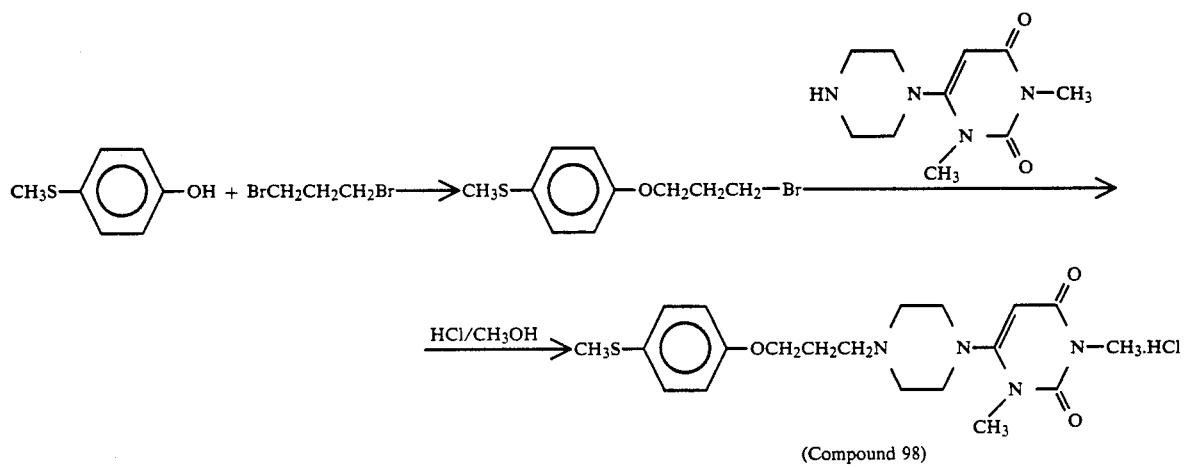

(Compound 98)

The same treatment as in Example 3 was effected except that 4-chlorophenol was replaced with 4-methylthiophenol, thereby obtaining 12.5 g of the crystals of 1,3-dimethyl-6-[4-(3-[4-methylthiophenoxy]propyl)piperazin-1-yl]-2,4(1H,3H)-pyrimidinedione.

Analytical results of the obtained pyrimidinedione derivative $^1$H-NMR (CDCl$_3$) δ ppm: 1.8–2.0 (m, 2H), 2.4–2.6 (m, 8H), 2.8–3.0 (m, 4H), 3.27 (s, 3H), 3.34 (s, 3H), 3.96 (t, 2H) 5.22 (s, 1H), 6.78 (d, 2H), 7.23 (d, 2H).

Values of elemental analysis (as $C_{20}H_{28}N_4O_3S$): Calcd. (%): C 59.38; H 6.98; N 13.85; S 7.93; Found (%): C 59.41; H 6.96; N 13.50; S 7.86.

1.3 g of this pyrimidinedione derivative was treated with a hydrochloric acid/methanol solution in an ordinary manner to obtain 0.6 g of the crystals of 1,3-dimethyl-6-[4-(3-[4-methylthiophenoxy]propyl)piperazin-1-yl]-2,4(1H,3H)-pyrimidinedione.hydrochloride (Compound 98).

Analytical results of the obtained Compound 98:
Melting point: 186°–188° C. (decomposed).
Values of elemental analysis (as $C_{20}H_{28}N_4O_3S \cdot HCl \cdot H_2O$): Calcd. (%): C 54.22; H 7.05; N 12.65; Cl 8.00; S 7.24; Found (%): C 54.59; H 6.87; N 12.68; Cl 8.21; S 7.22.

EXAMPLE 41

Synthesis of 1,3-dimethyl-6-[4-(3-[3,4-dichlorophenoxy]propyl)piperazin-1-yl]-2,4(1H,3H)-pyrimidinedione.hydrochloride (Compound 99)

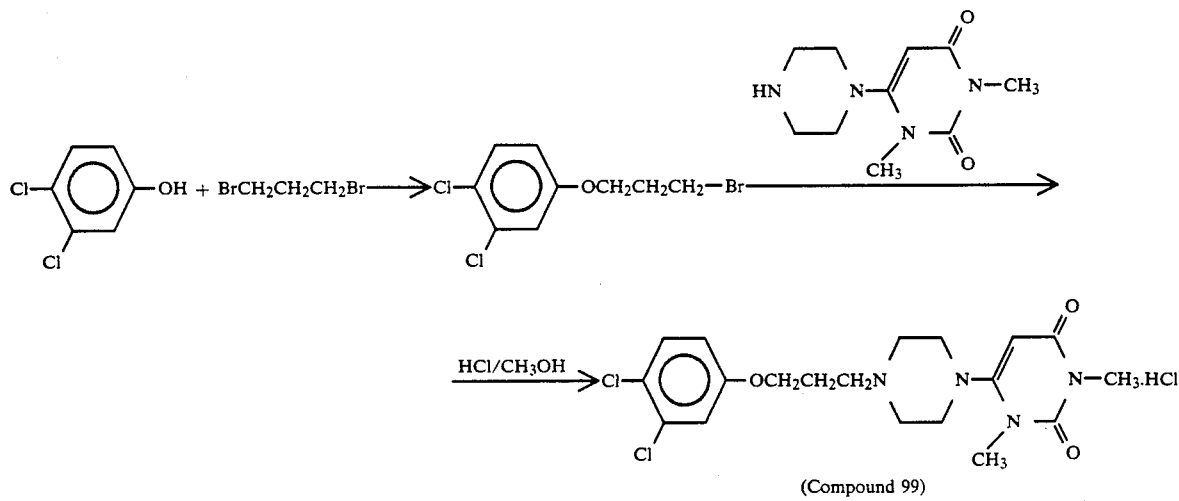

(Compound 99)

Melting point: 104°–106° C.

The same treatment as in Example 3 was effected except that 4-chlorophenol was replaced with 3,4-dichlorophenol, thereby obtaining 10.5 g of the crystals of 1,3-dimethyl-6-[4-(3-[3,4-dichlorophenoxy]propyl)-piperazin-1-yl]-2,4(1H,3H)-pyrimidinedione.

Analytical results of the obtained pyrimidinedione derivative

Melting point: 139°–140° C.

$^1$H-NMR (CDCl$_3$+DMSO-d$_3$) δ ppm: 1.8–2.1 (m, 2H), 2.4–2.7 (m, 6H), 2.8–3.3 (m, 4H), 3.25 (s, 3H), 3.36 (s, 3H), 4.05 (t, 2H), 5.20 (s, 1H), 6.84 (dd, 1H), 7.06 (d, 12H), 7.18 (d, 1H).

Values of elemental analysis (as C$_{19}$H$_{24}$N$_4$Cl$_2$O$_3$): Calcd. (%): C 53.40; H 5.66; N 13.11; Cl 16.59; Found (%): C 53.40; H 5.53; N 12.71; Cl 16.84.

2.0 g of this pyrimidinedione derivative was treated with a hydrochloric acid/methanol solution in an ordinary manner to obtain 2.0 g of the crystals of 1,3-dimethyl-6-[4-(3-[3,4-dichlorophenoxy]propyl)piperazin-1-yl]-2,4(1H,3H)-pyrimidinedione.hydrochloride (Compound 99).

Analytical results of the obtained Compound 99:

Melting point: 261°–263° C. (decomposed).

Values of elemental analysis (as C$_{19}$H$_{24}$N$_4$Cl$_2$O$_3$S.HCl.½H$_2$O): Calcd. (%): C 49.10; H 5.64; N 12.05; Cl 22.88; Found (%): C 49.07; H 5.61; N 11.92; Cl 22.64.

EXAMPLE 42

Synthesis of 1,3-dimethyl-6-[4-(3-[4-chlorobenzoyl-oxy]propyl)piperazin-1-yl]-2,4(1H,3H)-pyrimidinedione.hydrochloride (Compound 100)

ine, and 10 ml of a dioxane solution containing 1.05 g of 4-chlorobenzoyl chloride was further added dropwise. The solution was stirred at 50°–60° C. for 2 hours, and the solvent was then distilled off. Afterward, the resultant residue was dissolved in chloroform, washed with water, and then concentrated to dryness. The residue was purified through a silica gel column chromatograph (chloroform/methanol=100/1 to 100/3 in volume ratio), thereby obtaining 1.21 g of the crystals of 1,3-dimethyl-6-[4-(3-[4-chlorobenzoyloxy]propyl)piperazin-1-yl]-2,4(1H,3H)-pyrimidinedione.

Analytical results of the obtained pyrimidinedione derivative

Melting point: 68°–70° C.

1.2 g of this pyrimidinedione derivative was treated with a hydrochloric acid/methanol solution in an ordinary manner to obtain 1.19 g of the crystals of 1,3-dimethyl-6-[4-(3-[4-chlorobenzoyloxy]propyl)piperazin-1-yl]-2,4(1H,3H)-pyrimidinedione.hydrochloride (Compound 100).

Analytical results of the obtained Compound 100:

Melting point: 242°–244° C.

IR $ν_{max}^{KBr}$ (cm$^{-1}$): 1705, 1640, 1430, 1280, 1120, 975, 760.

Values of elemental analysis (as C$_{20}$H$_{25}$N$_4$O$_4$Cl.HCl.H$_2$O): Calcd. (%): C 50.53; H 6.15; N 11.79; Cl 14.92; Found (%): C 50.66; H 6.15; N 11.62; Cl 14.92.

EXAMPLE 43

Synthesis of

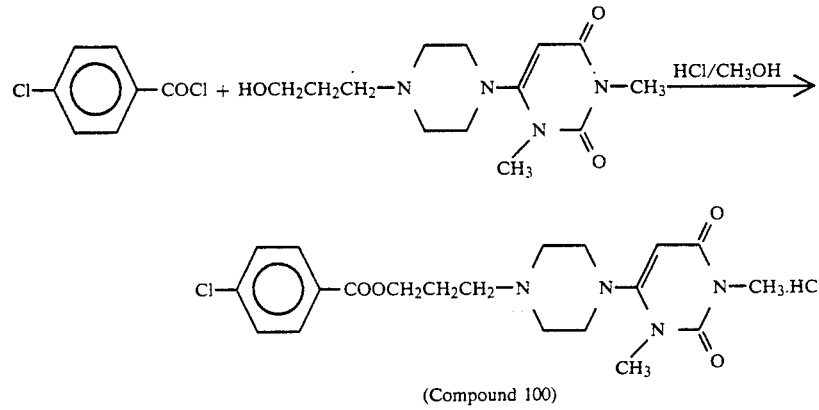

(Compound 100)

In 50 ml of dioxane were dissolved 1.45 g of 1,3-dimethyl-6-[4-(3-hydroxypropyl)piperazin-1-yl]-2,4(1H,3H)-pyrimidinedione and 1.5 ml of triethylamine 1,3-dimethyl-6-[4-(2-[4-methanesulfonamidobenzoyloxy]ethyl)piperazin-1-yl]-2,4(1H,3H)-pyrimidinedione (Compound 101)

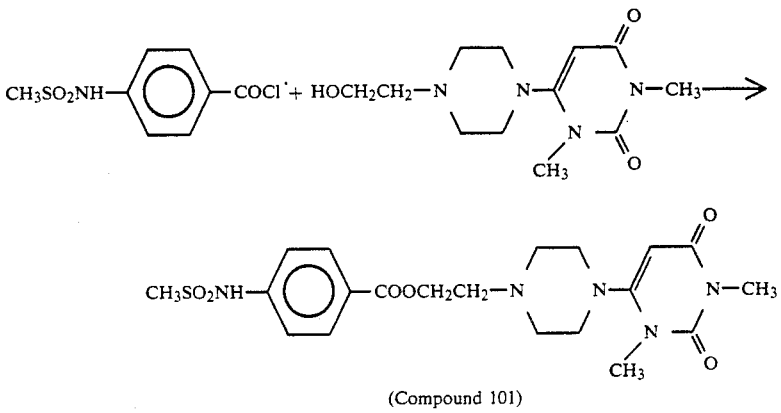

(Compound 101)

The same treatment as in Example 42 was effected except that 1,3-dimethyl-6-[4-(3-hydroxypropyl)piperazin-1-yl]-2,4(1H,3H)-pyrimidinedione was replaced with 1.35 g of 1,3-dimethyl-6-[4-(2-hydroxypropyl)piperazin-1-yl]-2,4(1H,3H)-pyrimidinedione and that 4-chlorobenzoyl chloride was replaced with 1.35 g of 4-methanesulfonamidebenzoyl chloride, thereby preparing 1.9 g of the crystals of 1,3-dimethyl-6-[4-(2-[4-methanesulfonamidobenzoyloxy]ethyl)piperazin-1-yl]-2,4(1H,3H)-pyrimidinedione (Compound 101).

Analytical results of the obtained Compound 101:
Melting point: 205°–208° C.

IR $\nu_{max}^{KBr}$ (cm$^{-1}$): 3440, 1720, 1700, 1610, 1360, 1170, 780.

$^1$H-NMR (CD$_3$OD) δ ppm: 2.8 (m, 10H), 3.04 (s, 3H), 3.16 (s, 3H), 3.30 (s, 3H), 4.4 (m, 2H), 5.14 (s, 1H), 7.30 (d, 2H), 7.88 (d, 2H).

EXAMPLE 44

Synthesis of
1,3-dimethyl-6-[4-(3-[2-acetonyloxyphenoxy]propyl)-piperazin-1-yl]-2,4(1H,3H)-pyrimidinedione.hydrochloride (Compound 102)

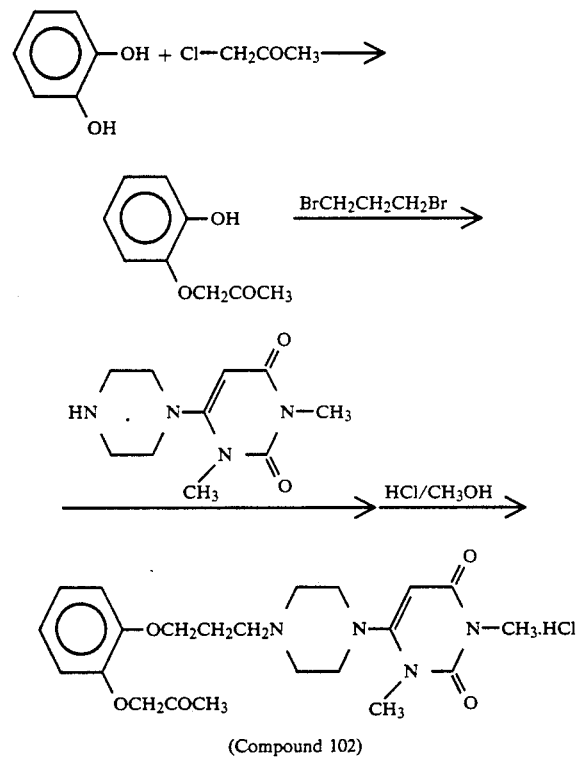

(Compound 102)

(1) Synthesis of 2-acetonyloxyphenol 11 g of catechol, 16.8 g of sodium hydrogencarbonate and 9.5 g of monochloroacetone were dissolved in a mixed solvent of 300 ml of water and 100 ml of isopropyl alcohol, and the solution was heated up to 50° to 60° C. and then stirred for 4 hours. Afterward, 50 ml of a 8% aqueous sodium hydroxide solution and 9.3 g of monochloroacetone were further added, followed by stirring at 50° C. for 5 hours. After standing for cooling, insolubles were removed from the solution by filtration, and the resultant filtrate was concentrated until the volume of the solution became about 300 ml, and then extracted with chloroform. The chloroform layer was washed with a dilute aqueous sodium hydroxide solution and then with water. The solvent was distilled off, and the residue was purified through a silica gel column chromatograph (chloroform/hexane=7/3 to chloroform alone in volume ratio), and then recrystallized from ether/hexane, thereby obtaining 7.73 g of crystals of 2-acetonyloxyphenol.

Analytical results of the obtained phenol derivative
Melting point: 99°–100° C.

(2) Synthesis of
1,3-dimethyl-6-[4-(3-[2-acetonyloxyphenoxy]propyl)-piperazin-1-yl]-2,4(1H,3H)-pyrimidinedione.hydrochloride (Compound 102):

In 50 ml of 2-butanone were suspended 3.32 g of 2-acetonyloxyphenol obtained in the previous section, 40.4 g of dibromopropane and 2.76 g of potassium carbonate, and the resultant suspension was then stirred under reflux for 7 hours. After standing for cooling, insolubles were removed from the suspension by filtration, and the filtrate was concentrated under reduced pressure. Next, the resultant residue was purified through a silica gel column chromatograph (chloroform/hexane=7/3 to 9/1 in volume ratio) to obtain 3.65 g of an oily product.

In 50 ml of dioxane were dissolved 1.44 g of this oily product, 1.12 g of 1,3-dimethyl-6-(1-piperazinyl)-2,4(1H,3H)-pyrimidinedione and 1 ml of triethylamine, and the solution was then heated under reflux for 5 hours. After standing, the reaction product was filtrated, and the filtrate was concentrated under reduced pressure and the resultant residue was dissolved in chloroform. The solution was washed with water and the solvent was distilled off, and the resultant residue was purified through a silica gel column chromatograph (chloroform/methanol=100/1 to 100/5 in volume ratio), and then recrystallized from ethanol, thereby obtaining 1.06 g of crystalline 1,3-dimethyl-6-[4-(3-[2-acetonyloxyphenoxy]-propyl)piperazin-1-yl]-2,4(1H,3H)-pyrimidinedione.

Analytical results of the obtained pyrimidinedione derivative
Melting point: 129°–130° C.

$^1$H-NMR (CD$_3$OD) δ ppm: 1.8–2.1 (m, 2H), 2.30 (s, 3H), 2.4–2.7 (m, 6H), 2.7–3.0 (m, 4H) 3.27 (s, 3H), 3.34 (s, 3H), 4.02 (t, 2H), 4.47 (s, 2H), 5.22 (s, 1H), 6.7–7.0 (m, 4H).

1.0 g of this pyrimidinedione derivative was treated with a hydrochloric acid/methanol solution in an ordinary manner to obtain 0.8 g of the crystals of 1,3-dimethyl-6-[4-(3-[2-acetonyloxyphenoxy]propyl)piperazin-1-yl]-2,4(1H,3H)-pyrimidinedione.hydrochloride (Compound 102).

Analytical results of the obtained Compound 102:
Melting point: 209°–211° C.

IR $\nu_{max}^{KBr}$ (cm$^{-1}$): 1720, 1695, 1635, 1500, 1270, 1200, 1115, 1045, 980, 780.

Values of elemental analysis (as $C_{22}H_{30}N_4O_5 \cdot HCl \cdot \frac{1}{2}H_2O$): Calcd. (%): C 55.52; H 6.78; N 11.77; Cl 7.45; Found (%): C 55.96; H 7.09; N 11.37; Cl 7.61.

EXAMPLE 45

Synthesis of 1,3-dimethyl-6-[4-(2-anilinoethyl)piperazin-1-yl]-2,4(1H,3H)-pyrimidinedione.oxalate (Compound 103)

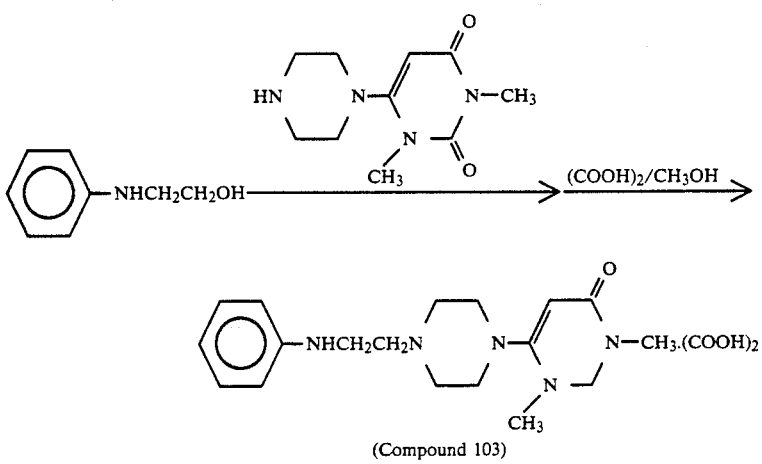

(Compound 103)

In 100 ml of acetonitrile were dissolved 13.7 g of anilinoethanol, 30.0 g of triphenylphosphine, 10.1 g of triethylamine and 15.4 g of carbon tetrachloride, and the solution was stirred at 5° C. for 16 hours. The formed crystals were collected by filtration, and the solvent was then distilled off under reduced pressure. The residue was poured into 200 ml of water and then extracted with ether. The resultant ether solution was dried over anhydrous sodium sulfate, and 200 ml of petroleum ether was added thereto and the solution was then allowed to stand at 0° C. for 20 hours. The precipitated crystals were filtered, and the filtrate was then concentrated to obtain 12.0 g of a colorless oily product. 100 mg of p-toluenesulfonic acid was added to 30 ml of a dioxane solution containing 1.5 g of this oily product and 2.0 g of 1,3-dimethyl-6-(1-piperazinyl)-2,4(1H,3H)-pyrimidinedione, followed by stirring for 1 hour. The reaction mixture was dissolved in 50 ml of chloroform and then washed with an aqueous saturated sodium hydrogencarbonate solution and a saturated sodium chloride solution, and the organic layer was dried over anhydrous sodium sulfate and then concentrated to dryness. The resultant residue was purified through a silica gel column chromatograph (chloroform/methanol=100/3 to 100/6 in volume ratio), thereby obtaining 2.9 g of 1,3-dimethyl-6-[4-(2-anilinoethyl)piperazin-1-yl]-2,4(1H,3H)-pyrimidinedione in a white crystalline state.

Analytical results of the obtained pyrimidinedione derivative $^1$H-NMR (CD$_3$OD) δ ppm: 2.4–3.3 (m, 12H), 3.32 (s, 3H), 3.38 (s, 3H), 4.20 (brs, 1H) 5.27 (s, 1H), 6.53–6.97 (m, 3H), 6.97–7.43 (m, 2H).

1.0 g of this pyrimidinedione derivative was treated with an oxalic acid/methanol solution in an ordinary manner to obtain 0.9 g of the crystals of 1,3-dimethyl-6-[4-(2-anilinoethyl)piperazin-1-yl]-2,4(1H,3H)-pyrimidinedione.oxalate (Compound 103).

Analytical results of the obtained Compound 103:
Melting point: 212°–214° C.

Values of elemental analysis (as C$_{18}$H$_{25}$N$_5$O$_2$.2-(CO$_2$H)$_2$): Calcd. (%): C 50.48; H 5.58; N 13.38; Found (%): C 50.02; H 5.12; N 13.80.

EXAMPLE 46

Synthesis of 1,3-dimethyl-6-[2-(4-[4-acetylphenyl]-piperazin-1-yl)ethylamino]-2,4(1H,3H)-pyrimidinedione.oxalate (Compound 104)

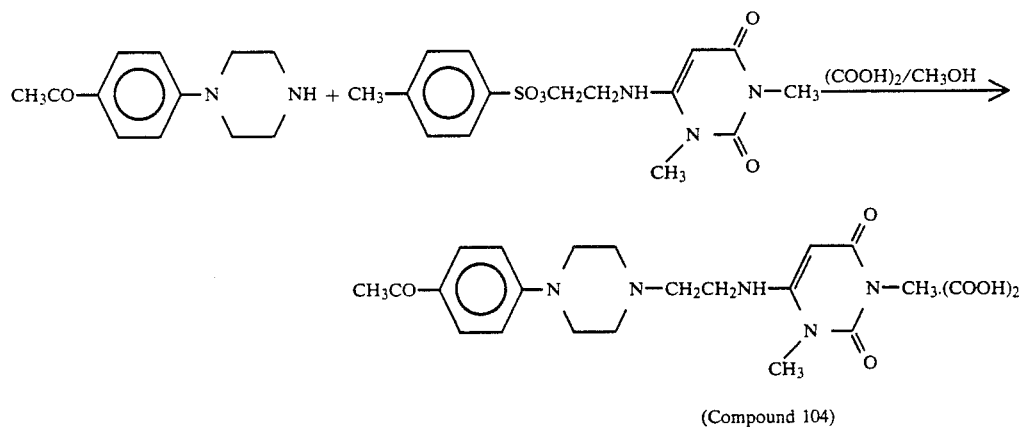

(Compound 104)

A mixture of 1.6 g of 1-(4-acetylphenyl)piperazine and 1.1 g of 1,3-dimethyl-6-[2-(p-toluenesulfonyloxy)-ethylamino]-2,4(1H,3H)-pyrimidinedione was heated at 80° C. for 6 hours, and after standing for cooling, the reaction solution was poured into a 5% aqueous sodium carbonate solution, stirred and then extracted with chloroform. The chloroform solution was washed with water and then concentrated, and the resultant residue was purified through a silica gel column chromatograph (chloroform/methanol=50/1 in volume ratio), thereby obtaining 0.5 g of 1,3-dimethyl-6-[2-(4-[4-acetylphenyl]-piperazin-1-yl)ethylamino]-2,4(1H,3H)-pyrimidinedione.

Analytical results of the obtained pyrimidinedione derivative $^1$H-NMR (CD$_3$OD) δ ppm: 2.55 (s, 3H), 2.4–3.0 (m, 10H), 3.0–3.2 (m, 2H), 3.33 (s, 3H), 3.38 (s, 3H), 4.83 (s, 1H), 5.56 (s, 1H), 6.92 (d, 2H), 7.86 (d, 2H).

0.5 g of this pyrimidinedione derivative was treated with an oxalic acid/methanol solution in an ordinary manner to obtain 0.47 g of the crystals of 1,3-dimethyl-6-[2-(4-[4-acetylphenyl]piperazin-1-yl)ethylamino]-2,4(1H,3H)-pyrimidinedione.oxalate (Compound 104).

Analytical results of the obtained Compound 104:
Melting point: 216°–217° C.
IR $\nu_{max}^{KBr}$(cm$^{-1}$): 2550, 1740, 1700, 1640, 1620, 820.
Values of elemental analysis (as C$_{20}$H$_{27}$N$_5$O$_3$·(CO$_2$H)$_2$·½H$_2$O): Calcd. (%): C 54.54; H 6.24; N 14.45; Found (%): C 54.27; H 6.23; N 14.01.

EXAMPLE 47

Synthesis of 1-methyl-6-[4-(3-phenoxypropyl)piperazin-1-yl]-2,4(1H,3H)-pyrimidinedione.oxalate (Compound 105)

to stand for cooling, and the solvent was distilled off. The resultant residue was dissolved in 100 ml of chloroform. The chloroform layer was washed with water, dried over anhydrous sodium sulfate and then concentrated under reduced pressure to obtain an oily product. This oily product was purified through a silica gel column chromatograph (chloroform/methanol=30/1 in volume ratio), thereby obtaining 0.73 g of 1-methyl-6-[4-(3-phenoxypropyl)piperazin-1-yl]-2,4(1H,3H)-pyrimidinedione.

Analytical results of the obtained pyrimidinedione derivative $^1$H-NMR (CD$_3$OD) δ ppm: 2.06 (m, 2H), 2.62–3.00 (m, 10H), 3.32 (s, 3H), 4.03 (t, 2H), 5.15 (s, 1H), 6.8–7.5 (m, 5H).

0.70 g of this pyrimidinedione derivative was treated with an oxalic acid/methanol solution in an ordinary manner to obtain 0.61 g of the crystals of 1-methyl-6-[4-(3-phenoxypropyl)piperazin-1-yl]-2,4(1H,3H)-pyrimidinedione.oxalate (Compound 105).

Analytical results of the obtained Compound 105:
Melting point: 211°–214° C.
IR $\nu_{max}^{KBr}$ (cm$^{-1}$): 2950, 1720, 1680, 1600, 750, 700.
Values of elemental analysis (as C$_{18}$H$_{24}$N$_4$O$_3$·(CO$_2$H)$_2$·H$_2$O): Calcd. (%): C 53.09; H 6.24; N 12.38; Found (%): C 52.77; H 6.08; N 12.42.

EXAMPLE 48

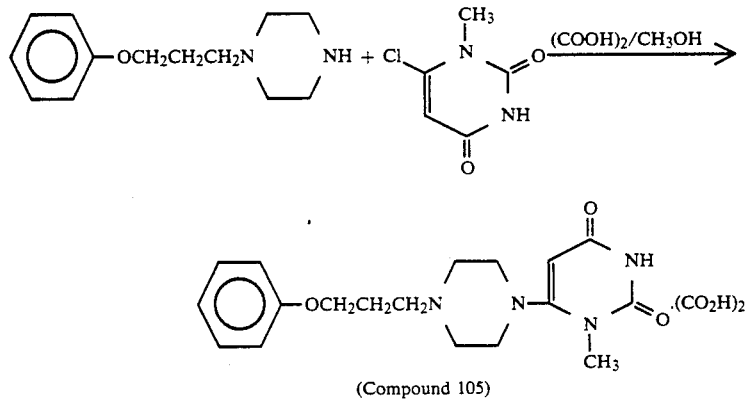

(Compound 105)

1.3 g of 1-(3-phenyloxypropyl)piperazine and 0.5 g of 6-chloro-1-methyl-2,4(1H,3H)-pyrimidinedione were dissolved in 15 ml of isopropanol, and 2.7 ml of triethylamine was then added. Next, the solution was heated under reflux with stirring for 12 hours and then allowed Synthesis of 1-methyl-6-[4-(3-[4-chlorophenoxy]-propyl)piperazin-1-yl]-2,4(1H,3H)-pyrimidinedione.oxalate (Compound 106)

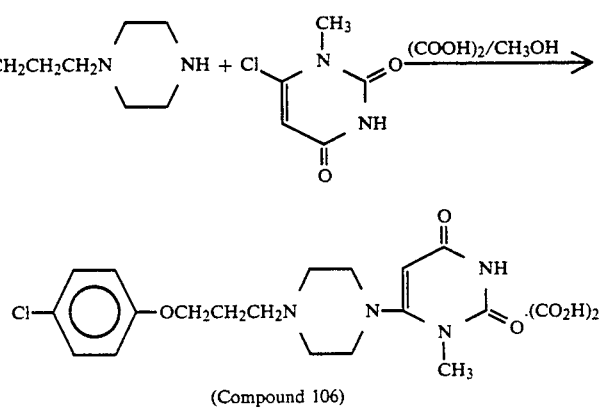

(Compound 106)

The same treatment as in Example 47 was effected except that 1-(3-phenyloxypropyl)piperazine was replaced with 1.5 g of 1-[3-(4-chlorophenyloxy)propyl]-piperazine, thereby preparing 0.77 g of 1-methyl-6-[4-(3-[4-chlorophenoxy]propyl)piperazin-1-yl]-2,4(1H,3H)-pyrimidinedione.

Analytical results of the obtained pyrimidinedione derivative $^1$H-NMR (CDCl$_3$) δ ppm: 1.96 (m, 2H), 2.5–2.8 (m, 10H), 3.29 (s, 1H), 4.03 (m, 2H), 5.06 (s, 1H), 6.88 (d, 2H), 7.32 (d, 2H).

0.70 g of this pyrimidinedione derivative was treated with an oxalic acid/methanol solution in an ordinary manner to obtain 0.67 g of the crystals of 1-methyl-6-[4-(3-[4-chlorophenoxy]propyl)piperazin-1-yl]-2,4(1H,3H)-pyrimidinedione.oxalate (Compound 106).

Analytical results of the obtained Compound 106:
Melting point: 204°–206° C.
IR $\nu_{max}^{KBr}$(cm$^{-1}$): 2900, 1720, 1680, 1640, 1600, 760, 670.
Values of elemental analysis (as C$_{18}$H$_{23}$N$_4$O$_3$Cl.(CO$_2$H)$_2$.H$_2$O): Calcd. (%): C 49.34; H 5.59; N 11.51; Cl 7.28; Found (%): C 49.76; H 5.60; N 11.60; Cl 7.23.

hours. Afterward, the solution was allowed to stand at room temperature overnight, and the resultant precipitate was then collected by filtration, dissolved in a small amount of water, and then acidified with 1N hydrochloric acid. Methanol was added to the solution and then stored in an icebox overnight. The precipitate was collected by filtration, and then washed with methanol/ether to prepare 0.71 g of crystalline 1,3-dimethyl-6-[4-(3-[2-carboxyphenoxy]propyl)piperazin-1-yl]-2,4(1H,3H)-pyrimidinedione.hydrochloride (Compound 107).

Analytical results of the obtained pyrimidinedione derivative

Melting point: 152°–154° C. (decomposed).
IR $\nu_{max}^{KBr}$(cm$^{-1}$): 3000, 2550, 1690, 1640, 1620.
Values of elemental analysis (as C$_{20}$H$_{26}$N$_4$O$_5$.HCl.3H$_2$O): Calcd. (%): C 48.73; H 6.75; N 11.37; Cl 7.19; Found (%): C 48.54; H 6.83; N 11.28; Cl 7.04.

EXAMPLE 50

Synthesis of 1,3-dimethyl-6-[4-(2-[2-methanesulfonyloxyphenyl]ethyl)piperazin-1-yl]-2,4(1H,3H)-pyrimidinedione.oxalate (Compound 108)

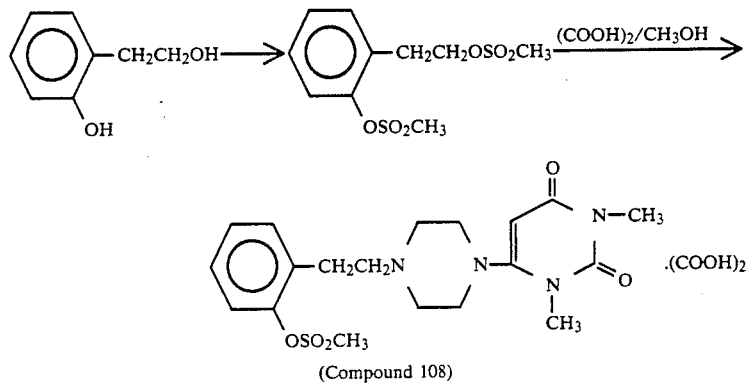

(Compound 108)

EXAMPLE 49

Synthesis of 1,3-dimethyl-6-[4-(3-[2-carboxyphenoxy]propyl)piperazin-1-yl]-2,4(1H,3H)-pyrimidinedione.hydrochloride (Compound 107)

(1) Synthesis of 2-(2-methanesulfonyloxyphenyl)ethylmethane sulfonate 1.5 ml of 2-(2-hydroxyphenyl)ethyl alcohol and 1 ml

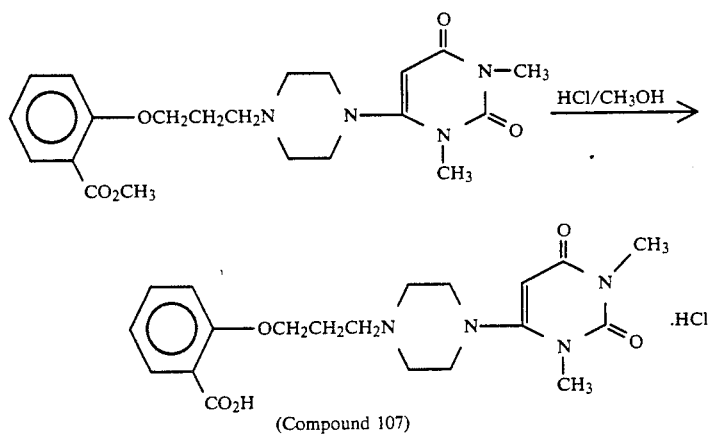

(Compound 107)

0.8 g of the Compound 21 prepared in Example 2 was dissolved in 13 ml of ethanol and 1 ml of a 20% aqueous potassium hydroxide solution was further added, and the solution was heated under reflux with stirring for 2 of pyridine were dissolved in 15 ml of tetrahydrofuran (THF), and 2.9 ml of methanesulfonyl chloride was added dropwise under ice cooling. After stirring overnight, 20 ml of ice water was added, and the solution was stirred vigorously and then extracted with chloroform. Next, the solution was washed with 1N HCl and water, dried over anhydrous sodium sulfate and then concentrated under reduced pressure to obtain 1.2 g of 2-(2-methanesulfonyloxyphenyl)ethylmethane sulfonate.

(2) Synthesis of 1,3-dimethyl-6-[4-(2-[2-methanesulfonyloxyphenyl]ethyl)piperazin-1-yl]-2,4(1H,3H)-pyrimidinedione.oxalate (Compound 108)

A mixture of 1 g of 2-(2-methanesulfonyloxyphenyl)ethylmethane sulfonate and 0.65 g of 1,3-dimethyl-6-(piperazin-1-yl)-2,4(1H,3H)-pyrimidinedione was stirred at 90° C. for 2 hours and then allowed to stand for cooling. The resultant reaction mixture was dissolved in 50 ml of chloroform, and then washed with 10 ml of a 1N aqueous sodium hydroxide solution. The chloroform layer was washed with water, dried over anhydrous sodium sulfate and then concentrated under reduced pressure, and the residue was purified through a silica gel column chromatograph (chloroform/methanol=40/1 in volume ratio), thereby obtaining 2.0 g of 1,3-dimethyl-6-[4-(2-[2-methanesulfonyloxyphenyl]ethyl)piperazin-1-yl]-2,4(1H,3H)-pyrimidinedione.

Analytical results of the obtained pyrimidinedione derivative $^1$H-NMR (CDCl$_3$) δ ppm: 2.6–3.1 (m, 12H), 3.25 (s, 3H), 3.32 (s, 3H), 3.38 (s, 3H), 5.23 (s, 1H), 7.28 (s, 4H).

1.80 g of this pyrimidinedione derivative was treated with an oxalic acid/methanol solution in an ordinary manner to obtain 1.5 g of the crystals of 1,3-dimethyl-6-[4-(2-[2-methanesulfonyloxyphenyl]ethyl)piperazin-1-yl]-2,4(1H,3H)-pyrimidinedione.oxalate (Compound 108).

Analytical results of the obtained pyrimidinedione derivative

Melting point: 219°–221° C. (decomposed).

IR $\nu_{max}^{KBr}$ (cm$^{-1}$): 2940, 1710, 1700, 1650, 1350, 1150, 780.

Values of elemental analysis (as C$_{19}$H$_{26}$N$_4$O$_5$S.(CO$_2$H)$_2$.½H$_2$O): Calcd. (%): C 48.36; H 5.60; N 10.74; S 6.15; Found (%): C 48.41; H 5.59; N 10.57; S 6.33.

EXAMPLE 51

Synthesis of 1,3-dimethyl-6-[4-(2-[2-(N,N-dimethylamino)phenyl]ethyl)piperazin-1-yl]-2,4(1H,3H)-pyrimidinedione.oxalate (Compound 109)

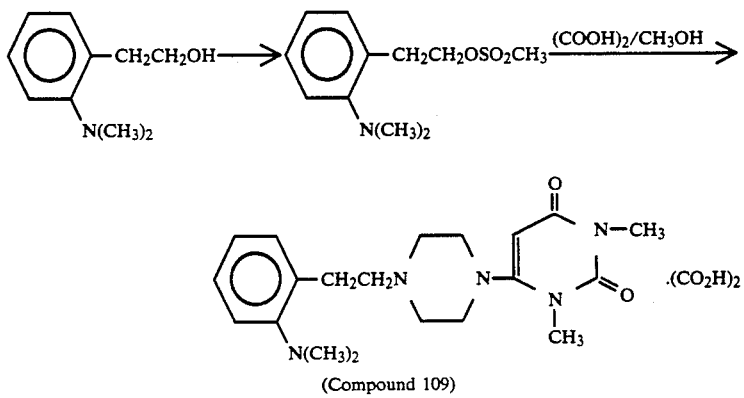

(Compound 109)

(1) Synthesis of 2-(2-dimethylaminophenyl)ethylmethanesulfonate

The same treatment as in the section (1) of Example 50 was effected except that 1 g of 2-(2-dimethylaminophenyl)ethyl alcohol and 0.52 ml of methanesulfonyl chloride were used, thereby obtaining 0.89 g of 2-(2-dimethylaminophenyl)ethylmethanesulfonate.

(2) Synthesis of 1,3-dimethyl-6-[4-(2-[2-(N,N-dimethylamino) phenyl]ethyl)piperazin-1-yl]-2,4(1H,3H)-pyrimidinedione.oxalate (Compound 109)

The same treatment as in the section (2) of Example 50 was effected except that 2-(2-methanesulfonyloxyphenyl)ethylmethanesulfonate was replaced with 0.82 g of 2-(2-dimethylaminophenyl)ethylmethane sulfonate, thereby obtaining 0.66 g of 1,3-dimethyl-6-[4-(2-[2-(N,N-dimethylamino)phenyl] ethyl)piperazin-1-yl]-2,4(1H,3H)-pyrimidinedione.

Analytical results of the obtained pyrimidinedione derivative $^1$H-NMR (CDCl$_3$) δ ppm: 3.0 (m, 10H), 3.3 (m, 2H), 3.02 (s, 3H), 3.25 (s, 3H), 3.29 (s, 3H), 3.37 (s, 3H), 5.22 (s, 1H), 7.35 (m, 4H).

0.60 g of this pyrimidinedione derivative was treated with an oxalic acid/methanol solution in an ordinary manner to obtain 1,3-dimethyl-6-[4-(2-[2-(N,N-dimethylamino)phenyl]ethyl)piperazin-1-yl]-2,4(1H,3H)-pyrimidinedione.oxalate (Compound 109).

Analytical results of the obtained Compound 109

Melting point: 248°–249° C. (decomposed).

IR $\nu_{max}^{KBr}$ (cm$^{-1}$): 2930, 2550, 1700, 1660, 1640, 760.

Values of elemental analysis (as C$_{20}$H$_{29}$N$_5$O$_2$.(CO$_2$H)$_2$.H$_2$O): Calcd. (%): C 49.82; H 6.27; N 12.10; Found (%): C 49.62; H 5.86; N 12.30.

EXAMPLE 52

Synthesis of 1,3-dimethyl-6-[4-(2-[2-acetylaminophenyl]ethyl)piperazin-1-yl]-2,4(1H,3H)-pyrimidinedione.oxalate (Compound 110)

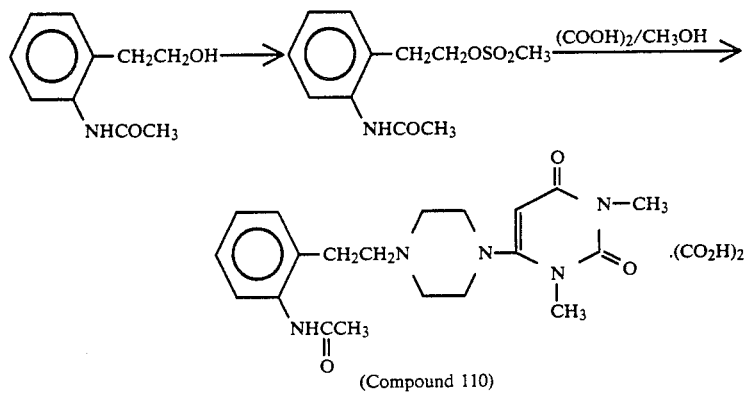

(Compound 110)

(1) Synthesis of 2-(2-acetylaminophenyl)ethylmethanesulfonate

The same treatment as in the section (1) of Example 50 was effected except that 1 g of 2-(2-acetylaminophenyl)ethyl alcohol and 0.52 ml of methanesulfonyl chloride were used, thereby obtaining 0.89 g of 2-(2-acetylaminophenyl)ethylmethanesulfonate.

(2) Synthesis of 1,3-dimethyl-6-[4-(2-[2-acetylaminophenyl]ethyl)piperazin-1-yl]-2,4(1H,3H)-pyrimidinedione.oxalate (Compound 110)

The same treatment as in the section (2) of Example 50 was effected except that 2-(2-methanesulfonyloxyphenyl)ethylmethanesulfonate was replaced with 0.87 g of 2-(2-acetylaminophenyl)ethylmethanesulfonate, thereby obtaining 0.45 g of 1,3-dimethyl-6-[4-(2-[2-acetylaminophenyl]ethyl)piperazin-1-yl]-2,4(1H,3H)-pyrimidinedione.

Analytical results of the obtained pyrimidinedione derivative $^1$H-NMR (CDCl$_3$) δ ppm: 2.5–3.1 (m, 12H) 2.44 (s, 3H), 3.30 (s, 3H), 3.38 (s, 3H), 5.18 (s, 3H), 7.2–7.4 (m, 4H).

0.41 g of this pyrimidinedione derivative was treated with an oxalic acid/methanol solution in an ordinary manner to obtain 0.34 g of 1,3-dimethyl-6-[4-(2-[2-acetylaminophenyl]ethyl)piperazin-1-yl]-2,4(1H,3H)-pyrimidinedione.oxalate (Compound 110).

Analytical results of the obtained Compound 110
Melting point: 152°–155° C.
IR $v_{max}^{KBr}$ (cm$^{-1}$): 2950, 2450, 1690, 1640, 1630, 1600, 850.
Values of elemental analysis (as C$_{20}$H$_{27}$N$_5$O$_3$.(CO$_2$H)$_2$.H$_2$O): Calcd. (%): C 53.54; H 6.33; N 14.19; Found (%): C 53.42; H 6.62; N 13.88.

EXAMPLE 53

Synthesis of 1,3-dimethyl-6-[4-(3-[2-chloro-4-methanesulfonamidophenoxy]propyl)piperazin-1-yl]-2,4(1H,3H)-pyrimidinedione.hydrochloride (Compound 111)

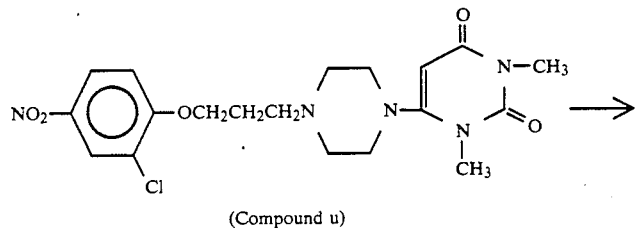

(Compound u)

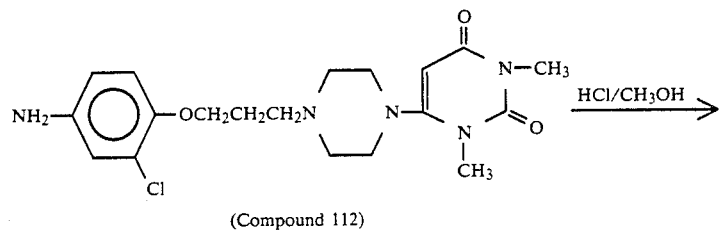

(Compound 112)

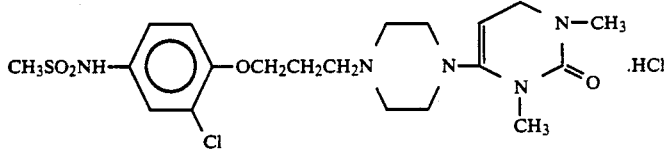

(Compound 111)

(1) Synthesis of 1,3-dimethyl-6-[4-(3-[4-amino-2-chlorophenoxy]-propyl)piperazin-1-yl]-2,4(1H,3H)-pyrimidinedione (Compound 112)

2.86 g of the Compound U obtained in Reference Example 16 was hydrogenated in the same manner as in Example 6 to obtain 2.49 g of crystalline 1,3-dimethyl-6-[4-(3-[4-amino-2-chlorophenoxy]propyl)piperazin-1-yl]-2,4(1H,3H)-pyrimidinedione (Compound 112).

Analytical results of the obtained pyrimidinedione derivative
Melting point: 143°–145° C.

(2) Synthesis of 1,3-dimethyl-6-[4-(3-[2-chloro-4-methanesulfonamidophenoxy]propyl)piperazin-1-yl]-2,4(1H,3H)-pyrimidinedione.hydrochloride (Compound 111)

2.04 g of the Compound 112 obtained above was treated in the same manner as in Example 7 to obtain 1.55 g of 1,3-dimethyl-6-[4-(3-[2-chloro-4-methanesulfonamidophenoxy]propyl)piperazin-1-yl]-2,4(1H,3H)-pyrimidinedione.

Analytical results of the obtained pyrimidinedione derivative
$^1$H-NMR (CDCl$_3$) δ ppm: 1.7–2.0 (m, 2H) 2.3–2.6 (m, 6H), 2.6–2.9 (m, 4H), 2.82 (s, 3H), 3.12 (s, 3H), 3.16 (s, 3H), 3.82 (t, 2H), 4.93 (s, 1H), 6.4–6.9 (m, 3H).

1.0 g of this pyrimidinedione derivative was treated with a hydrochloric acid/methanol solution in an ordinary manner to obtain 0.8 g of crystalline 1,3-dimethyl-6-[4-(3-[2-chloro-4-methanesulfonamidophenoxy]-propyl)piperazin-1-yl]-2,4(1H,3H)-pyrimidinedione.hydrochloride (Compound 111).

Analytical results of the obtained Compound 111:
Melting point: 244°–247° C.
IR $\nu_{max}^{KBr}$ (cm$^{-1}$): 1690, 1650, 1500, 1320, 1150, 1060, 970, 890, 760.
Values of elemental analysis (as $C_{20}H_{28}N_5O_5ClS \cdot HCl$): Calcd. (%): C 45.98; H 5.60; N 13.41; Cl 13.57; S 6.14; Found (%): C 45.91; H 5.94; N 13.42; Cl 13.82; S 6.37.

EXAMPLE 54

Synthesis of 1,3-dimethyl-6-[4-(3-[4-methylmercapto-2-methanesulfonamidophenoxy]propyl)piperazin-1-yl]-2,4(1H,3H)-pyrimidinedione.hydrochloride (Compound 113)

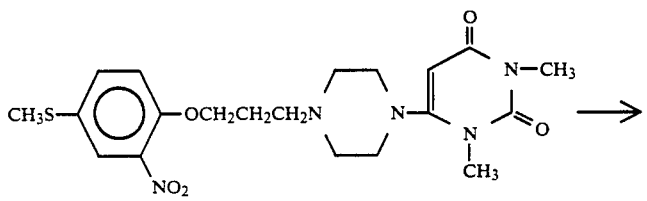

(Compound v)

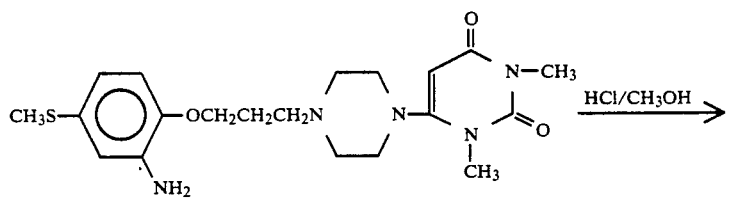

(Compound 114)

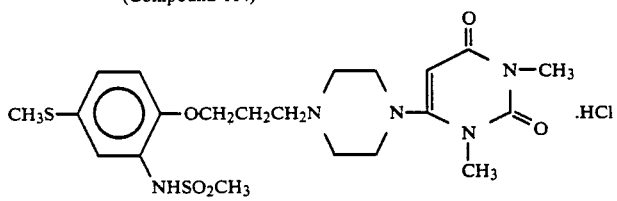

(Compound 113)

(1) Synthesis of 1,3-dimethyl-6-[4-(3-[2-amino-4-methylmercaptophenoxy]propyl)piperazin-1-yl]-2,4 (1H,3H)-pyrimidinedione (Compound 114)

2.0 g of the Compound v obtained in Reference Example 17 was dissolved in 20 ml of ethanol, and 4.5 g of stannic chloride (II) was added dropwise. The solution was heated up to 70° C. and then stirred for 30 minutes. The precipitated insolubles were removed by filtration, and the filtrate was then diluted with 100 ml of chloroform. Next, 20 ml of a 1N aqueous sodium hydroxide solution was added to the solution, followed by stirring vigorously. The formed insolubles were removed by filtration, and the resultant chloroform layer was separated, washed with water, dried over anhydrous sodium sulfate and then concentrated. The thus obtained oily product was purified through a silica gel column chromatograph (chloroform/methanol=100/1 in volume ratio), thereby obtaining 0.62 g of 1,3-dimethyl-6-[4-(3-[2-amino-4-methylmercaptophenoxy]propyl)piperazin-1-yl]-2,4(1H,3H)-pyrimidinedione (Compound 114).

Analytical results of the obtained Compound 114:
$^1$H-NMR (CDCl$_3$) δ ppm: 1.8–2.1 (m, 2H), 2.4–3.7 (m, 6H), 2.4 (s, 3H), 2.8–3.0 (m, 4H), 3.27 (s, 3H), 3.33 (s, 3H), 3.96 (t, 2H), 5.23 (s, 1H), 6.5–6.8 (m, 3H).

(2) Synthesis of 1,3-dimethyl-6-[4-(3-[4-methylmercapto-2-methanesulfonamidophenoxy]propyl)piperazin-1-yl]-2,4(1H,3H)-pyrimidinedione.hydrochloride (Compound 113)

0.57 g of the Compound 114 obtained above was treated in the same manner as in Example 7 to obtain 0.29 g of 1,3-dimethyl-6-[4-(3-[4-methylmercapto-2-methanesulfonamidophenoxy]propyl)piperazin-1-yl]-2,4(1H,3H)-pyrimidinedione.

Analytical results of the obtained pyrimidinedione derivative

Melting point: 55°–60° C.
$^1$H-NMR (CDCl$_3$) δ ppm: 1.8–2.2 (m, 2H), 2.3–2.7 (m, 6H), 2.43 (s, 3H), 2.7–3.1 (m, 4H), 2.95 (s, 3H), 3.28 (s, 3H), 3.34 (s, 3H), 4.03 (t, 2H), 5.18 (s, 1H), 6.7–7.5 (m, 3H).

This pyrimidinedione derivative was dissolved in a slightly excess hydrochloric acid/ethanol solution and then concentrated under reduced pressure, and the resultant residue was treated with ethanol to obtain 1,3-dimethyl-6-[4-(3-[4-methylmercapto-2-methanesulfonamidophenoxy]propyl)piperazin-1-yl]-2,4(1H,3H)-pyrimidinedione.hydrochloride (Compound 113).

Analytical results of the obtained Compound 113:
Melting point: 238°–241° C.
IR $\nu_{max}^{KBr}$ (cm$^{-1}$): 1965, 1635, 1490, 1330, 1250, 1160, 1140, 980, 760.
Values of elemental analysis (as C$_{21}$H$_{30}$N$_5$O$_5$S$_2$.HCl.1.5H$_2$O): Calcd. (%): C 45.03; H 6.12; N 12.50; S 11.45; Cl 6.33; Found (%): C 45.14; H 6.46; N 12.43; S 11.25; Cl 6.74.

EXAMPLE 55

Synthesis of 1,3-dimethyl-6-[4-(2-[2-methanesulfonamidophenyl]ethyl)piperazin-1-yl]-2,4(1H,3H)-pyrimidinedione.oxalate (Compound 115)

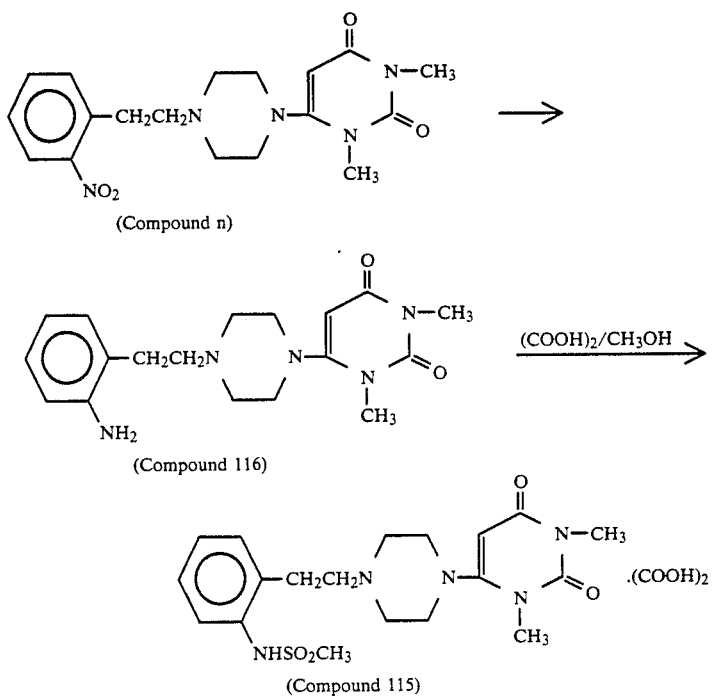

(1) Synthesis of 1,3-dimethyl-6-[4-(2-[2-aminophenyl]ethyl)piperazin-1-yl]-2,4(1H,3H)-pyrimidinedione.oxalate (Compound 116)

1.50 g of the Compound n obtained in Reference Example 9 was treated in the same manner as in Example 6, thereby preparing 1.0 g of crystalline 1,3-dimethyl-6-[4-(2-[2-aminophenyl]ethyl)piperazin-1-yl]-2,4(1H,3H)-pyrimidinedione (Compound 116).

Analytical results of the obtained Compound 116
NMR (CDCl$_3$/DMSO-d$^6$=1/1 in volume ratio) δ ppm: 2.7–3.0 (m, 10H), 3.1 (m, 2H), 3.29 (s, 3H), 3.38 (s, 3H), 5.08 (s, 1H), 7.72 (m, 4H).

0.40 g of this pyrimidinedione derivative was treated with an oxalic acid/methanol solution in an ordinary manner to obtain 0.21 g of 1,3-dimethyl-6-[4-[2-(2-[2-aminophenyl]ethyl)piperazin-1-yl]-2,4(1H,3H)-pyrimidinedione.oxalate.

Analytical results of the obtained pyrimidinedione derivative oxalate:
IR $\nu_{max}^{KBr}$ (cm$^{-1}$): 2950, 1690, 1660, 1600, 760.

Values of elemental analysis (as $C_{18}H_{25}N_5O_2 \cdot 2(CO_2H)_2 \cdot 2H_2O$): Calcd. (%): C 47.23; H 5.95; N 12.52; Found (%): C 46.89; H 5.92; N 12.26.

(2) Synthesis of 1,3-dimethyl-6-[4-(2-[2-methanesulfonamidophenyl]ethyl)piperazin-1-yl]-2,4(1H,3H)-pyrimidinedione.oxalate (Compound 115)

The Compound 116 obtained above was treated in the same manner as in Example 7 to obtain 1,3-dimethyl-6-[4-(2-[2-methanesulfonamidophenyl]ethyl)piperazin-1-yl]-2,4(1H,3H)-pyrimidinedione.

Analytical results of the obtained pyrimidinedione derivative $^1$H-NMR (CDCl$_3$) δ ppm: 2.8–3.0 (m, 10H), 3.1 (m, 2H), 3.07 (s, 3H), 3.29 (s, 3H), 3.35 (s, 3H), 5.02 (s, 1H), 7.50 (n, 4H).

0.60 g of this pyrimidinedione derivative was treated with an oxalic acid/methanol solution in an ordinary manner to obtain 0.32 g of 1,3-dimethyl-6-[4-(2-[2-methanesulfonamidophenyl]ethyl)piperazin-1-yl]-2,4(1H,3H)-pyrimidinedione.oxalate (Compound 115).

Analytical results of the obtained Compound 115:

IR $\nu_{max}^{KBr}$ (cm$^{-1}$): 3000, 2900, 1730, 1660, 1610, 1160, 750.

Values of elemental analysis (as $C_{19}H_{27}N_5O_4S \cdot (CO_2H)_2 \cdot 3H_2O$): Calcd. (%): C 44.60; H 6.24; N 12.38; S 5.67; Found (%): C 44.75; H 5.94; N 12.37; S 5.61.

EXAMPLE 56

Synthesis of 1,3-dimethyl-6-[2-(N-ethyl-3-[4-benzoylphenoxy]propylamino)ethylamino]-2,4(1H,3H)-pyrimidinedione.oxalate (Compound 117)

(2) Synthesis of N-ethyl-3-(4-benzoylphenyloxy)propylamine 1.0 g of 4-(3-bromopropyloxy)benzophenone was dissolved in a 70% aqueous ethylamine solution, and then stirred at 90° C. for 5 hours. The mixture was dissolved in 50 ml of chloroform, washed with water three times, dried over anhydrous sodium sulfate and then concentrated to obtain 0.9 g of N-ethyl-3-(4-benzoylphenyloxy)propylamine.

(3) Synthesis of 1,3-dimethyl-6-[2-(N-ethyl-3-[4-benzoylphenoxy]propylamino)ethylamino]-2,4(1H,3H)-pyrimidinedione.oxalate (Compound 117)

0.2 g of 6-(1-aziridinyl)-1,3-dimethyl-2,4(1H,3H)-pyrimidinedione (Compound j) obtained in Reference Example 7 and 0.8 g of N-ethyl-3-(4-benzoylphenyloxy)propylamine were dissolved in 20 ml of chloroform, and 0.1 g of p-toluenesulfonic acid was added. Afterward, the solution was concentrated, and the residue was then stirred at 80° C. for 3 hours. After standing for cooling, this mixture was dissolved in 50 ml of chloroform, washed with water, dried over anhydrous sodium sulfate and then concentrated. The resultant residue was purified through a silica gel column chromatograph (chloroform/methanol = 50/1 in volume ratio), thereby obtaining 0.48 g of 1,3-dimethyl-6-[2-(N-ethyl-3-[4-benzoylphenoxy]propylamino)ethylamino]-2,4(1H,3H)-pyrimidinedione.

Analytical results of the obtained pyrimidinedione derivative $^1$H-NMR (CDCl$_3$) δ ppm: 1.06 (t, 3H), 2.04 (m, 2H), 2.5–3.1 (m, 8H), 3.23 (s, 6H), 4.07 (t, 2H), 4.74 (s, 1H),

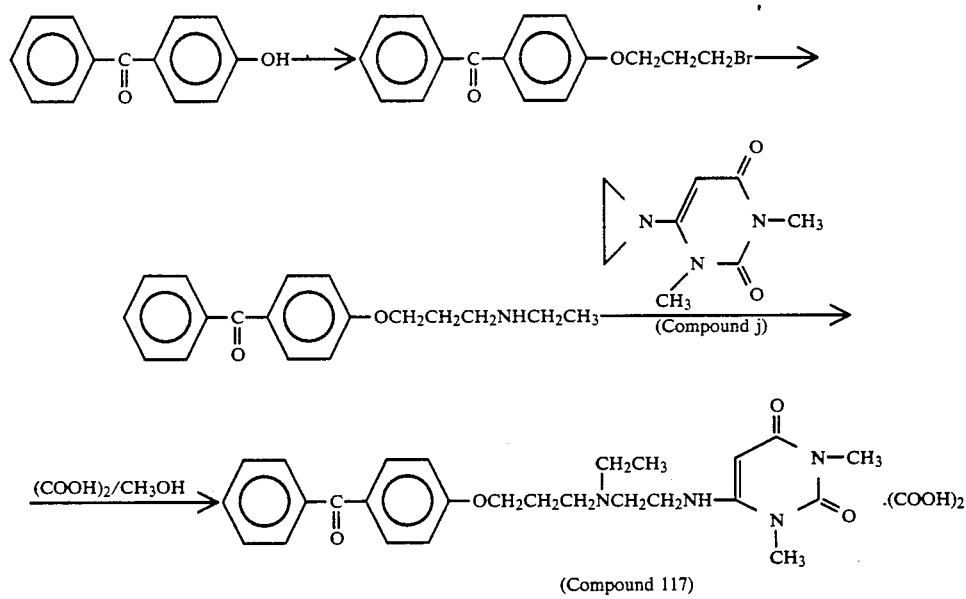

(Compound 117)

(1) Synthesis of 4-(3-bromopropyloxy)benzophenone 6 g of 4-hydroxybenzophenone, 12 ml of dibromopropane and 4.1 g of potassium carbonate were treated in 10 ml of 2-butanone in the same manner as in the section (1) of Reference Example 2, thereby obtaining 4.4 g of 4-(3-bromopropyloxy)benzophenone.

5.48 (m, 1H), 6.88 (m, 2H), 7.73 (m, 7H).

0.41 g of this pyrimidinedione derivative was treated with an oxalic acid/methanol solution in an ordinary manner to obtain 0.34 g of 1,3-dimethyl-6-[2-(N-ethyl-3-[4-benzoylphenoxy]propylamino)ethylamino]-2,4(1H,3H)-pyrimidinedione.oxalate (Compound 117).

Analytical results of the obtained pyrimidinedione derivative

IR $\nu_{max}^{KBr}$ (cm$^{-1}$): 3350, 2650, 1730, 1640, 1600, 1210, 770, 700.

Values of elemental analysis (as $C_{26}H_{32}N_4O_4$): Calcd. (%): C 54.80; H 6.18; N 8.81; Found (%): C 54.69; H 5.93; N 8.54.

EXAMPLE 57

Synthesis of 1,3-dimethyl-6-[2-(N-[2-hydroxyethyl]-3-(4-benzoyl-2-fluorophenoxy)propylamino)ethylamino]-2,4(1H,3H)-pyrimidinedione.oxalate (Compound 118)

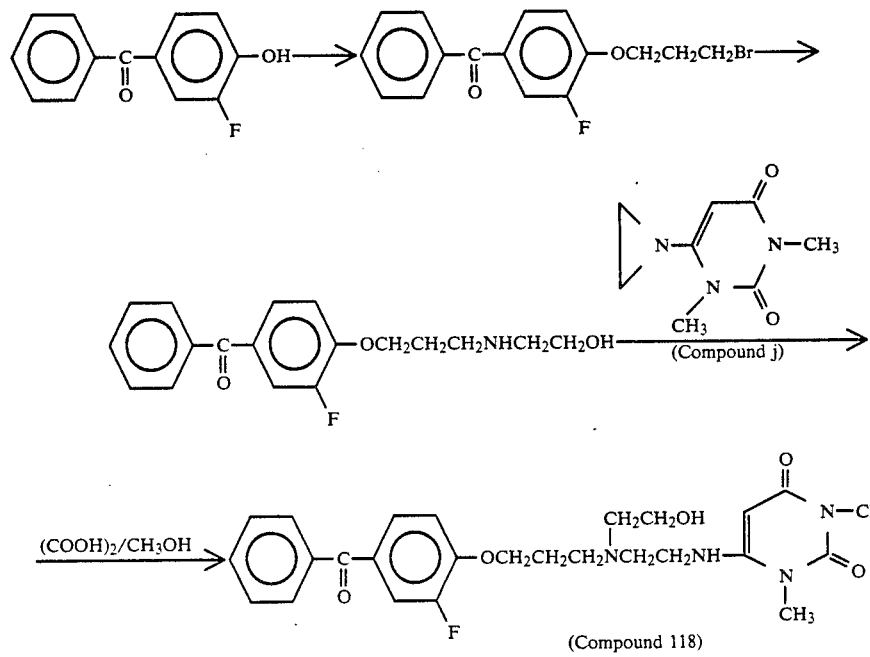

(1) Synthesis of 4-(3-bromopropyloxy)-3-fluorobenzophenone 1.5 g of 4-hydroxy-3-fluorobenzophenone, 2.9 ml of dibromopropane and 3.0 g of potassium carbonate were treated in 10 ml of 2-butanone in the same manner as in the section (1) of Reference Example 2, thereby obtaining 1.7 g of 4-(3-bromopropyloxy)-3-fluorobenzophenone.

(2) Synthesis of N-[2-hydroxyethyl 1-3-(4-benzoyl3-fluorophenyloxy)propylamine 1.7 g of 4-(3-bromopropyloxy)-3-fluorobenzophenone and 5.5 ml of ethanolamine were dissolved in 5 ml of dioxane, and the solution was then stirred at 90° C. for 3 hours. The mixture was allowed to stand for cooling, dissolved in 50 ml of chloroform, washed with water twice, dried over anhydrous sodium sulfate and then concentrated to obtain 1.2 g of N-[2-hydroxyethyl]-3-(4-benzoyl-3-fluorophenyloxy)propylamine.

(3) Synthesis of 1,3-dimethyl-6-[2-(N-[2-hydroxyethyl]-3-(4-benzoyl-2-fluorophenoxy)propylamino)ethylamino]-2,4(1H,3H)-pyrimidinedione.oxalate (Compound 118)

0.8 g of 6-(1-aziridinyl)-1,3-dimethyl-2,4(1H,3H)-pyrimidinedione (Compound j) obtained in Reference Example 7 and 1.0 g of N-(2-hydroxyethyl)-3-(4-benzoyl-2-fluorophenyloxy)propylamine were dissolved in 30 ml of chloroform, and 0.1 g of p-toluenesulfonic acid was added. The solution was then treated in the same manner as in the section (3) of Example 56 to prepare 1.3 g of 1,3-dimethyl-6-[2-(N-[2-hydroxyethyl]-3-(4-benzoyl-2-fluorophenoxy)propylamino)ethylamino]-2,4(1H,3H)-pyrimidinedione.

Analytical results of the obtained Compound $^1$H-NMR (CDCl$_3$) δ ppm: 2.1 (m, 2H), 2.5–3.3 (m, 8H), 3.36 (s, 3H), 3.42 (s, 3H), 4.2–4.4 (m, 4H), 4.91 (s, 1H), 6.9–7.8 (m, 8H).

1.00 g of this pyrimidinedione derivative was treated with an oxalic acid/methanol solution in an ordinary manner to obtain 0.97 g of 1,3-dimethyl-6-[2-(N-[2-hydroxyethyl]-3-(4-benzoyl-2-fluorophenoxy)-propylamino)ethylamino]-2,4(1H,3H)-pyrimidinedione.oxalate (Compound 118).

Analytical results of the obtained Compound 118

Melting point: 117°–120° C. (decomposed).

IR $\nu_{max}^{KBr}$(cm$^{-1}$): 3450, 1740, 1690, 1620, 1280, 1105 760.

Values of elemental analysis Calcd. (%): C 53.08; H 6.05; N 8.81; Found (%): C 52.34; H 5.80; N 9.08.

EXAMPLE 58

Synthesis of 1,3-dimethyl-6-[2-(N-[2-hydroxyethyl]-3-(4-acetyl-2-fluorophenoxy)propylamino)ethylamino]-2,4(1H,3H)-pyrimidinedione.oxalate (Compound 119)

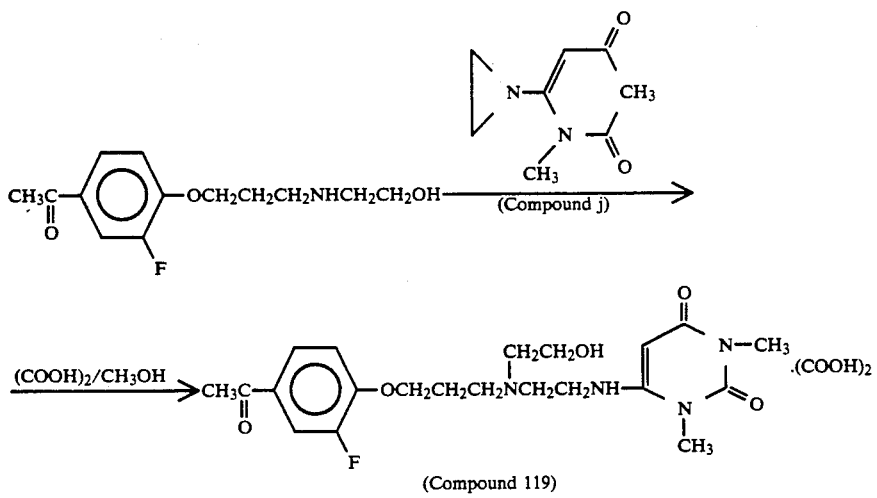

(1) Synthesis of 4-(3-bromopropyloxy)-3-fluoroacetophenone 5.0 g of 4-hydroxy-2-fluoroacetophenone, 15 ml of dibromopropane and 9.0 g of potassium carbonate were treated in 30 ml of 2-butanone in the same manner as in the section (1) of Reference Example 2, thereby obtaining 4.8 g of 4-(3-bromopropyloxy)-3-fluoroacetophenone.

(2) Synthesis of N-(2-hydroxyethyl)-3-(4-acetyl-3-fluorophenyloxy)-propylamine 2.0 g of 4-(3-bromopropyloxy)-3-fluoroactophenone and 7.9 ml of ethanolamine were dissolved in 7.2 ml of dioxane, and the solution was then treated in the same manner as in the section (2) of Example 57 to obtain 1.63 g of N-(2-hydroxyethyl)-3-(4-acetyl-2-fluorophenyloxy)propylamine.

(3) Synthesis of 1,3-dimethyl-6-[2-(N-[2-hydroxyethyl]-3-(4-acetyl-2-fluorophenoxy)propylamino)ethylamino]-2,4(1H,3H)-pyrimidinedione.oxalate (Compound 119)

1.0 g of 6-(1-aziridinyl)-1,3-dimethyl-2,4(1H,3H)-pyrimidinedione (Compound j) obtained in Reference Example 7 and 1.6 g of N-(2-hydroxyethyl)-3-(4-acetyl-2-fluorophenyloxy)propylamine were dissolved in 50 ml of chloroform, and 0.1 g of p-toluenesulfonic acid was added. The solution was then treated in the same manner as in the section (3) of Example 56 to prepare 1.41 g of 1,3-dimethyl-6-[2-(N-[2-hydroxyethyl]-3-(4-acetyl-2-fluorophenoxy)propylamino)ethylamino]-2,4(1H,3H)-pyrimidinedione.

Analytical results of the obtained pyrimidinedione derivative $^1$H-NMR (CDCl$_3$) δ ppm: 2.1 (m, 2H), 2.4–3.1 (m, 8H), 2.70 (s, 3H), 4.1–4.2 (m, 4H), 3.31 (s, 3H), 3.38 (s, 3H), 4.71 (s, 1H), 6.17 (m, 1H), 6.9–7.9 (m, 3H).

1.23 g of this pyrimidinedione derivative was treated with an oxalic acid/methanol solution in an ordinary manner to obtain 1.02 g of 1,3-dimethyl-6-[2-(N-[2-hydroxyethyl]-3-(4-acetyl-2-fluorophenoxy)-propylamino)ethylamino]-2,4(1H,3H)-pyrimidine-dione.oxalate (Compound 119).

Analytical results of the obtained Compound 119

Melting point: 163°–165° C. (decomposed).

IR $\nu_{max}^{KBr}$ (cm$^{-1}$): 3540, 2600, 1700, 1640, 1600, 1260, 860.

Values of elemental analysis (as C$_{21}$H$_{29}$N$_4$O$_5$F.(CO$_2$H)$_2$.½H$_2$O): Calcd. (%): C 51.59; H 6.02; N 10.46; Found (%): C 51.26; H 6.42; N 10.19.

EXAMPLE 59

Synthesis of 1,3-dimethyl-6-[2-(N-[2-hydroxyethyl]-3-phenyl-propylamino)ethylamino]-2,4(1H,3H)-pyrimidine-dione.oxalate (Compound 120)

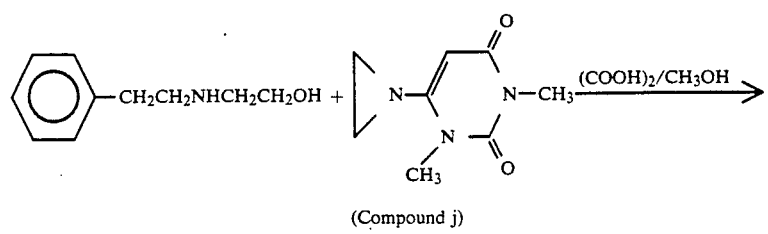

(Compound j)

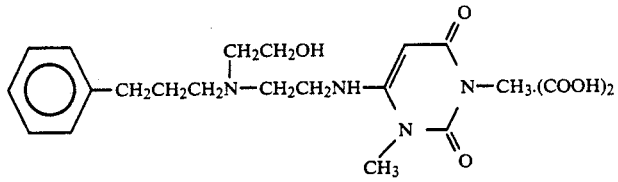

(Compound 120)

1.0 g of N-(2-hydroxyethyl)-3-phenylpropylamine and 1.02 g of 6-(1-aziridinyl)-1,3-dimethyl-2,4(1H,3H)-pyrimidinedione (Compound j) obtained in Reference Example 7 were dissolved in 80 ml of chloroform, and 0.2 g of p-toluenesulfonic acid was added. The solution was then treated in the same manner as in the section (3) of Example 56 to prepare 1.10 g of 1,3-dimethyl-6-[2-(N-[2-hydroxyethyl]-3-phenylpropylamino)ethylamino]-2,4(1H,3H)-pyrimidinedione.

Analytical results of the obtained pyrimidinedione derivative $^1$H-NMR (CDCl$_3$) δ ppm: 1.9 (m, 2H), 2.3–3.0 (m, 8H), 3.20 (s, 3H), 3.33 (s, 3H), 3.60 (t, 2H), 4.05 (m, 2H), 4.66 (s, 1H), 6.22 (m, 1H), 7.12 (s, 5H).

1.08 g of this pyrimidinedione derivative was treated with an oxalic acid/methanol solution in an ordinary manner to obtain 1.15 g of 1,3-dimethyl-6-[2-(N-[2-hydroxyethyl]-3-phenylpropylamino)ethylamino]-2,4(1H,3H)-pyrimidinedione-oxalate (Compound 120).

Analytical results of the obtained Compound 120

IR $v_{max}^{KBr}$ (cm$^{-1}$): 3350, 2900, 1690, 1590, 1200, 770, 700.

Values of elemental analysis (as C$_{19}$H$_{28}$N$_4$O$_3$·(CO$_2$H)$_2$·H$_2$O): Calcd. (%): C 53.84; H 6.88; N 11.96; Found (%): C 53.57; H 6.67; N 11.92.

EXAMPLE 60

Synthesis of 1,3-dimethyl-6-[2-(N-ethyl-3-phenylpropylamino)ethylamino]-2,4(1H,3H)-pyrimidinedione.oxalate (Compound 121)

Analytical results of the obtained pyrimidinedione derivative $^1$H-NMR (CDCl$_3$) δ ppm: 1.11 (t, 3H), 2.0 (m, 2H), 2.3–3.3 (m, 10H), 3.28 (s, 3H), 3.35 (s, 3H), 4.79 (s, 1H), 5.2 (m, 1H), 7.08 (m, 5H).

1.06 g of this pyrimidinedione derivative was treated with an oxalic acid/methanol solution in an ordinary manner to obtain 1.11 g of 1,3-dimethyl-6-[2-(N-ethyl-3-phenylpropylamino)ethylamino]-2,4(1H,3H)-pyrimidinedione.oxalate (Compound 121).

Analytical results of the obtained Compound 121

IR $v_{max}^{KBr}$ (cm$^{-1}$): 3300, 2900, 1690, 1600, 1440, 1200, 750, 700.

Values of elemental analysis (as C$_{19}$H$_{28}$N$_4$O$_2$·(CO$_2$H)$_2$·H$_2$O): Calcd. (%): C 55.74; H 7.13; N 12.38; Found (%): C 55.68; H 7.22; N 11.98.

EXAMPLE 61

Synthesis of 1,3-dimethyl-6-[4-(4-methanesulfonamidobenzoyl)piperazin-1-yl]-2,4(1H,3H)-pyrimidinedione (Compound 122)

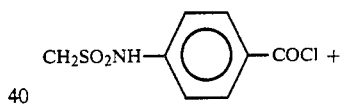

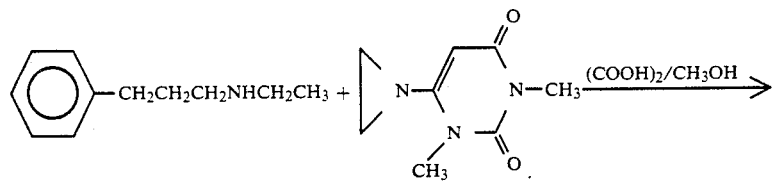

(Compound j)

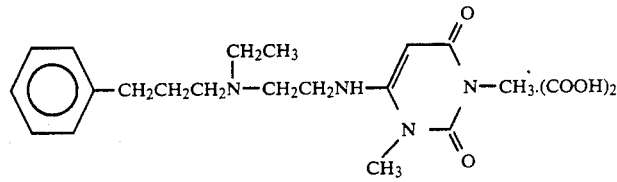

(Compound 121)

1.12 g of N-ethyl-3-phenylpropylamine and 0.91 g of 6-(1-aziridinyl)-1,3-dimethyl-2,4(1H,3H)-pyrimidinedione (Compound j) obtained in Reference Example 7 were dissolved in 80 ml of chloroform, and 0.2 g of p-toluenesulfonic acid was added. The solution was then treated in the same manner as in the section (3) of Example 56 to prepare 1.10 g of 1,3-dimethyl-6-[2-(N-

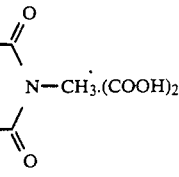

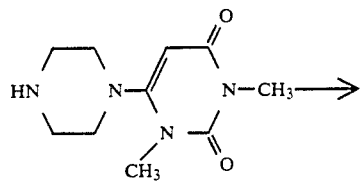

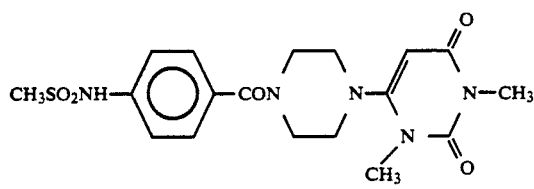

(Compound 122)

EXAMPLE 62

Synthesis of 1,3-dimethyl-6-[2-(4-methanesulfonamidobenzoylamino)ethylamino]-2,4(1H,3H)-pyrimidinedione.hydrochloride (Compound 123)

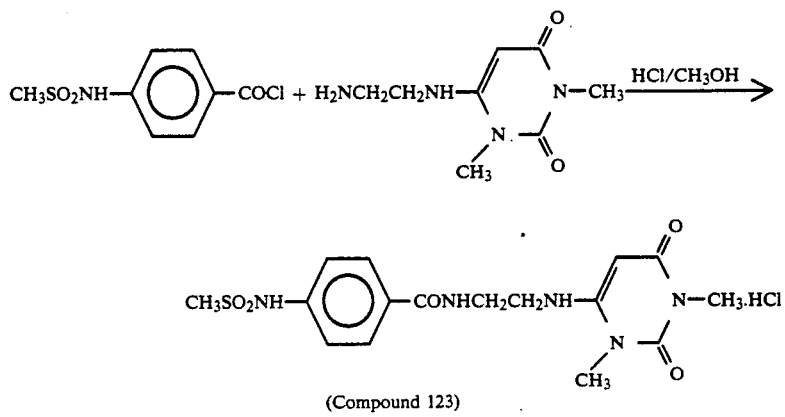

(Compound 123)

In 20 ml of tetrahydrofuran were dissolved 0.55 g of 4-methanesulfonylamidobenzoyl chloride, 0.53 g of 1,3-dimethyl-6-(1-piperazinyl)-2,4(1H,3H)-pyrimidinedione and 1.8 ml of triethylamine, and the solution was stirred at 0° C. for 30 minutes. A small amount of water was added to the solution, and the solvent was then distilled off. Methanol was poured into the resultant residue, and the formed crystals were collected by filtration, thereby obtaining 0.75 g of 1,3-dimethyl-6-[4-(4-methanesulfonamidobenzoyl)piperazin-1-yl]-2,4(1H,3H)-pyrimidinedione (Compound 122).

Analytical results of the obtained Compound 122
Melting point: 237°–238° C.

IR $\nu_{max}^{KBr}$ (cm$^{-1}$): 3350, 1700, 1640, 1620, 1340, 1160, 770.

$^1$H-NMR (CDCl$_3$) δ ppm: 3.16 (s, 3H), 3.22 (s, 3H), 3.46 (s, 3H), 3.0–3.9 (m, 8H), 5.28 (s, 1H), 7.53 (m, 4H).

The same treatment as in Example 61 was effected except that 1,3-dimethyl-6-(1-piperazinyl)-2,4(1H,3H)-pyrimidinedione was replaced with 0.48 g of 1,3-dimethyl-6-(2-aminoethylamino)-2,4(1H,3H)-pyrimidinedione, thereby obtaining 0.79 g of 1,3-dimethyl-6-[2-(4-methanesulfonamidobenzoylamino)ethylamino]-2,4(1H,3H)-pyrimidinedione.

Analytical results of the obtained pyrimidinedione derivative $^1$H-NMR (DMSO-d$_6$) δ ppm: 3.02 (s, 3H), 3.22 (s, 3H), 3.38 (s, 3H), 3.5 (m, 4H), 4.78 (s, 1H), 7.3 (d, 2H), 7.84 (d, 2H).

0.7 g of this pyrimidinedione derivative was treated with a hydrochloric acid/methanol solution in an ordinary manner to obtain 0.62 g of 1,3-dimethyl-6-[2-(4-methanesulfonamidobenzoylamino)ethylamino]-2,4(1H,3 H)-pyrimidinedione.hydrochloride (Compound 123).

Analytical results of the obtained Compound 123
Melting point: 213°–218° C.

IR $\nu_{max}^{KBr}$ (cm$^{-1}$): 3300, 3200, 1720, 1640, 1600, 1340, 1150, 770.

EXAMPLE 63

Synthesis of 1,3-dimethyl-6-[4-(3-[4-methanesulfonamidobenzoyloxy]propyl)piperazin-1-yl]-2,4(1H,3H)-pyrimidinedione.hydrochloride (Compound 124)

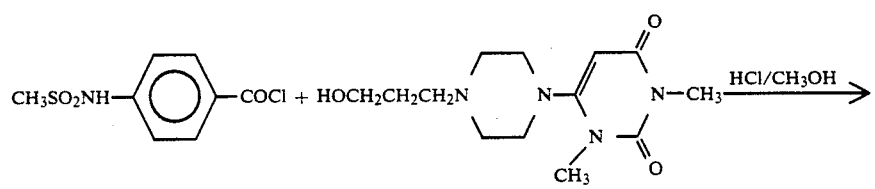

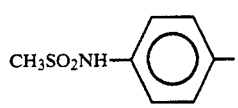

(Compound 124)

The same treatment as in Example 61 was effected except that 1,3-dimethyl-6-(1-piperazinyl)-2,4(1H,3H)-pyrimidinedione was replaced with 0.7 g of 1,3-dimethyl6-[4-(3-hydroxypropyl)piperazin-1-yl]-2,4(1H,3H)-pyrimidinedione, thereby obtaining 0.35 g of 1,3-dimethyl-6-[4-(3-[4-methanesulfonamidobenzoyloxy]-propyl)piperazin-1-yl]-2,4(1H,3H)-pyrimidinedione.

Analytical results of the obtained pyrimidinedione derivative $^1$H-NMR (DMSO-d$_6$) δ ppm: 1.7–2.1 (m, 2H), 2.4–3.1 (m, 10H), 3.02 (s, 3H), 3.28 (s, 3H), 3.33 (s, 3H), 4.28 (t, 2H), 5.24 (s, 1H), 7.3 (2d, 2H), 7.97 (d, 2H).

0.3 g of this pyrimidinedione derivative was treated with a hydrochloric acid/methanol solution in an ordinary manner to obtain 0.25 g of crystalline 1,3-dimethyl-6-[4-(3-[4-methanesulfonamidobenzoyloxy]propyl)piperazin-1-yl]-2,4(1H,3H)-pyrimidinedione.hydrochloride (Compound 124).

Analytical results of the obtained Compound 124
IR $\nu_{max}^{KBr}$ (cm$^{-1}$): 1705, 1640, 1330, 1280, 1150, 1120, 980, 760, 700.
Values of elemental analysis (as C$_{21}$H$_{29}$N$_5$O$_6$S.HCl.½H$_2$O): Calcd. (%): C 47.95; H 6.13; N 13.31; S 6.09; Cl 6.74; Found (%): C 47.86; H 6.58; N 13.76; S 5.70; Cl 6.65.

EXAMPLE 64

Synthesis of 1,3-dimethyl-6-[4-(2-[4-methanesulfonamidobenzoylamino] ethyl)piperazin-1-yl]-2,4(1H,3H)-pyrimidinedione.hydrochloride (Compound 125)

Analytical results of the obtained pyrimidinedione derivative
Melting point: 214°–217° C.
Values of elemental analysis (as C$_{20}$H$_{28}$N$_6$O$_5$S): Calcd. (%): C 51.70; H 6.07; N 18.12; S 6.90; Found (%): C 51.65; H 6.19; N 18.12; S 6.94.

0.3 g of this pyrimidinedione derivative was treated with a hydrochloric acid/methanol solution in an ordinary manner to obtain 0.28 g of crystalline 1,3-dimethyl-6-[4-(2-[4-methanesulfonamidobenzoylamino]ethyl)piperazin-1-yl]-2,4(1H,3H)-pyrimidinedione.hydrochloride (Compound 125).

Analytical results of the obtained Compound 125
Melting point: 250°–255° C.
IR $\nu_{max}^{KBr}$ (cm$^{-1}$): 2900, 2800, 1680, 1640, 1560, 1340, 1160, 760.
$^1$H-NMR (D$_2$O) δ ppm: 3.0 (m, 6H), 3.06 (s, 3H), 3.12 (s, 3H), 3.32 (s, 2H), 3.66 (m, 6H), 5.18 (s, 1H), 7.3 (d, 2H), 7.8 (d, 2H).

EXAMPLE 65

Synthesis of 1,3-dimethyl-6-[4-(3-[2-hydroxy-5-methanesulfonamidophenoxy]propyl)piperazin-1-yl]-2,4(1H,3H)-pyrimidinedione.hydrochloride (Compound 126)

(1) Synthesis of 1,3-dimethyl-6-[4-(3-[2-hydroxy-5-aminophenoxy]-propyl)piperazin-1-yl]-2,4(1H,3H)-pyrimidinedione (Compound 127)

The Compound y obtained in Reference Example 20 was hydrogenated in the same manner as in Example 6

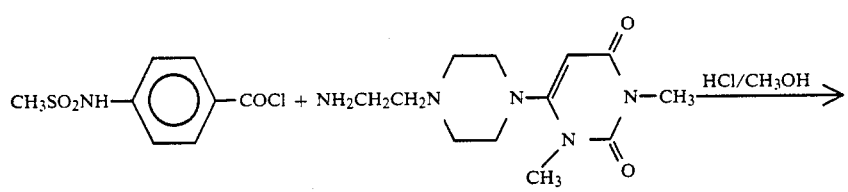

(Compound 125)

The same treatment as in Example 61 was effected except that 1,3-dimethyl-6-(1-piperazinyl)-2,4(1H,3H)-pyrimidinedione was replaced with 0.67 g of 1,3-dimethyl-6-[4-(2-aminoethyl)piperazin-1-yl]-2,4(1H,3H)-pyrimidinedlone, thereby obtaining 0.45 g of 1,3-dimethyl-6-[4-(2-[4-methanesulfonamidobenzoylamino]ethyl)piperazin-1-yl]-2,4(1H,3H)-pyrimidinedione.

to obtain crystalline 1,3-dimethyl-6-[4-(3-[2-hydroxy-5-aminophenoxy]propyl)piperazin-1-yl]-2,4(1H,3H)-pyrimidinedione (Compound 127).

Analytical results of the obtained compound 127
Melting point: 171°–172° C.
$^1$H-NMR (CDCl$_3$) δ ppm: 1.8–2.1 (m, 2H), 2.6–3.2 (m, 10H), 3.3 (s, 3H), 3.36 (s, 3H), 3.86 (t, 2H), 5.24 (s, 1H), 5.90–6.24 (m, 2H), 6.72 (d, 1H).

(2) Synthesis of
1,3-dimethyl-6-[4-(3-[2-hydroxy-5-methanesulfonamidophenoxy]propyl)piperazin-1-yl]-2,4(1H,3H)-pyrimidinedione.hydrochloride (Compound 126)

The Compound 127 obtained above was treated in the same manner as in Example 7, thereby obtaining the crystals of 1,3-dimethyl-6-[4-(3-[2-hydroxy-5-methanesulfonamidophenoxy]propyl)piperazin-1-yl]-2,4(1H,3H)-pyrimidinedione.

Analytical results of the obtained pyrimidinedione derivative $^1$H-NMR (CDCl$_3$) δ ppm: 1.7–2.05 (m, 2H), 2.40–3.04 (m, 10H), 2.86 (s, 3H), 3.14 (s, 3H), 3.28 (s, 3H), 3.90 (t, 2H), 5.14 (s, 1H), 6.44–6.90 (m, 3H), 9.12 (s, 2H).

IR $\nu_{max}^{KBr}$ (cm$^{-1}$): 1680, 1600, 1510, 1490, 1440, 1200, 1150.

This pyrimidinedione derivative was treated with a hydrochloric acid/methanol solution in an ordinary manner to obtain the crystals of 1,3-dimethyl-6-[4-(3-[2-hydroxy-5-methanesulfonamidophenoxy]propyl)piperazin-1-yl]-2,4(1H,3H)-pyrimidinedione.hydrochloride (Compound 126).

Analytical results of the obtained Compound 126
Values of elemental analysis (as C$_{20}$H$_{29}$N$_5$O$_6$S.HCl.1.5H$_2$O): Calcd. (%): C 44.46; H 6.06; N 12.96; Cl 9.84; S 5.93; Found (%): C 44.23; H 6.31; N 12.62; Cl 9.52; S 5.90.

EXAMPLE 66

Synthesis of
1,3-dimethyl-6-[4-(2-[4-methanesulfonamidophenyl]ethyl)piperazin-1-yl]-2,4(1H,3H)-pyrimidinedione.hydrochloride (Compound 128)

(1) Synthesis of
1,3-dimethyl-6-[4-(2-[4-aminophenyl]ethyl)piperazin-1-yl]-2,4(1H,3H)-pyrimidinedione (Compound 129)

The Compound i obtained in Reference Example 6 was hydrogenated in the same manner as in Example 6 to obtain the crystals of 1,3-dimethyl-6-[4-(2-[4-aminophenyl]-ethyl)piperazin-1-yl]-2,4(1H,3H)-pyrimidinedione (Compound 129).

Analytical results of the obtained Compound 129
$^1$H-NMR (CDCl$_3$) δ ppm: 2.68 (m, 6H) 3.00 (m, 4H), 3.33 (s, 3H), 3.40 (s, 3H), 3.62 (m, 2H), 5.28 (s, 1H), 6.50–7.30 (m, 4H).

IR $\nu_{max}^{KBr}$ (cm$^{-1}$): 3420, 3330, 2920, 2850, 2800, 1690, 1650, 1610, 1515, 1465, 1440, 1250, 1195, 1000, 800, 760.

(2) Synthesis of
1,3-dimethyl-6-[4-(2-[4-methanesulfonamidophenyl]ethyl)piperazin-1-yl]-2,4(1H,3H)-pyrimidinedione.hydrochloride (Compound 128)

The Compound 129 obtained above was treated in the same manner as in Example 7, thereby obtaining the crystals of 1,3-dimethyl-6-[4-(2-[4-methanesulfonamidophenyl]ethyl)piperazin-1-yl]-2,4(1H,3H)-pyrimidinedione. Furthermore, this pyrimidinedione derivative was treated with a hydrochloric acid/methanol solution in an ordinary manner to obtain the crystals of 1,3-dimethyl-6-[4-(2-[4-methanesulfonamidophenyl]ethyl)-piperazin-1-yl]-2,4(1H,3H)-pyrimidinedione.hydrochloride (Compound 128).

Analytical results of the obtained Compound 128
Values of elemental analysis (as C$_{19}$H$_{27}$N$_5$O$_4$S.HCl.½H$_2$O): Calcd. (%): C 48.87; H 6.26; N 15.00; Cl 7.59; S 6.87; Found (%): C 49.26; H 6.66; N 14.73; Cl 7.59; S 6.73.

IR $\nu_{max}^{KBr}$ (cm$^{-1}$): 1700, 1650, 1610, 1480, 1435, 1330, 1230, 1160, 1115, 1030, 1000, 790, 760, 700.

EXAMPLE 67

Synthesis of
1,3-dimethyl-6-[4-(4-[4-methanesulfonamidophenyl]butyl)piperazin-1-yl]-2,4(1H,3H)-pyrimidinedione.hydrochloride (Compound 130):

(1) Synthesis of
1,3-dimethyl-6-[4-(4-[4-aminophenyl]butyl)piperazin-1-yl]-2,4(1H,3H)-pyrimidinedione (Compound 131)

The Compound o obtained in Reference Example 6 was hydrogenated in the same manner as in Example 6 to obtain the crystals of 1,3-dimethyl-6-[4-(4-[4-aminophenyl]-butyl)piperazin-1-yl]-2,4(1H,3H)-pyrimidinedione (Compound 131).

Analytical results of the obtained Compound 131
$^1$H-NMR (CDCl$_3$) δ ppm: 1.50 (m, 4H), 2.2–2.6 (m, 8H), 2.88 (m, 4H), 3.27 (s, 3H), 3.32 (s, 3H), 3.52 (s, 2H), 5.24 (s, 1H), 6.56 (d, 2H), 6.90 (d, 2H).

IR $\nu_{max}^{KBr}$ (cm$^{-1}$): 3440, 3370, 2940, 1700, 1645, 1615, 1500, 1440, 1380, 1220, 1130, 1000.

(2) Synthesis of
1,3-dimethyl-6-[4-(4-[4-methanesulfonamidophenyl]butyl)piperazin-1-yl]-2,4(1H,3H)-pyrimidinedione.hydrochloride (Compound 130)

The Compound 131 obtained above was treated in the same manner as in Example 7, thereby obtaining the crystals of 1,3-dimethyl-6-[4-(4-[4-methanesulfonamidophenyl]butyl)piperazin-1-yl]-2,4(1H,3H)-pyrimidinedione.

Analytical results of the obtained pyrimidinedione derivative

IR $\nu_{max}^{KBr}$ (cm$^{-1}$): 3450, 1695, 1645, 1600, 1490, 1445, 1340, 1160, 970, 805, 770, 560.

$^1$H-NMR (CDCl$_3$) δ ppm: 1.54 (m, 4H), 2.2–2.68 (m, 8H), 2.96 (m, 7H), 3.30 (s, 3H), 3.30 (s, 3H), 5.23 (s, 1H), 7.19 (s, 4H).

Furthermore, this pyrimidinedione derivative was treated with a hydrochloric acid/methanol solution in an ordinary manner to obtain crystalline 1,3-dimethyl-6-[4-(4-[4-methanesulfonamidophenyl]butyl)piperazin-1-yl]-2,4(1H,3H)-pyrimidinedione.hydrochloride (Compound 130).

Values of elemental analysis (as C$_{21}$H$_{31}$N$_5$O$_4$S.HCl): Calcd. (%): C 51.90; H 6.64; N 14.41; Cl 7.29; S 6.60; Found (%): C 51.58; H 6.96; N 14.06; Cl 7.25; S 6.53.

IR $\nu_{max}^{KBr}$ (cm$^{-1}$): 3450, 1705, 1660, 1615, 1435, 1335, 1160.

EXAMPLE 63

Synthesis of
1,3-dimethyl-6-[4-(3-[4-benzoyl-2-methanesulfonamidophenoxy]propyl)piperazin-1-yl]-2,4(1H,3H)-pyrimidinedione.hydrochloride (Compound 132)

(1) Synthesis of
1,3-dimethyl-6-[4-(3-[2-amino-4-benzoylphenoxy]propyl)piperazin-1-yl]-2,4(1H,3H)-pyrimidinedione (Compound 133)

The Compound r obtained in Reference Example 13 was hydrogenated in the same manner as in Example 6 to obtain the crystals of 1,3-dimethyl-6-[4-(3-[2-amino- 4-benzoylphenoxy]propyl)piperazin-1-yl]-2,4(1H,3H)-pyrimidinedione (Compound 133).

Analytical results of the obtained Compound 133

$^1$H-NMR (CDCl$_3$+DMSO-d$_6$) δ ppm: 2.0 (m, 2H), 2.6–3.0 (m, 10H), 3.26 (s, 3H), 3.33 (s, 3H), 4.10 (t, 2H), 5.22 (s, 1H), 6.9–7.8 (m, 8H).

IR $\nu_{max}^{KBr}$ (cm$^{-1}$): 3400, 2550, 1700, 1650, 1440, 1290, 810, 790, 760, 710.

(2) Synthesis of 1,3-dimethyl-6-[4-(3-[4-benzoyl-2-methanesulfonamidophenoxy]propyl)piperazin-1-yl]-2,4(1H,3H)-pyrimidinedione.hydrochloride (Compound 132)

The Compound 132 obtained above was treated in the same manner as in Example 7, thereby obtaining the crystals of 1,3-dimethyl-6-[4-(3-[4-benzoyl-2-methanesulfonaminophenoxy]propyl)piperazin-1-yl]-2,4(1H,3H)-pyrimidinedione.

Analytical results of the obtained pyrimidinedione derivative $^1$H-NMR (CDCl$_3$) δ ppm: 2.1 (m, 2H), 2.3–3.1 (m, 10H), 3.03 (s, 3H), 3.33 (s, 3H), 3.41 (s, 3H), 4.28 (t, 2H), 5.44 (s, 1H), 7.1–8.1 (m, 8H).

Furthermore, this pyrimidinedione derivative was treated with a hydrochloric acid/methanol solution in an ordinary manner to obtain the crystals of 1,3-dimethyl-6-[4-(3-[4-benzoyl-2-methanesulfonamidophenoxy]-propyl)piperazin-1-yl]-2,4(1H,3H)-pyrimidinedione.hydrochloride (Compound 132).

Analytical results of the obtained Compound 132

Values of elemental analysis (as C$_{27}$H$_{33}$N$_5$O$_6$S.HCl.1.5H$_2$O): Calcd. (%): C 52.38; H 6.02; N 11.31; Cl 5.73; S 5.18; Found (%): C 52.12; H 5.75; N 11.29; Cl 5.92; S 5.28.

IR $\nu_{max}^{KBr}$ (cm$^{-1}$): 3450, 2550, 1700, 1640, 1600, 1330, 1120, 980, 820, 760.

EXAMPLE 69

Synthesis of 1,3-dimethyl-6-[2-(3-[4-aminophenyl]-N-(2-hydroxyethyl)propylamino)ethylamino]-2,4(1H,3H)-pyrimidinedione.oxalate (Compound 134)

The Compound l obtained in Reference Example 8 was hydrogenated in the same manner as in Example 6 to obtain the crystals of 1,3-dimethyl-6-[2-(3-[4-aminophenyl]-N-(2-hydroxyethyl)propylamino)ethylamino]-2,4(1H,3H)-pyrimidinedione. This pyrimidinedione derivative was further treated with an oxalic acid/methanol solution in an ordinary manner to obtain the crystals of 1,3-dimethyl-6-[2-(3-[4-aminophenyl]-N-(2-hydroxyethyl)propylamino) ethylamino]-2,4(1H,3H)-pyrimidinedione.oxalate (Compound 134).

Analytical results of the obtained Compound 134

Values of elemental analysis (as C$_{19}$H$_{29}$N$_5$O$_3$.2-(COOH)$_2$.½H$_2$O): Calcd. (%): C 48.93; H 6.07; N 12.41; Found (%): C 48.73; H 6.07; N 12.30.

IR $\nu_{max}^{KBr}$ (cm$^{-1}$): 3270, 2850, 2600, 1690, 1600, 1540, 1440, 1195, 1060, 710.

EXAMPLE 70

Synthesis of 1,3-dimethyl-6-[4-(3-[4-aminophenyl]-propyl)piperazin-1-yl]-2,4(1H,3H)-pyrimidinedione.hydrochloride (Compound 135)

The Compound p obtained in Reference Example 11 was hydrogenated in the same manner as in Example 6 to obtain the crystals of 1,3-dimethyl-6-[4-(3-[4-aminophenyl]-propyl)piperazin-1-yl]-2,4(1H,3H)-pyrimidinedione.

Analytical results of the obtained pyrimidinedione derivative $^1$H-NMR (CDCl$_3$) δ ppm: 1.9 (m, 2H), 2.6 (m, 8H), 2.9 (m, 4H), 3.30 (s, 3H), 3.35 (s, 3H), 5.21 (s, 1H), 6.23 (d, 2H), 6.92 (d, 2H).

Furthermore, this pyrimidinedione derivative was treated with a hydrochloric acid/methanol solution in an ordinary manner to obtain the crystals of 1,3-dimethyl-6-[4-(3-[4-aminophenyl]propyl)piperazin-1-yl]-2,4(1H,3H)-pyrimidinedione.hydrochloride (Compound 135).

Analytical results of the obtained Compound 135

IR $\nu_{max}^{KBr}$ (cm$^{-1}$): 3400, 2700, 1700, 1620, 1440, 1210, 990, 810, 760.

Values of elemental analysis (as C$_{19}$H$_{27}$N$_5$O$_2$.2HCl.½H$_2$O): Calcd. (%): C 51.94; H 6.88; N 15.94; Cl 16.14; Found (%): C 51.97; H 6.93; N 15.94; Cl 15.96.

EXAMPLE 71

Synthesis of 1,3-dimethyl-6-[4-(2-[4-methanesulfonamidophenoxy]ethyl)piperazin-1-yl]-2,4(1H,3H)-pyrimidinedione.hydrochloride (Compound 136)

The Compound x obtained in Reference Example 19 was hydrogenated in the same manner as in Example 6 and then methane-sulfonated in the same manner as in Example 7 to obtain the crystals of 1,3-dimethyl-6-[4-(2-[4-methanesulfonamidophenoxy]ethyl)piperazin-1-yl]-2,4(1H,3H)-pyrimidinedione. This pyrimidinedione derivative was treated with a hydrochloric acid/methanol solution in an ordinary manner to obtain the crystals of 1,3-dimethyl-6-[4-(2-[4-methanesulfonamidophenoxy]ethyl)piperazin-1-yl]-2,4(1H,3H)-pyrimidinedione.hydrochloride (Compound 136).

Analytical results of the obtained Compound 136

Values of elemental analysis (as C$_{19}$H$_{27}$N$_5$O$_5$S.HCl.1.5H$_2$O): Calcd. (%): C 45.55; H 6.24; N 13.98; Cl 7.08; S 6.40; Found (%): C 45.06; H 6.38; N 12.59; Cl 7.27; S 6.64.

IR $\nu_{max}^{KBr}$ (cm$^{-1}$): 3450, 1690, 1645, 1515, 1330, 1155, 980, 765.

EXAMPLE 72

Synthesis of 1,3-dimethyl-6-[4-(3-[2-methoxy-4-methanesulfonamidophenoxy]propyl)piperazin-1-yl]-2,4(1H,3H)-pyrimidinedione.hydrochloride (Compound 137)

The Compound w obtained in Reference Example 18 was hydrogenated in the same manner as in Example 6 and then methane-sulfonated in the same manner as in Example 7 to obtain the crystals of 1,3-dimethyl-6-[4-(3-[2-methoxy-4-methanesulfonamidophenoxy]propyl)piperazin-1-yl]-2,4(1H,3H)-pyrimidinedione.

Analytical results of the obtained pyrimidinedione derivative $^1$H-NMR (CDCl$_3$) δ ppm: 2.00 (m, 2H), 2.60 (m, 6H), 2.98 (m, 7H), 3.34 (s, 3H), 3.40 (s, 3H), 3.88 (s, 3H), 4.10 (t, 2H), 5.30 (s, 1H), 6.92 (d, 2H), 7.40 (d, 2H).

This pyrimidinedione derivative was treated with a hydrochloric acid/methanol solution in an ordinary manner to obtain the crystals of 1,3-dimethyl-6-[4-(3-[2-methoxy-4-methanesulfonamidophenoxy]propyl)piperazin-1-yl]-2,4(1H,3H)-pyrimidinedione.hydrochloride (Compound 137).

Analytical results of the obtained Compound 137

Values of elemental analysis (as $C_{21}H_{31}N_5O_6S \cdot HCl \cdot 3H_2O$): Calcd. (%): C 44.09; H 6.69; N 12.24; Cl 6.19; S 5.60; Found (%): C 43.89; H 6.47; N 12.06; Cl 6.41; S 5.72.

EXAMPLE 73

Synthesis of 1,3-dimethyl-6-[4-(3-[4-chloro-2-methanesulfonamidophenoxy]propyl)piperazin-1-yl]-2,4(1H,3H)-pyrimidinedione.hydrochloride (Compound 138)

The Compound t obtained in Reference Example 15 was hydrogenated in the same manner as in Example 6 and then methane-sulfonated in the same manner as in Example 7. Furthermore, the compound was treated with a hydrochloric acid/methanol solution in an ordinary manner to obtain the crystals of 1,3-dimethyl-6-[4-(3-[4-chloro-2-methanesulfonamidophenoxy]propyl)-piperazin-1-yl]-2,4(1H,3H)-pyrimidinedione.hydrochloride (Compound 138).

Analytical results of the obtained Compound 138
Melting point: 275°–277° C. (decomposed).
Values of elemental analysis (as $C_{20}H_{28}ClN_5O_5S \cdot HCl$): Calcd. (%): C 45.98; H 5.60; N 13.41; Cl 13.57; S 5.60; Found (%): C 45.71; H 5.89; N 13.40; Cl 13.45; S 5.71.

EXAMPLE 74

Synthesis of 1,3-dimethyl-6-[4-(3-[2-benzoyl-4-methanesulfonamidophenoxy]propyl)piperazin-1-yl]-2,4(1H,3H)-pyrimidinedione.oxalate (Compound 139)

The Compound s obtained in Reference Example 14 was hydrogenated in the same manner as in Example 6 and then methane-sulfonated in the same manner as in Example 7 to obtain the crystals of 1,3-dimethyl-6-[4-(3-[2-benzoyl-4-methanesulfonamidophenoxy]propyl)piperazin-1-yl]-2,4(1H,3H)-pyrimidinedione.

Analytical results of the obtained pyrimidinedione derivative
$^1$H-NMR (CDCl$_3$) δ ppm: 2.0 (m, 2H), 2.4–2.8 (m, 10H), 2.84 (s, 3H), 3.32 (s, 3H), 3.44 (s, 3H), 4.04 (t, 2H), 5.16 (s, 1H), 6.7–8.0 (m, 8H).

This pyrimidinedione derivative was treated with an oxalic acid/methanol solution in an ordinary manner to obtain the crystals of 1,3-dimethyl-6-[4-(3-[2-benzoyl-4-methanesulfonamidophenoxy]propyl)piperazin-1-yl]-2,4(1H,3H)-pyrimidinedione.oxalate (Compound 139).

Analytical results of the obtained Compound 139
Values of elemental analysis (as $C_{27}H_{33}N_5O_6S \cdot (COOH)_2 \cdot 2.5H_2O$): Calcd. (%): C 50.34; H 5.84; N 10.14; S 4.62; Found (%): C 50.09; H 5.69; N 10.34; S 4.72.
IR $\nu_{max}^{KBr}$(cm$^{-1}$): 1710, 1650, 1590, 1330, 1160, 700.

EXAMPLE 75

Synthesis of 1,3-dimethyl-6-[2-(3-[2-fluorophenyl]-N-(2-hydroxyethyl)propylamino)ethylamino]-2,4(1H,3H)-pyrimidinedione.oxalate (Compound 140)

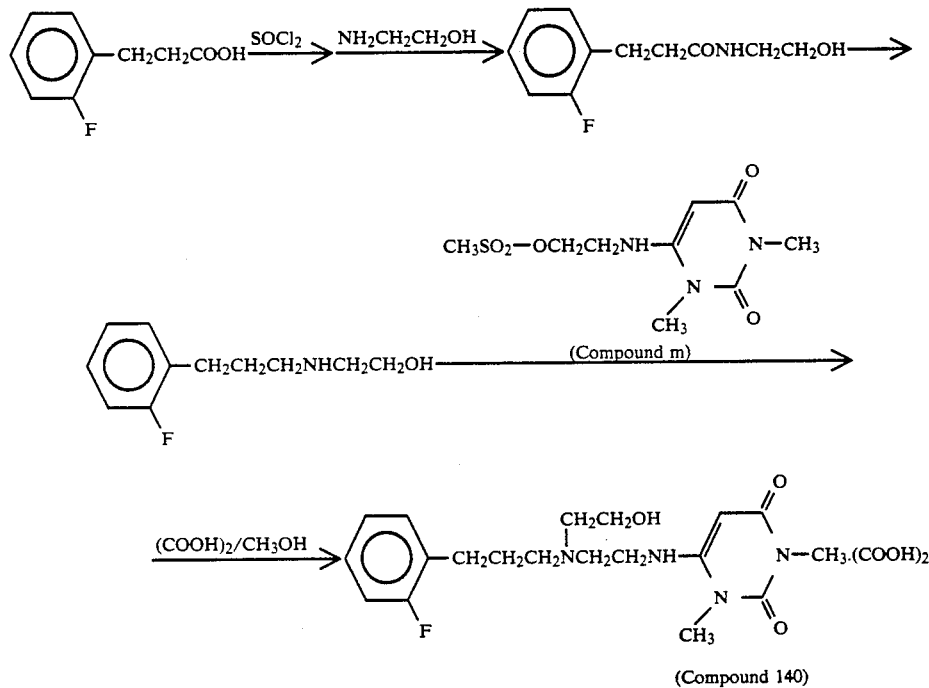

(Compound 140)

The same treatment as in Reference Example 8 was effected except that 3-(4-nitrophenyl)propionic acid was replaced with 3-(2-fluorophenyl)propionic acid, thereby obtaining 1,3-dimethyl-6-[2-(3-[2-fluorophenyl]-N-(2-hydroxyethyl) propylamino)ethylamino]-2,4(1H,3H)-pyrimidinedlone.

Analytical results of the obtained pyrimidinedione derivative
$^1$H-NMR (CDCl$_3$) δ ppm: 2.1 (m, 2H), 2.5–3.1 (m, 10H), 3.30 (s, 3H), 3.41 (s, 3H), 3.6–4.2 (m, 2H), 4.70 (s, 1H), 6.31 (s, 1H), 6.9–7.2 (m, 4H).

This pyrimidinedione derivative was treated with an oxalic acid/methanol solution in an ordinary manner to obtain the crystals of 1,3-dimethyl-6-[2-(3-[2-fluorophenyl]-N-(2-hydroxyethyl)propylamino)ethylamino]-2,4(1H,3H)-pyrimidinedione.oxalate (Compound 140).

EXAMPLE 76

Synthesis of 1,3-dimethyl-6-[2-(3-[2-fluorophenyl]-N-(2-benzolyoxyethyl)propylamino)ethylamino]-2,4(1H,3H)-pyrimidinedione.oxalate (Compound 141)

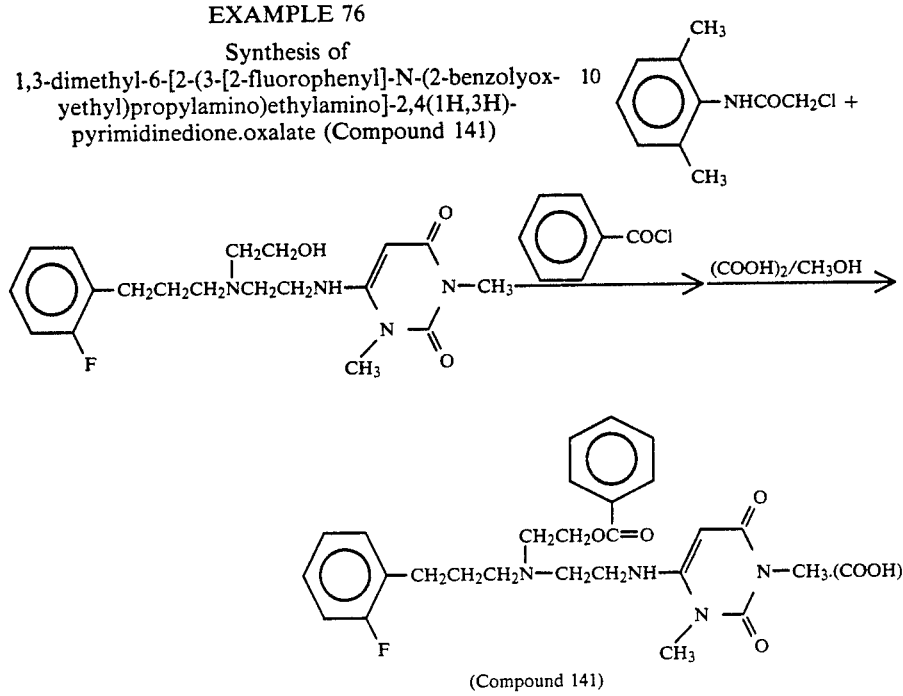

(Compound 141)

In 20 ml of pyridine were dissolved 1.68 g of 1,3-dimethyl-6-[2-(3-[2-fluorophenyl]-N-(2-hydroxyethyl)-propylamino)ethylamino]-2,4(1H,3H)-pyrimidinedione obtained in Example 75 and 2.0 g of benzoyl chloride, and the solution was then stirred at room temperature overnight. Pyridine was distilled off under reduced pressure from the reaction solution, and the resultant residue was purified through a silica gel column chromatograph (chloroform/methanol=50/1 in volume ratio), thereby obtaining 1.5 g of 1,3-dimethyl-6-[2-(3-[2-fluorophenyl]-N-(2-benzolyoxyethyl)propylamino)ethylamino]-2,4(1H,3H)-pyrimidinedione.

Analytical results of the obtained pyrimidinedione derivative $^1$H-NMR (CDCl$_3$) δ ppm: 1.9 (m, 2H), 2.4–3.1 (m, 10H), 3.06 (s, 3H), 3.20 (s, 3H), 4.36 (t, 2H), 4.92 (s, 1H), 5.52 (s, 1H), 6.9–7.6 (m, 7H), 7.9–8.1 (m, 2H).

1.4 g of this pyrimidinedione derivative was treated with an oxalic acid/methanol solution in an ordinary manner to obtain 1.29 g of crystalline 1,3-dimethyl-6-2-(3-[2-fluorophenyl]-N-(2-benzolyoxyethyl)-propylamino)ethylamino]-2,4(1H,3H)-pyrimidinedione.oxalate (Compound 141) in a crystalline state.

Analytical results of the obtained Compound 141
Melting point: 142°–144° C. (decomposed).

IR $\nu_{max}^{KBr}$ (cm$^{-1}$). 3350, 1740, 1700, 1630, 1540, 1270, 760, 710.

Values of elemental analysis (as C$_{26}$H$_{31}$N$_4$O$_4$F.(COOH)$_2$.½H$_2$O): Calcd. (%): C 57.82; H 5.89; N 9.63; Found (%): C 58.09; H 5.91; N 9.88.

Analytical results of the obtained Compound 140
IR $\nu_{max}^{KBr}$ (cm$^{-1}$): 3300, 2950, 1700, 1640, 1420, 1220, 980, 760, 700.

Values of elemental analysis (as C$_{19}$H$_{27}$N$_4$O$_3$F.(COO)$_2$.½H$_2$O): Calcd. (%): C 52.82; H 6.33; N 11.73; Found (%): C 52.70; H 6.07; N 11.52.

EXAMPLE 77

Synthesis of 1,3-dimethyl-6-[4-(N-[2,6-dimethylphenyl]carbamoylmethyl)piperazin-1-yl]-2,4(1H,3H)-pyrimidinedione.hydrochloride (Compound 142)

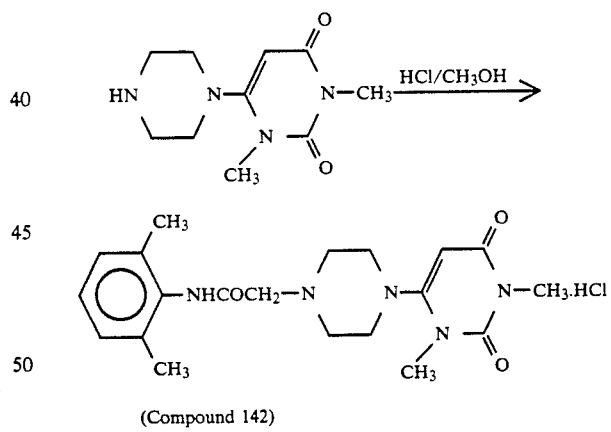

(Compound 142)

In 50 ml of ethanol were dissolved 0.99 g of N-[2,6-dimethylphenyl]carbamoylmethyl chloride, 1.12 g of 1,3-dimethyl-6-(1-piperazinyl)-2,4(1H,3H)-pyrimidinedione and 2 g of triethylamine, and the solution was then heated under reflux for 15 hours. After standing for cooling, the precipitated crystals were collected by filtration, and the crystals were then recrystallized from ethanol/n-hexane, thereby obtaining 1.04 g of 1,3-dimethyl-6-[4-(N-[2,6-dimethylphenyl]carbamoylmethyl)piperazin-1-yl]-2,4(1H,3H)-pyrimidinedione.

Analytical results of the obtained pyrimidinedione derivative $^1$H-NMR (CDCl$_3$) δ ppm: 2.24 (s, 6H), 2.6–3.1 (m, 10H), 3.30 (s, 3H), 3.39 (s, 3H), 5.22 (s, 1H), 7.08 (s, 3H), 8.44 (s, 1H).

This pyrimidinedione derivative was treated with a hydrochloric acid/methanol solution in an ordinary manner to obtain the crystals of 1,3-dimethyl-6-[4-(N-[2,6-dimethylphenyl]carbamoylmethyl)piperazin-1-yl]-2,4-(1H,3H)-pyrimidinedione.hydrochloride (Compound 142):

Analytical results of the obtained Compound 142

Values of elemental analysis (as $C_{20}H_{27}N_5O_3 \cdot HCl \cdot H_2O$): Calcd. (%): C 54.60; H 6.87; N 15.92; Cl 8.06; Found (%): C 54.40; H 6.72; N 15.61; Cl 7.90.

Melting point: 170°–173° C. (decomposed).

EXAMPLE 78

Synthesis of 1,3-dimethyl-6-[4-(3-[2-(4-nitrocinnamoyl)phenoxy]-propyl)piperazin-1-yl]-2,4(1H,3H)-pyrimidinedione.hydrochloride (Compound 143)

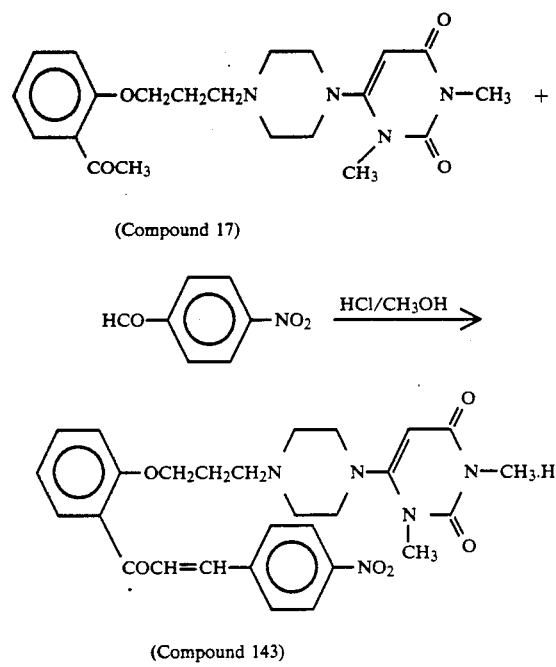

0.96 g of NaOH was dissolved in a mixed solvent of 10 ml of water and 5 ml of ethanol, and at room temperature, the mixture was then added to a solution which was prepared by dissolving 1.0 g of 1,3-dimethyl-6-[4-(3-[2-acetylphenoxy)propyl)piperazin-1-yl]-2,4(1H,3H)-pyrimidinedione (Compound 17) obtained in Example 17 and 0.42 g of p-nitrobenzaldehyde in a mixed solvent of 6 ml of chloroform and 14 ml of ethanol. Afterward, the solution was stirred at the same temperature for 2 hours, and 50 ml of chloroform and 200 ml of water were added to the reaction mixture. Next, the resultant organic layer was separated, washed with an aqueous saturated sodium chloride solution and then dried over anhydrous sodium sulfate, and the solvent was distilled off under reduced pressure. The resultant residue was purified through a silica gel column chromatograph (ethyl acetate/methanol=20/1 to 10/1 in volume ratio), thereby obtaining 0.93 g of 1,3-dimethyl-6-[4-(3-[2-(4-nitrocinnamoyl)phenoxy]-propyl)piperazin-1-yl]-2,4(1H,3H)-pyrimidinedione.

Analytical results of the obtained pyrimidinedione derivative $^1$H-NMR (CDCl$_3$) δ ppm: 1.96 (m, 2H), 2.46 (m, 6H), 2.86 (m, 4H), 3.28 (s, 3H), 3.32 (s, 3H), 4.15 (t, 2H), 5.16 (s, 1H), 6.92–7.12 (m, 2H), 7.36–7.80 (m, 6H), 8.15–8.32 (d, 2H).

This pyrimidinedione derivative was treated with a hydrochloric acid/methanol solution in an ordinary manner to obtain the crystals of 1,3-dimethyl-6-[4-(3-[2-(4-nitrocinnamoyl)phenoxy]propyl)piperazin-1-yl]-2,4(1H,3H)-pyrimidinedione.hydrochloride (Compound 143).

Analytical results of the obtained Compound 143

Values of elemental analysis (as $C_{21}H_{31}N_5O_4S \cdot HCl$): Calcd. (%): C 59.00; H 5.66; N 12.29; Cl 6.22; Found (%): C 59.21; H 5.82; N 12.01; Cl 6.21.

EXAMPLE 79

Synthesis of 1,3-dimethyl-6-[4-(3-{2-[3-(4-pyridyl)-acryloyl]phenoxy}propyl)piperazin-1-yl]-2,4(1H,3H)-pyrimidinedione.oxalate (Compound 144)

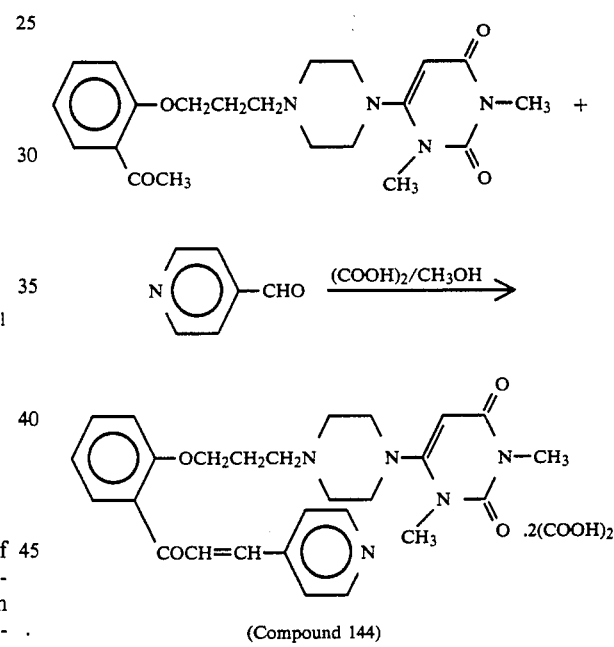

The same treatment as in Reference Example 78 was effected except that p-nitrobenzaldehyde was replaced with 4-pyridinecarboxylaldehyde, thereby obtaining 1,3-dimethyl-6-[4-(3-{2-[3-(4-pyridyl)acryloyl]phenoxy}-propyl)piperazin-1-yl]-2,4(1H,3H)-pyrimidinedione. Furthermore, this pyrimidinedione derivative was treated with an oxalic acid/methanol solution in an ordinary manner to obtain 1,3-dimethyl-6-[4-(3-{2-[3-(4-pyridyl)-acryloyl]phenoxy}propyl)piperazin-1-yl]-2,4(1H,3H)-pyrimidinedione.oxalate (Compound 144).

Analytical results of the obtained Compound 144

Melting point: 202°–204.5° C.

Values of elemental analysis (as $C_{27}H_{31}N_5O_4 \cdot 2(COOH)_2$): Calcd. (%): C 55.60; H 5.27; N 10.46; Found (%): C 55.97; H 5.55; N 10.56.

EXAMPLE 80

Synthesis of
1,3-dimethyl-6-[4-(3-[2-(3,4,5-trimethoxycinnamoyl)-
phenoxy]propyl)piperazin-1-yl]2,4(1H,3H)-pyrimidine-
dione.hydrochloride (Compound 145)

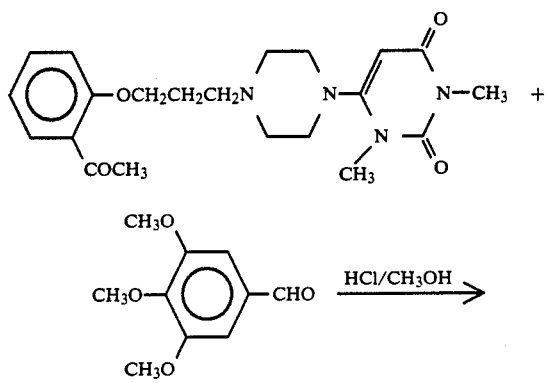

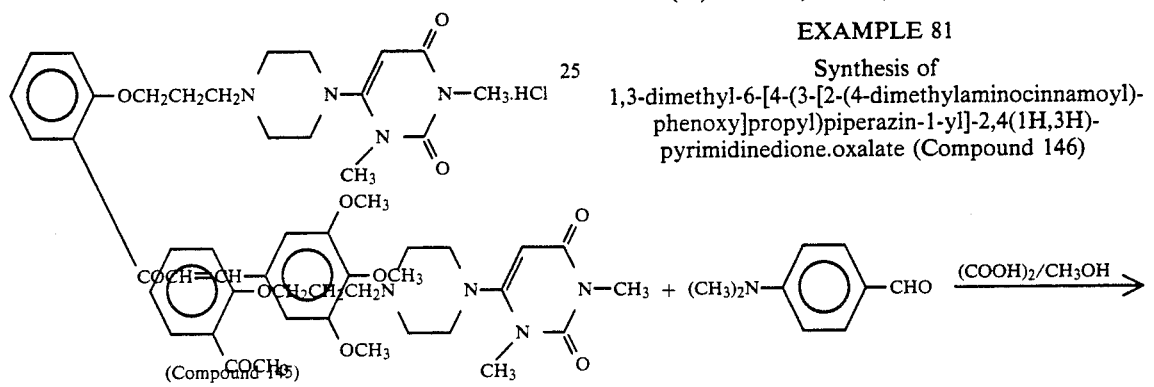

In 30 ml of anhydrous tetrahydrofuran were suspended 1.50 g of 1,3-dimethyl-6-[4-(3-[2-acetylphenoxy)propyl)-piperazin-1-yl]-2,4(1H,3H)-pyrimidinedione (Compound 17) obtained in Example 2 and 0.7 g of 3,4,5-trimethoxybenzaldehyde, and 0.19 ml of sodium hydride (60% and oily) was added to the suspension under ice cooling. Afterward, the suspension was stirred at the same temperature for 1 hour, and 1.0 ml of anhydrous ethanol was then added dropwise thereto, followed by stirring at room temperature for 3 hours. Next, 1 ml of water was added to the reaction solution, and this solution was then concentrated to dryness under reduced pressure and the resultant residue was dissolved in 50 ml of chloroform. The chloroform solution was washed with an aqueous saturated sodium chloride solution and then dried over anhydrous sodium sulfate, and the solvent was distilled off under reduced pressure. The resultant residue was purified through a silica gel column chromatograph (chloroform/methanol=50/1 to 10/1 in volume ratio), thereby obtaining 1.65 g of crystalline 1,3-dimethyl-6-[4-(3-[2-(3,4,5-trimethoxycinnamoyl)phenoxy]propyl)piperazin-1-yl]-2,4(1H,3H)-pyrimidinedione. Furthermore, this pyrimidinedione derivative was treated with a hydrochloric acid/methanol solution in an ordinary manner to obtain the crystals of 1,3-dimethyl-6-[4-(3-[2-(3,4,5-trimethoxycinnamoyl)phenoxy]propyl)piperazin-1-yl]-2,4(1H,3H)-pyrimidinedione.hydrochloride (Compound 145).

Analytical results of the obtained Compound 145
Melting point: 257°-258° C.
Values of elemental analysis (as $C_{31}H_{36}N_4O_7 \cdot HCl \cdot \frac{1}{2} H_2O$): Calcd. (%): C 59.85; H 6.16; N 9.01; Cl 5.70; Found (%): C 59.63; H 6.11; N 9.11; Cl 5.73.

EXAMPLE 81

Synthesis of
1,3-dimethyl-6-[4-(3-[2-(4-dimethylaminocinnamoyl)-
phenoxy]propyl)piperazin-1-yl]-2,4(1H,3H)-
pyrimidinedione.oxalate (Compound 146)

The same treatment as in Example 80 was effected except that 3,4,5-trimethoxybenzaldehyde was replaced with 4-dimethylaminobenzaldehyde, thereby obtaining 1,3-dimethyl-6-[4-(3-[2-(4-dimethylaminocinnamoyl)-phenoxy]-propyl)piperazin-1-yl]-2,4(1H,3H)-pyrimidinedione. Furthermore, this pyrimidinedione derivative was treated with an oxalic acid/methanol solution in an ordinary manner to obtain 1,3-dimethyl-6-[4-(3-[2-(4-dimethylaminocinnamoyl)phenoxy]propyl)piperazin-1-yl]-2,4(1H,3H)-pyrimidinedione.oxalate (Compound 146).

Analytical results of the obtained Compound 146
Values of elemental analysis (as $C_{30}H_{37}N_5O_4 \cdot (COOH)_2$): Calcd. (%): C 61.82; H 6.32; N 11.27; Found (%): C 61.81; H 6.64; N 11.20.

EXAMPLE 82

Synthesis of 1,3-dimethyl-6-[4-(3-{2-[3-(4-methylthiophenyl)acryloyl]phenoxy}propyl)piperazin-1-yl]-2,4(1H,3H)-pyrimidinedione.oxalate (Compound 147)

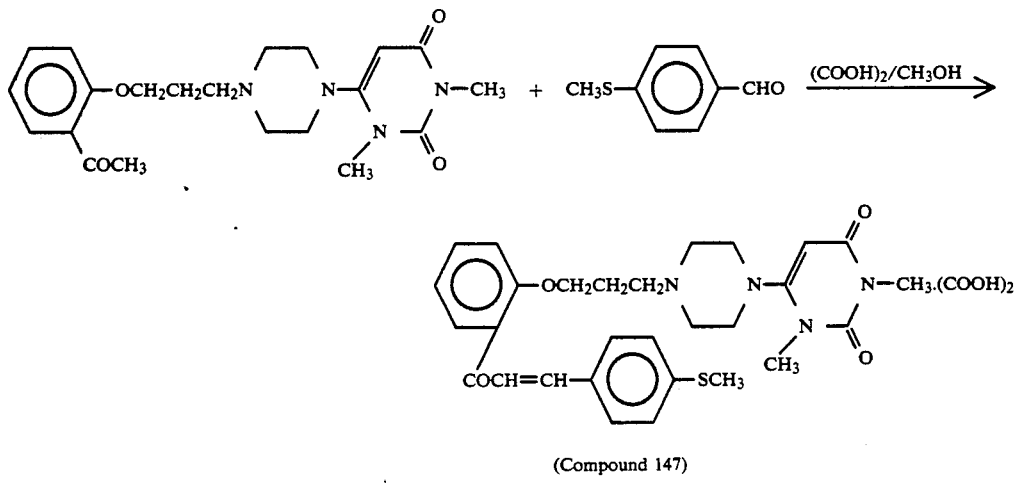

(Compound 147)

The same treatment as in Example 80 was effected except that 3,4,5-trimethoxybenzaldehyde was replaced with 4-methylthiobenzaldehyde, thereby obtaining 1,3-dimethyl-6-[4-(3-{2-[3-(4-methylthiophenyl)acryloyl]-phenoxy}propyl)piperazin-1-yl]-2,4(1H,3H)-pyrimidinedione. Furthermore, this pyrimidinedione derivative was treated with an oxalic acid/methanol solution in an ordinary manner to obtain 1,3-dimethyl-6-[4-(3-{2-[3-(4-methylthiophenyl)acryloyl]phenoxy}propyl)piperazin-1-yl]-2,4(1H,3H)-pyrimidinedione.oxalate (Compound 147).

Analytical results of the obtained Compound 147
Melting point: 86°–93° C.
Values of elemental analysis (as $C_{29}H_{34}N_4O_4S.2(COO)_2.\tfrac{1}{2}H_2O$): Calcd. (%): C 58.76; H 5.89; N 8.84; S 5.06; Found (%): C 58.77; H 6.12; N 8.64; S 5.05.

PHARMACOLOGICAL TEST EXAMPLE 1

(1) Influence on Myocardial Action Potential Duration Time ($APD_{75}$)

To a hybrid adult dog, 30 mg/kg of pentobarbital was administered through a vein, and after being anesthetized, the heart was removed. Afterward, the right ventricular free wall of the heart was cut and taken out in a Tyrode solution.

The taken right ventricular free wall was fixed in an incubator at 37° C., and a nutritional solution (20 ml of the Tyrode solution) was refluxed.

In this isolated condition, myocardial action potential duration times ($APD_{75}$) were measured before and after the administration of the respective compounds prepared in the above examples in Table A and d-sotalol as a control medicine, and $APD_{75}(\%)$ was calculated from the measured results in accordance with the formula:

$$APD_{75}(\%)=(B-A)/A\times 100$$

A: $APD_{75}$ before administration
B: $APD_{75}$ after administration

Here, $APD_{75}$ was measured as follows: A field stimulation of 1 Hz was given to the right ventricular free wall, and any variation of an action potential was depicted on an oscilloscope via a glass microelectrode (10 to 20 MΩ) thrust into a Purkinje fiber of the free wall and via an amplifier. Afterward, a waveform on the oscilloscope was analyzed by the use of a computer, and the time of from a point of the action potential generation to a point of 75% repolarization was measured.

This measured time was regarded as the myocardial action potential duration time ($APD_{75}$).

The compounds and d-sotalol shown in Table A were separately added to the refluxing nutritional solution (20 ml), and after 20 minutes' incubation, $APD_{75}$ after the administration was calculated from the variation of the myocardial action potential duration time.

Incidentally, this test was carried out in accordance with a Sato et al's method [H. Sato, K. Hashimoto, Arzneimeittel Forschung, 34 (1), 3a, 376–380 (1984)].

The obtained results are set forth in Table A.

(2) Influence on Ventricular Muscle Refractory Period

Refractory periods were measured in the following manner before and after each of the compounds and d-sotalol shown an Table A was separately administered to a vein or a duodenum, and ERP (%; extensibility of refractory period) was calculated from the measured values in accordance with the following formula:

$$ERP(\%)=(W-Y)/Y\times 100$$

W: Refractory period after administration
Y: Refractory period before administration To a mongrel adult dog, 30 mg/kg of pentobarbital was administered intravenously, and after being anesthetized, a pair of silver-silver chloride electrodes separated by 3 mm was sewn on an opened right ventricule, and electrical stimulation was given at an interval of 400 msec at a duration time of 4 msec under a current twice as much as the threshold. Afterward, a small amount of alcohol was injected into a sinus artery in order to extinguish a pacemaker activity, and the ventricular refractory period (ERP) was measured under ventricule pacing.

That is, 1 train comprised 10 stimulations, and an interval between two of the trains was usually 400 msec. At the time of the refractory period measurement, however, the above interval was shortened every 10 smec, and the interval between the trains at the time when reaction to the first stimulation of the train disappeared was regarded as the refractory period.

In this case, the electrical stimulation was fed in accordance with a program by a heart stimulation device (Diamedical Co., Ltd.; DHM-226-3).

The results are set forth in Tables A-1 and A-2.

TABLE A-1

(results of pharmacological test)

| Compound No. | APD75 (%) Dose (μg, ml) | | | | ERP (%) Dose (i.V., mg/kg) | | | |
|---|---|---|---|---|---|---|---|---|
| | 0.3 | 1.0 | 3.0 | 10.0 | 0.1 | 0.3 | 1.0 | 3.0 |
| 1 | | 17 | 22 | 30 | 6 | 12 | 15.8 | 24.3 |
| 4' | | 5 | 8 | | | | | |
| 6' | | 5 | 10 | 25 | 0 | 0 | 0 | 6.2 |
| 9' | | 6 | 21 | 30 | 5.6 | 5.6 | 11.1 | 16.7 |
| 12' | | 4 | 11 | 28 | 0 | 2.1 | 4.3 | 17 |
| 16' | | 6 | 14 | 23 | 0 | 0 | 6.7 | 10 |
| 17' | | 28 | 43 | 59 | 3.5 | 8.3 | 13.5 | 17.3 |
| 18' | | | 11 | 22 | | 6.3 | 12.5 | |
| 21' | | 11 | 23 | 26 | 7.1 | 7.1 | 7.1 | 14.3 |
| 25' | | 13 | 26 | | 0 | 0 | 0 | 7.6 |
| 31' | | 13 | 16 | | 0 | 0 | 6.3 | 12.9 |
| 36' | | | 17 | | 0 | 7.1 | 7.1 | 14.3 |
| 37' | | | 10 | 21 | | | | |
| 39' | | | 26 | 48 | | | | |
| 43' | | | 13 | 18 | 0 | 0 | 7.7 | 19.3 |
| 45' | | 42 | 71 | 75 | 0. | 2.4 | 9.5 | 18.6 |
| 50' | | 6 | 15 | 26 | 0 | 5.6 | 5.6 | 11.1 |
| 51' | 11 | 19 | 24 | | 0 | 6.3 | 6.3 | 12.5 |

TABLE A-2

(results of pharmacological test)

| Compound No. | APD75 (%) Dose (μg, ml) | | | | ERP (%) Dose (i.V., mg/kg) | | | |
|---|---|---|---|---|---|---|---|---|
| | 0.3 | 1.0 | 3.0 | 10.0 | 0.1 | 0.3 | 1.0 | 3.0 |
| 52' | | | 9 | 14 | 18 | | | |
| 53' | | | 25 | 33 | | | | |
| 58' | | | 19 | 29 | 36 | | | |
| 60' | | | 15 | 30 | 67 | 0 | 6 | 13 | 19 |
| 64 | 7 | 14 | 25 | | 2 | 6.3 | 13 | 24.3 |
| 65 | | | 14 | 17 | 0 | 0 | 0 | 0 |
| 69 | | | 24 | 34 | 0 | 6.3 | 12.5 | |
| 82 | | 16 | 28 | 43 | | | | |
| 88 | | | 26 | 49 | 2 | 6 | 11.7 | |
| 89 | | 15 | 26 | 31 | 0 | 5.7 | 9.7 | 14 |
| 91 | | 13 | 25 | | 3.5 | 6.5 | 14.5 | |
| 98 | | 4 | 13 | 25 | 0 | 0 | 7.7 | 15.4 |
| 111 | | | 19 | 36 | 0 | 2.4 | 8.6 | 15.2 |
| 113 | | 2 | 17 | 26 | 0 | 0 | 11.8 | 17.6 |
| 117 | | 17 | 23 | | 3.2 | 3.2 | 6.9 | 16.1 |
| 120 | | 6 | 14 | 26 | | | | |
| 121 | | 9 | 14 | 16 | | | | |
| d-sota- | 0 | 3 | 7.4 | 15.8 | 1.7 | 6.7 | 8.7 | 15.5 |

Toxicity Test 1

Each of the compounds prepared in the above-mentioned examples shown in Table B was administered into a mouse (ddy strain, male). In each case, the administration was effected by oral administration in a dose of 300 mg/kg.

A mortality rate (number of specimens: one group=2 to 4 mice) of the mice 24 hours after the administration was calculated, and the results are set forth in Table B.

TABLE B (results of toxicity test)

| Compound Number | Mortality Rate (%) 300 mg/kg (P.O) |
|---|---|
| 2 | 50 |
| 4' | 0 |
| 6' | 0 |

TABLE B-continued (results of toxicity test)

| Compound Number | Mortality Rate (%) 300 mg/kg (P.O) |
|---|---|
| 7' | 0 |
| 21' | 0 |
| 29' | 0 |
| 37' | 0 |
| 45' | 50 |
| 60' | 0 |
| 64 | 0 |
| 69 | 0 |
| 82 | 0 |
| 85 | 0 |

What is claimed is:

1. A pyrimidinedione derivative which is represented by the formula (I)

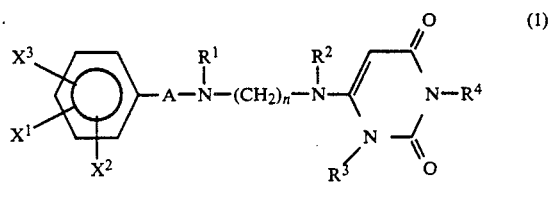

wherein A is $-(CH_2)_m-$, $-B-(CH_2)_k-$, $D-(CH_2)_l-$ or

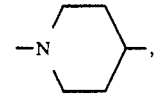

B is an oxygen atom, sulfur atom,

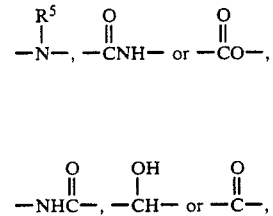

and D is

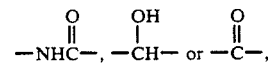

$R^1$ and $R^2$ are so linked with each other as to make an alkylene chain and thus form a heterocyclic structure, each of $R^3$ and $R^4$ is independently a hydrogen atom or lower alkyl group, each of $X^1$, $X^2$ and $X^3$ is independently a hydrogen atom, $-CO-R^6$, halogen atom, lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^5$ is a hydrogen atom, lower alkylsulfonyl group or lower alkyl group, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, m is 0, 1, 2, 3 or 4, k is 2, 3 or 4, and l is 0, 1, 2, 3 or 4.

2. A pyrimidinedione derivative described in claim 1 which is represented by the formula (2)

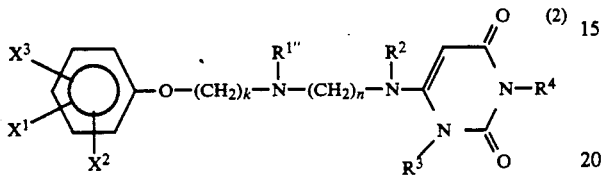

wherein $R^{1''}$ and $R^2$ are so linked with each other as to make an alkylene chain and thus form a heterocyclic structure, each of $R^3$ and $R^4$ is independently a hydrogen atom or a lower alkyl group, each of $X^1$, $X^2$ and $X^3$ is independently a hydrogen atom, $-CO-R^6$, halogen atom, lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, and k is 2, 3 or 4.

3. A pyrimidinedione derivative described in claim 1 which is represented by the formula (3)

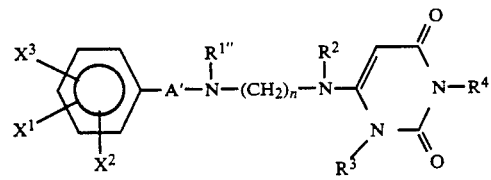

wherein A' is $-(CH_2)_m-$, $-B'-(CH_2)_k-$ or

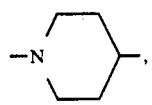

B' is an oxygen atom, sulfur atom or

$R^{1''}$ and $R^2$ are so linked with each other as to make an alkylene chain and thus form a heterocyclic structure, each of $R^3$ and $R^4$ is independently a hydrogen atom or lower alkyl group, each of $X^1$, $X^2$ and $X^3$ is independently a hydrogen atom, $-CO-R^6$, halogen atom, lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^{5'}$ is a hydrogen atom, lower alkylsulfonyl group or lower alkyl group, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, m is 0, 1, 2, 3 or 4, and k is 2, 3 or 4.

4. A pyrimidinedione derivative described in claim 1 which is represented by the formula (4)

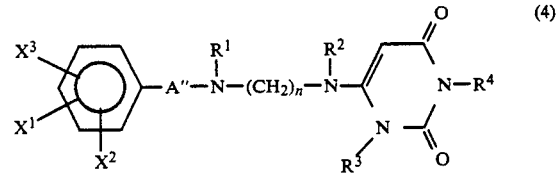

wherein A'' is $-B''-(CH_2)_k-$ or

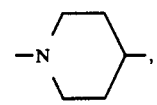

B'' is an oxygen atom, sulfur atom or

$R^1$ and $R^2$ are so linked with each other as to make an alkylene chain and thus form a heterocyclic structure, each of $R^3$ and $R^4$ is independently a hydrogen atom or lower alkyl group, each of $X^1$, $X^2$ and $X^3$ is independently a hydrogen atom, $-CO-R^6$, halogen atom, lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^5$ is a hydrogen atom, lower alkylsulfonyl group or lower alkyl group, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, and k is 2, 3 or 4.

5. A pyrimidinedione derivative described in claim 1 which is represented by the formula (6)

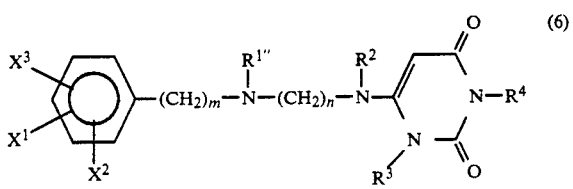

wherein $R^{1''}$ and $R^2$ are so linked with each other as to make an alkylene chain and thus form a heterocyclic structure, each of $R^3$ and $R^4$ is independently a hydrogen atom or lower alkyl group, each of $X^1$, $X^2$ and $X^3$ is independently a hydrogen atom, —CO—$R^6$, halogen atom, lower alkyl group, halogen-substituted lower alkyl group, hydroxyl group, lower alkyloxy group, lower alkylthio group, lower alkyloxycarbonyl group, carboxyl group, cyano group, amino group, lower alkanoyloxy group, lower alkanoylamino group, lower alkylsulfonamido group, lower alkylsulfonyl group, ureido group, lower alkylsulfinyl group, sulfamoyl group, heterocyclic ring, mono- or di-lower alkylamino group, phenyl-substituted lower alkylamino group, trifluoroacetylamino group, trifluoromethylsulfonamido group, phenylsulfonamido group or unsaturated lower alkyloxy group, $R^6$ is a lower alkyl group (which may be substituted by a halogen atom, phenyl group or lower alkyloxycarbonyl group), unsaturated lower alkyl group (which may be substituted by a phenyl group or substituted phenyl group), cycloalkyl group, phenyl group or heterocyclic ring, n is 2 or 3, and m is 0, 1, 2, 3 or 4.

6. A pharmaceutically acceptable acid addition salt of the pyrimidinedione derivative described in any one of claims 1 to 5.

7. An antiarrhythmic agent containing, as an effective ingredient, the pyrimidinedione derivative of any one of claims 1 to 5.

8. A method of treating cardiac arrhythmias comprising administering to a person in need of same an effective amount of the compound of any one of claims 1 to 5.

9. A pyrimidinedione derivative described in claim 1 which is 6-[4-(3-[4-chlorolphenoxy]propyl)-piperazin-1-yl]-1,3-dimethyl-2,4(1H,3H)-pyrimidinedione.hydrochloride.

10. An antiarrhythmic agent containing, as an effective ingredient, a pharmaceutically acceptable addition salt of a pyrimidinedione derivative of claim 6.

11. A method of treating cardiac arrhythmias comprising administering to a person in need of same an effective amount of an acid addition salt of claim 6.

* * * * *